US011203587B2

(12) United States Patent
Kirschberg et al.

(10) Patent No.: US 11,203,587 B2
(45) Date of Patent: Dec. 21, 2021

(54) THYROID HORMONE RECEPTOR BETA AGONIST COMPOUNDS

(71) Applicant: Terns, Inc., Foster City, CA (US)

(72) Inventors: Thorsten A. Kirschberg, San Carlos, CA (US); Randall Halcomb, Foster City, CA (US); Yingzi Xu, Palo Alto, CA (US); F. Anthony Romero, Redwood City, CA (US)

(73) Assignee: TERNS, INC., Foster City, CA (US)

( * ) Notice: Subject to any disclaimer, the term of this patent is extended or adjusted under 35 U.S.C. 154(b) by 0 days.

(21) Appl. No.: 16/598,978

(22) Filed: Oct. 10, 2019

(65) Prior Publication Data

US 2020/0115362 A1   Apr. 16, 2020

Related U.S. Application Data

(60) Provisional application No. 62/745,195, filed on Oct. 12, 2018.

(51) Int. Cl.
| | | |
|---|---|---|
| *C07D 403/12* | (2006.01) | |
| *C07D 413/10* | (2006.01) | |
| *A61P 1/16* | (2006.01) | |
| *A61P 3/06* | (2006.01) | |

(52) U.S. Cl.
CPC .............. *C07D 403/12* (2013.01); *A61P 1/16* (2018.01); *A61P 3/06* (2018.01); *C07D 413/10* (2013.01)

(58) Field of Classification Search
CPC ..... C07D 403/12; C07D 413/10; A61K 31/53
USPC .......................................... 544/182; 514/242
See application file for complete search history.

(56) References Cited

U.S. PATENT DOCUMENTS

| | | | |
|---|---|---|---|
| 7,807,674 | B2 | 10/2010 | Haynes |
| 8,791,266 | B2 | 7/2014 | Kawata |
| 10,800,767 | B2 | 10/2020 | Kirschberg |
| 2004/0157844 | A1 | 8/2004 | Dow |
| 2005/0085541 | A1 | 4/2005 | Shiohara |
| 2008/0167313 | A1 | 7/2008 | Dupont-passelaigue |
| 2009/0005383 | A1 | 1/2009 | Haynes |
| 2009/0247539 | A1 | 10/2009 | Bell |
| 2010/0004271 | A1 | 1/2010 | Collazo et al. |
| 2012/0129812 | A1 | 5/2012 | Kawata et al. |
| 2014/0275077 | A1 | 9/2014 | Dandu |
| 2015/0368205 | A1 | 12/2015 | Ji |
| 2017/0050949 | A1 | 2/2017 | Dandu |
| 2017/0334883 | A1 | 11/2017 | Albrecht |
| 2020/0190064 | A1 | 6/2020 | Yu |
| 2020/0399249 | A1 | 12/2020 | Yu |

FOREIGN PATENT DOCUMENTS

| | | |
|---|---|---|
| CN | 111484481 A | 8/2020 |
| WO | 2003094845 A2 | 11/2003 |
| WO | 2007009913 A1 | 1/2007 |
| WO | 2010122980 A1 | 10/2010 |
| WO | 2011038207 A1 | 3/2011 |
| WO | 2018075650 A1 | 4/2018 |
| WO | 2019144835 A1 | 8/2019 |
| WO | 2019240938 A1 | 12/2019 |
| WO | 2020073974 A1 | 4/2020 |
| WO | 2020169069 A1 | 8/2020 |
| WO | 2020239076 A1 | 12/2020 |

OTHER PUBLICATIONS

Kowalik et al. Frontiers in Endocrinology, 2018, vol. 9, Article 382, pp. 1-11.*
Basnak, I. et al. (1975). "Synthesis of 5-cyclopropyl-6-azauracil," Collect. Czech Chem. Commun. 40(4):1038-1042.
Dermer, G.B. et al. (Mar. 1994). "Another Anniversary for the War on Cancer," Bio/Technology 12:320, 1 page.
Freshney, R.I. et al. (1983). Culture of Animal Cells, A Manual of Basic Technique, Alan R. Liss, Inc., 1983, New York, p. 4. and pp. 129-133, 9 pages.
Hill, S.R. Jr. et al. (1960). "The Metabolic Effects of the Acetic and Propionic Acid Analogs of Thyroxine and Triiodothyronine," J. Clin. Invest. 39:523-533.
International Search Report and Written Opinion of the International Searching Authority dated Jan. 23, 2020, for Patent Application No. PCT/US19/55689, filed Oct. 10, 2019, 13 pages.
Invitation to Pay Additional Fees dated Nov. 21, 2019, for Patent Application No. PCT/US19/55689, filed Oct. 10, 2019, 2 pages.
Kelly, M.J. et al. (May 22, 2014, e-pub. Apr. 8, 2014). "Discovery of 2-[3,5-dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia," J. Med . Chem. 57(10):3912-3923.
Klein, I. et al. (Oct. 9, 2007). "Cardiovascular Involvement in General Medical Conditions: Thyroid Disease and the Heart," Circulation 116:1725-1735.
Kogler, M. (Mar. 2012). "Synthesis and Evaluation of 6-aza-2'-deoxyuridine Monophosphate Analogs as Inhibitors pf Thymidylate Synthases, and as Substrates or Inhibitors of Thymidine Monophosphate Kinase in *Mycobacterium tuberculosis*," Chem. Biodivers. 9(3):536-556.
Simone, J.V. et al. (1996). "Oncology," Part XIV in Cecil Textbook of Medicine, 20th edition, Bennet, J.C. et al. eds., W.B. Saunders Company, pp. 1004-1010.
Sinha, R. A et al. (May 2018, e-pub. Feb. 23, 2018). "Direct Effects of Thyroid Hormones on Hepatic Lipid Metabolism," Nat. Rev. Endocrinology 14(5):259-269, 26 pages.
PUBCHEM (Jan. 12, 2016). "4-(1,2,4-Benzotriazin-3-Yloxy)-N-Methylaniline," CID: 103204817, 7 pages.

* cited by examiner

*Primary Examiner* — Susanna Moore

(74) *Attorney, Agent, or Firm* — Morrison & Foerster LLP

(57) ABSTRACT

Provided herein are compounds, preferably thyroid hormone receptor beta (THR beta) agonist compounds, compositions thereof, methods of their preparation, and methods of agonizing THR beta and methods for treating disorders mediated by THR beta.

21 Claims, No Drawings

THYROID HORMONE RECEPTOR BETA AGONIST COMPOUNDS

CROSS-REFERENCE TO RELATED APPLICATIONS

This application claims priority to U.S. Provisional Application No. 62/745,195, filed Oct. 12, 2018, the disclosure of which is hereby incorporated by reference in its entirety for all purposes.

FIELD OF THE INVENTION

This invention relates to compounds, preferably thyroid hormone receptor beta (THR beta) agonist compounds, compositions thereof, and methods of their preparation, and methods of agonizing THR beta and methods for treating disorders benefiting from THR beta agonism.

BACKGROUND OF THE INVENTION

The beneficial effects arising from treating hyperthyroid or hypothyroid patients with T3/T4 endogenous ligands or early analogs of these endogenous ligands have been described in the literature (Richardson Hill Jr., S. et al. *J. Clin. Invest.* 1960, 39, 523-533). These early studies, as well as similar follow-up studies, established the heart as a major organ for the manifestation of side effects of both hyperthyroidism and hypothyroidism (Klein, I. et al. *Circulation*, 2007, 1725-1735). In particular, tachycardia, hypertrophism, atrial dysrhythmias, and atrial fibrillation are serious concerns. In addition, increased bone turn-over leading to decreased bone mineral density has also been noted. Negative effects at both sites, heart and bone, have been linked to the agonism of the THR alpha isoform, whereas the beneficial effects of THR agonism in the liver are largely linked to the THR beta isoform (Sinha, R. A. et al. *Nat. Rev. Endocrinology* 2018, 14, 259-269).

Diseases or disorders associated with THR beta include non-alcoholic steatohepatitis (NASH), non-alcoholic fatty liver disease (NAFLD), metabolic syndrome, dyslipidemia, hypertriglyceridemia, and hypercholesterolemia. There is a need to develop new thyroid hormone analogs that are selective agonists for THR beta, and preferably those that avoid the undesirable effects associated with agonism of THR alpha, and maintain the beneficial effects of thyroid hormones, e.g., for the treatment for patients with non-alcoholic steatohepatitis (NASH), non-alcoholic fatty liver disease (NAFLD), metabolic syndrome, dyslipidemia, hypertriglyceridemia, or hypercholesterolemia.

BRIEF SUMMARY OF THE INVENTION

In one aspect, provided herein is a compound of formula (I):

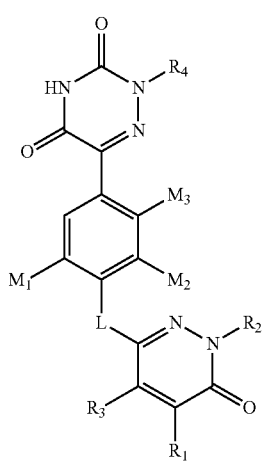

(I)

wherein:
$R_1$ is substituted or unsubstituted $C_1$-$C_6$ alkyl, substituted or unsubstituted $C_3$-$C_6$ cycloalkyl, —C(O)N($R_7$)($R_8$), —N($R_9$)C(O)($R_{10}$), or halo;
$R_2$ is H, substituted or unsubstituted $C_1$-$C_6$ alkyl, or substituted or unsubstituted $C_3$-$C_6$ cycloalkyl;
$R_3$ is H or halo;
$R_4$ is H, or substituted or unsubstituted linear $C_1$-$C_3$ alkyl;
L is —O—, —S—, —S(O)—, —S(O)$_2$—, —C(O)—, or —C($R_5$)($R_6$)—;
$R_5$ and $R_6$ are independently H, halo, —CN, or substituted or unsubstituted $C_1$-$C_6$ alkyl, or $R_5$ and $R_6$ are taken together with the carbon atom to which they are attached to form a substituted or unsubstituted $C_3$-$C_6$ cycloalkyl;
$R_7$ and $R_8$ are independently H, or substituted or unsubstituted $C_1$-$C_6$ alkyl, or $R_7$ and $R_8$ are taken together with the nitrogen atom to which they are attached to form a substituted or unsubstituted 3- to 7-membered heterocycloalkyl;
$R_9$ is H, substituted or unsubstituted $C_1$-$C_6$ alkyl, or substituted or unsubstituted $C_3$-$C_6$ cycloalkyl;
$R_{10}$ is substituted or unsubstituted $C_1$-$C_6$ alkyl, substituted or unsubstituted $C_3$-$C_6$ cycloalkyl, —N($R_7$)($R_8$), or —O($R_{11}$);
$R_{11}$ is substituted or unsubstituted $C_1$-$C_6$ alkyl, or substituted or unsubstituted $C_3$-$C_6$ cycloalkyl;
$M_1$ and $M_2$ are independently halo, or substituted or unsubstituted $C_1$-$C_6$ alkyl; and
$M_3$ is H, halo, or substituted or unsubstituted $C_1$-$C_6$ alkyl, or $M_3$ is taken together with $M_2$ and the carbon atoms to which they are attached to form a 5- to 7-membered ring containing 0, 1, or 2 heteroatoms selected from the group consisting of N, O, and S,
or a pharmaceutically acceptable salt thereof.

In some embodiments, provided herein is a compound of formula (I), or a pharmaceutically acceptable salt thereof, wherein:
$R_1$ is $C_1$-$C_6$ alkyl, $C_3$-$C_6$ cycloalkyl, —C(O)N($R_7$)($R_8$), —N($R_9$)C(O)($R_{10}$), or halo, wherein $C_1$-$C_6$ alkyl and $C_3$-$C_6$ cycloalkyl are optionally substituted by 1-5 substituents selected from the group consisting of —OH, oxo, —CN, and halo;
$R_2$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;
$R_3$ is H or halo;
$R_4$ is H or linear $C_1$-$C_3$ alkyl optionally substituted by 1-5 substituents selected from the group consisting of —OH, oxo, —CN, halo, and —O($C_1$-$C_2$ alkyl);
L is —O—, —S—, —S(O)—, —S(O)$_2$—, —C(O)—, or —C($R_5$)($R_6$)—;
$R_5$ and $R_6$ are independently H, halo, —CN, or $C_1$-$C_6$ alkyl, or $R_5$ and $R_6$ are taken together with the carbon atom to which they are attached to form a $C_3$-$C_6$ cycloalkyl, wherein each $C_1$-$C_6$ alkyl or $C_3$-$C_6$ cycloalkyl is optionally independently substituted by 1-5 substituents selected from the group consisting of —OH, —CN, and halo;
$R_7$ and $R_8$ are independently H or $C_1$-$C_6$ alkyl, or $R_7$ and $R_8$ are taken together with the nitrogen atom to which they are attached to form a 3- to 7-membered heterocycloalkyl, wherein each $C_1$-$C_6$ alkyl or 3- to 7-membered heterocycloalkyl is optionally independently substituted by 1-5 substituents selected from the group consisting of —OH, —CN, and halo;

$R_9$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;

$R_{10}$ is $C_1$-$C_6$ alkyl, $C_3$-$C_6$ cycloalkyl, —N($R_7$)($R_8$), or —O($R_{11}$), wherein $C_1$-$C_6$ alkyl and $C_3$-$C_6$ cycloalkyl are optionally substituted by 1-5 substituents selected from the group consisting of —OH, —CN, and halo;

$R_{11}$ is $C_1$-$C_6$ alkyl or $C_3$-$C_6$ cycloalkyl, each of which is optionally substituted by 1-5 substituents selected from the group consisting of —OH, —CN, and halo;

$M_1$ and $M_2$ are independently halo or $C_1$-$C_6$ alkyl optionally substituted by 1-5 substituents selected from the group consisting of —OH, —CN, and halo; and $M_3$ is H, halo, or $C_1$-$C_6$ alkyl optionally substituted by 1-5 substituents selected from the group consisting of —OH, —CN, and halo, or $M_3$ is taken together with $M_2$ and the carbon atoms to which they are attached to form a 5- to 7-membered ring containing 0, 1, or 2 heteroatoms selected from the group consisting of N, O, and S.

In some embodiments, $R_1$ is $C_1$-$C_6$ alkyl or $C_3$-$C_6$ cycloalkyl, each of which is optionally substituted by 1-5 substituents selected from the group consisting of —OH, oxo, —CN, and halo. In some embodiments, $R_1$ is cyclopropyl, isopropyl, ethyl, —CH(CH$_2$CH$_3$)$_2$, —CH(CH$_3$)(CH$_2$OH), —CH(OH)(CH$_2$CH$_3$), —CH(OH)(CH$_3$), —CH(CH$_3$)(CH$_2$CH$_3$), or —C(O)(CH$_3$).

In some embodiments, $R_2$ is H or $C_1$-$C_6$ alkyl optionally substituted by 1-5 substituents selected from the group consisting of —OH, —CN, and halo. In some embodiments, $R_2$ is H or methyl.

In some embodiments, $R_3$ is H.

In some embodiments, $R_4$ is H or linear $C_1$-$C_3$ alkyl optionally substituted by 1-3 substituents selected from the group consisting of —OH, oxo, —CN, halo, and —O($C_1$-$C_2$ alkyl). In some embodiments, $R_4$ is H, methyl, ethyl, —CH$_2$C(O)O(CH$_2$CH$_3$), —CH$_2$CF$_3$, —CH$_2$CN, or —CH$_2$CHF$_2$.

In some embodiments, L is —O—, —C(O)—, or —CH$_2$—.

In some embodiments, $M_1$ and $M_2$ are independently halo or $C_1$-$C_3$ alkyl optionally substituted by 1-3 substituents selected from the group consisting of —OH, —CN, and halo. In some embodiments, $M_1$ and $M_2$ are independently halo or methyl. In some embodiments, $M_1$ and $M_2$ are each chloro. In some embodiments, $M_1$ and $M_2$ are each methyl.

In some embodiments, $M_3$ is H, halo, or $C_1$-$C_3$ alkyl optionally substituted by 1-3 substituents selected from the group consisting of —OH, —CN, and halo. In some embodiments, $M_3$ is H, F, or methyl.

In some embodiments, provided herein is a compound selected from Compounds 1-3 and 5-35, or a pharmaceutically acceptable salt thereof.

Further provided is a pharmaceutical composition comprising a compound described herein, or a pharmaceutically acceptable salt thereof, and a pharmaceutically acceptable excipient.

In another aspect, provided herein is a method of agonizing thyroid hormone receptor beta (THR beta) comprising contacting an effective amount of a compound described herein, or a pharmaceutically acceptable salt thereof, or an effective amount of the pharmaceutical composition comprising a compound described herein, with the THR beta.

In another aspect, provided herein is a method of treating a disorder which is mediated by THR beta in a patient in need thereof, comprising administering to the patient a therapeutically effective amount of a compound described herein, or a pharmaceutically acceptable salt thereof, or a therapeutically effective amount of the pharmaceutical composition comprising a compound described herein. In some embodiments, the disorder is non-alcoholic steatohepatitis (NASH).

DETAILED DESCRIPTION OF THE INVENTION

Definitions

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention. Thus, it is understood that aspects and embodiments described herein as "comprising" include "consisting of" and "consisting essentially of" embodiments.

"Effective amount" or dose of a compound or a composition, refers to that amount of the compound, or a pharmaceutically acceptable salt thereof, or the composition that results in an intended result as desired based on the disclosure herein. Effective amounts can be determined by standard pharmaceutical procedures in cell cultures or experimental animals, e.g., and without limitation, by determining the LD$_{50}$ (the dose lethal to 50% of the population) and the ED$_{50}$ (the dose therapeutically effective in 50% of the population).

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than employing the corresponding drug. For illustration and without limitation, prodrugs include, carboxy esters, linear and cyclic phosphate esters and phosphoramide and phosphoramidates, carbamates, preferably phenolic carbamates (i.e., carbamates where the hydroxy group is part of an aryl or heteroaryl moiety, where the aryl and heteroaryl may be optionally substituted), and the likes.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

"Therapeutically effective amount" or dose of a compound or a composition refers to that amount of the compound or the composition that results in reduction or inhibition of symptoms or a prolongation of survival in a patient. The results may require multiple doses of the compound or the composition.

As used herein, "treatment" or "treating" is an approach for obtaining beneficial or desired results including clinical results. For purposes of this invention, beneficial or desired results include, but are not limited to, one or more of the following: decreasing one more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the invention contemplate any one or more of these aspects of treatment.

An "isotopomer" of a compound is a compound in which one or more atoms of the compound have been replaced with isotopes of those same atoms. For example, where H has been replaced by D or T, or $^{12}C$ has been replaced by $^{11}C$ or $^{14}N$ has been replaced by $^{15}N$. For example, and without limitation, replacement of with D can in some instances lead to reduced rates of metabolism and therefore longer half-lives. Replacement of H with T can provide radioligands potentially useful in binding studies. Replacement of $^{12}C$ with the short-lived isotope $^{11}C$ can provide ligands useful in Positron Emission Tomography (PET) scanning. Replacement of $^{14}N$ with $^{15}N$ provides compounds that can be detected/monitored by $^{15}N$ NMR spectroscopy. For example, an isotopomer of a compound containing —$CH_2CH_3$ is that compound but containing —$CD_2CD_3$ instead of the —$CH_2CH_3$.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Alkyl" refers to monovalent saturated aliphatic hydrocarbyl groups having from 1 to 12 carbon atoms, preferably from 1 to 10 carbon atoms, and more preferably from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). $C_x$ alkyl refers to an alkyl group having x number of carbon atoms.

"Alkenyl" refers to straight or branched monovalent hydrocarbyl groups having from 2 to 6 carbon atoms and preferably 2 to 4 carbon atoms and having at least 1 and preferably from 1 to 2 sites of vinyl ($>C=C<$) unsaturation. Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH). C$_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxyl or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluoromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(O)—.

"Acylamino" refers to the groups —NR$^{30}$C(O)alkyl, —NR$^{30}$C(O) substituted alkyl, —NR$^{30}$C(O)cycloalkyl, —NR$^{30}$C(O) substituted cycloalkyl, —NR$^{30}$C(O)alkenyl, —NR$^{30}$C(O) substituted alkenyl, alkoxy, substituted alkoxy-NR$^{30}$C(O)alkynyl, —NR$^{30}$C(O) substituted alkynyl, —NR$^{30}$C(O)aryl, —NR$^{30}$C(O) substituted aryl, —NR$^{30}$C(O)heteroaryl, —NR$^{30}$C(O) substituted heteroaryl, —NR$^{30}$C(O)heterocyclic, and —NR$^{30}$C(O) substituted heterocyclic wherein R$^{30}$ is hydrogen, alkyl, substituted alkyl, aryl, substituted aryl, heteroaryl, substituted heteroaryl, cycloalkyl, or substituted cycloalkyl; and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O) O—, aryl-C(O)O—, substituted aryl-C(O)O—, cycloalkyl-C(O)O—, substituted cycloalkyl-C(O)O—, heteroaryl-C(O) O—, substituted heteroaryl-C(O)O—, heterocyclic-C(O) O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{31}$R$^{32}$ where R$^{31}$ and R$^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, arylamino, substituted arylamino, heteroarylamino, substituted heteroarylamino, cycloalkylamino, substituted cycloalkylamino, heterocycloalkylamino, substituted heterocyclylamino, sulfonylamino, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —C(O)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{30}$C(O)NR$^{33}$R$^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{30}$C(S)NR$^{33}$R$^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Arylamino" refers to the group —NR$^{37}$(aryl), where aryl is as defined herein and R$^{37}$ is hydrogen, alkyl, or substituted alkyl.

"Substituted arylamino" refers to the group —NR$^{37}$(substituted aryl), where R$^{37}$ is hydrogen, alkyl, or substituted alkyl where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to saturated or unsaturated but non-aromatic cyclic alkyl groups of from 3 to 10 carbon atoms, preferably from 3 to 8 carbon atoms, and more preferably from 3 to 6 carbon atoms, having single or multiple cyclic rings including fused, bridged, and spiro ring systems. C$_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more of the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylamino" refers to the group —$NR^{37}$(cycloalkyl) where $R^{37}$ is hydrogen, alkyl, or substituted alkyl.

"Substituted cycloalkylamino" refers to the group —$NR^{37}$(substituted cycloalkyl) where $R^{37}$ is hydrogen, alkyl, or substituted alkyl and substituted cycloalkyl is as defined herein.

"Cycloalkylthio" refers to —S-cycloalkyl.

"Substituted cycloalkylthio" refers to —S-(substituted cycloalkyl).

"Guanidino" refers to the group —NHC(=NH)$NH_2$.

"Substituted guanidino" refers to —$NR^{36}$C(=$NR^{36}$)N($R^{36}$)$_2$ where each $R^{36}$ is independently selected from the group consisting of hydrogen, alkyl, substituted alkyl, aryl, substituted aryl, heteroaryl, substituted heteroaryl, heterocyclic, and substituted heterocyclic and two $R^{36}$ groups attached to a common guanidino nitrogen atom are optionally joined together with the nitrogen bound thereto to form a heterocyclic or substituted heterocyclic group, provided that at least one $R^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroalkylene" refers to an alkylene group wherein one or more carbons is replaced with —O—, —S—, —$SO_2$—, —$NR^Q$—,

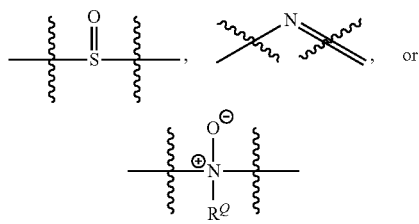

moieties where $R^Q$ is H or $C_1$-$C_6$ alkyl. "Substituted heteroalkylene" refers to heteroalkynylene groups having from 1 to 3 substituents, and preferably 1 to 2 substituents, selected from the substituents disclosed for substituted alkylene.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, thiophenyl, and furanyl. Other preferred heteroaryls include 9 or 10 membered heteroaryls, such as indolyl, quinolinyl, quinolonyl, isoquinolinyl, and isoquinolonyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heteroarylamino" refers to the group —$NR^{37}$(heteroaryl) where $R^{37}$ is hydrogen, alkyl, or substituted alkyl.

"Substituted heteroarylamino" refers to the group —$NR^{37}$(substituted heteroaryl), where $R^{37}$ is hydrogen, alkyl, or substituted alkyl and substituted heteroaryl is defined as herein.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, or oxygen. $C_x$ heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Heterocyclylene" refers to a divalent saturated or partially saturated, but not aromatic, group having from 1 to 10 ring carbon atoms and from 1 to 4 ring heteroatoms selected from the group consisting of nitrogen, sulfur, or oxygen. "Substituted heterocyclylene" refers to heterocyclylene groups that are substituted with from 1 to 5 or preferably 1 to 3 of the same substituents as defined for substituted cycloalkyl.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

"Heterocyclylamino" refers to the group —$NR^{37}$(heterocyclyl) where $R^{37}$ is hydrogen, alkyl, or substituted alkyl.

"Substituted heterocyclylamino" refers to the group —$NR^{37}$(substituted heterocyclyl), where $R^{37}$ is hydrogen, alkyl, or substituted alkyl and substituted heterocyclyl is defined as herein.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Nitro" refers to the group —$NO_2$.

"Oxo" refers to the atom (=O) or (O).

"Spiro ring systems" refers to bicyclic ring systems that have a single ring carbon atom common to both rings.

"Sulfinyl" refers to the divalent group —S(O)— or —S(=O)—.

"Sulfonyl" refers to the divalent group —$S(O)_2$— or —$S(=O)_2$—.

"Substituted sulfonyl" refers to the group —$SO_2$-alkyl, —$SO_2$-substituted alkyl, —$SO_2$—OH, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-$SO_2$—, phenyl-$SO_2$—, and 4-methylphenyl-$SO_2$—. Preferred substituted alkyl groups on the substituted alkyl-$SO_2$— include halogenated alkyl groups and particularly halogenated methyl groups such as trifluoromethyl, difluoromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluoromethyl, fluoromethyl and the like.

"Sulfonyloxy" or "substituted sulfonyloxy" refers to the group —$OSO_2$-alkyl, —$OSO_2$-substituted alkyl, —$OSO_2$—OH, —$OSO_2$-alkenyl, —$OSO_2$-substituted alkenyl, —$OSO_2$-cycloalkyl, —$OSO_2$-substituted cycloalkyl, —$OSO_2$-aryl, —$OSO_2$-substituted aryl, —$OSO_2$-heteroaryl, —$OSO_2$-substituted heteroaryl, —$OSO_2$-heterocyclic, —$OSO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the group —$NR^{37}$(substituted sulfonyl) where $R^{37}$ is hydrogen, alkyl, or substituted alkyl and substituted sulfonyl is as defined here.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluoromethyl, fluoromethyl and the like.

"Vinyl" refers to unsaturated hydrocarbon radical —CH=$CH_2$, derived from ethylene.

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

The term "optionally substituted" refers to a substituted or unsubstituted group. The substituted group (e.g., the alkyl group in "substituted alkyl") may be substituted with one or more substituents, such as e.g., 1, 2, 3, 4 or 5 substituents, which may be the same or different. Preferably, the substituents are selected from the functional groups provided herein. In certain more preferred embodiments, the substituents are selected from oxo, halo, —CN, $NO_2$, —$CO_2R^{100}$, —$OR^{100}$, —$SR^{100}$, —$SOR^{100}$, —$SO_2R^{100}$, —$NR^{101}R^{102}$, —$CONR^{101}R^{102}$, —$SO_2NR^{101}R^{102}$, $C_1$-$C_6$ alkyl, $C_1$-$C_6$ alkoxy, —$CR^{100}$=$C(R^{100})_2$, —$CCR^{100}$, $C_3$-$C_{10}$ cycloalkyl, $C_4$-$C_{10}$ heterocyclyl, $C_6$-$C_{14}$ aryl and $C_5$-$C_{12}$ heteroaryl, wherein each $R^{100}$ independently is hydrogen or $C_1$-$C_8$ alkyl; $C_3$-$C_{12}$ cycloalkyl; $C_4$-$C_{10}$ heterocyclyl; $C_6$-$C_{14}$ aryl; or $C_2$-$C_{12}$ heteroaryl; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups. More preferably, the substituents are selected from the group consisting of chloro, fluoro, —$OCH_3$, methyl, ethyl, iso-propyl, cyclopropyl, —$OCF_3$, —$CF_3$ and —$OCHF_2$.

$R^{101}$ and $R^{102}$ independently are hydrogen; $C_1$-$C_8$ alkyl, optionally substituted with —$CO_2H$ or an ester thereof, $C_1$-$C_6$ alkoxy, oxo, —$CR^{103}$=$C(R^{103})_2$, —CCR, $C_3$-$C_{10}$ cycloalkyl, $C_3$-$C_{10}$ heterocyclyl, $C_6$-$C_{14}$ aryl, or $C_2$-$C_{12}$ heteroaryl, wherein each $R^{103}$ independently is hydrogen or $C_1$-$C_8$ alkyl; $C_3$-$C_{12}$ cycloalkyl; $C_4$-$C_{10}$ heterocyclyl; $C_6$-$C_{14}$ aryl; or $C_2$-$C_{12}$ heteroaryl; wherein each cycloalkyl, heterocyclyl, aryl, or heteroaryl is optionally substituted with 1-3 alkyl groups or 1-3 halo groups, or $R^{101}$ and $R^{102}$ together with the nitrogen atom they are attached to form a 5-7 membered heterocycle.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

In some embodiments of a substituted moiety, the moiety is substituted with a group that may also be substituted with a further group, but the further group cannot be additionally substituted. For example, in some embodiments of "substituted alkyl", the alkyl moiety is substituted with a group that may be further substituted (e.g., substituted alkoxy, substituted amino, substituted aryl, substituted aryloxy, substituted arylthio, substituted arylamino, substituted heteroarylamino, substituted cycloalkylamino, substituted heterocyclylamino, substituted cycloalkyl, substituted cycloalkyloxy, substituted cycloalkylthio, substituted guanidino, substituted heteroaryl, substituted heteroaryloxy, substituted heteroarylthio, substituted heterocyclic, substituted heterocyclyloxy, substituted heterocyclylthio, substituted sulfonyl, substituted alkylthio), but the substituted alkoxy, substituted amino, substituted aryl, substituted aryloxy, substituted arylthio, substituted arylamino, substituted heteroarylamino, substituted cycloalkylamino, substituted heterocyclylamino, substituted cycloalkyl, substituted cycloalkyloxy, substituted cycloalkylthio, substituted guanidino, substituted heteroaryl, substituted heteroaryloxy, substituted heteroarylthio, substituted heterocyclic, substituted heterocyclyloxy, substituted heterocyclylthio, substituted sulfonyl or substituted alkylthio on the alkyl moiety is not substituted with a moiety that is itself further substituted. Although "substituted alkyl" is provided as an example, such an embodiment is intended for each substituted moiety described herein.

In some embodiments of a substituted moiety, the moiety is substituted with a group that is not further substituted. Thus, in some embodiments, "substituted alkyl" is an alkyl moiety substituted with one or more, and in some aspects, 1 or 2 or 3 or 4 or 5 moieties independently selected from the group consisting of alkoxy, acyl, acylamino, acyloxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, aryloxy, arylthio, arylamino, heteroarylamino, cycloalkylamino, heterocycloalkylamino, carboxyl, carboxyl ester, (carboxyl ester)amino, (carboxyl ester)oxy, cyano, cycloalkyl, cycloalkyloxy, cycloalkylthio, guanidino, halo, hydroxy, heteroaryl, heteroaryloxy, heteroarylthio, heterocyclic, heterocyclyloxy, heterocyclylthio, nitro, $SO_3H$, sulfonyloxy, sulfonylamino, thioacyl, thiol, and alkylthio. Although "substituted alkyl" is provided as an example, such an embodiment is intended for each substituted moiety described herein.

It is understood that the above definitions are not intended to include impermissible substitution patterns (e.g., methyl substituted with 4 fluoro groups). Such impermissible substitution patterns are well known to the skilled artisan.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Compounds

In one aspect, provided herein is a compound of formula (I):

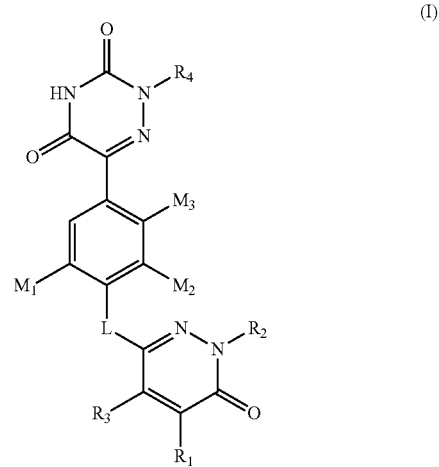

wherein:
$R_1$ is substituted or unsubstituted $C_1$-$C_6$ alkyl, substituted or unsubstituted $C_3$-$C_6$ cycloalkyl, —C(O)N($R_7$)($R_8$), —N($R_9$)C(O)($R_{10}$), or halo;
$R_2$ is H, substituted or unsubstituted $C_1$-$C_6$ alkyl, or substituted or unsubstituted $C_3$-$C_6$ cycloalkyl;
$R_3$ is H or halo;
$R_4$ is H, or substituted or unsubstituted linear $C_1$-$C_3$ alkyl;
L is —O—, —S—, —S(O)—, —S(O)$_2$—, —C(O)—, or —C($R_5$)($R_6$)—;
$R_5$ and $R_6$ are independently H, halo, —CN, or substituted or unsubstituted $C_1$-$C_6$ alkyl, or $R_5$ and $R_6$ are taken together with the carbon atom to which they are attached to form a substituted or unsubstituted $C_3$-$C_6$ cycloalkyl;
$R_7$ and $R_8$ are independently H, or substituted or unsubstituted $C_1$-$C_6$ alkyl, or $R_7$ and $R_8$ are taken together with the nitrogen atom to which they are attached to form a substituted or unsubstituted 3- to 7-membered heterocycloalkyl;

$R_9$ is H, substituted or unsubstituted $C_1$-$C_6$ alkyl, or substituted or unsubstituted $C_3$-$C_6$ cycloalkyl;

$R_{10}$ is substituted or unsubstituted $C_1$-$C_6$ alkyl, substituted or unsubstituted $C_3$-$C_6$ cycloalkyl, —N($R_7$)($R_8$), or —O($R_{11}$);

$R_{11}$ is substituted or unsubstituted $C_1$-$C_6$ alkyl, or substituted or unsubstituted $C_3$-$C_6$ cycloalkyl;

$M_1$ and $M_2$ are independently halo, or substituted or unsubstituted $C_1$-$C_6$ alkyl; and $M_3$ is H, halo, or substituted or unsubstituted $C_1$-$C_6$ alkyl, or $M_3$ is taken together with $M_2$ and the carbon atoms to which they are attached to form a 5- to 7-membered ring containing 0, 1, or 2 heteroatoms selected from the group consisting of N, O, and S, or a pharmaceutically acceptable salt thereof.

In some embodiments, provided herein in the compound of formula (I), or a pharmaceutically acceptable salt thereof, wherein:

$R_1$ is $C_1$-$C_6$ alkyl, $C_3$-$C_6$ cycloalkyl, —C(O)N($R_7$)($R_8$), —N($R_9$)C(O)($R_{10}$), or halo, wherein $C_1$-$C_6$ alkyl and $C_3$-$C_6$ cycloalkyl are optionally substituted by 1-5 substituents selected from the group consisting of —OH, oxo, —CN, and halo;

$R_2$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;

$R_3$ is H or halo;

$R_4$ is H or linear $C_1$-$C_3$ alkyl optionally substituted by 1-5 substituents selected from the group consisting of —OH, oxo, —CN, halo, and —O($C_1$-$C_2$ alkyl);

L is —O—, —S—, —S(O)—, —S(O)$_2$—, —C(O)—, or —C($R_5$)($R_6$)—;

$R_5$ and $R_6$ are independently H, halo, —CN, or $C_1$-$C_6$ alkyl, or $R_5$ and $R_6$ are taken together with the carbon atom to which they are attached to form a $C_3$-$C_6$ cycloalkyl, wherein each $C_1$-$C_6$ alkyl or $C_3$-$C_6$ cycloalkyl is optionally independently substituted by 1-5 substituents selected from the group consisting of —OH, —CN, and halo;

$R_7$ and $R_8$ are independently H or $C_1$-$C_6$ alkyl, or $R_7$ and $R_8$ are taken together with the nitrogen atom to which they are attached to form a 3- to 7-membered heterocycloalkyl, wherein each $C_1$-$C_6$ alkyl or 3- to 7-membered heterocycloalkyl is optionally independently substituted by 1-5 substituents selected from the group consisting of —OH, —CN, and halo;

$R_9$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;

$R_{10}$ is $C_1$-$C_6$ alkyl, $C_3$-$C_6$ cycloalkyl, —N($R_7$)($R_8$), or —O($R_{11}$), wherein $C_1$-$C_6$ alkyl and $C_3$-$C_6$ cycloalkyl are optionally substituted by 1-5 substituents selected from the group consisting of —OH, —CN, and halo;

$R_{11}$ is $C_1$-$C_6$ alkyl or $C_3$-$C_6$ cycloalkyl, each of which is optionally substituted by 1-5 substituents selected from the group consisting of —OH, —CN, and halo;

$M_1$ and $M_2$ are independently halo or $C_1$-$C_6$ alkyl optionally substituted by 1-5 substituents selected from the group consisting of —OH, —CN, and halo; and $M_3$ is H, halo, or $C_1$-$C_6$ alkyl optionally substituted by 1-5 substituents selected from the group consisting of —OH, —CN, and halo, or $M_3$ is taken together with $M_2$ and the carbon atoms to which they are attached to form a 5- to 7-membered ring containing 0, 1, or 2 heteroatoms selected from the group consisting of N, O, and S.

In some embodiments, $R_1$ is $C_1$-$C_6$ alkyl or $C_3$-$C_6$ cycloalkyl, each of which is optionally substituted by 1-5 substituents selected from the group consisting of —OH, oxo, —CN, and halo. In some embodiments, $R_1$ is cyclopropyl, isopropyl, ethyl, —CH(CH$_2$CH$_3$)$_2$, —CH(CH$_3$)(CH$_2$OH), —CH(OH)(CH$_2$CH$_3$), —CH(OH)(CH$_3$), —CH(CH$_3$)(CH$_2$CH$_3$), or —C(O)(CH$_3$).

In some embodiments, $R_1$ is substituted or unsubstituted $C_1$-$C_6$ alkyl. In some embodiments, $R_1$ is $C_1$-$C_6$ alkyl optionally substituted by 1 to 4 halogen atoms. In some embodiments, $R_1$ is $C_1$-$C_6$ alkyl optionally substituted by 1 to 4 chloro or fluoro atoms. In some embodiments, $R_1$ is methyl, ethyl, propyl, isopropyl, butyl, pentyl, or hexyl. In some embodiments, $R_1$ is substituted or unsubstituted $C_3$-$C_6$ alkyl, such as an unsubstituted $C_3$-$C_6$ alkyl which in one aspect is a branched $C_3$-$C_6$ alkyl. In some embodiments, $R_1$ is isopropyl. In some embodiments, $R_1$ is substituted or unsubstituted $C_1$-$C_3$ alkyl, such as an unsubstituted $C_1$-$C_3$ alkyl which in one aspect is a linear $C_1$-$C_3$ alkyl. In some embodiments, $R_1$ is $C_1$-$C_6$ alkyl optionally substituted by 1-5 substituents selected from the group consisting of —OH, oxo, —CN, and halo. In some embodiments, $R_1$ is $C_1$-$C_6$ alkyl optionally substituted by 1-3 substituents selected from the group consisting of —OH, oxo, —CN, and halo. In some embodiments, $R_1$ is $C_1$-$C_6$ alkyl optionally substituted by 1-2 —OH groups. In some embodiments, $R_1$ is $C_1$-$C_6$ alkyl substituted by one —OH group, such as —CH(CH$_3$)(CH$_2$OH), —CH(OH)(CH$_2$CH$_3$), or —CH(OH)(CH$_3$). In some embodiments, $R_1$ is $C_1$-$C_6$ alkyl optionally substituted by one oxo group. In some embodiments, $R_1$ is $C_1$-$C_6$ alkyl substituted by one oxo group, such as —C(O)(CH$_3$). In some embodiments, $R_1$ is unsubstituted $C_1$-$C_6$ alkyl, such as methyl, ethyl, isopropyl, —CH(CH$_2$CH$_3$)$_2$, or —CH(CH$_3$)(CH$_2$CH$_3$). In some embodiments, $R_1$ is isopropyl, ethyl, —CH(CH$_2$CH$_3$)$_2$, —CH(CH$_3$)(CH$_2$OH), —CH(OH)(CH$_2$CH$_3$), —CH(OH)(CH$_3$), —CH(CH$_3$)(CH$_2$CH$_3$), or —C(O)(CH$_3$).

In some embodiments, $R_1$ is substituted or unsubstituted $C_3$-$C_6$ cycloalkyl. In some embodiments, $R_1$ is $C_3$-$C_6$ cycloalkyl optionally substituted by 1 to 4 halogen atoms and/or 1 to 4 $C_1$-$C_6$ alkyl groups. In some embodiments, $R_1$ is $C_3$-$C_6$ cycloalkyl optionally substituted by 1 to 4 chloro or fluoro atoms. In some embodiments, $R_1$ is $C_3$-$C_6$ cycloalkyl optionally substituted by 1 to 4 $C_1$-$C_6$ alkyl groups. In some embodiments, $R_1$ is $C_3$-$C_6$ cycloalkyl optionally substituted by 1 or 2 methyl, ethyl, or propyl groups. In some embodiments, $R_1$ is cyclopropyl, cyclobutyl, cyclopentyl, or cyclohexyl. In some embodiments, $R_1$ is cyclopropyl. In some embodiments, $R_1$ is $C_3$-$C_6$ cycloalkyl optionally substituted by 1-5 substituents selected from the group consisting of —OH, oxo, —CN, and halo. In some embodiments, $R_1$ is $C_3$-$C_6$ cycloalkyl optionally substituted by 1-3 substituents selected from the group consisting of —OH, oxo, —CN, and halo. In some embodiments, $R_1$ is unsubstituted $C_3$-$C_6$ cycloalkyl.

In some embodiments, $R_1$ is halo. In some embodiments, $R_1$ is fluoro, chloro, bromo, or iodo. In some embodiments, $R_1$ is fluoro or chloro. In some embodiments, $R_1$ is chloro.

In some embodiments, $R_1$ is —C(O)N($R_7$)($R_8$). In some embodiments, $R_7$ and $R_8$ are independently H or substituted or unsubstituted $C_1$-$C_6$ alkyl. In some embodiments, $R_7$ and $R_8$ are each H. In some embodiments, $R_7$ is H, and $R_8$ is substituted or unsubstituted $C_1$-$C_6$ alkyl. In some embodiments, $R_7$ is H, and $R_8$ is methyl, ethyl, propyl, isopropyl, or butyl. In some embodiments, $R_7$ and $R_8$ are independently substituted or unsubstituted $C_1$-$C_6$ alkyl. In some embodiments, $R_7$ and $R_8$ are independently methyl, ethyl, propyl, isopropyl, or butyl. In any of these variations wherein $R_7$ and/or $R_8$ is $C_1$-$C_6$ alkyl, the $C_1$-$C_6$ alkyl group is optionally substituted by 1 to 4 halogen atoms. In some embodiments, $R^7$ and $R^8$ are taken together with the nitrogen atom to which they are attached to form a 3- to 7-membered heterocycloalkyl optionally substituted by 1 to 4 halogen atoms and/or 1 to 4 $C_1$-$C_6$ alkyl groups. In some embodiments, $R^7$ and $R^8$ are taken together with the nitrogen atom to which they are attached to form a 3- to 5-membered heterocycloalkyl optionally substituted by 1 to 4 halogen atoms and/or 1 to 4 $C_1$-$C_6$ alkyl groups.

In some embodiments, $R_1$ is —N($R_9$)C(O)($R_{10}$). In some embodiments, $R_9$ is H. In some embodiments, $R_9$ is substituted or unsubstituted $C_1$-$C_6$ alkyl. In some embodiments, $R_9$ is methyl, ethyl, propyl, isopropyl, or butyl. In some embodiments, $R_9$ is substituted or unsubstituted $C_3$-$C_6$ cycloalkyl. In some embodiments, $R_9$ is cyclopropyl, cyclobutyl, cyclopentyl, or cyclohexyl. In some embodiments, $R_{10}$ is substituted or unsubstituted $C_1$-$C_6$ alkyl. In some embodiments, $R_{10}$ is methyl, ethyl, propyl, isopropyl, or butyl. In some embodiments, $R_{10}$ is substituted or unsubstituted $C_3$-$C_6$ cycloalkyl. In some embodiments, $R_{10}$ is cyclopropyl, cyclobutyl, cyclopentyl, or cyclohexyl. In any of these variations wherein $R_9$ and/or $R_{10}$ is $C_1$-$C_6$ alkyl, the $C_1$-$C_6$ alkyl group is optionally substituted by 1 to 4 halogen atoms. In any of these variations wherein $R_9$ and/or $R_{10}$ is $C_3$-$C_6$ cycloalkyl, the $C_3$-$C_6$ cycloalkyl group is optionally substituted by 1 to 4 halogen atoms and/or 1 to 4 $C_1$-$C_6$ alkyl groups. In some embodiments, $R_9$ is H and $R_{10}$ is substituted or unsubstituted $C_1$-$C_6$ alkyl. In some embodiments, $R_9$ is H and $R_{10}$ is methyl. In some embodiments, $R_9$ is substituted or unsubstituted $C_1$-$C_6$ alkyl and $R_{10}$ is substituted or unsubstituted $C_1$-$C_6$ alkyl. In some embodiments, $R_9$ and $R_{10}$ are each methyl.

In some embodiments where $R_1$ is —N($R_9$)C(O)($R_{10}$), $R_{10}$ is —N($R_7$)($R_8$). In some embodiments, $R_7$ and $R_8$ are independently H or substituted or unsubstituted $C_1$-$C_6$ alkyl. In some embodiments, $R_7$ and $R_8$ are each H. In some embodiments, $R_7$ is H, and $R_8$ is substituted or unsubstituted $C_1$-$C_6$ alkyl. In some embodiments, $R_7$ is H, and $R_8$ is methyl, ethyl, propyl, isopropyl, or butyl. In some embodiments, $R_7$ and $R_8$ are independently substituted or unsubstituted $C_1$-$C_6$ alkyl. In some embodiments, $R_7$ and $R_8$ are independently methyl, ethyl, propyl, isopropyl, or butyl. In any of these variations wherein $R_7$ and/or $R_8$ is $C_1$-$C_6$ alkyl, the $C_1$-$C_6$ alkyl group is optionally substituted by 1 to 4 halogen atoms. In some embodiments, $R^7$ and $R^8$ are taken together with the nitrogen atom to which they are attached to form a 3- to 7-membered heterocycloalkyl optionally substituted by 1 to 4 halogen atoms and/or 1 to 4 $C_1$-$C_6$ alkyl groups. In some embodiments, $R^7$ and $R^8$ are taken together with the nitrogen atom to which they are attached to form a 3- to 5-membered heterocycloalkyl optionally substituted by 1 to 4 halogen atoms and/or 1 to 4 $C_1$-$C_6$ alkyl groups.

In some embodiments where $R_1$ is —N($R_9$)C(O)($R_{10}$), $R_{10}$ is —O($R_{11}$). In some embodiments, $R_{11}$ is substituted or unsubstituted $C_1$-$C_6$ alkyl. In some embodiments, $R_{11}$ is $C_1$-$C_6$ alkyl optionally substituted by 1 to 4 halogen atoms. In some embodiments, $R_{11}$ is methyl, ethyl, propyl, isopropyl, or butyl. In some embodiments, $R_{11}$ is substituted or unsubstituted $C_3$-$C_6$ cycloalkyl. In some embodiments, $R_{11}$ is cyclopropyl, cyclobutyl, cyclopentyl, or cyclohexyl. In some embodiments, $R_{11}$ is $C_3$-$C_6$ cycloalkyl optionally substituted by 1 to 4 halogen atoms and/or 1 to 4 $C_1$-$C_6$ alkyl groups.

In some embodiments, $R_2$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo. In some embodiments, $R_2$ is H or $C_1$-$C_6$ alkyl optionally substituted by 1-5 substituents selected from the group consisting of —OH, —CN, and halo. In some embodiments, $R_2$ is H or methyl.

In some embodiments, $R_2$ is H. In some embodiments, $R_2$ is substituted or unsubstituted $C_1$-$C_6$ alkyl. In some embodiments, $R_2$ is $C_1$-$C_6$ alkyl optionally substituted by 1 to 4 halogen atoms. In some embodiments, $R_2$ is $C_1$-$C_6$ alkyl optionally substituted by 1 or 2 chloro or fluoro atoms. In some embodiments, $R_2$ is methyl, ethyl, propyl, isopropyl, butyl, or pentyl. In some embodiments, $R_2$ is methyl. In some embodiments, $R_2$ is $C_1$-$C_6$ alkyl optionally substituted by 1-5 substituents selected from the group consisting of —OH, —CN, and halo. In some embodiments, $R_2$ is $C_1$-$C_6$ alkyl optionally substituted by 1-3 substituents selected from the group consisting of —OH, —CN, and halo. In some embodiments, $R_2$ is unsubstituted $C_1$-$C_6$ alkyl.

In some embodiments, $R_3$ is H. In some embodiments, $R_3$ is halo. In some embodiments, $R_3$ is fluoro, chloro, bromo, or iodo. In some embodiments, $R_3$ is fluoro or chloro.

In some embodiments, $R_4$ is H or linear $C_1$-$C_3$ alkyl optionally substituted by 1-5 substituents selected from the group consisting of —OH, oxo, —CN, halo, and —O($C_1$-$C_2$ alkyl). In some embodiments, $R_4$ is H or linear $C_1$-$C_3$ alkyl optionally substituted by 1-3 substituents selected from the group consisting of —OH, oxo, —CN, halo, and —O($C_1$-$C_2$ alkyl). In some embodiments, $R_4$ is H, methyl, ethyl, —CH$_2$C(O)OCH$_2$CH$_3$, —CH$_2$CF$_3$, —CH$_2$CN, or —CH$_2$CHF$_2$.

In some embodiments, $R_4$ is H.

In some embodiments, $R_4$ is substituted or unsubstituted linear $C_1$-$C_3$ alkyl. In some embodiments, $R_4$ is linear $C_1$-$C_3$ alkyl optionally substituted by 1 to 4 halogen atoms and/or 1 to 4 hydroxyl groups. In some embodiments, $R_4$ is linear $C_1$-$C_3$ alkyl optionally substituted by 1 to 2 halogen atoms and/or 1 to 2 hydroxyl groups. In some embodiments, $R_4$ is linear $C_1$-$C_3$ alkyl optionally substituted by 1 or 2 chloro or fluoro atoms. In some embodiments, $R_4$ is linear $C_1$-$C_3$ alkyl optionally substituted by 1 or 2 hydroxyl groups. In some embodiments, $R_4$ is substituted or unsubstituted linear $C_1$-$C_2$ alkyl. In some embodiments, $R_4$ is linear $C_1$-$C_2$ alkyl optionally substituted by 1 to 2 halogen atoms and/or 1 to 2 hydroxyl groups. In some embodiments, $R_4$ is unsubstituted linear $C_1$-$C_3$ alkyl. In some embodiments, $R_4$ is unsubstituted linear $C_1$-$C_2$ alkyl. In some embodiments, $R_4$ is methyl, ethyl, or propyl. In some embodiments, $R_4$ is methyl. In some embodiments, $R_4$ is linear $C_1$-$C_3$ alkyl optionally substituted by 1-5 substituents selected from the group consisting of —OH, oxo, —CN, halo, and —O($C_1$-$C_2$ alkyl). In some embodiments, $R_4$ is linear $C_1$-$C_3$ alkyl optionally substituted by 1-3 substituents selected from the group consisting of —OH, oxo, —CN, halo, and —O($C_1$-$C_2$ alkyl). In some embodiments, $R_4$ is linear $C_1$-$C_3$ alkyl optionally substituted by 1-3 halo groups, such as chloro or fluoro. In some embodiments, $R_4$ is linear $C_1$-$C_3$ alkyl optionally substituted by 1-3 fluoro groups. In some embodiments, $R_4$ is —CF$_3$, —CH$_2$CF$_3$, or —CH$_2$CHF$_2$. In some embodiments, $R_4$ is linear $C_1$-$C_3$ alkyl optionally substituted by one oxo group. In some embodiments, $R_4$ is —CH$_2$C(O)CH$_3$, —C(O)CH$_2$CH$_3$, or —C(O)CH$_3$. In some embodiments, $R_4$ is linear $C_1$-$C_3$ alkyl optionally substituted with one —O($C_1$-$C_2$ alkyl). In some embodiments, $R_4$ is —CH$_2$OCH$_3$, —CH$_2$OCH$_2$CH$_3$, or —CH$_2$CH$_2$OCH$_3$. In some embodiments, $R_4$ is linear $C_1$-$C_3$ alkyl optionally substituted by one oxo group and one —O($C_1$-$C_2$ alkyl) group. In some embodiments, $R_4$ is —CH$_2$C(O)OCH$_3$, —C(O)OCH$_3$, or —C(O)OCH$_2$CH$_3$. In some embodiments, $R_4$ is linear $C_1$-$C_3$ alkyl optionally substituted by 1-2 cyano groups. In some embodiments, $R_4$ is linear $C_1$-$C_3$ alkyl optionally substituted by one cyano group. In some embodiments, $R_4$ is —$CH_2CN$ or —$CH_2CH_2CN$. It will be understood that when $R_4$ is linear $C_1$-$C_3$ alkyl optionally substituted by a carbon-containing moiety, such as —CN and —$O(C_1$-$C_2$ alkyl), the total number of carbon atoms of $R_4$ may exceed three. In some embodiments, $R_4$ is —$CH_2CH_2CH_2CN$. In some embodiments, $R_4$ is —$CH_2C(O)OCH_2CH_3$, —$CH_2CH_2C(O)OCH_2CH_3$, or —$CH_2CH_2C(O)OCH_3$. In some embodiments, $R_4$ is methyl, ethyl, —$CH_2C(O)OCH_2CH_3$, —$CH_2CF_3$, —$CH_2CN$, or —$CH_2CHF_2$.

In some embodiments, L is —O— or —C(O)—. In some embodiments, L is —O—. In some embodiments, L is —C(O)—. In some embodiments, L is —S—, —S(O)—, or —S(O)$_2$—. In some embodiments, L is —C($R_5$)($R_6$)—. In some embodiments, $R_5$ and $R_6$ are independently H, halo, —CN, or substituted or unsubstituted $C_1$-$C_6$ alkyl. In some embodiments, $R_5$ and $R_6$ are each H. In some embodiments, $R_5$ and $R_6$ are independently $C_1$-$C_6$ alkyl optionally substituted by 1 to 4 halogen atoms. In some embodiments, $R_5$ is H and $R_6$ is substituted or unsubstituted $C_1$-$C_6$ alkyl. In some embodiments, $R_5$ and $R_6$ are taken together with the carbon atom to which they are attached to form a substituted or unsubstituted $C_3$-$C_6$ cycloalkyl. In some embodiments, $R_5$ and $R_6$ are taken together with the carbon atom to which they are attached to form a $C_3$-$C_6$ cycloalkyl optionally substituted by 1 to 4 halogen atoms and/or 1 to 4 $C_1$-$C_6$ alkyl groups. In some embodiments, L is —O—, —C(O)—, or —$CH_2$—.

In some embodiments, $M_1$ and $M_2$ are independently halo or $C_1$-$C_6$ alkyl optionally substituted by 1-5 substituents selected from the group consisting of —OH, —CN, and halo. In some embodiments, $M_1$ and $M_2$ are independently halo or methyl. In some embodiments, $M_1$ and $M_2$ are each chloro. In some embodiments, $M_1$ and $M_2$ are each methyl.

In some embodiments, $M_1$ and $M_2$ are independently halo, or substituted or unsubstituted $C_1$-$C_6$ alkyl. In some embodiments, $M_1$ and $M_2$ are independently halo. In some embodiments, $M_1$ and $M_2$ are independently fluoro, chloro, bromo, or iodo. In some embodiments, $M_1$ and $M_2$ are independently fluoro or chloro. In some embodiments, $M_1$ and $M_2$ are each chloro. In some variations, at least one of $M_1$ and $M_2$ is substituted or unsubstituted $C_1$-$C_6$ alkyl. In some embodiments, at least one of $M_1$ and $M_2$ is $C_1$-$C_6$ alkyl optionally substituted by 1 to 4 halogen atoms. In some embodiments, at least one of $M_1$ and $M_2$ is $C_1$-$C_6$ alkyl optionally substituted by 1 or 2 halogen atoms. In some embodiments, at least one of $M_1$ and $M_2$ is $C_1$-$C_4$ alkyl optionally substituted by 1 or 2 fluoro or chloro atoms. In some embodiments, $M_1$ and $M_2$ are independently $C_1$-$C_6$ alkyl optionally substituted by 1-5 substituents selected from the group consisting of —OH, —CN, and halo. In some embodiments, $M_1$ and $M_2$ are independently $C_1$-$C_6$ alkyl optionally substituted by 1-3 substituents selected from the group consisting of —OH, —CN, and halo. In some embodiments, $M_1$ and $M_2$ are independently unsubstituted $C_1$-$C_6$ alkyl. In some embodiments, $M_1$ and $M_2$ are independently unsubstituted $C_1$-$C_3$ alkyl. In some embodiments, $M_1$ and $M_2$ are each methyl. In some embodiments, $M_1$ and $M_2$ are the same. In other embodiments, $M_1$ and $M_2$ are different. In some embodiments, $M_1$ is methyl and $M_2$ is ethyl. In some embodiments, $M_1$ is ethyl and $M_2$ is methyl. In some embodiments, $M_1$ is methyl and $M_2$ is chloro. In some embodiments, $M_1$ is chloro and $M_2$ is methyl.

In some embodiments, $M_3$ is H, halo, or $C_1$-$C_6$ alkyl optionally substituted by 1-5 substituents selected from the group consisting of —OH, —CN, and halo, or $M_3$ is taken together with $M_2$ and the carbon atoms to which they are attached to form a 5- to 7-membered ring containing 0, 1, or 2 heteroatoms selected from the group consisting of N, O, and S. In some embodiments, $M_3$ is H, halo, or $C_1$-$C_3$ alkyl optionally substituted by 1-3 substituents selected from the group consisting of —OH, —CN, and halo. In some embodiments, $M_3$ is H, F, or methyl.

In some embodiments, $M_3$ is H, halo, or substituted or unsubstituted $C_1$-$C_6$ alkyl. In some embodiments, $M_3$ is H. In some embodiments, $M_3$ is halo. In some embodiments, $M_3$ is fluoro, chloro, bromo, or iodo. In some embodiments, $M_3$ is fluoro. In some embodiments, $M_3$ is substituted or unsubstituted $C_1$-$C_6$ alkyl. In some embodiments, $M_3$ is $C_1$-$C_6$ optionally substituted by 1 to 4 halogen atoms. In some embodiments, $M_3$ is $C_1$-$C_6$ optionally substituted by 1 or 2 fluoro or chloro atoms. In some embodiments, $M_3$ is methyl, ethyl, propyl, isopropyl, butyl, or pentyl. In some embodiments, $M_3$ is methyl. In some embodiments, $M_3$ is $C_1$-$C_6$ alkyl optionally substituted by 1-5 substituents selected from the group consisting of —OH, —CN, and halo. In some embodiments, $M_3$ is $C_1$-$C_6$ alkyl optionally substituted by 1-3 substituents selected from the group consisting of —OH, —CN, and halo. In some embodiments, $M_3$ is —$CH_2CN$, —$CH_2CH_2CN$, —$CH_2CH_2CH_2CN$, —$CH_2OH$, —$CH_2CH_2OH$, —$CH_2CH_2CH_2OH$, —$CF_3$, —$CHF_2$, —$CH_2F$, —$CCl_3$, or —$CHCl_2$. In some embodiments, $M_3$ is unsubstituted $C_1$-$C_6$ alkyl.

In some embodiments, $M_3$ is taken together with $M_2$ and the carbon atoms to which they are attached to form a 5- to 7-membered ring containing 0, 1, or 2 heteroatoms selected from the group consisting of N, O, and S. In some embodiments, $M_3$ is taken together with $M_2$ and the carbon atoms to which they are attached to form a 5- to 7-membered ring containing 0 heteroatoms. In some embodiments, $M_3$ is taken together with $M_2$ and the carbon atoms to which they are attached to form a 5- to 7-membered ring containing 1 or 2 heteroatoms selected from the group consisting of N, O, and S. In some embodiments, $M_3$ is taken together with $M_2$ and the carbon atoms to which they are attached to form a 5- to 7-membered ring containing 1 or 2 heteroatoms selected from the group consisting of N and O. In some embodiments, $M_3$ is taken together with $M_2$ and the carbon atoms to which they are attached to form a 5- to 7-membered ring containing 1 heteroatom selected from the group consisting of N and O. In some embodiments, $M_3$ is taken together with $M_2$ and the carbon atoms to which they are attached to form a saturated 5- to 7-membered ring containing 0, 1, or 2 heteroatoms selected from the group consisting of N, O, and S. In some embodiments, $M_3$ is taken together with $M_2$ and the carbon atoms to which they are attached to form a partially unsaturated 5- to 7-membered ring containing 0, 1, or 2 heteroatoms selected from the group consisting of N, O, and S. In some embodiments, $M_3$ is taken together with $M_2$ and the carbon atoms to which they are attached to form an aromatic 5- to 7-membered ring containing 0, 1, or 2 heteroatoms selected from the group consisting of N, O, and S.

It is intended and understood that where present each and every variation of L described for formula (I) may be combined with each and every variation of $R_1$, $R_2$, $R_3$, $R_4$, $R_5$, $R_6$, $R_7$, $R_8$, $R_9$, $R_{10}$, $R_{11}$, $M_1$, $M_2$ and $M_3$ described for formula (I) the same as if each and every combination is specifically and individually described. Similarly, it is intended and understand that each variable described for formula (I) may be combined with each and every variable described for formula (I-a), (I-b), (I-c), and (I-d) below the same as if each and every combination is specifically and individually described. In addition, all subcombinations of the chemical groups listed in the embodiments describing such variables are also specifically embraced by the present invention and are disclosed herein just as if each and every such sub-combination of chemical groups was individually and explicitly disclosed herein.

In some embodiments, the compound of formula (I) is of formula (I-a):

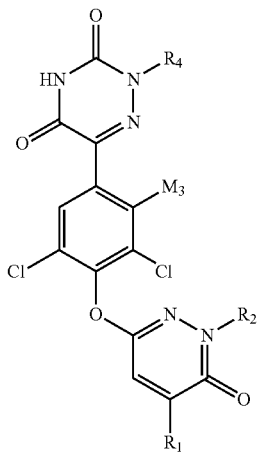

(I-a)

or a pharmaceutically acceptable salt thereof, wherein $R_1$, $R_2$, $R_4$, and $M_3$ are as defined for the compound of formula (I). In some embodiments, $R_1$ is $C_1$-$C_3$ alkyl or $C_3$-$C_5$ cycloalkyl. In some embodiments, $R_1$ is isopropyl. In some embodiments, $R_1$ is cyclopropyl. In some embodiments, $R_1$ is $C_1$-$C_6$ alkyl optionally substituted by 1-5 substituents selected from the group consisting of —OH, oxo, —CN, and halo. In some embodiments, $R_1$ is ethyl, —CH($CH_2CH_3$)$_2$, —CH($CH_3$)($CH_2OH$), —CH(OH)($CH_2CH_3$), —CH(OH)($CH_3$), —CH($CH_3$)($CH_2CH_3$), or —C(O)($CH_3$). In some embodiments, $R_2$ is H or $C_1$-$C_3$ alkyl. In some embodiments, $R_2$ is H. In some embodiments, $R_2$ is methyl. In some embodiments, $R_4$ is H or linear $C_1$-$C_3$ alkyl. In some embodiments, $R_4$ is H. In some embodiments, $R_4$ is methyl. In some embodiments, $R_4$ is linear $C_1$-$C_3$ alkyl optionally substituted by 1-5 substituents selected from the group consisting of —OH, oxo, —CN, halo, and —O($C_1$-$C_2$ alkyl). In some embodiments, ethyl, —CH$_2$C(O)O(CH$_2$CH$_3$), —CH$_2$CF$_3$, —CH$_2$CN, or —CH$_2$CHF$_2$. In some embodiments, $M_3$ is H or $C_1$-$C_3$ alkyl. In some embodiments, $M_3$ is H. In some embodiments, $M_3$ is methyl. In some embodiments, $M_3$ is halo. In some embodiments, $M_3$ is F.

In some embodiments, the compound of formula (I) is of formula (I-b):

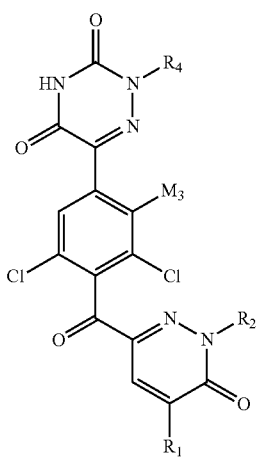

(I-b)

or a pharmaceutically acceptable salt thereof, wherein $R_1$, $R_2$, $R_4$, and $M_3$ are as defined for the compound of formula (I). In some embodiments, $R_1$ is $C_1$-$C_3$ alkyl. In some embodiments, $R_1$ is isopropyl. In some embodiments, $R_2$ is H or $C_1$-$C_3$ alkyl. In some embodiments, $R_2$ is H. In some embodiments, $R_2$ is methyl. In some embodiments, $R_4$ is H or linear $C_1$-$C_3$ alkyl. In some embodiments, $R_4$ is H. In some embodiments, $R_4$ is methyl. In some embodiments, $M_3$ is H or $C_1$-$C_3$ alkyl. In some embodiments, $M_3$ is H. In some embodiments, $M_3$ is methyl.

In some embodiments, the compound of formula (I) is of formula (I-c):

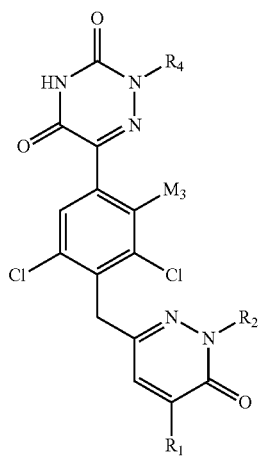

(I-c)

or a pharmaceutically acceptable salt thereof, wherein $R_1$, $R_2$, $R_4$, and $M_3$ are as defined for the compound of formula (I). In some embodiments, $R_1$ is $C_1$-$C_3$ alkyl. In some embodiments, $R_1$ is isopropyl. In some embodiments, $R_2$ is H or $C_1$-$C_3$ alkyl. In some embodiments, $R_2$ is H. In some embodiments, $R_2$ is methyl. In some embodiments, $R_4$ is H or linear $C_1$-$C_3$ alkyl. In some embodiments, $R_4$ is H. In some embodiments, $R_4$ is methyl. In some embodiments, $M_3$ is H or $C_1$-$C_3$ alkyl. In some embodiments, $M_3$ is H. In some embodiments, $M_3$ is methyl.

In some embodiments, the compound of formula (I) is of formula (I-d):

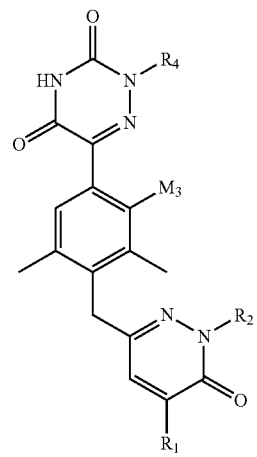

(I-d)

or a pharmaceutically acceptable salt thereof, wherein $R_1$, $R_2$, $R_4$, and $M_3$ are as defined for the compound of formula (I). In some embodiments, $R_1$ is $C_1$-$C_3$ alkyl. In some embodiments, $R_1$ is isopropyl. In some embodiments, $R_2$ is H or $C_1$-$C_3$ alkyl. In some embodiments, $R_2$ is H. In some embodiments, $R_2$ is methyl. In some embodiments, $R_4$ is H or linear $C_1$-$C_3$ alkyl. In some embodiments, $R_4$ is H. In some embodiments, $R_4$ is methyl. In some embodiments, $M_3$ is H or $C_1$-$C_3$ alkyl. In some embodiments, $M_3$ is H. In some embodiments, $M_3$ is methyl.

In some embodiments, the compound of formula (I) is an agonist of THR beta. In some embodiments, the compound of formula (I) is an agonist of THR beta and is selective over THR alpha. In some embodiments, the compound of formula (I) has at least 2-fold selectivity for THR beta over THR alpha. In some embodiments, the compound of formula (I) has at least 5-fold selectivity for THR beta over THR alpha. In some embodiments, the compound of formula (I) has at least 10-fold selectivity for THR beta over THR alpha. In some embodiments, the compound of formula (I) has at least 20-fold selectivity for THR beta over THR alpha. In some embodiments, the compound of formula (I) has at least 50-fold selectivity for THR beta over THR alpha. In some embodiments, the compound of formula (I) has at least 75-fold selectivity for THR beta over THR alpha. In some embodiments, the compound of formula (I) has at least 100-fold selectivity for THR beta over THR alpha. In some embodiments, the compound of formula (I) has at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, or 100-fold selectivity for THR beta over THR alpha. In any such embodiment, in one aspect selectivity is assessed via a biochemical assay, such as the TR-FRET assay described in Example B1.

In one embodiment, provided herein is a compound of formula (I) selected from those listed in Table 1 below, or a pharmaceutically acceptable salt thereof:

TABLE 1-continued

Compound Structure and Number

TABLE 1-continued

Compound Structure and Number (Structures 22–31, 31 P1, 31 P3 — chemical structure images not extracted)

TABLE 1-continued

Compound Structure and Number

[Structure 32]

[Structure 33 P1]

[Structure 33 P2]

[Structure 34]

[Structure 35]

\* Compound 4 does not fall within the scope of formula (I) and is provided for comparative purposes only.

\*\* Biological data reported in Table 2 for the compounds whose stereochemistry is arbitrarily assigned in Table 1 can be associated with the appropriate compound of Table 1 by reference to the corresponding synthetic example details. It is thus possible that the compound associated with a given chiral chromatography elution pattern and biological data set will have the same absolute stereochemistry or a different absolute stereochemistry from the compound whose stereochemistry is arbitrarily assigned in Table 1.

In some embodiments, the compound of formula (I) is selected from Compounds 1-3 and 5-35, or a pharmaceutically acceptable salt thereof.

In some embodiments, provided herein is a compound selected from the group consisting of:

[Structure 1]

[Structure 2]

[Structure 3]

[Structure 5]

[Structure 6]

[Structure 7]

8
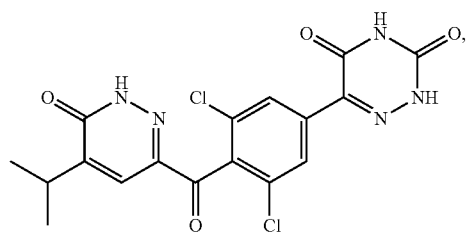
9
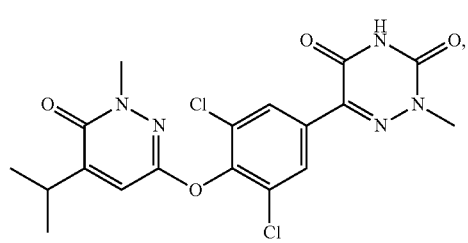
10
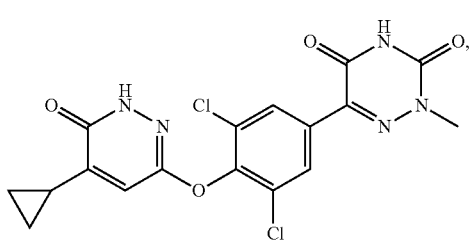
11
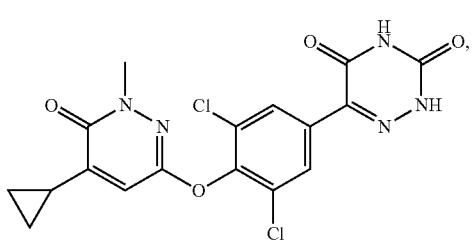
12
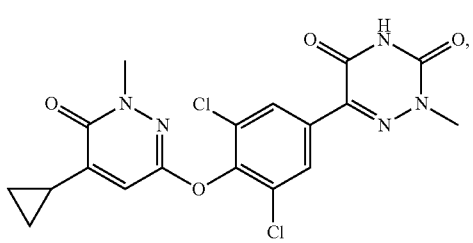
13
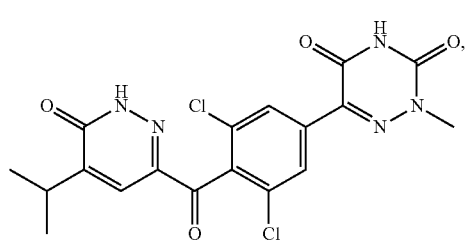
14
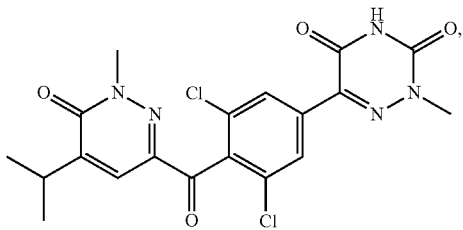
15
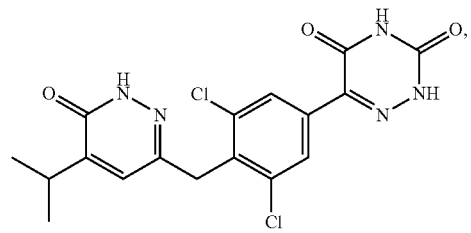
16
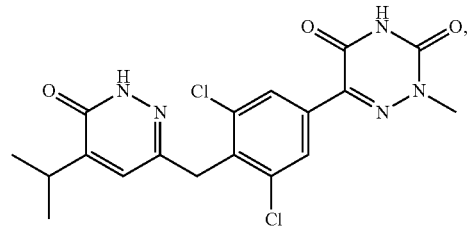
17
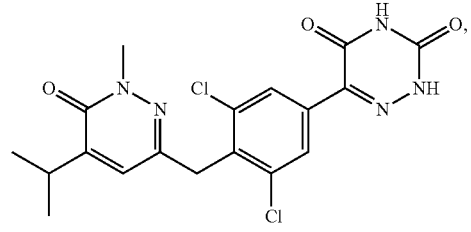
18
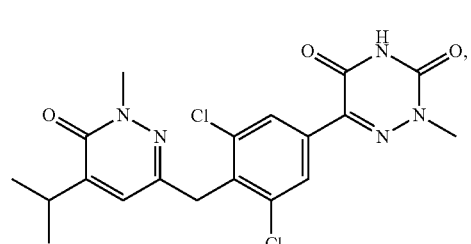
19
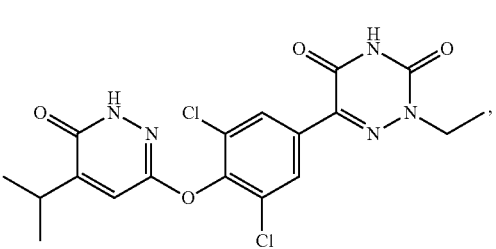

37
-continued
20
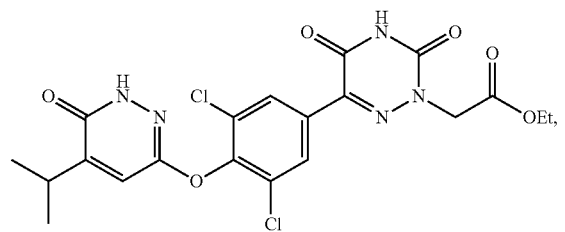 [SMILES: CCOC(=O)Cn1nc(-c2cc(Cl)c(Oc3cc(C(C)C)c(=O)[nH]n3)c(Cl)c2)c(=O)[nH]c1=O]
21
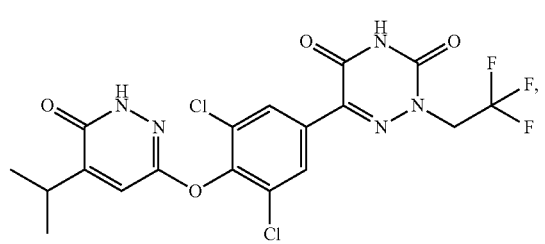
22
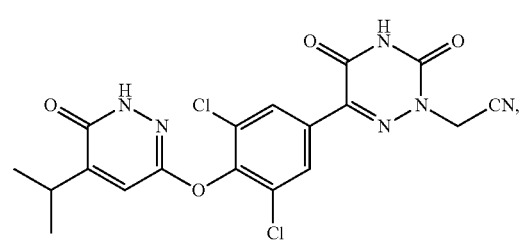 [SMILES: CC(C)c1cc(Oc2c(Cl)cc(-c3nn(CC#N)c(=O)[nH]c3=O)cc2Cl)n[nH]c1=O]
23
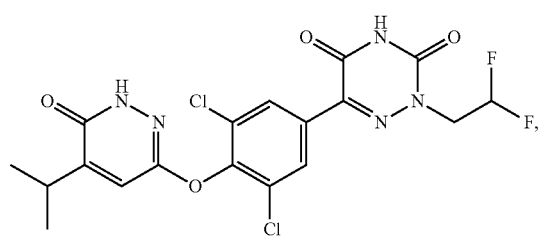
24
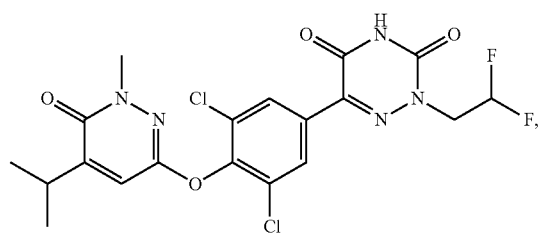
25
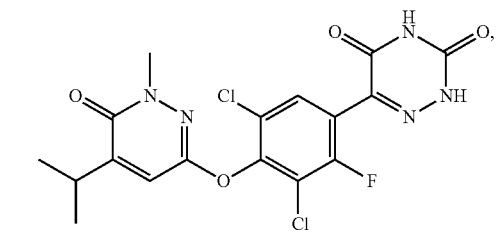
38
-continued
26
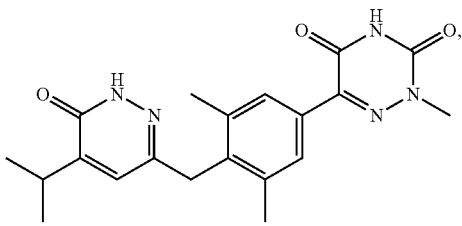
27
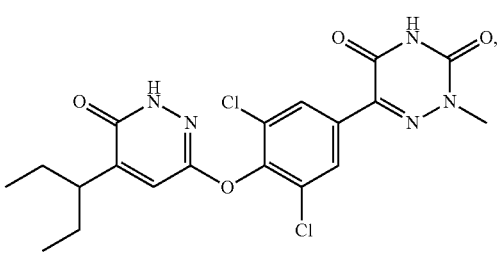
28
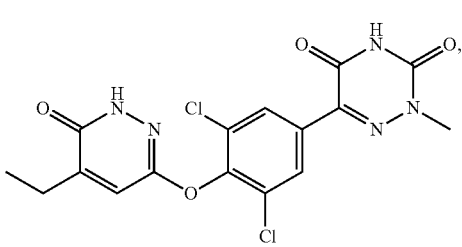
29
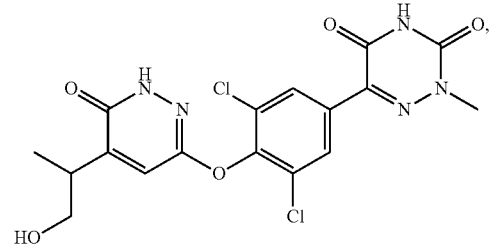
30
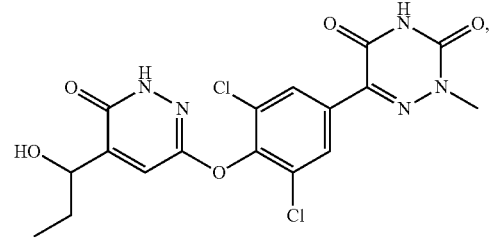
31
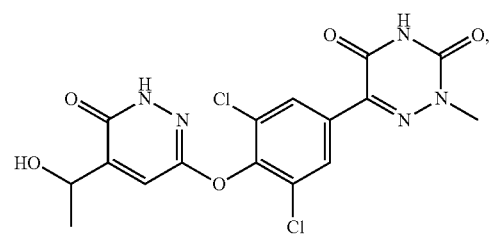

31 P1
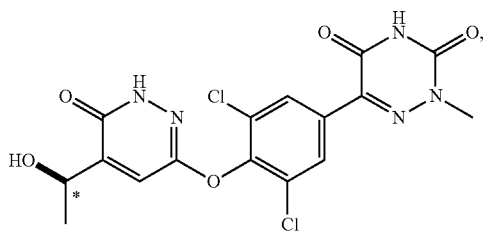

31 P2
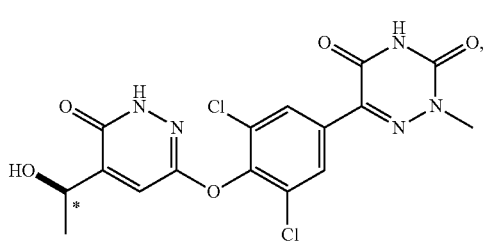

32
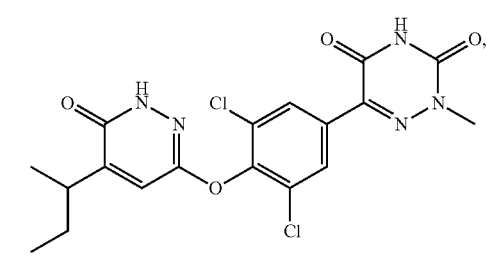

33 P1
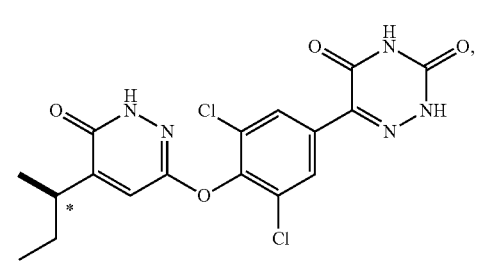 [SMILES: CC[C@@H](C)c1cc(Oc2c(Cl)cc(-c3n[nH]c(=O)[nH]c3=O)cc2Cl)n[nH]c1=O]

33 P2
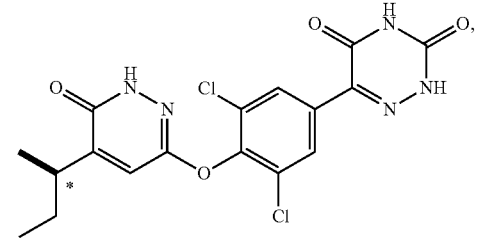 [SMILES: CC[C@@H](C)c1cc(Oc2c(Cl)cc(-c3n[nH]c(=O)[nH]c3=O)cc2Cl)n[nH]c1=O]

34
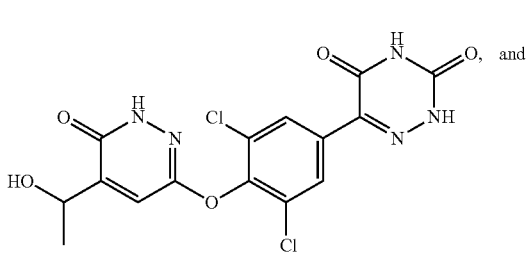
and

35
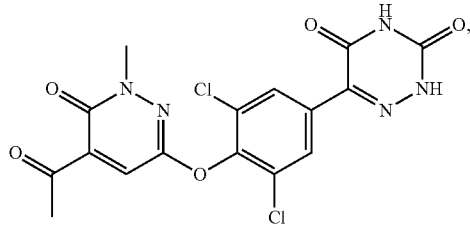

or a pharmaceutically acceptable salt thereof.

The invention also includes all salts, such as pharmaceutically acceptable salts, of compounds referred to herein. The invention also includes any or all of the stereochemical forms, including any enantiomeric or diastereomeric forms, and any tautomers or other forms, such as N-oxides, solvates, prodrugs, or isotopomers, of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

Methods of Synthesis—General Schemes

Schemes S1-S8 below show synthetic routes for preparing the compounds of the present disclosure. In each of Schemes S1-S8, variables $R_1$, $R_2$, $R_3$, $R_4$, $M_1$, $M_2$, and $M_3$ are as defined for the compound of formula (I), unless specified otherwise; additional variables V, T, and W (where EWG is an appropriate electron-withdrawing group) are as defined in the specific schemes; and variable R is H or a suitable boronic ester protecting group, such as an alkyl.

Scheme S1 shows a general synthesis for compounds of formula (I) wherein L is O or S.

Scheme S1

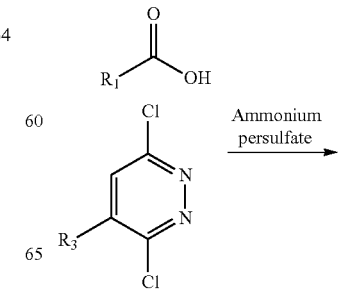

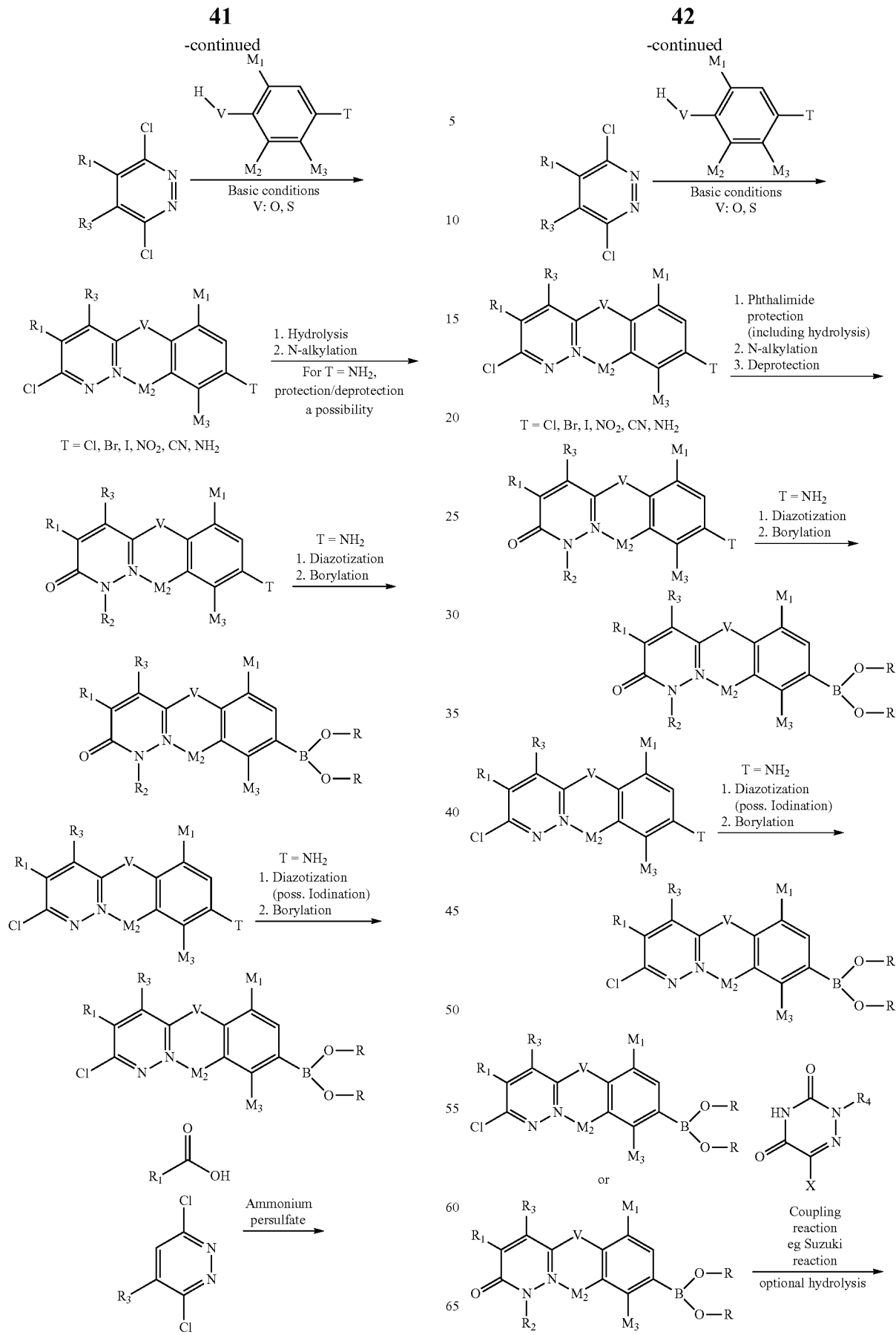

-continued
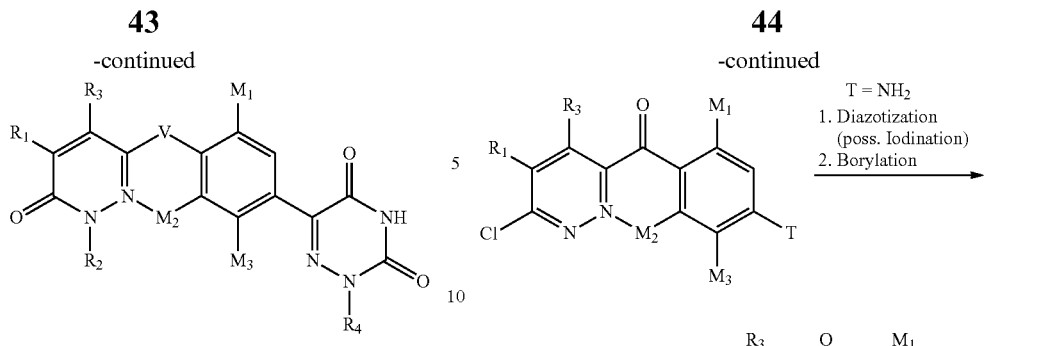
Scheme S2 outlines a general synthesis for compounds of formula (I) wherein L is —C(O)—.
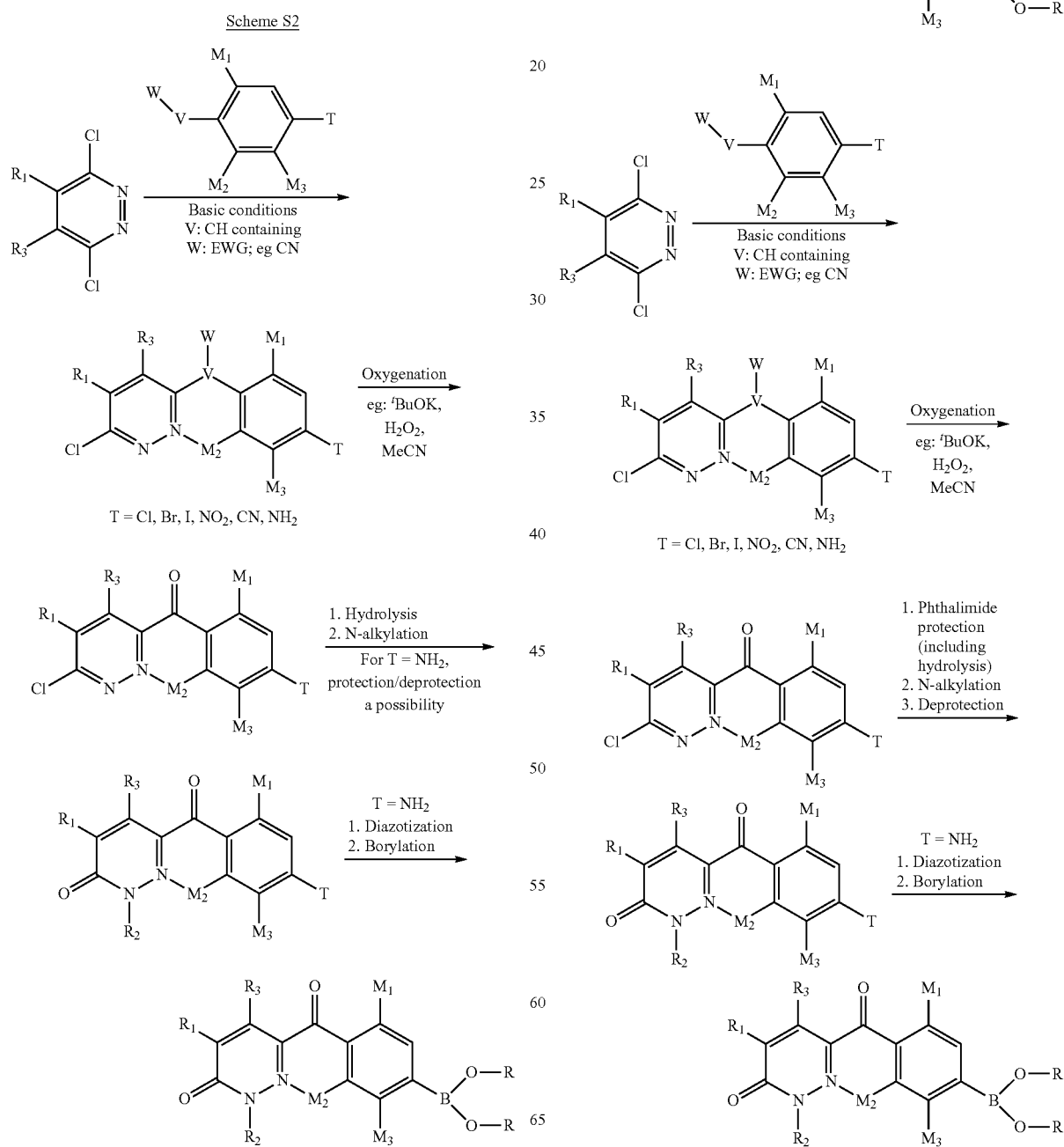

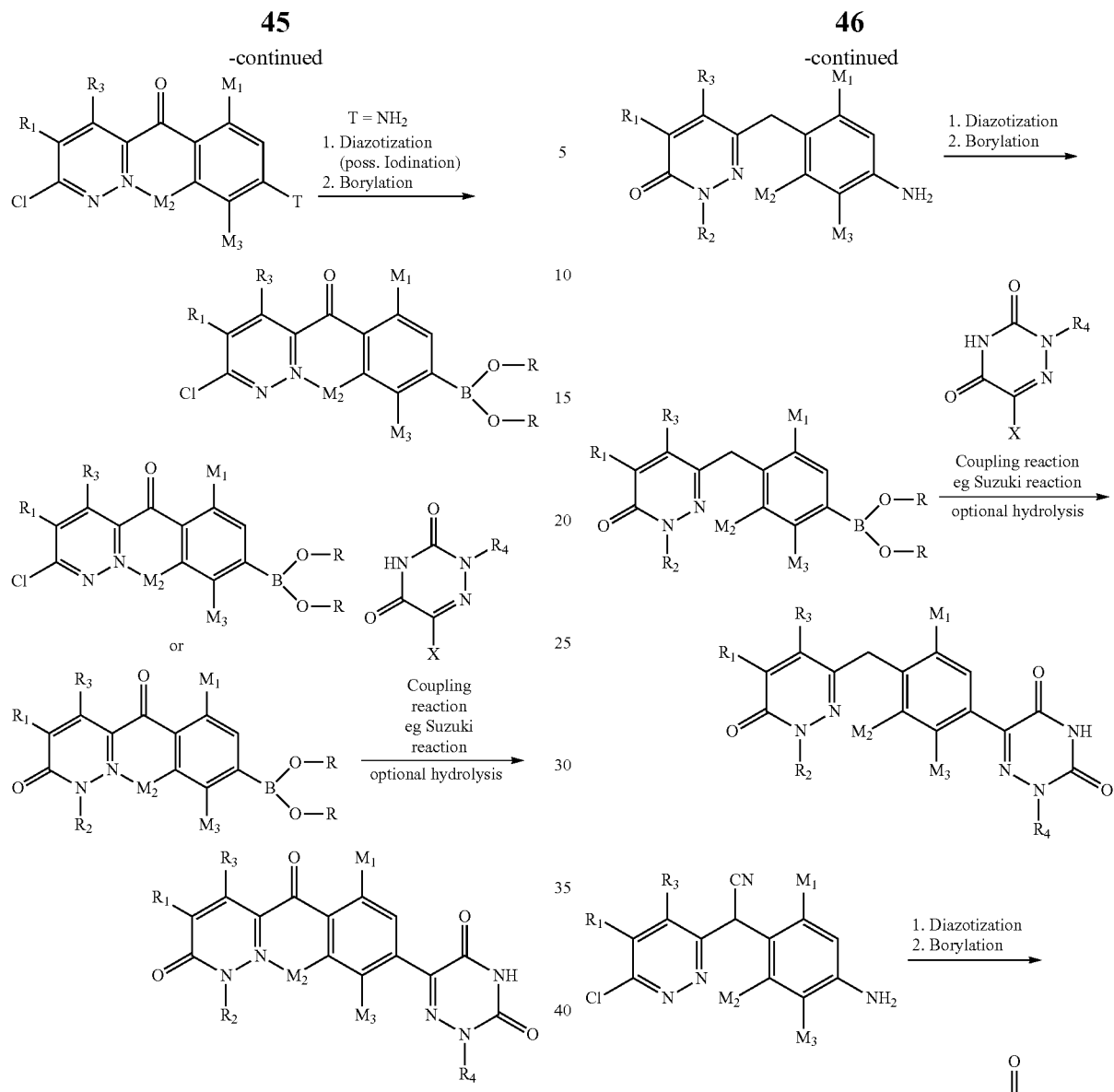
Scheme S3 shows a general synthesis for compounds of formula (I) wherein L is —CH$_2$—.
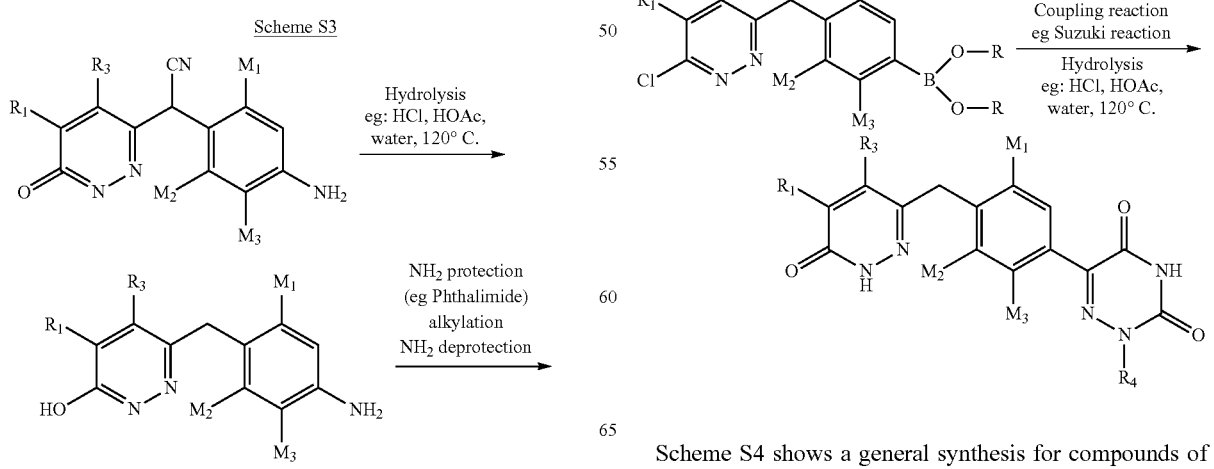
Scheme S4 shows a general synthesis for compounds of formula (I) wherein L is —S(O)— or —S(O)$_2$—.

Scheme S4

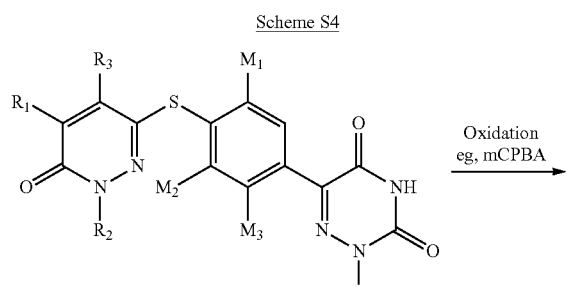

n = 1, 2

Scheme S5 shows a general synthesis for compounds of formula (I) wherein L is —CHF—.

Scheme S5

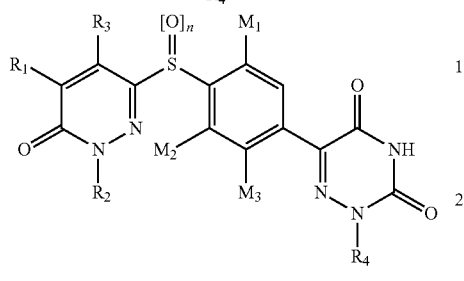

including single isomer synthesis/separation

Scheme S6 shows a general synthesis for compounds of formula (I) wherein L is —CF$_2$—.

Scheme S6

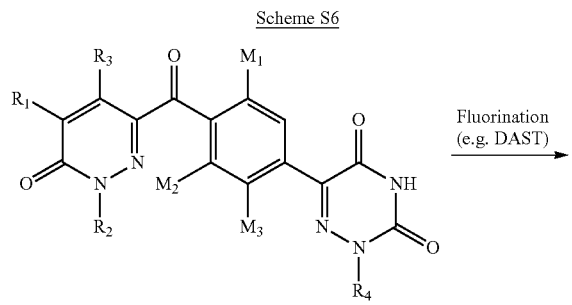

Scheme S7 outlines a general synthesis for compounds of formula (I) wherein L is —CH(CH$_3$)—.

Scheme S7

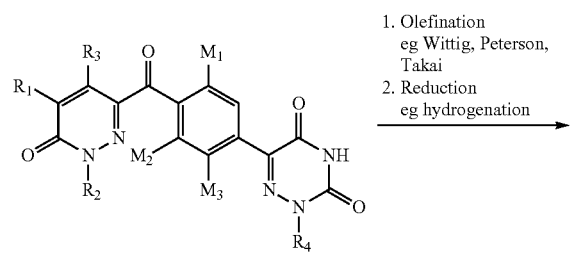

including single isomer separation

Scheme S8 shows a general synthesis for compounds of formula (I) wherein L is

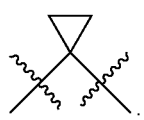 [SMILES: *C1(*)CC1]

.

Scheme S8

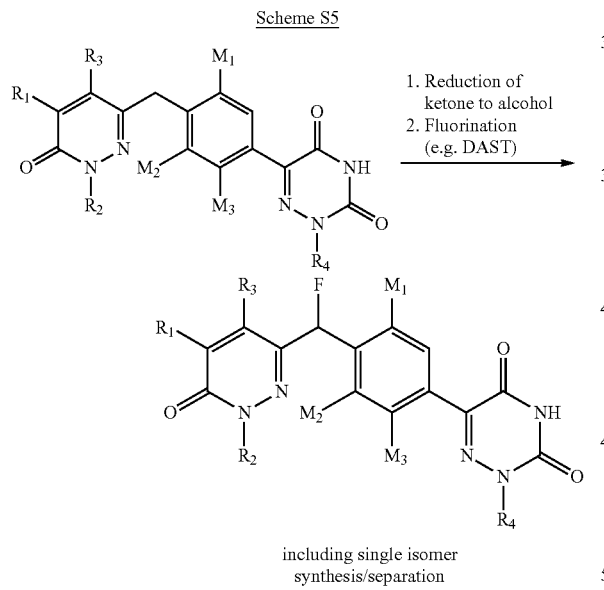

-continued

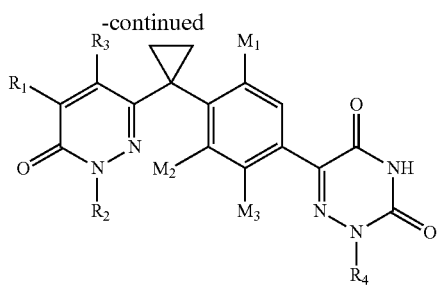

Synthesis of certain compounds provided herein are schematically illustrated above and provided in the Examples section below. Synthesis of other compounds provided herein will be apparent to the skilled artisan based on the guidance provided herein and based on synthetic methods well known to the skilled artisan.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

It is understood that the synthetic process disclosed here may be modified to arrive at various compounds of the invention by selection of appropriate reagents and starting materials. It is also understood that where protection of certain active or incompatible groups (e.g., an amine or a carboxylic acid) is required, the formulae in e.g., the scheme(s) provided here intend and include compounds where such active or incompatible groups are in appropriate protected forms. For a general description of protecting groups and their use, see P. G. M. Wuts and T. W. Greene, Greene's Protective Groups in Organic Synthesis 4$^{th}$ edition, Wiley-Interscience, New York, 2006.

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 10% impurity, wherein the impurity denotes a compound other than the compound comprising the majority of the composition or a salt thereof. For example, a composition of a substantially pure compound selected from a compound of Table 1 intends a composition that contains no more than 10% impurity, wherein the impurity denotes a compound other than the compound or a salt thereof. In one variation, a composition of substantially pure compound or a salt thereof is provided wherein the composition contains no more than 5% impurity. In another variation, a composition of substantially pure compound or a salt thereof is provided wherein the composition contains or no more than 2% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 10% or preferably no more than 5% or more preferably no more than 1% or even more preferably no more than 0.5% and most preferably no more than 0.1% impurity, which impurity may be the compound in a different stereochemical form. For instance, and without limitation, a composition of substantially pure (S) compound means that the composition contains no more than 10% or no more than 5% or no more than 3% or no more than 1% or no more than 0.5% of the (R) form of the compound.

In one variation, the compounds herein are synthetic compounds prepared for administration to a patient such as a human. In another variation, pharmaceutical compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, 21$^{st}$ ed. (2005), which is incorporated herein by reference.

Compounds as described herein may be administered to patients (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described.

Pharmaceutical compositions, such as pharmaceutical compositions, comprising a compound provided herein, or a pharmaceutically acceptable salt thereof, are also described. In one variation, the composition comprises a compound, or a pharmaceutically acceptable salt thereof, and a pharmaceutically acceptable carrier or excipient. In another variation, a composition of substantially pure compound, or a pharmaceutically acceptable salt thereof, is provided.

Methods of Use/Treatment

Compounds and compositions detailed herein, such as a pharmaceutical composition containing a compound of any formula provided herein, or a pharmaceutically acceptable salt thereof, and a pharmaceutically acceptable carrier or excipient, may be used in methods of administration and treatment as provided herein. The compounds and compositions may also be used in in vitro methods, such as in vitro methods of administering a compound, or a salt thereof, or composition to cells for screening purposes and/or for conducting quality control assays.

In one aspect, provided herein is a method of agonizing thyroid hormone receptor beta (THR beta) comprising contacting either an effective amount of a compound provided herein, or a salt thereof, such as a pharmaceutically acceptable salt thereof, or an effective amount of a pharmaceutical composition provided herein, with the THR beta. In one aspect, provided herein is a method of selectively agonizing THR beta over THR alpha comprising contacting either an effective amount of a compound provided herein, or a pharmaceutically acceptable salt thereof, or an effective amount of a pharmaceutical composition provided herein, with the THR beta. In one such aspect, the method selectively agonizes THR beta over THR alpha by at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, or 100-fold. In any such embodiment, in one aspect selectivity is assessed via a biochemical assay, such as the TR-FRET assay described in Example B1.

In one aspect, provided herein is a method of treating a disease or disorder that is mediated by THR beta in a patient in need thereof, comprising administering to the patient a therapeutically effective amount of a compound provided herein, or a therapeutically effective amount of a composition provided herein. In one aspect, the disease or disorder is a liver disease or disorder. In one aspect, provided herein is a method of treating a disease or disorder of the liver associated with sub-optimal THR beta agonism in a patient in need thereof, comprising administering to the patient a compound of formula (I), or a pharmaceutically acceptable salt thereof, wherein the compound selectively agonizes THR beta over THR alpha.

In one aspect, provided herein is a method of treating non-alcoholic fatty liver disease in a patient in need thereof, comprising administering to the patient a therapeutically effective amount of a compound provided herein, or a therapeutically effective amount of a composition provided herein. In one aspect, provided herein is a method of treating non-alcoholic steatohepatitis (NASH) in a patient in need thereof, comprising administering to the patient a therapeutically effective amount of a compound provided herein, or a therapeutically effective amount of a composition provided herein. In one aspect, provided herein is a method of treating metabolic syndrome in a patient in need thereof, comprising administering to the patient a therapeutically effective amount of a compound provided herein, or a therapeutically effective amount of a composition provided herein. In one aspect, provided herein is a method of treating dyslipidemia in a patient in need thereof, comprising administering to the patient a therapeutically effective amount of a compound provided herein, or a therapeutically effective amount of a composition provided herein. In one aspect, provided herein is a method of treating hypertriglyceridemia in a patient in need thereof, comprising administering to the patient a therapeutically effective amount of a compound provided herein, or a therapeutically effective amount of a composition provided herein. In one aspect, provided herein is a method of treating hypercholesterolemia in a patient in need thereof, comprising administering to the patient a therapeutically effective amount of a compound provided herein, or a therapeutically effective amount of a composition provided herein.

In any of the embodiments described herein, a patient having a disease or disorder associated with THR beta agonism may include, but is not limited to, a patient with an underlying hypothyroid disorder.

In another aspect is provided a method of delaying the onset and/or development of a disease or disorder that is mediated by THR beta in a patient (such as a human) who is at risk for developing the disease or disorder. It is appreciated that delayed development may encompass prevention in the event the individual does not develop the disease or disorder. An individual at risk of developing a disease or disorder that is mediated by THR beta in one aspect has one or more risk factors for developing the disease or disorder, such as age, increased waist circumference, high body to mass index or the presence of an associated comorbidity.

In one aspect, provided herein is a method of delaying the onset and/or development of non-alcoholic fatty liver disease in a patient in need thereof, comprising administering to the patient a therapeutically effective amount of a compound provided herein, or a therapeutically effective amount of a composition provided herein. In one aspect, provided herein is a method of delaying the onset and/or development of non-alcoholic steatohepatitis (NASH) in a patient in need thereof, comprising administering to the patient a therapeutically effective amount of a compound provided herein, or a therapeutically effective amount of a composition provided herein. In one aspect, provided herein is a method of delaying the onset and/or development of metabolic syndrome in a patient in need thereof, comprising administering to the patient a therapeutically effective amount of a compound provided herein, or a therapeutically effective amount of a composition provided herein. In one aspect, provided herein is a method of delaying the onset and/or development of dyslipidemia in a patient in need thereof, comprising administering to the patient a therapeutically effective amount of a compound provided herein, or a therapeutically effective amount of a composition provided herein. In one aspect, provided herein is a method of delaying the onset and/or development of hypertriglyceridemia in a patient in need thereof, comprising administering to the patient a therapeutically effective amount of a compound provided herein, or a therapeutically effective amount of a composition provided herein. In one aspect, provided herein is a method of delaying the onset and/or development of hypercholesterolemia in a patient in need thereof, comprising administering to the patient a therapeutically effective amount of a compound provided herein, or a therapeutically effective amount of a composition provided herein.

In one aspect, provided herein is a compound of formula (I) or any variation thereof, or a pharmaceutically acceptable salt thereof, for use in therapy. In some embodiments, provided herein is a compound of formula (I) or any variation thereof, or a pharmaceutically acceptable salt thereof, or a pharmaceutical composition comprising such compound or a pharmaceutically acceptable salt thereof, for use in the treatment of non-alcoholic fatty liver disease. In some embodiments, provided herein is a compound of formula (I) or any variation thereof, or a pharmaceutically acceptable salt thereof or pharmaceutical composition comprising such compound, or a pharmaceutically acceptable salt thereof, for use in the treatment of non-alcoholic steatohepatitis (NASH). In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of metabolic syndrome. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of dyslipidemia. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of hypertriglyceridemia. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of hypercholesterolemia.

In another embodiment, provided herein is a compound of formula (I) or any variation thereof, or a pharmaceutically acceptable salt thereof, for use in the manufacture of a medicament for the treatment of non-alcoholic fatty liver disease. In another embodiment, provided herein is a compound of formula (I) or any variation thereof, or a pharmaceutically acceptable salt thereof, for use in the manufacture of a medicament for the treatment of non-alcoholic steatohepatitis (NASH). In another embodiment, provided herein is a compound of formula (I) or any variation thereof, or a pharmaceutically acceptable salt thereof, for use in the manufacture of a medicament for the treatment of metabolic syndrome. In some embodiments, the medicament is for the treatment of dyslipidemia. In some embodiments, the medicament is for the treatment of hypertriglyceridemia. In some embodiments, the medicament is for the treatment of dyslipidemia. In some embodiments, the medicament is for the treatment of hypercholesterolemia.

In some embodiments, the individual is a mammal. In some embodiments, the individual is a primate, dog, cat, rabbit, or rodent. In some embodiments, the individual is a primate. In some embodiments, the individual is a human. In some embodiments, the human is at least about or is about any of 18, 21, 30, 50, 60, 65, 70, 75, 80, or 85 years old. In some embodiments, the human is a child. In some embodiments, the human is less than about or about any of 21, 18, 15, 10, 5, 4, 3, 2, or 1 years old.

Dosing and Method of Administration

The dose of a compound described herein, or a stereoisomer, tautomer, solvate, or salt thereof, administered to an individual (such as a human) may vary with the particular compound or salt thereof, the method of administration, and the particular disease or disorder, such as non-alcoholic fatty liver disease, non-alcoholic steatohepatitis (NASH), metabolic syndrome, hypertriglyceridemia, dyslipidemia, or hypercholesterolemia, being treated. In some embodiments, the amount of the compound, or a stereoisomer, tautomer, solvate, or salt thereof, is a therapeutically effective amount.

The compounds provided herein, or a salt thereof, may be administered to an individual via various routes, including, e.g., intravenous, intramuscular, subcutaneous, oral, and transdermal.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein, or a stereoisomer, tautomer, solvate, or salt thereof, and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule.

The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound described herein, or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein, or a pharmaceutically acceptable salt thereof, or a composition comprising a compound described herein, or a pharmaceutically acceptable salt thereof. The kits may employ any of the compounds disclosed herein or a pharmaceutically acceptable salt thereof. In one variation, the kit employs a compound described herein or a pharmaceutically acceptable salt thereof. The kits may be used for any one or more of the uses described herein, and, accordingly, may contain instructions for the treatment of any disease or described herein, for example for the treatment of non-alcoholic steatohepatitis (NASH).

Kits generally comprise suitable packaging. The kits may comprise one or more containers comprising any compound described herein or a pharmaceutically acceptable salt thereof. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein, or a pharmaceutically acceptable salt thereof, and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

EXEMPLARY EMBODIMENTS

The present disclosure is further described by the following embodiments. The features of each of the embodiments are combinable with any of the other embodiments where appropriate and practical.

Embodiment 1

A compound of formula (I):

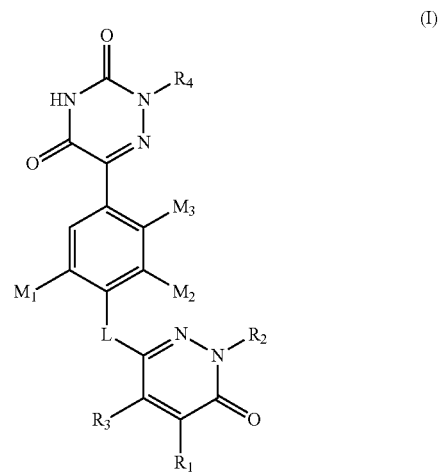

wherein:

$R_1$ is substituted or unsubstituted $C_1$-$C_6$ alkyl, substituted or unsubstituted $C_3$-$C_6$ cycloalkyl, —C(O)N($R_7$)($R_8$), —N($R_9$)C(O)($R_{10}$), or halo;

$R_2$ is H, substituted or unsubstituted $C_1$-$C_6$ alkyl, or substituted or unsubstituted $C_3$-$C_6$ cycloalkyl;

$R_3$ is H or halo;

$R_4$ is H, or substituted or unsubstituted linear $C_1$-$C_3$ alkyl;

L is —O—, —S—, —S(O)—, —S(O)$_2$—, —C(O)—, or —C($R_5$)($R_6$)—;

$R_5$ and $R_6$ are independently H, halo, —CN, or substituted or unsubstituted $C_1$-$C_6$ alkyl, or $R_5$ and $R_6$ are taken together with the carbon atom to which they are attached to form a substituted or unsubstituted $C_3$-$C_6$ cycloalkyl;

$R_7$ and $R_8$ are independently H, or substituted or unsubstituted $C_1$-$C_6$ alkyl, or $R_7$ and $R_8$ are taken together with the nitrogen atom to which they are attached to form a substituted or unsubstituted 3- to 7-membered heterocyloalkyl;

$R_9$ is H, substituted or unsubstituted $C_1$-$C_6$ alkyl, or substituted or unsubstituted $C_3$-$C_6$ cycloalkyl;

$R_{10}$ is substituted or unsubstituted $C_1$-$C_6$ alkyl, substituted or unsubstituted $C_3$-$C_6$ cycloalkyl, —N($R_7$)($R_8$), or —O($R_{11}$);

$R_{11}$ is substituted or unsubstituted $C_1$-$C_6$ alkyl, or substituted or unsubstituted $C_3$-$C_6$ cycloalkyl;

$M_1$ and $M_2$ are independently halo, or substituted or unsubstituted $C_1$-$C_6$ alkyl; and $M_3$ is H, halo, or substituted or unsubstituted $C_1$-$C_6$ alkyl, or $M_3$ is taken together with $M_2$ and the carbon atoms to which they are attached to form a 5- to 7-membered ring containing 0, 1, or 2 heteroatoms selected from the group consisting of N, O, and S, or a pharmaceutically acceptable salt thereof.

Embodiment 2

The compound of embodiment 1, or a pharmaceutically acceptable salt thereof, wherein $R_1$ is substituted or unsubstituted $C_1$-$C_6$ alkyl or substituted or unsubstituted $C_3$-$C_6$ cycloalkyl.

Embodiment 3

The compound of embodiment 2, or a pharmaceutically acceptable salt thereof, wherein $R_1$ is isopropyl.

Embodiment 4

The compound of embodiment 2, or a pharmaceutically acceptable salt thereof, wherein $R_1$ is cyclopropyl.

Embodiment 5

The compound of any one of embodiments 1-4, or a pharmaceutically acceptable salt thereof, wherein $R_2$ is substituted or unsubstituted $C_1$-$C_6$ alkyl.

Embodiment 6

The compound of embodiment 5, or a pharmaceutically acceptable salt thereof, wherein $R_2$ is methyl.

Embodiment 7

The compound of any one of embodiments 1-4, or a pharmaceutically acceptable salt thereof, wherein $R_2$ is H.

Embodiment 8

The compound of any one of embodiments 1-7, or a pharmaceutically acceptable salt thereof, wherein $R_3$ is H.

Embodiment 9

The compound of any one of embodiments 1-8, or a pharmaceutically acceptable salt thereof, wherein $R_4$ is H.

Embodiment 10

The compound of any one of embodiments 1-8, or a pharmaceutically acceptable salt thereof, wherein $R_4$ is substituted or unsubstituted linear $C_1$-$C_3$ alkyl.

Embodiment 11

The compound of embodiment 10, or a pharmaceutically acceptable salt thereof, wherein $R_4$ is methyl.

Embodiment 12

The compound of any one of embodiments 1-11, or a pharmaceutically acceptable salt thereof, wherein L is —O—.

Embodiment 13

The compound of any one of embodiments 1-11, or a pharmaceutically acceptable salt thereof, wherein L is —C(O)—.

Embodiment 14

The compound of any one of embodiments 1-11, or a pharmaceutically acceptable salt thereof, wherein L is —CH$_2$—.

Embodiment 15

The compound of any one of embodiments 1-14, or a pharmaceutically acceptable salt thereof, wherein $M_1$ and $M_2$ are independently halo.

Embodiment 16

The compound of embodiment 15, or a pharmaceutically acceptable salt thereof, wherein $M_1$ and $M_2$ are each chloro.

Embodiment 17

The compound of any one of embodiments 1-16, or a pharmaceutically acceptable salt thereof, wherein $M_3$ is H.

Embodiment 18

The compound of any one of embodiments 1-16, or a pharmaceutically acceptable salt thereof, wherein $M_3$ is substituted or unsubstituted $C_1$-$C_6$ alkyl.

Embodiment 19

The compound of embodiment 18, or a pharmaceutically acceptable salt thereof, wherein $M_3$ is methyl.

Embodiment 20

A compound selected from the group consisting of:

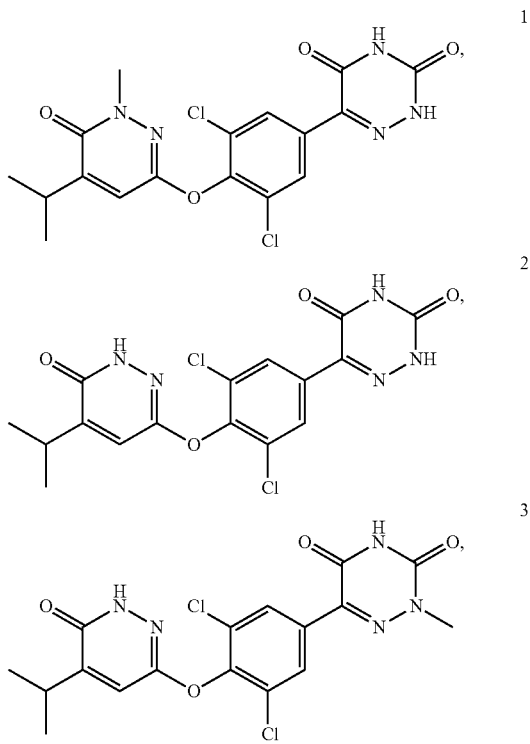

5 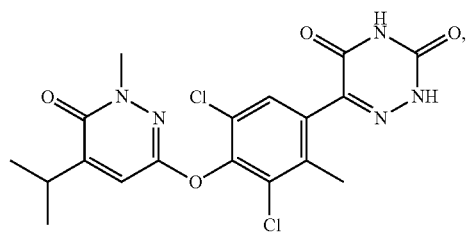
6 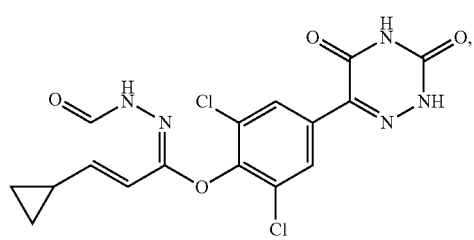
7 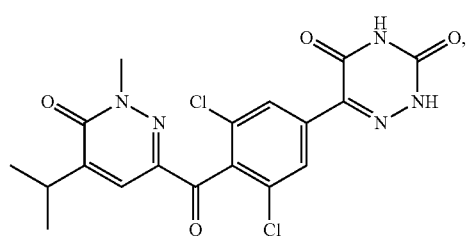
8 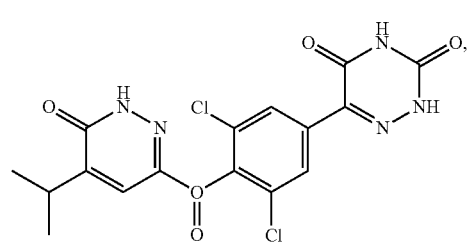
9 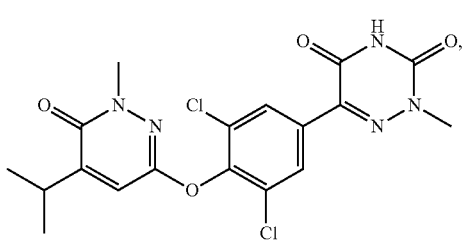
10 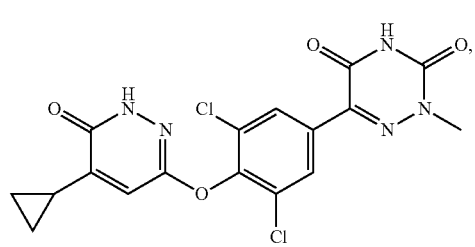
11 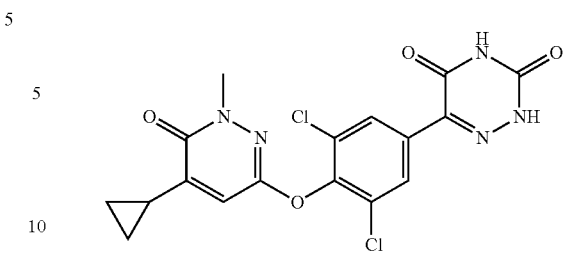
12 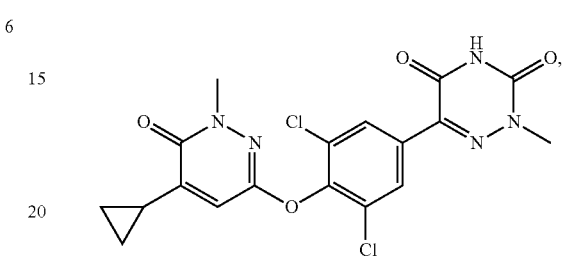
13 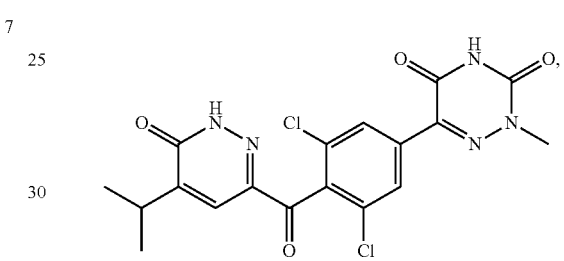
14 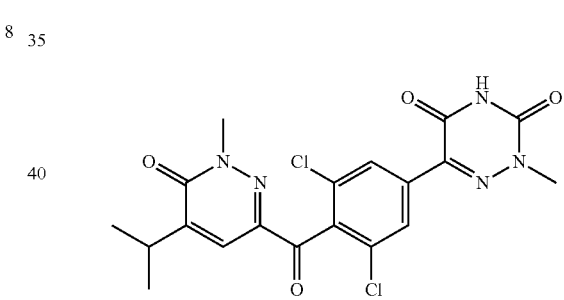
15 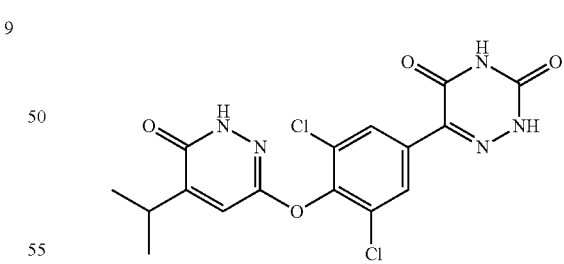
16 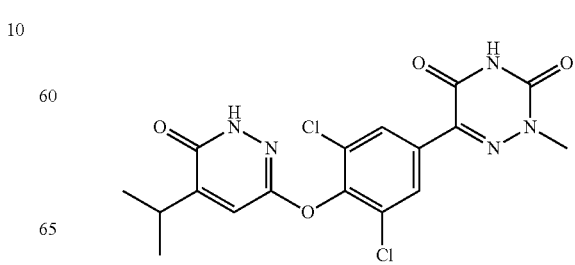

-continued

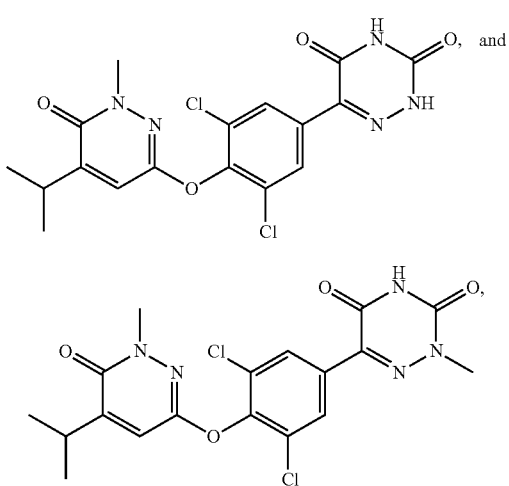

or a pharmaceutically acceptable salt thereof.

Embodiment 21

A pharmaceutical composition comprising the compound of any one of embodiments 1-20, or a pharmaceutically acceptable salt thereof, and a pharmaceutically acceptable excipient.

Embodiment 22

A method of agonizing thyroid hormone receptor beta (THR beta) comprising contacting an effective amount of the compound of any one of embodiments 1-20, or a pharmaceutically acceptable salt thereof, or an effective amount of the pharmaceutical composition of embodiment 21, with the THR beta.

Embodiment 23

A method of treating a disorder which is mediated by THR beta in a patient in need thereof, comprising administering to the patient a therapeutically effective amount of the compound of any one of embodiments 1-20, or a pharmaceutically acceptable salt thereof, or a therapeutically effective amount of the pharmaceutical composition of embodiment 21.

Embodiment 24

A compound of formula (I):

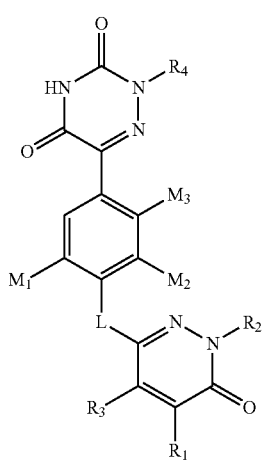

(I)

wherein:

$R_1$ is substituted or unsubstituted $C_1$-$C_6$ alkyl, substituted or unsubstituted $C_3$-$C_6$ cycloalkyl, —C(O)N($R_7$)($R_8$), —N($R_9$)C(O)($R_{10}$), or halo;

$R_2$ is H, substituted or unsubstituted $C_1$-$C_6$ alkyl, or substituted or unsubstituted $C_3$-$C_6$ cycloalkyl;

$R_3$ is H or halo;

$R_4$ is H, or substituted or unsubstituted linear $C_1$-$C_3$ alkyl; L is —O—, —S—, —S(O)—, —S(O)$_2$—, —C(O)—, or —C($R_5$)($R_6$)—;

$R_5$ and $R_6$ are independently H, halo, —CN, or substituted or unsubstituted $C_1$-$C_6$ alkyl, or $R_5$ and $R_6$ are taken together with the carbon atom to which they are attached to form a substituted or unsubstituted $C_3$-$C_6$ cycloalkyl;

$R_7$ and $R_8$ are independently H, or substituted or unsubstituted $C_1$-$C_6$ alkyl, or $R_7$ and $R_8$ are taken together with the nitrogen atom to which they are attached to form a substituted or unsubstituted 3- to 7-membered heterocycloalkyl;

$R_9$ is H, substituted or unsubstituted $C_1$-$C_6$ alkyl, or substituted or unsubstituted $C_3$-$C_6$ cycloalkyl;

$R_{10}$ is substituted or unsubstituted $C_1$-$C_6$ alkyl, substituted or unsubstituted $C_3$-$C_6$ cycloalkyl, —N($R_7$)($R_8$), or —O($R_{11}$);

$R_{11}$ is substituted or unsubstituted $C_1$-$C_6$ alkyl, or substituted or unsubstituted $C_3$-$C_6$ cycloalkyl;

$M_1$ and $M_2$ are independently halo, or substituted or unsubstituted $C_1$-$C_6$ alkyl; and $M_3$ is H, halo, or substituted or unsubstituted $C_1$-$C_6$ alkyl, or $M_3$ is taken together with $M_2$ and the carbon atoms to which they are attached to form a 5- to 7-membered ring containing 0, 1, or 2 heteroatoms selected from the group consisting of N, O, and S, or a pharmaceutically acceptable salt thereof.

Embodiment 25

The compound of embodiment 24, or a pharmaceutically acceptable salt thereof, wherein:

$R_1$ is $C_1$-$C_6$ alkyl, $C_3$-$C_6$ cycloalkyl, —C(O)N($R_7$)($R_8$), —N($R_9$)C(O)($R_{10}$), or halo, wherein $C_1$-$C_6$ alkyl and $C_3$-$C_6$ cycloalkyl are optionally substituted by 1-5 substituents selected from the group consisting of —OH, oxo, —CN, and halo;

$R_2$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;

$R_3$ is H or halo;

$R_4$ is H or linear $C_1$-$C_3$ alkyl optionally substituted by 1-5 substituents selected from the group consisting of —OH, oxo, —CN, halo, and —O($C_1$-$C_2$ alkyl);

L is —O—, —S—, —S(O)—, —S(O)$_2$—, —C(O)—, or —C($R_5$)($R_6$)—;

$R_5$ and $R_6$ are independently H, halo, —CN, or $C_1$-$C_6$ alkyl, or $R_5$ and $R_6$ are taken together with the carbon atom to which they are attached to form a $C_3$-$C_6$ cycloalkyl, wherein each $C_1$-$C_6$ alkyl or $C_3$-$C_6$ cycloalkyl is optionally independently substituted by 1-5 substituents selected from the group consisting of —OH, —CN, and halo;

$R_7$ and $R_8$ are independently H or $C_1$-$C_6$ alkyl, or $R_7$ and $R_8$ are taken together with the nitrogen atom to which they are attached to form a 3- to 7-membered heterocycloalkyl, wherein each $C_1$-$C_6$ alkyl or 3- to 7-membered heterocycloalkyl is optionally independently substituted by 1-5 substituents selected from the group consisting of —OH, —CN, and halo;

$R_9$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;

$R_{10}$ is $C_1$-$C_6$ alkyl, $C_3$-$C_6$ cycloalkyl, —N($R_7$)($R_8$), or —O($R_{11}$), wherein $C_1$-$C_6$ alkyl and $C_3$-$C_6$ cycloalkyl are optionally substituted by 1-5 substituents selected from the group consisting of —OH, —CN, and halo;

$R_{11}$ is $C_1$-$C_6$ alkyl or $C_3$-$C_6$ cycloalkyl, each of which is optionally substituted by 1-5 substituents selected from the group consisting of —OH, —CN, and halo;

$M_1$ and $M_2$ are independently halo or $C_1$-$C_6$ alkyl optionally substituted by 1-5 substituents selected from the group consisting of —OH, —CN, and halo; and $M_3$ is H, halo, or $C_1$-$C_6$ alkyl optionally substituted by 1-5 substituents selected from the group consisting of —OH, —CN, and halo, or $M_3$ is taken together with $M_2$ and the carbon atoms to which they are attached to form a 5- to 7-membered ring containing 0, 1, or 2 heteroatoms selected from the group consisting of N, O, and S.

Embodiment 26

The compound of embodiment 24 or 25, or a pharmaceutically acceptable salt thereof, wherein:
$R_1$ is $C_1$-$C_6$ alkyl or $C_3$-$C_6$ cycloalkyl, each of which is optionally substituted by 1-5 substituents selected from the group consisting of —OH, oxo, —CN, and halo;

Embodiment 27

The compound of embodiment 26, or a pharmaceutically acceptable salt thereof, wherein:
$R_1$ is cyclopropyl, isopropyl, ethyl, —CH(CH$_2$CH$_3$)$_2$, —CH(CH$_3$)(CH$_2$OH), —CH(OH)(CH$_2$CH$_3$), —CH(OH)(CH$_3$), —CH(CH$_3$)(CH$_2$CH$_3$), or —C(O)(CH$_3$).

Embodiment 28

The compound of any one of embodiments 24-27, or a pharmaceutically acceptable salt thereof, wherein:
$R_2$ is H or $C_1$-$C_6$ alkyl optionally substituted by 1-5 substituents selected from the group consisting of —OH, —CN, and halo.

Embodiment 29

The compound of embodiment 28, or a pharmaceutically acceptable salt thereof, wherein:
$R_2$ is H or methyl.

Embodiment 30

The compound of any one of embodiments 24-29, or a pharmaceutically acceptable salt thereof, wherein:
$R_3$ is H.

Embodiment 31

The compound of any one of embodiments 24-30, or a pharmaceutically acceptable salt thereof, wherein:
$R_4$ is H or linear $C_1$-$C_3$ alkyl optionally substituted by 1-3 substituents selected from the group consisting of —OH, oxo, —CN, halo, and —O($C_1$-$C_2$ alkyl).

Embodiment 32

The compound of embodiment 31, or a pharmaceutically acceptable salt thereof, wherein:

$R_4$ is H, methyl, ethyl, —CH$_2$C(O)OCH$_2$CH$_3$, —CH$_2$CF$_3$, —CH$_2$CN, or —CH$_2$CHF$_2$.

Embodiment 33

The compound of any one of embodiments 24-32, or a pharmaceutically acceptable salt thereof, wherein:
L is —O—, —C(O)—, or —CH$_2$—.

Embodiment 34

The compound of any one of embodiments 24-33, or a pharmaceutically acceptable salt thereof, wherein:
$M_1$ and $M_2$ are independently halo or $C_1$-$C_3$ alkyl optionally substituted by 1-3 substituents selected from the group consisting of —OH, —CN, and halo.

Embodiment 35

The compound of embodiment 34, or a pharmaceutically acceptable salt thereof, wherein:
$M_1$ and $M_2$ are independently halo or methyl.

Embodiment 36

The compound of embodiment 35, or a pharmaceutically acceptable salt thereof, wherein:
$M_1$ and $M_2$ are each chloro.

Embodiment 37

The compound of embodiment 35, or a pharmaceutically acceptable salt thereof, wherein:
$M_1$ and $M_2$ are each methyl.

Embodiment 38

The compound of any one of embodiments 24-37, or a pharmaceutically acceptable salt thereof,
$M_3$ is H, halo, or $C_1$-$C_3$ alkyl optionally substituted by 1-3 substituents selected from the group consisting of —OH, —CN, and halo.

Embodiment 39

The compound of embodiment 38, or a pharmaceutically acceptable salt thereof, wherein:
$M_3$ is H, F, or methyl.

Embodiment 40

A compound selected from Compounds 1-3 and 5-35, or a pharmaceutically acceptable salt thereof.

Embodiment 41

A pharmaceutical composition comprising the compound of any one of embodiments 24-40, or a pharmaceutically acceptable salt thereof, and a pharmaceutically acceptable excipient.

Embodiment 42

A method of agonizing thyroid hormone receptor beta (THR beta) comprising contacting an effective amount of the compound of any one of embodiments 24-40, or a pharmaceutically acceptable salt thereof, or an effective amount of the pharmaceutical composition of embodiment 41, with the THR beta.

Embodiment 43

A method of treating a disorder which is mediated by THR beta in a patient in need thereof, comprising administering to the patient a therapeutically effective amount of the compound of any one of embodiments 24-40, or a pharmaceutically acceptable salt thereof, or a therapeutically effective amount of the pharmaceutical composition of embodiment 41.

Embodiment 44

The method of embodiment 43, wherein the disorder is non-alcoholic steatohepatitis (NASH).

EXAMPLES

The following abbreviations may be relevant for the application.

Abbreviations

Ac: acetyl
ACN: acetonitrile
Boc: tertiarybutyloxycarbonyl
BSA: bis(trimethylsilyl)acetamide
Bu: butyl
CAN: ceric ammonium nitrate
DBA: dibenzylideneacetone
DCM: dichloromethane
DMAP: dimethylaminopyridine
DMF: dimethylformamide
DMF-DMA: dimethylformamide dimethylacetal
DMSO: dimethylsulfoxide
DSC: disuccinimidylcarbonate
Et: ethyl
HPLC: high-performance liquid chromatography
MeOH: methanol
OAc: acetate
Pr: propyl
Py or Pyr: pyridine
rt: room temperature
SEMCI: 2-(Trimethylsilyl)ethoxymethyl chloride
SFC: supercritical fluid chromatography
TEA: triethylamine
THF: tetrahydrofuran
TFA: trifluoroacetic acid
Si-TMT: silica bound 2,4,6-trimercaptotriazine
Tol.: toluene
Ts: tosyl
t-Bu Xphos: 2-Di-tert-butylphosphino-2',4',6'-triisopropylbiphenyl Synthetic Examples Example S1: 6-(3,5-dichloro-4-((5-isopropyl-1-methyl-6-oxo-1,6-dihydropyridazin-3-yl)oxy)phenyl)-1,2,4-triazine-3,5(2H,4H)-dione (Compound 1

Scheme 1

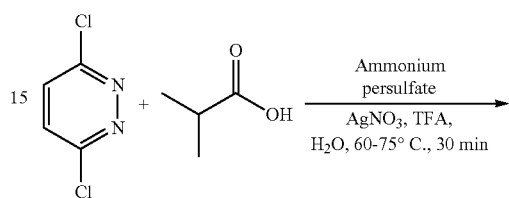

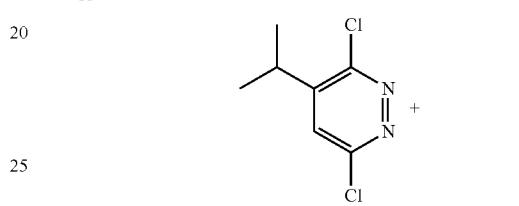

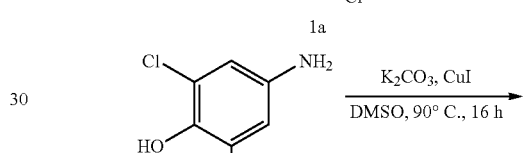

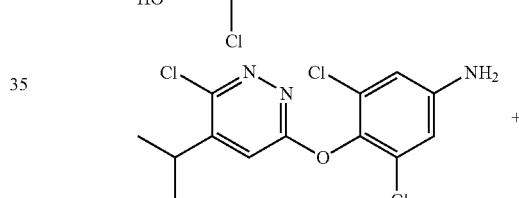

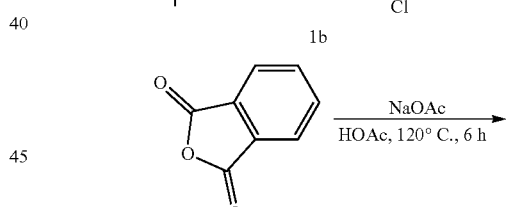

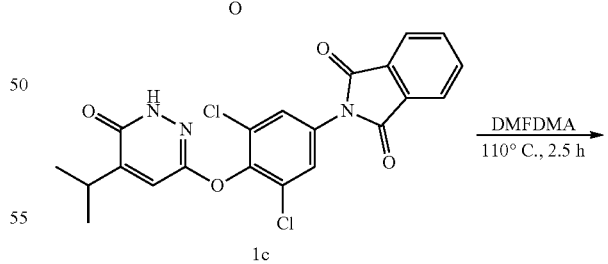

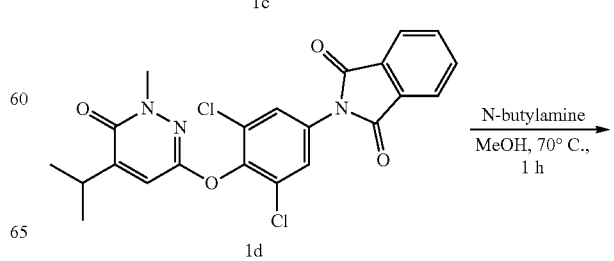

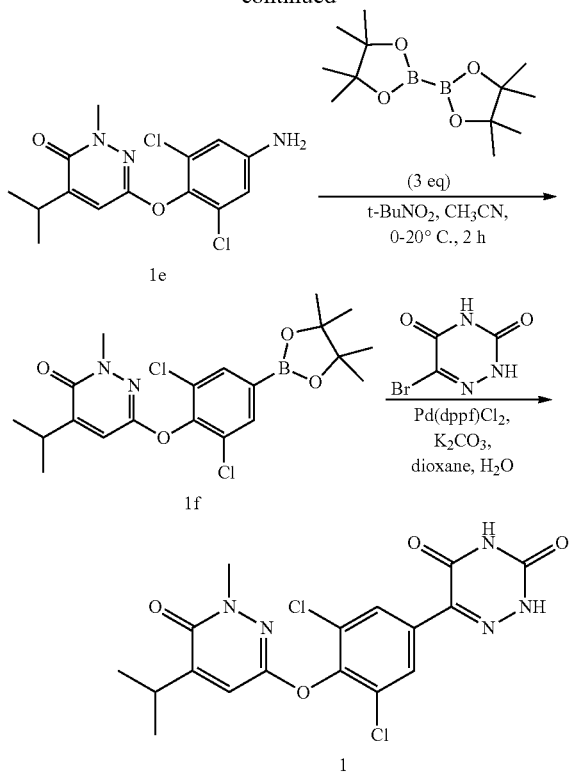

3,6-dichloro-4-isopropylpyridazine (1a)

Sulfuric acid (19.75 g, 201.37 mmol, 10.73 mL) was added to a mixture of 3,6-dichloropyridazine (10 g, 67.12 mmol), 2-methylpropanoic acid (6.21 g, 70.48 mmol, 6.54 mL) and AgNO$_3$ (5.70 g, 33.56 mmol, 5.64 mL) in H$_2$O (200 mL) at 60° C. Then a solution of ammonium persulfate (45.95 g, 201.37 mmol) in H$_2$O (100 mL) was added by drop-wise to the mixture at 75° C., the resulting mixture was stirred at 75° C. for 30 min. TLC showed the reaction was completed. After cooling the mixture, it was adjusted to pH=9-10 with NH$_3$/H$_2$O. The mixture was extracted with ethyl acetate (200 mL*2), the organic phases were washed with brine (100 mL), dried over Na$_2$SO$_4$, filtered and concentrated to give 1a (11 g, 57.57 mmol, 85.77% yield) as light yellow oil. The product was used directly in the next step. MS mass calculated for [M+1]$^+$ (C$_7$H$_8$Cl$_2$N$_2$) requires m/z 191.1, LCMS found m/z 191.1; $^1$H NMR (400 MHz, CDCl$_3$) δ 7.38 (s, 1H), 3.24-3.31 (m, 1H), 1.31 (d, J=6.8 Hz, 6H).

3,5-dichloro-4-((6-chloro-5-isopropylpyridazin-3-yl)oxy)aniline (1b)

To a solution of 4-amino-2,6-dichlorophenol (3 g, 16.85 mmol) and 3,6-dichloro-4-isopropylpyridazine (1a) (3.22 g, 16.85 mmol) in DMSO (30 mL) was added K$_2$CO$_3$ (9.32 g, 67.41 mmol) and CuI (1.93 g, 10.11 mmol). Then the mixture was degassed and purged with N$_2$ 3 times, and stirred at 90° C. for 16 hours under N$_2$ atmosphere. TLC and LCMS showed the starting material was consumed completely and desired MS was detected. The mixture was concentrated in vacuo. The residue was partitioned between ethyl acetate (1000 mL*2) and H$_2$O (500 mL). The combined organic layers were washed with brine (50 mL*3), dried with anhydrous Na$_2$SO$_4$, filtered and concentrated in vacuo. The residue was purified by column chromatography (SiO$_2$, petroleum ether/ethyl acetate=10:1 to 3:1, according TLC) to give 1b (3.5 g, 10.52 mmol, 62.44% yield) as a light brown oil. MS mass calculated for [M+1]$^+$ (C$_{13}$H$_{12}$C$_{13}$N$_3$O) requires m/z 332.0, LCMS found m/z 332.0; $^1$H NMR (400 MHz, DMSO-d6) δ 7.66 (s, 1H), 6.67-6.76 (m, 2H), 5.67 (s, 2H), 3.11-3.21 (m, 1H), 1.28 (d, J=6.85 Hz, 6H).

2-(3,5-dichloro-4-((5-isopropyl-6-oxo-1,6-dihydropyridazin-3-yl)oxy)phenyl)isoindoline-1,3-dione (1c To a mixture of 3,5-dichloro-4-((6-chloro-5-isopropylpyridazin-3-yl)oxy)aniline (1b) (2.6 g, 7.82 mmol) and isobenzofuran-1,3-dione (1.16 g, 7.82 mmol) in HOAc (5 mL) was added NaOAc (3.21 g, 39.08 mmol). The mixture was stirred at 120° C. for 6 hours. LCMS showed the starting material was consumed completely and desired MS was detected. The reaction mixture was concentrated under reduced pressure to remove AcOH. The solid was dissolved in water and the pH was adjusted to ~9 with saturated NaHCO$_3$ solution (10 mL). Then the mixture was partitioned with ethyl acetate (30 mL*2) and H$_2$O (30 mL). The combined organic layers were washed with brine (10 mL*3), dried with anhydrous Na$_2$SO$_4$, filtered and concentrated in vacuo. The solid was diluted with ethyl acetate (10 mL), and then petroleum ether (50 mL) was added to the mixture. The mixture was filtered to collect the solid. The solid was dried to give 1c (2.48 g, 3.65 mmol, 46.71% yield) as a brown solid. MS mass calculated for [M+1]$^+$ (C$_{21}$H$_{15}$Cl$_2$N$_3$O$_4$) requires m/z 444.0, LCMS found m/z 444.1; $^1$H NMR (400 MHz, DMSO-d6) δ 12.21 (s, 1H), 7.98-8.06 (m, 2H), 7.90-7.97 (m, 2H), 7.78-7.83 (m, 2H), 7.46 (s, 1H), 3.03-3.10 (m, 1H), 1.20 (d, J=6.85 Hz, 6H).

2-(3,5-dichloro-4-((5-isopropyl-1-methyl-6-oxo-1,6-dihydropyridazin-3-yl)oxy)phenyl)isoindoline-1,3-dione (1d A solution of 2-(3,5-dichloro-4-((5-isopropyl-6-oxo-1,6-dihydropyridazin-3-yl)oxy)phenyl)iso-indoline-1,3-dione (1c) (500 mg, 1.13 mmol) in DMF-DMA (4 mL) was stirred at 110° C. for 2.5 hours. TLC showed the starting material was consumed completely and two new spots formed. The mixture was concentrated in vacuo. The residue was partitioned between ethyl acetate (10 mL*2) and H$_2$O (3 mL). The combined organic layers were washed with brine (5 mL*3), dried with anhydrous Na$_2$SO$_4$, filtered and concentrated in vacuo to give 1d as a yellow solid. The product was used directly in the next step without further purification.

6-(4-amino-2,6-dichlorophenoxy)-4-isopropyl-2-methylpyridazin-3(2H),-one (1e A mixture of 2-(3,5-dichloro-4-((5-isopropyl-1-methyl-6-oxo-1,6-dihydropyridazin-3-yl)oxy)phenyl)isoindoline-1,3-dione (1d) (700 mg, 1.53 mmol) and butyl-1-amine (335.13 mg, 4.58 mmol) in MeOH (10 mL) was stirred at 70° C. for 1 hour. TLC (petroleum ether:ethyl acetate=1:1, P1:R$_f$=0.6) and LCMS showed the starting material was consumed completely and desired MS was detected. The mixture was concentrated in vacuo to give a residue. The residue was purified by preparative TLC (petroleum ether:ethyl acetate=1:1, P1:R$_f$=0.6) to give 1e (285 mg, 868.39 umol, 56.85% yield) as a white solid. MS mass calculated for [M+1]$^+$ (C$_{14}$H$_{15}$Cl$_2$N$_3$O$_2$) requires m/z 328.1, LCMS found m/z 328.2; $^1$H NMR (400 MHz, MeOH-d4) δ 7.22 (s, 1H) 6.70 (s, 1H) 3.52 (s, 3H) 3.17 (dt, J=13.81, 7.13 Hz, 1H) 1.43 (s, 2H) 1.25 (d, J=6.58 Hz, 6H).

6-(2,6-dichloro-4-(4,4,5,5-tetramethyl-1,3,2-dioxaborolan-2-yl)phenoxy)-4-isopropyl-2-methylpyridazin-3(2H)-one (1f To a solution of 6-(4-amino-2,6-dichloro-phenoxy)-4-isopropyl-2-methyl-pyridazin-3-one (1e) (50 mg, 152.35 umol) and 4,4,5,5-tetramethyl-2-(4,4,5,5-tetramethyl-1,3,2-dioxaborolan-2-yl)-1,3,2-dioxaborolane (116.06 mg, 457.05 umol) in CH$_3$CN (3 mL) was added tert-butyl nitrite (23.57 mg, 228.52 umol, 27.18 uL) drop-wise at 20° C. And the mixture was stirred at 20° C. for 2 hours. LCMS and TLC (petroleum ether:ethyl acetate=5:1, R$_f$=0.6) showed the reaction was completed, and desired MS was detected. The mixture was extracted with EtOAc (10 mL) and the organic layer was washed with H$_2$O (5 mL). The organic layer was dried over Na$_2$SO$_4$, filtered and concentrated in vacuo. The residue was purified by Prep-TLC (petroleum ether:ethyl acetate=5:1, R$_f$=0.6) to give 1f (40 mg, crude) as a light yellow solid. MS mass calculated for [M+1]$^+$ (C$_{20}$H$_{25}$BCl$_2$N$_2$O$_4$) requires m/z 439.1, LCMS found m/z 439.0 and 356.9 (MS of boric acid); $^1$H NMR (400 MHz, CDCl$_3$) δ 7.79 (s, 1H), 7.01-7.09 (m, 1H), 3.46-3.55 (m, 2H), 3.18-3.32 (m, 1H,) 1.36 (s, 5H), 1.21-1.29 (m, 12H).

6-(3,5-dichloro-4-((5-isopropyl-1-methyl-6-oxo-1,6-dihydropyridazin-3-yl)oxy)phenyl)-1,2,4-triazine-3,5(2H,4H)-dione (1

To a mixture of 6-[2,6-dichloro-4-(4,4,5,5-tetramethyl-1,3,2-dioxaborolan-2-yl)phenoxy]-4-isopropyl-2-methyl-pyridazin-3-one (if) (40 mg, 91.09 umol) and 6-bromo-2H-1,2,4-triazine-3,5-dione (26.23 mg, 136.63 umol) in dioxane (3 mL) and H$_2$O (1.5 mL) was added K$_2$CO$_3$ (25.18 mg, 182.17 umol). Then Pd(dppf)Cl$_2$ (6.66 mg, 9.11 umol) was added to the mixture under N$_2$. Then the mixture was stirred at 80° C. under N$_2$ for 2 hours. LCMS and TLC (petroleum ether:ethyl acetate=0:1, R$_f$=0.6) showed the reaction was completed, and desired MS was detected. The mixture was concentrated in vacuo, and the residue was extracted with EtOAc (10 mL) and H$_2$O (5 mL). The organic layer was dried over Na$_2$SO$_4$, filtered and concentrated in vacuo. The residue was purified by Prep-HPLC (column: Luna C18 100*30 5 u; mobile phase: [water (0.1% TFA)-ACN]; B %: 36-66%, 10 min) to give 1 (4.5 mg, 10.52 umol, 11.55% yield). MS mass calculated for [M+1]$^+$ (C$_{20}$H$_{25}$BCl$_2$N$_2$O$_4$) requires m/z 424.1, LCMS found m/z 424.0; $^1$H NMR (400 MHz, MeOH-d4) δ 8.18 (s, 2H), 7.34 (d, J=0.74 Hz, 1H), 3.50 (s, 3H), 3.10-3.25 (m, 1H), 1.28 (d, J=6.8 Hz, 6H).

Example S2: 6-(3,5-dichloro-4-((5-isopropyl-6-oxo-1,6-dihydropyridazin-3-yl)oxy)phenyl)-1,2,4-triazine-3,5(2H,4H)-dione (Compound 2

Scheme 2

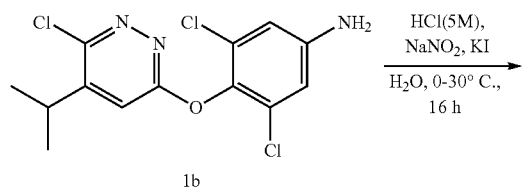

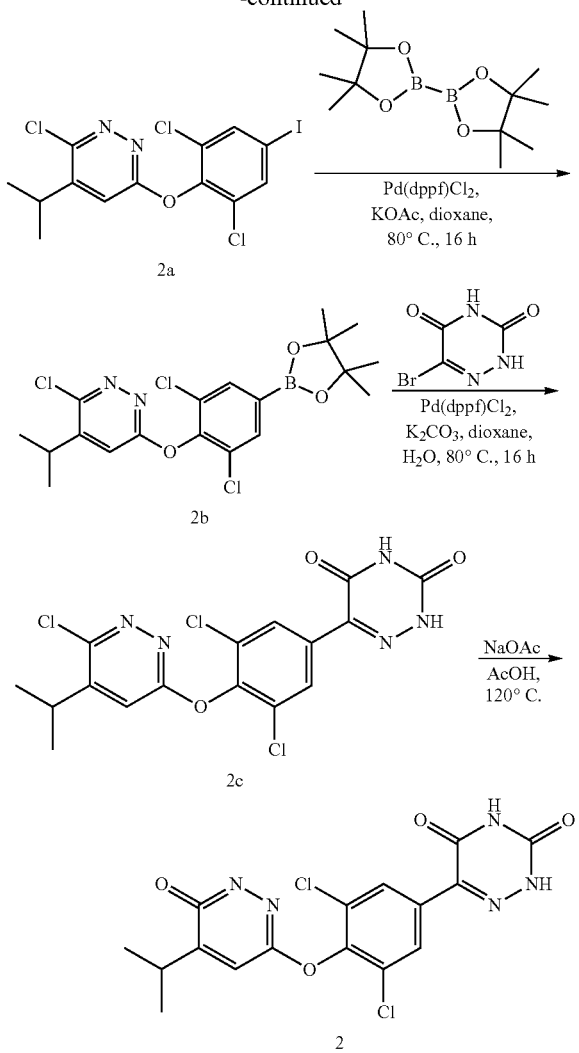

3-chloro-6-(2,6-dichloro-4-iodophenoxy)-4-isopropylpyridazine (2a

To a solution of 3,5-dichloro-4-(6-chloro-5-isopropyl-pyridazin-3-yl)oxy-aniline (1b) (500 mg, 1.50 mmol) in HCl (15.03 mmol, 5 M, 1.79 mL) was added NaNO$_2$ (124.47 mg, 1.80 mmol) at 0° C. Then the mixture was stirred at 0° C. for 0.5 hours. Then a solution of KI (499.08 mg, 3.01 mmol) in H$_2$O (5 mL) was added, and the mixture was stirred at 20° C. for another 16 hours. TLC (petroleum ether:ethyl acetate=3:1, R$_f$=0.6) indicated 1b was consumed completely. The reaction mixture was extracted with EtOAc (10 mL*3). The combined organic layers were washed with brine (5 mL*2), dried over Na$_2$SO$_4$, filtered and concentrated under reduced pressure. The residue was purified by column chromatography (SiO$_2$, petroleum ether:ethyl acetate=10:1 to 1:1) to give 2a (340 mg, 613.31 umol, 40.80% yield) as a light yellow solid.

3-chloro-6-(2,6-dichloro-4-(4,4,5,5-tetramethyl-1,3,2-dioxaborolan-2-yl)phenoxy)-4-isopropylpyridazine (2b To a solution of 3-chloro-6-(2,6-dichloro-4-iodo-phenoxy)-4-isopropyl-pyridazine (2a) (340 mg, 766.64 umol)

and 4,4,5,5-tetramethyl-2-(4,4,5,5-tetramethyl-1,3,2-dioxaborolan-2-yl)-1,3,2-dioxaborolane (584.04 mg, 2.30 mmol) in dioxane (10 mL) was added Pd(dppf)Cl$_2$ (28.05 mg, 38.33 umol) and KOAc (376.19 mg, 3.83 mmol). The mixture was degassed and purged with N$_2$ for 3 times and stirred at 90° C. for 16 hours. TLC (petroleum ether:ethyl acetate=5:1, R$_f$=0.5) indicated 2a was consumed completely. The suspension was filtered through a pad of Celite and the pad cake was washed with EtOAc (10 mL*3). The combined filtrates were concentrated in vacuo. The residue was purified by prep-TLC (SiO$_2$, Petroleum ether:Ethyl acetate=5:1) to give 2b (380 mg, 685.37 umol, 89.40% yield) as a white gum. MS mass calculated for [M+1]+(C$_{19}$H$_{22}$BCl$_3$N$_2$O$_3$) requires m/z 443.1, LCMS found m/z 443.1. $^1$H NMR (400 MHz, CDCl$_3$) δ 7.82-7.80 (m, 2H), 7.22-7.20 (m, 1H), 3.31-3.23 (m, 1H), 1.36-1.36 (m, 3H), 1.36-1.35 (m, 12H), 1.35-1.34 (m, 3H).

6-(3,5-dichloro-4-((6-chloro-5-isopropylpyridazin-3-yl)oxy)phenyl)-1,2,4-triazine-3,5(2H,4H)-dione (2c To a solution of 3-chloro-6-[2,6-dichloro-4-(4,4,5,5-tetramethyl-1,3,2-dioxaborolan-2-yl)phenoxy]-4-isopropyl-pyridazine (2b) (70 mg, 157.81 umol) and 6-bromo-2H-1,2,4-triazine-3,5-dione (45.44 mg, 236.72 umol) in dioxane (4 mL) and H$_2$O (1 mL) was added Pd(dppf)Cl$_2$ (11.55 mg, 15.78 umol) and K$_2$CO$_3$ (65.43 mg, 473.44 umol). The mixture was degassed and purged with N$_2$ 3 times, and then was stirred at 80° C. for 16 hours under N$_2$ atmosphere. TLC (petroleum ether:ethyl acetate=1:1, R$_f$=0.30) showed the reaction was completed. The suspension was filtered through a pad of Celite and the filter cake was washed with EtOAc (5 mL*4). The combined filtrates were concentrated in vacuo, and the residue was purified by prep-TLC (SiO$_2$, petroleum ether:ethyl acetate=1:1) to give 2c (10.5 mg, 22.05 umol, 13.97% yield) as a light yellow solid. MS mass calculated for [M+1]$^+$ (C$_{16}$H$_{12}$C$_{13}$N$_5$O$_3$) requires m/z 428.0, LCMS found m/z 428.1/430.1.

6-(3,5-dichloro-4-((5-isopropyl-6-oxo-1,6-dihydro-pyridazin-3-yl)oxy)phenyl)-1,2,4-triazine-3,5(2H, 4H)-dione (2

To a solution of 6-[3,5-dichloro-4-(6-chloro-5-isopropyl-pyridazin-3-yl)oxy-phenyl]-2H-1,2,4-triazine-3,5-dione (2c) (10 mg, 21.00 umol) in AcOH (2 mL) was added NaOAc (6.89 mg, 83.98 umol). The mixture was stirred at 120° C. for 2 hours. LCMS showed ~10% of 2c was remained and desired MS was detected. The reaction mixture was concentrated under reduced pressure. The residue was purified by Prep-HPLC (column: Luna C18 100*30 5 u; mobile phase: [water (0.2% FA)-ACN]; B %: 25-50%, 12 min) to give 2 (2.56 mg, 6.24 umol, 29.72% yield). MS mass calculated for [M+1]$^+$ (C$_{16}$H$_{13}$Cl$_2$N$_5$O$_4$) requires m/z 410.0, LCMS found m/z 410.1/412.1. $^1$H NMR (400 MHz, CDCl$_3$) δ 8.15 (s, 2H), 7.34 (s, 1H), 3.12-3.18 (m, 1H), 1.27-1.29 (d, J=8.0 Hz, 6H).

Example S3: 6-(3,5-dichloro-4-((5-isopropyl-6-oxo-1,6-dihydropyridazin-3-yl)oxy)phenyl)-2-methyl-1, 2,4-triazine-3,5(2H,4H)-dione (Compound 3

Scheme 3a

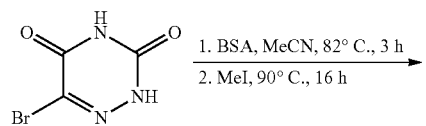

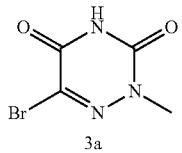

6-bromo-2-methyl-1,2,4-triazine-3,5(2H,4H)-dione (3a

To a solution of 6-bromo-2H-1,2,4-triazine-3,5-dione (200 mg, 1.04 mmol) in MeCN (5 mL) was added BSA (529.85 mg, 2.60 mmol). The mixture was heated at 82° C. for 3 hours. Then MeI (221.81 mg, 1.56 mmol) was added to the mixture, and the resulting mixture was stirred at 90° C. for another 16 hours. TLC (petroleum ether:ethyl acetate=1:1, product R$_f$=0.5) indicated starting material was consumed completely. The reaction mixture was extracted with EtOAc (10 mL*3). The combined organic layers were filtered and concentrated under reduced pressure. The residue was purified by prep-TLC (SiO$_2$, petroleum ether:ethyl acetate=1:1, according TLC) to give 3a (170 mg, 660.20 umol, 63.37% yield) as a white solid. $^1$H NMR (400 MHz, DMSO-d6) δ 12.53-12.45 (m, 1H), 3.43 (s, 3H).

Scheme 3b

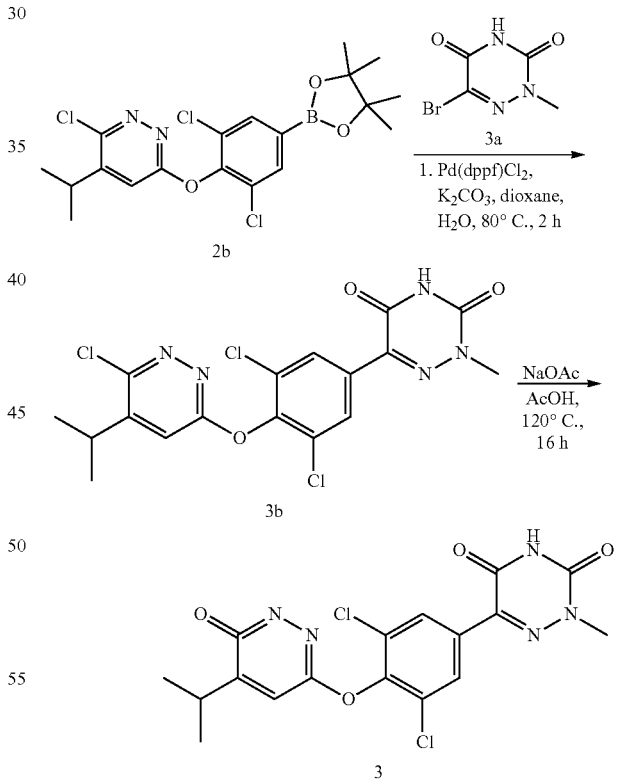

6-(3,5-dichloro-4-((6-chloro-5-isopropylpyridazin-3-yl)oxy)phenyl)-2-methyl-1,2,4-triazine-3,5(2H,4H)-dione (3b To a solution of 6-bromo-2-methyl-1,2,4-triazine-3,5(2H, 4H)-dione (3a) (50 mg, 112.72 umol) and 3-chloro-6-(2,6- dichloro-4-(4,4,5,5-tetramethyl-1,3,2-dioxaborolan-2-yl)phenoxy)-4-isopropylpyridazine (2b) (69.66 mg, 338.17 umol) in dioxane (4 mL) was added Pd(dppf)Cl$_2$ (8.25 mg, 11.27 umol) and K$_2$CO$_3$ (46.74 mg, 338.17 umol) in H$_2$O (1 mL). The mixture was stirred at 80° C. for 2 hours. TLC (petroleum ether:ethyl acetate=5:1, R$_f$=0.4) indicated 2b was consumed completely. The suspension was filtered through a pad of Celite and the filter cake was washed with EtOAc (10 mL*3). The combined filtrates were concentrated to dryness to give a residue. The residue was purified by prep-TLC (SiO$_2$, petroleum ether:ethyl acetate=5:1, according TLC) to give 3b (21 mg, 37.95 umol, 33.67% yield) as a white solid. MS mass calculated for [M+1]+ (C$_{17}$H$_{14}$Cl$_3$N$_5$O$_3$) requires m/z 442.0, LCMS found m/z 444.0.

6-(3,5-dichloro-4-((5-isopropyl-6-oxo-1,6-dihydropyridazin-3-yl)oxy)phenyl)-2-methyl-1,2,4-triazine-3,5(2H,4H)-dione (3

To a solution of 6-(3,5-dichloro-4-((6-chloro-5-isopropylpyridazin-3-yl)oxy)phenyl)-2-methyl-1,2,4-triazine-3,5(2H,4H)-dione (3b) (17 mg, 38.40 umol) in HOAc (5 mL) was added NaOAc (15.75 mg, 192.01 umol). The mixture was stirred at 120° C. for 16 hours. LCMS showed 3b was consumed completely and one main peak with desired MS was detected. The reaction mixture was concentrated under reduced pressure to give the crude residue. The residue was purified by prep-HPLC (column: Luna C18 100*30 5 u; mobile phase: [water (0.225% FA)-ACN]; B %: 30-70%, 15 min) to give 3 (2.57 mg, 5.82 umol, 15.14% yield). MS mass calculated for [M+1]+(C$_{17}$H$_{15}$Cl$_2$N$_5$O$_4$) requires m/z 424.1, LCMS found m/z 424.0. $^1$H NMR (400 MHz, CDCl$_3$) δ 8.21-8.16 (m, 2H), 7.37-7.34 (m, 1H), 3.69-3.66 (m, 3H), 3.21-3.13 (m, 1H), 1.31-1.27 (m, 6H).

Example S4: 6-(3,5-dichloro-4-((5-isopropyl-6-oxo-1,6-dihydropyridazin-3-yl)oxy)phenyl)-2-isopropyl-1,2,4-triazine-3,5(2H,4H)-dione (Compound 4

Scheme 4a

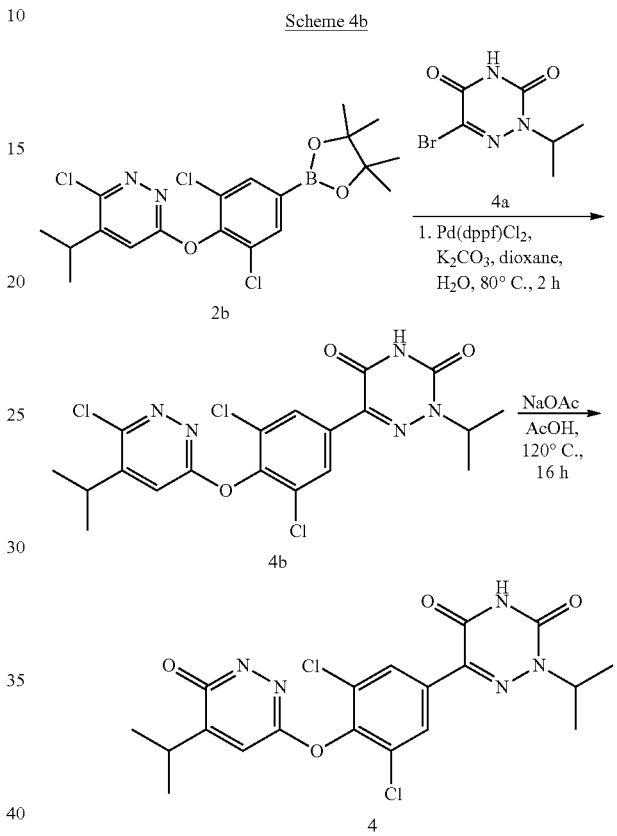

6-bromo-2-isopropyl-1,2,4-triazine-3,5(2H,4H)-dione (4a

To a solution of 6-bromo-2H-1,2,4-triazine-3,5-dione (150 mg, 781.37 umol) in ACN (6 mL) was added BSA (397.38 mg, 1.95 mmol). The mixture was heated at 82° C. for 3 hours, and then 2-iodopropane (199.24 mg, 1.17 mmol) was added in the mixture. The resulting mixture was stirred at 82° C. for another 16 hours. TLC (ethyl acetate:petroleum ether=2:1, R$_f$=0.6) showed starting material was consumed completely. The reaction mixture was concentrated under reduced pressure to give a residue. The residue was purified by prep-TLC (SiO$_2$, ethyl acetate:petroleum ether=1:1, according TLC) to give 4a (155 mg, 629.14 umol, 80.52% yield) as a white solid. $^1$H NMR (400 MHz, DMSO-d6) δ 12.50-12.28 (m, 1H), 4.76-4.67 (m, 1H), 1.23-1.20 (m, 6H).

Scheme 4b

6-(3,5-dichloro-4-((6-chloro-5-isopropylpyridazin-3-yl)oxy)phenyl)-2-isopropyl-1,2,4-triazine-3,5(2H,4H)-dione (4b To a solution of 3-chloro-6-(2,6-dichloro-4-(4,4,5,5-tetramethyl-1,3,2-dioxaborolan-2-yl)phenoxy)-4-isopropylpyridazine (2b) (100 mg, 225.45 umol) and 6-bromo-2-isopropyl-1,2,4-triazine-3,5(2H,4H)-dione (4a) (105.53 mg, 450.90 umol) in dioxane (4 mL) was added Pd(dppf)Cl$_2$ (16.50 mg, 22.54 umol) and K$_2$CO$_3$ (93.48 mg, 676.35 umol) in H$_2$O (1 mL). The mixture was stirred at 80° C. for 2 hours. TLC (petroleum ether:ethyl acetate=1:1, R$_f$=0.3) and LCMS showed 2b was consumed completely and the desired mass was detected. The suspension was filtered through a pad of Celite and the filter cake was washed with EtOAc (10 mL*3). The combined filtrates were concentrated to dryness to give a residue. The residue was purified by prep-TLC (SiO$_2$, petroleum ether:ethyl acetate=1:1, according TLC) to give 4b (50 mg, 84.97 umol, 37.69% yield) as a white solid. MS mass calculated for [M+1]+ (C$_{19}$H$_{18}$Cl$_3$N$_5$O$_3$) requires m/z 470.0, LCMS found m/z 470.1.

6-(3,5-dichloro-4-((5-isopropyl-6-oxo-1,6-dihydro-pyridazin-3-yl)oxy)phenyl)-2-isopropyl-1,2,4-triazine-3,5(2H,4H)-dione (4

To a solution of 6-(3,5-dichloro-4-((6-chloro-5-isopropylpyridazin-3-yl)oxy)phenyl)-2-isopropyl-1,2,4-triazine-3,5(2H,4H)-dione (4b) (50 mg, 106.22 umol) in HOAc (5 mL) was added NaOAc (43.56 mg, 531.08 umol). The mixture was stirred at 120° C. for 16 hours. LCMS showed 4b was consumed completely and one main peak with desired MS was detected. The reaction mixture was concentrated under reduced pressure to remove AcOH. The residue was purified by prep-HPLC (column: Luna C18 100*30 5 u; mobile phase: [water (0.225% FA)-ACN]; B %: 20-60%, 15 min) to give 4 (9.21 mg, 20.16 umol, 18.98% yield). MS mass calculated for [M+1]+($C_{19}H_{19}Cl_2N_5O_4$) requires m/z 452.1, LCMS found m/z 452.0. $^1$H NMR (400 MHz, MeOH-d4) δ 8.19-8.16 (m, 2H), 7.37-7.34 (m, 1H), 5.01-4.95 (m, 1H), 3.21-3.13 (m, 1H), 1.43-1.40 (m, 6H), 1.30-1.28 (m, 6H).

Example S5: 6-(3,5-dichloro-4-((5-isopropyl-1-methyl-6-oxo-1,6-dihydropyridazin-3-yl)oxy)-2-methylphenyl)-1,2,4-triazine-3,5(2H,4H)-dione (Compound 5

Scheme 5

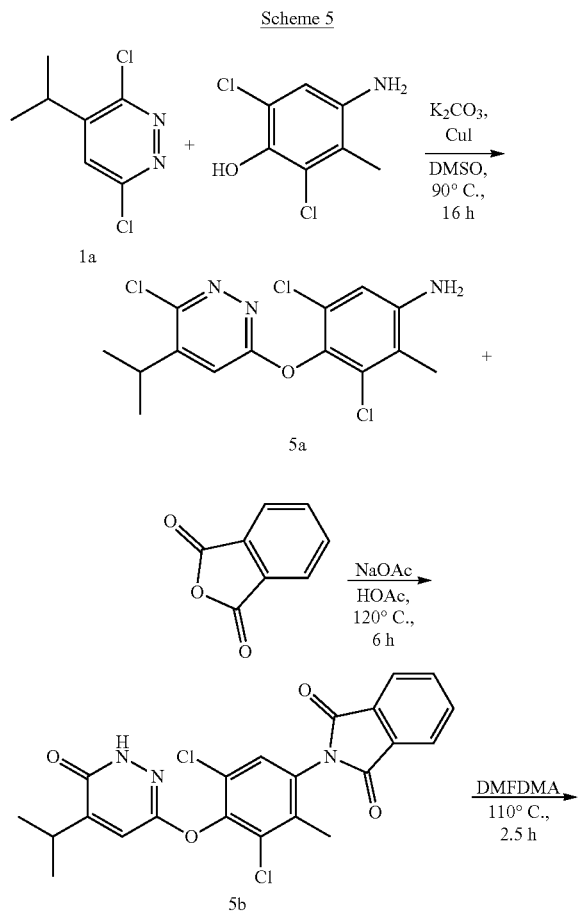

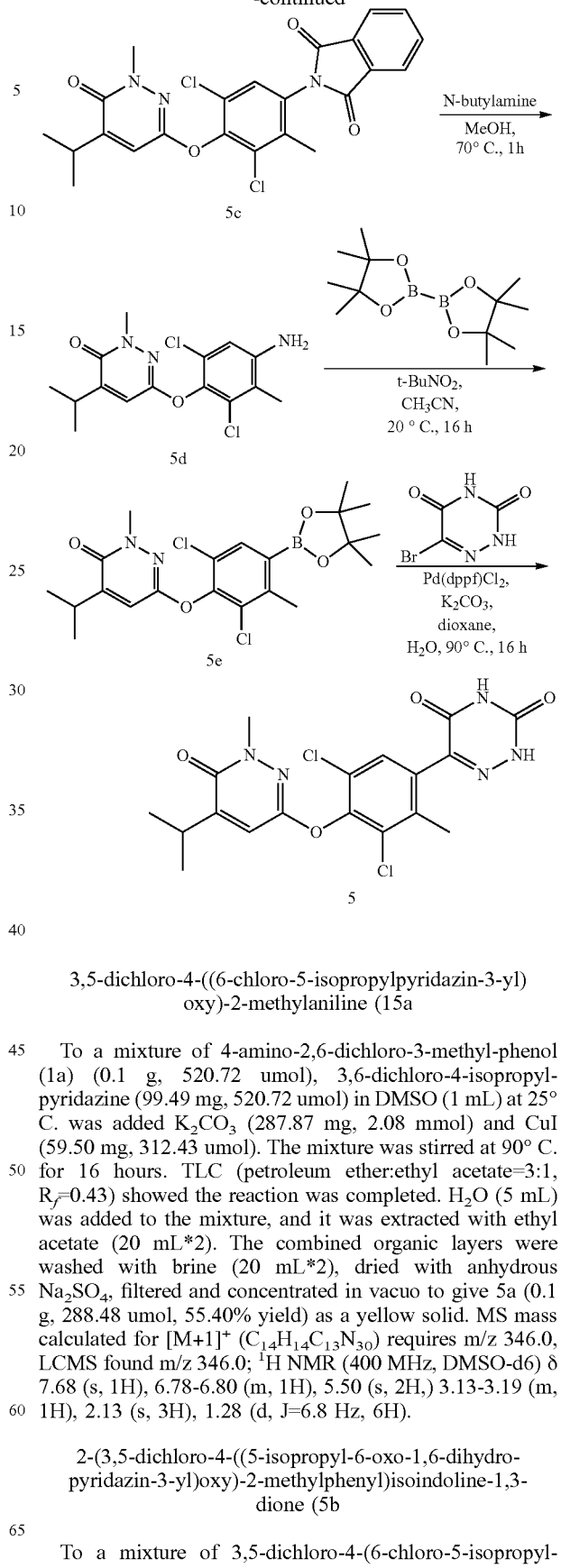

3,5-dichloro-4-((6-chloro-5-isopropylpyridazin-3-yl)oxy)-2-methylaniline (15a To a mixture of 4-amino-2,6-dichloro-3-methyl-phenol (1a) (0.1 g, 520.72 umol), 3,6-dichloro-4-isopropylpyridazine (99.49 mg, 520.72 umol) in DMSO (1 mL) at 25° C. was added $K_2CO_3$ (287.87 mg, 2.08 mmol) and CuI (59.50 mg, 312.43 umol). The mixture was stirred at 90° C. for 16 hours. TLC (petroleum ether:ethyl acetate=3:1, $R_f$=0.43) showed the reaction was completed. $H_2O$ (5 mL) was added to the mixture, and it was extracted with ethyl acetate (20 mL*2). The combined organic layers were washed with brine (20 mL*2), dried with anhydrous $Na_2SO_4$, filtered and concentrated in vacuo to give 5a (0.1 g, 288.48 umol, 55.40% yield) as a yellow solid. MS mass calculated for [M+1]$^+$ ($C_{14}H_{14}Cl_3N_3O$) requires m/z 346.0, LCMS found m/z 346.0; $^1$H NMR (400 MHz, DMSO-d6) δ 7.68 (s, 1H), 6.78-6.80 (m, 1H), 5.50 (s, 2H,) 3.13-3.19 (m, 1H), 2.13 (s, 3H), 1.28 (d, J=6.8 Hz, 6H).

2-(3,5-dichloro-4-((5-isopropyl-6-oxo-1,6-dihydropyridazin-3-yl)oxy)-2-methylphenyl)isoindoline-1,3-dione (5b To a mixture of 3,5-dichloro-4-(6-chloro-5-isopropyl-pyridazin-3-yl)oxy-2-methyl-aniline (5a) (0.1 g, 288.48 umol) and isobenzofuran-1,3-dione (42.73 mg, 288.48 umol) in AcOH (3 mL) was added NaOAc (94.66 mg, 1.15 mmol) at 25° C., the mixture was stirred at 120° C. for 6 hours. LCMS showed the reaction was completed. The mixture was concentrated to get residue. To the residue was added H$_2$O (10 mL) and extracted with ethyl acetate (20 mL*2). The combined organic layers were washed with brine (20 mL*2), dried with anhydrous Na$_2$SO$_4$, filtered and concentrated in vacuo. The residue was diluted with MTBE (5 mL) and filtered. The filter cake was dried in vacuo to give 5b (0.05 g, 109.10 umol, 37.82% yield) as yellow solid. MS mass calculated for [M+1]$^+$ (C$_{22}$H$_{17}$Cl$_2$N$_3$O$_4$) requires m/z 458.1, LCMS found m/z 458.0; $^1$H NMR (400 MHz, CDCl$_3$) δ 9.91 (br s, 1H), 8.00 (dd, J=5.5, 3.0 Hz, 2H), 7.85 (dd, J=5.5, 3.0 Hz, 2H), 7.30 (s, 1H), 7.16 (s, 1H), 3.23-3.29 (m, 1H), 3.22 (s, 1H), 2.25 (s, 3H), 1.30 (d, J=6.85 Hz, 6H).

2-(3,5-dichloro-4-((5-isopropyl-1-methyl-6-oxo-1,6-dihydropyridazin-3-yl)oxy)-2-methylphenyl)isoindoline-1,3-dione (5c A mixture of 2-[3,5-dichloro-4-[(5-isopropyl-6-oxo-1H-pyridazin-3-yl)oxy]-2-methyl-phenyl]isoindoline-1,3-dione (5b) (0.37 g, 807.34 umol) in DMF-DMA (5 mL) was stirred at 105° C. for 4 hours. LCMS showed the reaction was completed. H$_2$O (20 mL) was added to the mixture and it was extracted with ethyl acetate (20 mL*2). The combined organic layers were washed with brine (20 mL*2), dried with anhydrous Na$_2$SO$_4$, filtered and concentrated in vacuo to give 5c as yellow solid. The crude was used in the next step directly. MS mass calculated for [M+1]$^+$ (C$_{23}$H$_{19}$Cl$_2$N$_3$O$_4$) requires m/z 472.1, LCMS found m/z 472.1.

6-(4-amino-2,6-dichloro-3-methylphenoxy)-4-isopropyl-2-methylpyridazin-3(2H)-one (5d To a solution of 2-[3,5-dichloro-4-(5-isopropyl-1-methyl-6-oxo-pyridazin-3-yl)oxy-2-methyl-phenyl]isoindoline-1,3-dione (5c) (440 mg, 931.57 umol) in MeOH (1 mL) was added butyl-1-amine (2 M, 1.40 mL) at 70° C. The mixture was stirred at 70° C. for 1 h. TLC (petroleum ether:ethyl acetate=1:1, R$_f$=0.6) and LCMS showed the starting material was consumed completely and desired MS was detected. The mixture was concentrated in vacuo. The residue was purified by prep-TLC (SiO$_2$, petroleum ether/ethyl acetate=1:1) to give 5d as a white solid. MS mass calculated for [M+1]$^+$ (C$_{15}$H$_{17}$Cl$_2$N$_3$O$_2$) requires m/z 341.1, LCMS found m/z 342.1; $^1$H NMR (400 MHz, MeOH-d4) δ 7.22 (s, 1H), 6.77 (s, 1H), 3.50 (s, 3H), 3.17 (td, J=6.8, 13.8 Hz, 1H), 2.20 (s, 3H), 1.26 (d, J=6.6 Hz, 6H).

6-(2,6-dichloro-3-methyl-4-(4,4,5,5-tetramethyl-1,3,2-dioxaborolan-2-yl)phenoxy)-4-isopropyl-2-methylpyridazin-3(2H)-one (5e To a mixture of 6-(4-amino-2,6-dichloro-3-methylphenoxy)-4-isopropyl-2-methylpyridazin-3(2H)-one (5d) (20 mg, 58.44 umol) and 4,4,5,5-tetramethyl-2-(4,4,5,5-tetramethyl-1,3,2-dioxaborolan-2-yl)-1,3,2-dioxaborolane (742.03 mg, 2.92 mmol) in CH$_3$CN (8 mL) was added t-BuONO (12.05 mg, 116.88 umol, 13.90 uL) at 20° C. Then the mixture was stirred at 20° C. for 16 hours. TLC (petroleum ether:ethyl acetate=5:1, R$_f$=0.4) and LCMS showed the starting material was consumed completely and the desired MS was found. The mixture was concentrated in vacuo. The residue was purified by prep-TLC (SiO$_2$, petroleum ether:ethyl acetate=5:1, P1:R$_f$=0.4) to give 5e (25 mg, crude) as a white solid. MS mass calculated for [M+1]$^+$ (C$_{21}$H$_{27}$BCl$_2$N$_2$O$_4$) requires m/z 453.2, LCMS found m/z 453.0; $^1$H NMR (400 MHz, CDCl$_3$) δ 7.76 (s, 1H), 7.04 (s, 1H), 3.58-3.63 (m, 3H), 3.49-3.51 (m, 5H), 3.24 (s, 1H), 2.62 (s, 3H), 1.21-1.30 (m, 6H).

6-(3,5-dichloro-4-((5-isopropyl-1-methyl-6-oxo-1,6-dihydropyridazin-3-yl)oxy)-2-methylphenyl)-1,2,4-triazine-3,5(2H,4H)-dione (5

To a mixture of 6-(2,6-dichloro-3-methyl-4-(4,4,5,5-tetramethyl-1,3,2-dioxaborolan-2-yl)phenoxy)-4-isopropyl-2-methylpyridazin-3 (2H)-one (5e) (25 mg, 55.17 umol) and 6-bromo-2H-1,2,4-triazine-3,5-dione (10.59 mg, 55.17 umol) in dioxane (2 mL) and H$_2$O (0.5 mL) was added K$_2$CO$_3$ (22.87 mg, 165.50 umol) and Pd(dppf)Cl$_2$ (4.04 mg, 5.52 umol). The mixture was degassed and purged with N$_2$ for 3 times, and then it was stirred at 90° C. for 16 hours under N$_2$ atmosphere. HPLC and LCMS showed the starting material was consumed completely and desired MS was detected. The reaction mixture was concentrated in vacuo to give a residue. The residue was purified by Prep-HPLC (column: Luna C18 100*30 5 u; mobile phase: [water(0.1% TFA)-ACN]; B %: 25-60%, 12 min) to give the desired compound (20 mg, 40.77 umol, 73.89% yield, 89.33% purity). Then the product was re-purified by Prep-HPLC (column: HUAPU C8 Extreme BDS 150*30 5 u; mobile phase: [water(10 mM NH$_4$HCO$_3$)-ACN]; B %: 20%-50%, 10 min) to give 5 (0.26 mg, 2.60% yield). MS mass calculated for [M+1]$^+$ (C$_{18}$H$_{17}$Cl$_2$N$_5$O$_4$) requires m/z 438.3, LCMS found m/z 438.0; $^1$H NMR (400 MHz, DMSO-d6) δ 7.57 (s, 1H), 7.46 (s, 1H), 3.39 (br s, 3H), 3.08 (s, 1H), 2.25 (s, 3H), 1.19 (d, J=7.0 Hz, 6H).

Example S6: 6-(3,5-dichloro-4-((5-cyclopropyl-6-oxo-1,6-dihydropyridazin-3-yl)oxy)phenyl)-1,2,4-triazine-3,5(2H,4H)-dione (Compound 6

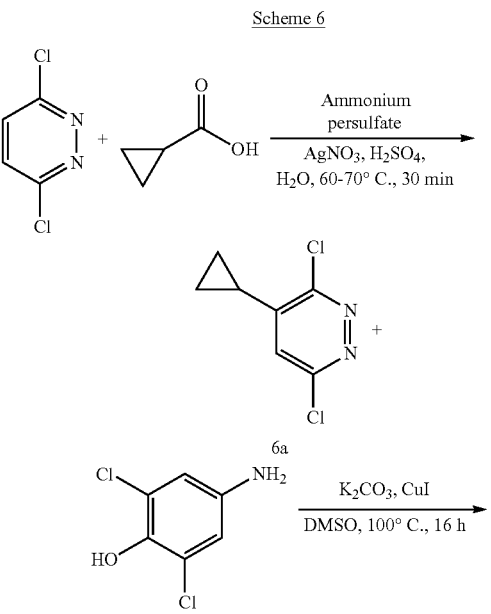

Scheme 6

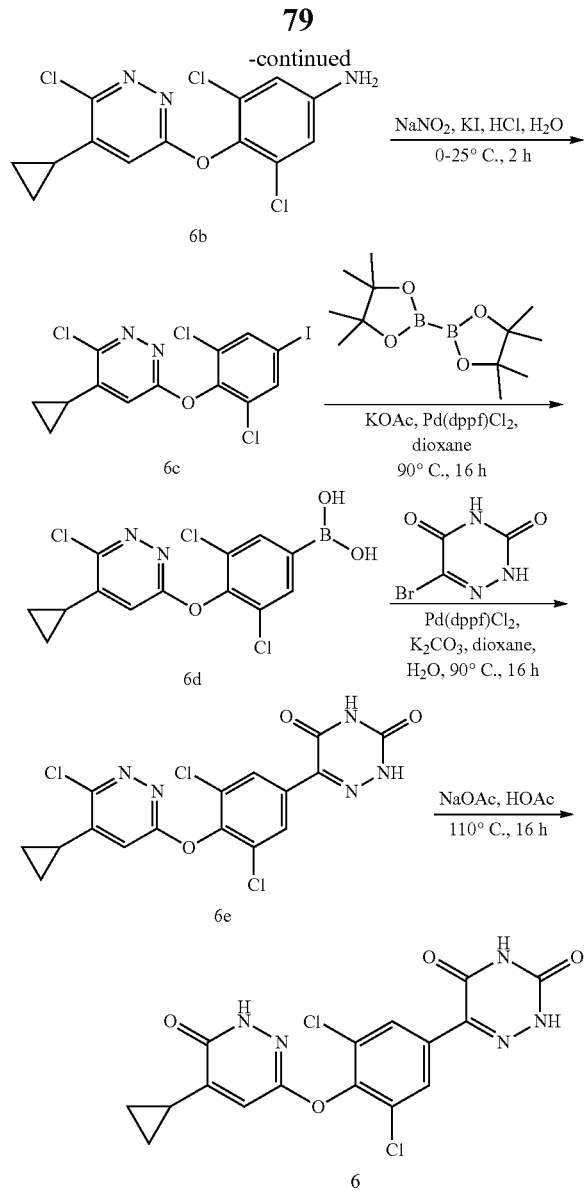

3,6-dichloro-4-cyclopropylpyridazine (6a)

H$_2$SO$_4$ (1.98 g, 20.14 mmol, 1.07 mL) was added to a solution of 3,6-dichloropyridazine (1 g, 6.71 mmol), cyclopropanecarboxylic acid (577.86 mg, 6.71 mmol, 530.15 uL) and AgNO$_3$ (1.14 g, 6.71 mmol) in H$_2$O (20 mL) at 60° C., then ammonium persulfate (4.60 g, 20.14 mmol, 4.38 mL) in H$_2$O (10 mL) was added to the mixture at 70° C., the resulting mixture was stirred at 70° C. for 30 min. TLC (petroleum ether:ethyl acetate=5:1, R$_f$=0.5) showed the reaction was completed, the mixture was extracted with ethyl acetate (20 mL*2), the combined organic layers were washed with brine (20 mL), dried over Na$_2$SO$_4$, filtered and concentrated. The residue was purified by MPLC (SiO$_2$, petroleum ether:ethyl acetate=5:1) to give 6a (0.64 g, 3.39 mmol, 50.44% yield) as colorless oil. MS mass calculated for [M+1]+(C$_7$H$_6$Cl$_2$N$_2$) requires m/z 189.0, LCMS found m/z 189.1; $^1$H NMR (400 MHz, CDCl$_3$) δ 6.94 (s, 1H), 2.22 (tt, J=5.0, 8.4 Hz, 1H), 1.37-1.28 (m, 2H), 0.93-0.83 (m, 2H).

3,5-dichloro-4-((6-chloro-5-cyclopropylpyridazin-3-yl)oxy)aniline (6b 3,6-dichloro-4-cyclopropylpyridazine (6a) (0.3 g, 1.59 mmol), 4-amino-2,6-dichlorophenol (282.50 mg, 1.59 mmol), K$_2$CO$_3$ (328.99 mg, 2.38 mmol) and CuI (60.45 mg, 317.39 umol) in DMA (5 mL) was de-gassed and then heated to 100° C. for 16 hours under N$_2$. LCMS showed desired MS, TLC (petroleum ether:ethyl acetate=3:1, R$_f$=0.33) showed one new spot. The mixture was filtered; the filtrate was extracted with water (20 mL) and ethyl acetate (15 mL*2). The combined organic layers were washed with brine (20 mL), dried over Na$_2$SO$_4$, filtered and concentrated, the residue was purified by Prep-TLC (petroleum ether:ethyl acetate=5:1) to give 6b (0.3 g, 907.45 umol, 57.18% yield) as a yellow solid. MS mass calculated for [M+1]+ (C$_{13}$H$_{10}$C$_{13}$N$_{30}$) requires m/z 330.0, LCMS found m/z 330.1; $^1$H NMR (400 MHz, DMSO-d6) δ 7.34 (s, 1H), 6.70 (s, 2H), 5.67 (s, 2H), 2.17-2.11 (m, 1H), 1.23-1.19 (m, 2H), 1.07-1.01 (m, 2H).

3-chloro-4-cyclopropyl-6-(2,6-dichloro-4-iodophenoxy)pyridazine (6c

To a solution of 3,5-dichloro-4-((6-chloro-5-cyclopropylpyridazin-3-yl)oxy)aniline (6b) (0.1 g, 302.48 umol) in conc. HCl (2 mL) and H$_2$O (2 mL) was added NaNO$_2$ (31.30 mg, 453.72 umol) in portions at 0° C. and stirred for 30 min, then KI (100.43 mg, 604.97 umol) in H$_2$O (1 mL) was added dropwise to the mixture, the resulting mixture was stirred at 25° C. for 1.5 hr to give a brown suspension. LCMS showed desired MS was detected, TLC (petroleum ether:ethyl acetate=5:1, R$_f$=0.59) showed the reaction was completed, the mixture was filtered, the filter cake washed with water (2 mL*2) and dried, the solid was purified by prep-TLC (petroleum ether:ethyl acetate=5:1) to give 6c (0.11 g, 249.16 umol, 82.37% yield) as a yellow solid. MS mass calculated for [M+1]+ (C$_{13}$H$_8$C$_{13}$IN$_2$O) requires m/z 440.9, LCMS found m/z 440.9; $^1$H NMR (400 MHz, CDCl$_3$) δ 7.77-7.69 (m, 2H), 6.78 (s, 1H), 2.25-2.18 (m, 1H), 1.31-1.26 (m, 2H), 0.94-0.89 (m, 2H).

(3,5-dichloro-4-((6-chloro-5-cyclopropylpyridazin-3-yl)oxy)phenyl)boronic acid (6d). 3-chloro-4-cyclopropyl-6-(2,6-dichloro-4-iodophenoxy)pyridazine (6c) (0.11 g, 249.16 umol), 4,4,4',4',5,5,5',5'-octamethyl-2,2'-bi(1,3,2-dioxaborolane) (189.82 mg, 747.49 umol, 3 eq), KOAc (146.72 mg, 1.49 mmol) and Pd(dppf)Cl$_2$ (18.23 mg, 24.92 umol) in dioxane (5 mL) was de-gassed and then heated to 90° C. for 16 hours under N$_2$. LCMS showed desired MS was detected, TLC (petroleum ether:ethyl acetate=3:1, R$_f$=0.35) showed new spot. The mixture was filtered, the filter cake was washed with ethyl acetate (10 mL*2), and the filtrate was concentrated. The residue was purified by prep-TLC (petroleum ether:ethyl acetate=3:1) to give 6d (85 mg, 236.51 umol, 94.92% yield) as white solid. MS mass calculated for [M+1]+ (C$_{13}$H$_{10}$BCl$_3$N$_2$O$_3$) requires m/z 359.0, LCMS found m/z 359.0;

6-(3,5-dichloro-4-((6-chloro-5-cyclopropylpyridazin-3-yl)oxy)phenyl)-1,2,4-triazine-3,5(2H,4H)-dione (6e (3,5-dichloro-4-((6-chloro-5-cyclopropylpyridazin-3-yl)oxy)phenyl)boronic acid (6d) (85 mg, 236.51 umol), 6-bromo-2H-1,2,4-triazine-3,5-dione (59.02 mg, 307.46 umol), Pd(dppf)Cl$_2$ (17.31 mg, 23.65 umol) and K$_2$CO$_3$ (65.37 mg, 473.01 umol) in dioxane (5 mL) and H$_2$O (0.5 mL) was de-gassed and then heated to 90° C. for 16 hours under N₂. LCMS showed desired MS was found, TLC (DCM:MeOH=10:1, R_f=0.42) showed a new spot was formed. The mixture was filtered and the filtrate was concentrated. The residue was purified by prep-TLC (DCM:MeOH=10:1) to give 6e (30 mg, 70.32 umol, 29.73% yield) as a yellow solid. MS mass calculated for [M+1]⁺ (C₁₆H₁₀Cl₃N₅O₃) requires m/z 426.0, LCMS found m/z 426.0; ¹H NMR (400 MHz, MeOH-d4) δ 8.23 (s, 2H), 7.26 (s, 1H), 2.33-2.26 (m, 1H), 1.33-1.30 (m, 2H), 1.08-1.02 (m, 2H).

6-(3,5-dichloro-4-((5-cyclopropyl-6-oxo-1,6-dihydropyridazin-3-yl)oxy)phenyl)-1,2,4-triazine-3,5(2H,4H)-dione (6

A mixture of 6-(3,5-dichloro-4-((6-chloro-5-cyclopropylpyridazin-3-yl)oxy)phenyl)-1,2,4-triazine-3,5 (2H,4H)-dione (6e) (30 mg, 70.32 umol) and NaOAc (28.84 mg, 351.58 umol) in HOAc (3 mL) was heated to 110° C. for 16 hours, LCMS showed the reaction was completed, and desired MS was found. The mixture was concentrated. The residue was purified by prep-HPLC (FA) to give 6 (10.19 mg, 24.96 umol, 35.50% yield). MS mass calculated for [M+1]⁺ (C₁₆H₁₀Cl₃N₅O₃) requires m/z 408.0, LCMS found m/z 408.0; ¹H NMR (400 MHz, DMSO-d6) δ 12.60 (s, 1H), 12.18 (br s, 1H), 8.01 (s, 2H), 7.15 (s, 1H), 2.12 (br s, 1H), 1.06 (br d, J=6.8 Hz, 2H), 0.99 (br s, 2H).

Example S7: 6-(3,5-dichloro-4-(5-isopropyl-1-methyl-6-oxo-1,6-dihydropyridazine-3-carbonyl)phenyl)-1,2,4-triazine-3,5(2H,4H)-dione (Compound 7)

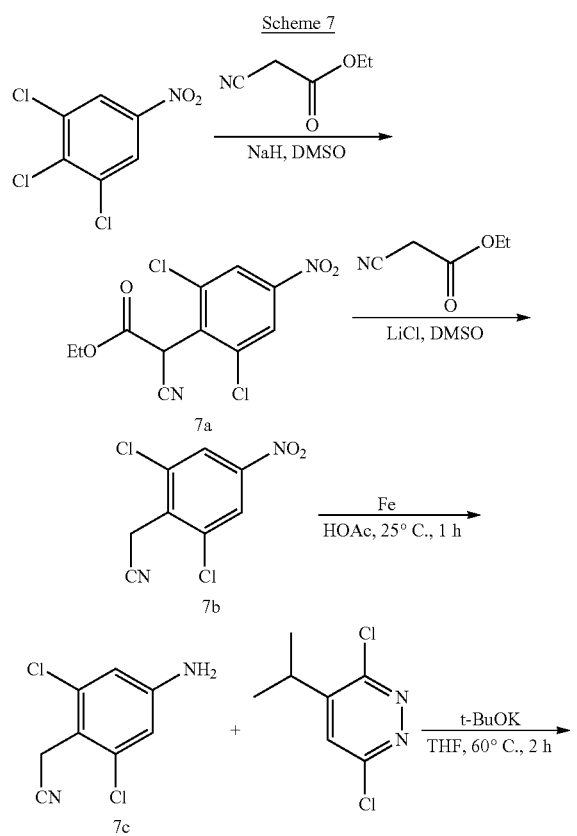

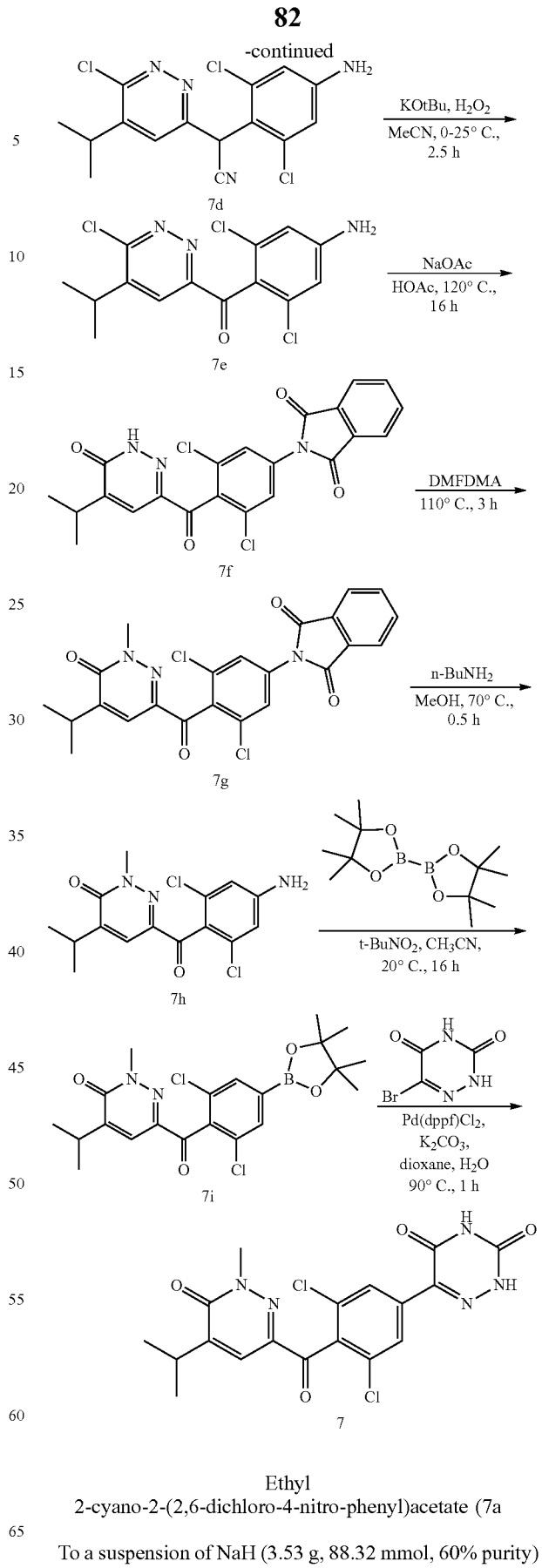

Ethyl 2-cyano-2-(2,6-dichloro-4-nitro-phenyl)acetate (7a

To a suspension of NaH (3.53 g, 88.32 mmol, 60% purity) in DMSO (100 mL) at 0° C. was added ethyl 2-cyanoacetate (9.99 g, 88.32 mmol, 9.42 mL) drop-wise and then the mixture was stirred at 25° C. for 30 min. Then 1,2,3-trichloro-5-nitro-benzene (10 g, 44.16 mmol) was added to the mixture, and the resulting mixture was stirred at 25° C. for 16 hours. TLC (petroleum ether:ethyl acetate=5:1, $R_f$=0.49) showed the reaction was completed. The reaction mixture was quenched by addition of water (100 mL) at 25° C. Then adjusted to pH=1 with HCl (4 M) and the yellow precipitate was collected by suction filtration and dried under vacuum to give 7a (12.5 g, 41.24 mmol, 93.39% yield) as a yellow solid. The product was used directly in the next step without further purification.

2-(2,6-dichloro-4-nitro-phenyl)acetonitrile (7b

A mixture of ethyl 2-cyano-2-(2,6-dichloro-4-nitro-phenyl)acetate (7a) (12.5 g, 41.24 mmol) and LiCl (2.62 g, 61.86 mmol) in DMSO (16 mL) and $H_2O$ (6 mL) was heated to 165° C. for 1 hour. TLC (petroleum ether:ethyl acetate=3:1, $R_f$=0.8) the reaction was completed, and one new spot was formed. The reaction was clean according to TLC. After cooling, the mixture was quenched with water (100 mL*4) and extracted with ethyl acetate (50 mL*4). The combined organic phases were washed with brine (20 mL*2), dried over $Na_2SO_4$, filtered and concentrated in vacuo to give 7b (9.2 g, 39.82 mmol, 96.56% yield) as a brown solid. The product was used directly in the next step without further purification. $^1$H NMR (400 MHz, $CDCl_3$) δ 8.33-8.21 (m, 2H), 4.11-4.07 (m, 3H).

2-(4-amino-2,6-dichloro-phenyl)acetonitrile (7c

To a solution of 2-(2,6-dichloro-4-nitro-phenyl)acetonitrile (7b) (5 g, 21.64 mmol) in HOAc (30 mL) was added iron powder (6.04 g, 108.21 mmol). The mixture was stirred at 25° C. for 1 hour. TLC (petroleum ether:ethyl acetate=3:1, $R_f$=0.4) showed the reaction was completed, and one new spot was formed. The mixture was filtered; the filtrate was extracted with water (100 mL*4) and ethyl acetate (50 mL*4). The combined organic layers were neutralized with sat. $NaHCO_3$ (30 ml*5), washed with brine (30 mL*2), dried over $Na_2SO_4$, filtered and concentrated to give 7c (4.2 g, 20.89 mmol, 96.53% yield) as a brown solid. The product was used in next step without further purification. $^1$H NMR (400 MHz, $CDCl_3$) δ 6.67 (s, 2H), 3.88 (s, 2H).

2-(4-amino-2,6-dichloro-phenyl)-2-(6-chloro-5-isopropyl-pyridazin-3-yl)acetonitrile (7d To a solution of 2-(4-amino-2,6-dichloro-phenyl)acetonitrile (7c) (4.2 g, 20.89 mmol) and 3,6-dichloro-4-isopropyl-pyridazine (3.99 g, 20.89 mmol) in THF (20 mL) was added t-BuOK (1 M in THF, 41.78 mL) by drop-wise at 60° C. The resulting mixture was stirred at this temperature for 2 hours. TLC (petroleum ether:ethyl acetate=2:1, $R_f$=0.49) indicated one new major spot with lower polarity was detected. After cooling the mixture, it was exacted with ethyl acetate (100 mL*3) and the organic layers were washed with brine (50 mL*2). The combined organic layers were dried over $Na_2SO_4$, filtered and concentrated in vacuo. The residue was purified by column chromatography ($SiO_2$, petroleum ether:ethyl acetate=10:1 to 1:1) to give 7d (4 g, 11.25 mmol, 53.84% yield) as an orange solid. $^1$H NMR (400 MHz, $CDCl_3$) δ 7.62-7.56 (m, 1H), 6.68 (s, 2H), 6.32 (s, 1H), 3.35-3.27 (m, 1H), 1.33-1.28 (m, 6H).

(4-amino-2,6-dichloro-phenyl)-(6-chloro-5-isopropyl-pyridazin-3-yl)methanone (7e To a solution of 2-(4-amino-2,6-dichloro-phenyl)-2-(6-chloro-5-isopropyl-pyridazin-3-yl)acetonitrile (7d) (2.2 g, 6.19 mmol) in MeCN (15 mL) was added t-BuOK (1 M in THF, 6.19 mL) at 25° C. The mixture was stirred at this temperature for 0.5 hours, and then it was cooled to 0° C., $H_2O_2$ (1.40 g, 12.37 mmol, 1.19 mL, 30% purity) was added to the mixture by drop-wise at 0° C. The resulting mixture was stirred at 25° C. for 2 hours. TLC (petroleum ether:ethyl acetate=2:1, $R_f$=0.69) showed one new spot was formed. LCMS showed the desired mass was found. The reaction mixture was quenched by the addition of $Na_2SO_3$ (5 mL), and then stirred at 20° C. for 1 hour. Then the mixture was concentrated in vacuo. The residue was extracted with ethyl acetate (20 mL*2). The combined organic layers were washed with brine, dried over $Na_2SO_4$, filtered and concentrated in vacuo. The residue was purified by prep-TLC (petroleum ether:ethyl acetate=2:1) to give 7e (885 mg, 2.57 mmol, 41.51% yield) as a light yellow solid. MS mass calculated for [M+1]+($C_{14}H_{12}Cl_3N_3O$) requires m/z 344.0, LCMS found m/z 344.1. $^1$H NMR (400 MHz, MeOH-d4) δ 8.23-8.21 (m, 1H), 6.69-6.66 (m, 2H), 3.44-3.36 (m, 1H), 1.40-1.36 (m, 6H).

2-[3,5-dichloro-4-(5-isopropyl-6-oxo-1H-pyridazine-3-carbonyl)phenyl]isoindoline-1,3-dione (7f To a solution of (4-amino-2,6-dichloro-phenyl)-(6-chloro-5-isopropyl-pyridazin-3-yl)methanone (7e) (250 mg, 725.43 umol) in HOAc (10 mL) was added NaOAc (297.55 mg, 3.63 mmol) and isobenzofuran-1,3-dione (107.45 mg, 725.43 umol). The mixture was stirred at 120° C. for 16 hours. TLC (petroleum ether:ethyl acetate=2:1, $R_f$=0.31) showed one new spot was formed. LCMS showed the desired mass was detected. The mixture was concentrated in vacuo, and the residue was diluted with $H_2O$ (50 mL) and aqueous $NaHCO_3$ (50 mL). Then the mixture was extracted with ethyl acetate (30 mL*2). The combined organic layers were concentrated in vacuo to give 7f (200 mg, 438.33 umol, 60.42% yield) as a white solid. The crude product was used into the next step without further purification. MS mass calculated for [M+1]+($C_{22}H_{15}Cl_2N_3O_4$) requires m/z 456.0, LCMS found m/z 456.1.

2-[3,5-dichloro-4-(5-isopropyl-1-methyl-6-oxo-pyridazine-3-carbonyl)phenyl]isoindoline-1,3-dione (7g A solution of 2-[3,5-dichloro-4-(5-isopropyl-6-oxo-1H-pyridazine-3-carbonyl)phenyl]isoindoline-1,3-dione (7f) (350 mg, 767.08 umol) in DMF-DMA (10 mL) was stirred at 110° C. for 3 hours. LCMS showed the reaction was completed, and the desired mass was found. The reaction mixture was partitioned between $H_2O$ (50 mL*2) and ethyl acetate (50 mL*2). The organic phase was concentrated in vacuo to give 7 g (300 mg, 637.89 umol, 83.16% yield) as a white solid. The product was used in next step without further purification. MS mass calculated for [M+1]+ ($C_{23}H_{17}Cl_2N_3O_4$) requires m/z 470.1, LCMS found m/z 470.1.

6-(4-amino-2,6-dichloro-benzoyl)-4-isopropyl-2-methyl-pyridazin-3-one (7h

To a solution of 2-[3,5-dichloro-4-(5-isopropyl-1-methyl-6-oxo-pyridazine-3-carbonyl)phenyl]isoindoline-1,3-dione (7 g) (300 mg, 637.89 umol) in MeOH (2 mL) was added N-butylamine (285.58 mg, 1.91 mmol, 307.08 uL). The mixture was stirred at 70° C. for 0.5 hours. TLC (petroleum ether:ethyl acetate=2:1) showed two new spots (R$_f$=0.41, 0.31) was formed. The mixture was concentrated in vacuo. The residue was purified by prep-TLC (Petroleum ether: Ethyl acetate=2:1) to give 7h (122 mg, 358.61 umol, 56.22% yield) as a light yellow solid. $^1$H NMR (400 MHz, CDCl$_3$) δ 7.84 (d, J=1.0 Hz, 1H), 6.65-6.61 (m, 2H), 3.77-3.74 (m, 3H), 3.27-3.18 (m, 1H), 1.27 (d, J=6.8 Hz, 6H).

6-[2,6-dichloro-4-(4,4,5,5-tetramethyl-1,3,2-dioxaborolan-2-yl)benzoyl]-4-isopropyl-2-methyl-pyridazin-3-one (7i To a solution of 6-(4-amino-2,6-dichloro-benzoyl)-4-isopropyl-2-methyl-pyridazin-3-one (7h) (40 mg, 117.58 umol) and 4,4,5,5-tetramethyl-2-(4,4,5,5-tetramethyl-1,3,2-dioxaborolan-2-yl)-1,3,2-dioxaborolane (89.57 mg, 352.73 umol) in MeCN (2 mL) was added t-BuONO (24.25 mg, 235.15 umol, 27.97 uL). The mixture was stirred at 25° C. for 16 hours. LCMS showed the reaction was completed. The reaction mixture was concentrated under reduced pressure to remove MeCN. The residue was purified by prep-TLC (petroleum ether:ethyl acetate=4:1) to give 7i (31 mg, 68.71 umol, 58.44% yield) as a light yellow solid. MS mass calculated for [M+1]$^+$ (C$_{21}$H$_{24}$BCl$_2$N$_2$O$_4$) requires m/z 451.1, LCMS found m/z 451.2. $^1$H NMR (400 MHz, CDCl$_3$) δ 7.86 (d, J=0.6 Hz, 1H), 7.75 (s, 2H), 3.71 (s, 3H), 3.27-3.19 (m, 1H), 1.37 (s, 12H), 1.29-1.27 (m, 6H).

6-[3,5-dichloro-4-(5-isopropyl-1-methyl-6-oxo-pyridazine-3-carbonyl)phenyl]-2H-1,2,4-triazine-3,5-dione (7

A mixture of 7i (30 mg, 66.50 umol, 6-bromo-2H-1,2,4-triazine-3,5-dione (12.77 mg, 66.50 umol) in dioxane (4 mL) and H$_2$O (1 mL) was degassed and purged with N$_2$ 3 times, and then Pd(dppf)Cl$_2$ (4.87 mg, 6.65 umol) and K$_2$CO$_3$ (27.57 mg, 199.49 umol) were added. Then the mixture was stirred at 90° C. for 1 hour under N$_2$ atmosphere. LCMS showed the desired mass was found. The mixture was filtered and the filtrate was concentrated. The residue was purified by prep-HPLC (NH$_4$CO$_3$) to give 7 (7.65 mg, 17.44 umol, 26.23% yield). MS mass calculated for [M+1]$^+$ (C$_{18}$H$_{15}$Cl$_2$N$_5$O$_4$) requires m/z 436.2, LCMS found m/z 436.0. $^1$H NMR (400 MHz, MeOH-d4) δ 8.16 (s, 2H), 7.93-7.91 (m, 1H), 3.72-3.68 (m, 3H), 3.24-3.16 (m, 1H), 1.29 (d, J=6.8 Hz, 6H).

Example S8: 6-(3,5-dichloro-4-(5-isopropyl-6-oxo-1,6-dihydropyridazine-3-carbonyl)phenyl)-1,2,4-triazine-3,5(2H,4H)-dione (Compound 8

Scheme 8

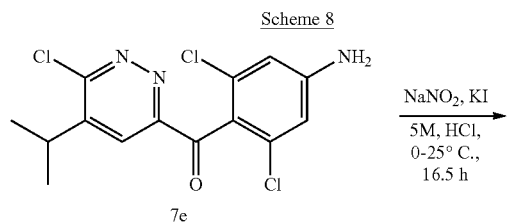

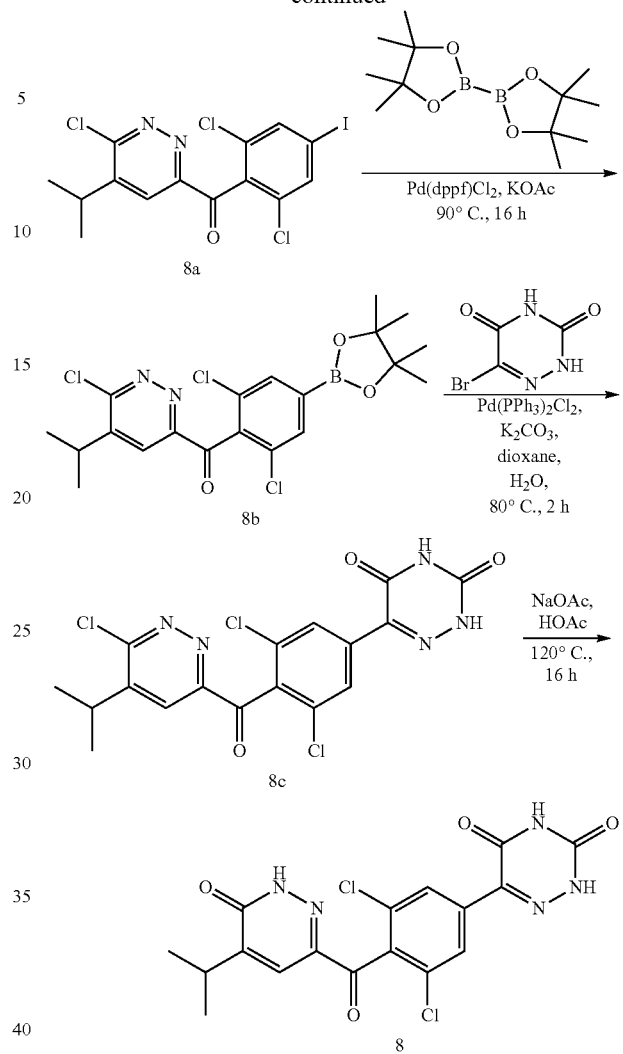

(6-chloro-5-isopropylpyridazin-3-yl)(2,6-dichloro-4-iodophenyl)methanone (8a

To a solution of (4-amino-2,6-dichlorophenyl)(6-chloro-5-isopropylpyridazin-3-yl)methanone (7e) (120 mg, 348.21 umol) in HCl (5 M, 2 mL) was added NaNO$_2$ (28.83 mg, 417.85 umol) at 0° C., the mixture was stirred for 0.5 hours. Then to the mixture was added a solution of KI (115.60 mg, 696.41 umol) in H$_2$O (5 mL), the resulting mixture was stirred at 20° C. for another 16 hours. TLC (petroleum ether:ethyl acetate=5:1, R$_f$=0.6) indicated 7e was consumed completely. The reaction mixture was extracted with EtOAc (10 mL*3). The combined organic layers were washed with brine (10 mL), dried over Na$_2$SO$_4$, filtered and concentrated under reduced pressure. The residue was purified by prep-TLC (SiO$_2$, petroleum ether:ethyl acetate=5:1, according TLC) to give 8a (75 mg, 131.72 umol, 37.83% yield) as a white solid. MS mass calculated for [M+1]+ (C$_{14}$H$_1$C$_{13}$IN$_2$O) requires m/z 454.9, LCMS found m/z 454.9.

(6-chloro-5-isopropylpyridazin-3-yl)(2,6-dichloro-4-(4,4,5,5-tetramethyl-1,3,2-dioxaborolan-2-yl)phenyl)methanone (8b To a solution of (6-chloro-5-isopropylpyridazin-3-yl)(2,6-dichloro-4-iodophenyl)methanone (8a) (100 mg, 219.54 umol) and 4,4,4',4',5,5,5',5'-octamethyl-2,2'-bi(1,3,2-dioxaborolane) (167.25 mg, 658.61 umol) in dioxane (3 mL) was added Pd(dppf)Cl$_2$ (8.03 mg, 10.98 umol) and KOAc (107.73 mg, 1.10 mmol). The mixture was degassed and purged with N$_2$ 3 times and stirred at 90° C. for 16 hours. TLC (petroleum ether:ethyl acetate=5:1, R$_f$=0.5) and LCMS showed 8a was consumed completely and the desired mass was detected. The suspension was filtered through a pad of Celite and the pad cake was washed with EtOAc (10 mL*3). The combined filtrates were concentrated in vacuo. The residue was purified by prep-TLC (SiO$_2$, petroleum ether:ethyl acetate=5:1, according TLC) to give 8b (150 mg, crude) as a white solid. MS mass calculated for [M+1]+ (C$_{20}$H$_{22}$BCl$_3$N$_2$O$_3$) requires m/z 455.1, LCMS found m/z 455.0. $^1$H NMR (400 MHz, CDCl$_3$) δ 8.20-8.18 (m, 1H), 7.79-7.74 (m, 2H), 3.40-3.32 (m, 1H), 1.38-1.34 (m, 18H).

6-(3,5-dichloro-4-(6-chloro-5-isopropylpyridazine-3-carbonyl)phenyl)-1,2,4-triazine-3,5(2H,4H)-dione (8c To a solution of (6-chloro-5-isopropylpyridazin-3-yl)(2,6-dichloro-4-(4,4,5,5-tetramethyl-1,3,2-dioxaborolan-2-yl)phenyl)methanone (8b) (50 mg, 109.75 umol) and 6-bromo-1,2,4-triazine-3,5(2H,4H)-dione (63.21 mg, 329.26 umol) in dioxane (4 mL) was added Pd(dppf)Cl$_2$ (8.03 mg, 10.98 umol) and K$_2$CO$_3$ (45.51 mg, 329.26 umol) in H$_2$O (1 mL). The mixture was stirred at 80° C. for 2 hours. TLC (petroleum ether:ethyl acetate=5:1) and LCMS showed 18b was consumed completely and the desired mass was detected. The suspension was filtered through a pad of Celite and the pad cake was washed with EtOAc (10 ml*3). The combined filtrates were concentrated to dryness to give a residue. The residue was purified by prep-TLC (SiO$_2$, DCM:MeOH=20:1, according TLC) to give 8c (25 mg, 28.37 umol, 25.85% yield) as a white solid. MS mass calculated for [M+1]+ (C$_{17}$H$_{12}$C$_{13}$N$_5$O$_3$) requires m/z 440.0, LCMS found m/z 442.0.

6-(3,5-dichloro-4-(5-isopropyl-6-oxo-1,6-dihydropyridazine-3-carbonyl)phenyl)-1,2,4-triazine-3,5(2H,4H)-dione (8

To a solution of 6-(3,5-dichloro-4-(6-chloro-5-isopropylpyridazine-3-carbonyl)phenyl)-1,2,4-triazine-3,5(2H,4H)-dione (8c) (25 mg, 56.73 umol) in HOAc (3 mL) was added NaOAc (23.27 mg, 283.66 umol). The mixture was stirred at 120° C. for 16 hours. LCMS showed 8c was consumed completely and one major peak with desired MS was detected. The reaction mixture was concentrated under reduced pressure to remove AcOH. The residue was purified by prep-HPLC (column: Nano-Micro UniSil 5-100 C18 ULTRA 100*250 mm 5 um; mobile phase: [water (0.225% FA)-ACN]; B %: 25-65%, 10 min) to give 8 (1.86 mg, 4.19 umol, 7.38% yield). MS mass calculated for [M+1]+ (C$_{17}$H$_{13}$Cl$_2$N$_5$O$_4$) requires m/z 422.0, LCMS found m/z 422.1. $^1$H NMR (400 MHz, MeOH-d4) δ 8.16-8.12 (m, 2H), 7.92-7.90 (m, 1H), 3.21-3.12 (m, 1H), 1.29 (d, J=7.0 Hz, 6H).

Example S9: 6-(3,5-dichloro-4-((5-isopropyl-1-methyl-6-oxo-1,6-dihydropyridazin-3-yl)oxy)phenyl)-2-methyl-1,2,4-triazine-3,5(2H,4H)-dione (Compound 9

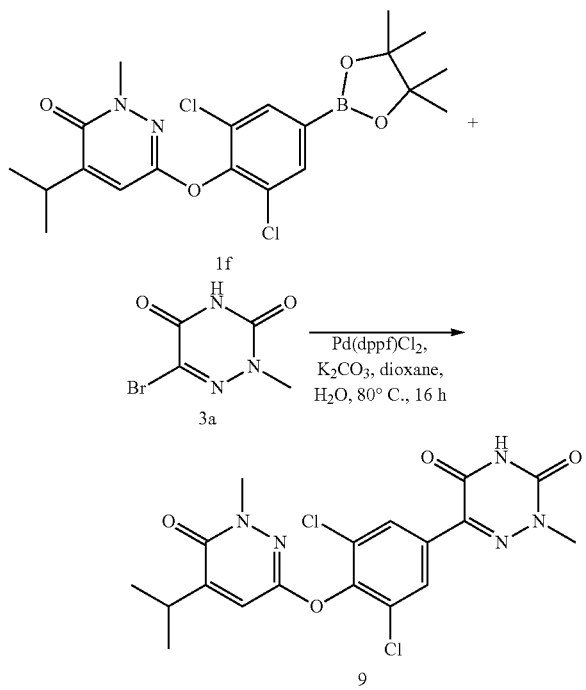

6-(3,5-dichloro-4-((5-isopropyl-1-methyl-6-oxo-1,6-dihydropyridazin-3-yl)oxy)phenyl)-2-methyl-1,2,4-triazine-3,5(2H,4H)-dione (9

To a solution of 6-(2,6-dichloro-4-(4,4,5,5-tetramethyl-1,3,2-dioxaborolan-2-yl)phenoxy)-4-isopropyl-2-methylpyridazin-3 (2H)-one (1f) (30 mg, 68.32 umol) and 6-bromo-2-methyl-1,2,4-triazine-3,5(2H,4H)-dione (3a) (42.22 mg, 204.95 umol) in dioxane (2 mL) was added Pd (dppf) Cl$_2$ (5.00 mg, 6.83 umol) and a solution of K$_2$CO$_3$ (28.33 mg, 204.95 umol) in H$_2$O (0.5 mL). The mixture was stirred at 80° C. for 3 hours. LCMS showed 1f was consumed completely and the desired mass was detected. To the mixture was added palladium scavenger Si-TMT (1g) and stirred at 20° C. for 2 hours. The mixture was filtered and the filtrate was concentrated under reduced pressure. The residue was purified by Prep-HPLC (column: Waters Xbridge 150*25 5 u; mobile phase: [water (10 mM NH$_4$HCO$_3$)-ACN]) to give 9. MS mass calculated for [M+1]+ (C$_{18}$H$_{17}$Cl$_2$N$_5$O$_4$) requires m/z 438.1, LCMS found m/z 438.0. $^1$H NMR (400 MHz, MeOH-d4) δ 8.14-8.24 (m, 2H), 7.32-7.35 (m, 1H), 3.64-3.72 (m, 3H), 3.49 (s, 3H), 3.20 (td, J=7.0, 13.6 Hz, 1H), 1.28 (d, J=6.8 Hz, 6H).

Example S10: 6-(3,5-dichloro-4-((5-cyclopropyl-6-oxo-1,6-dihydropyridazin-3-yl)oxy)phenyl)-2-methyl-1,2,4-triazine-3,5(2H,4H)-dione (Compound 10

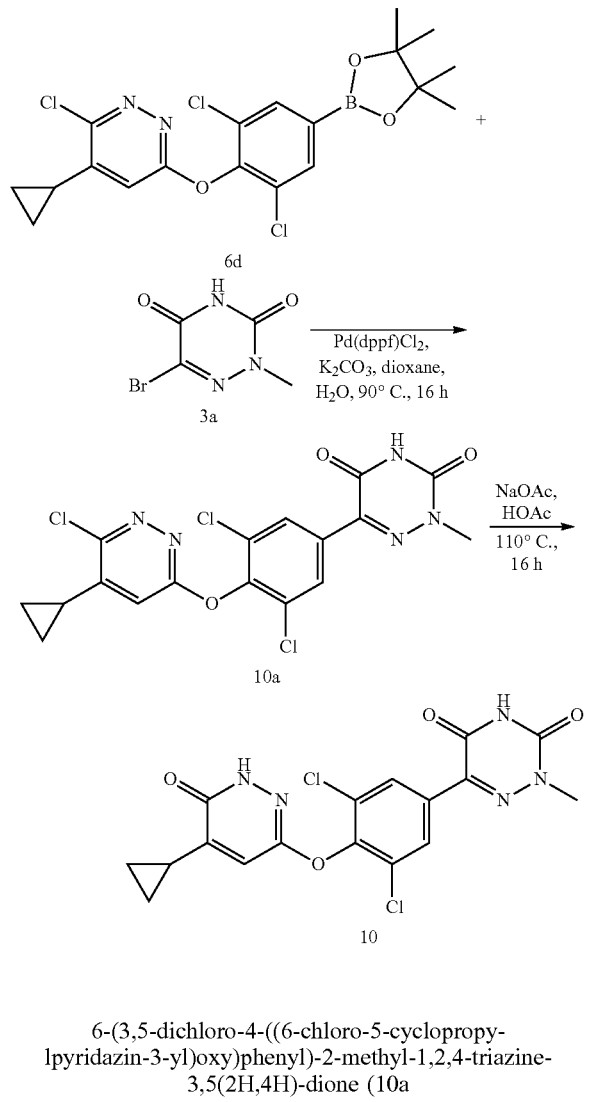

6-(3,5-dichloro-4-((6-chloro-5-cyclopropylpyridazin-3-yl)oxy)phenyl)-2-methyl-1,2,4-triazine-3,5(2H,4H)-dione (10a The mixture of 3-chloro-4-cyclopropyl-6-(2,6-dichloro-4-(4,4,5,5-tetramethyl-1,3,2-dioxaborolan-2-yl)phenoxy)pyridazine (6d) (75 mg, 169.86 umol), 6-bromo-2-methyl-1,2,4-triazine-3,5(2H,4H)-dione (3a) (45.49 mg, 220.82 umol), Pd(dppf)Cl$_2$ (12.43 mg, 16.99 umol) and K$_2$CO$_3$ (46.95 mg, 339.72 umol, 2 eq) in dioxane (5 mL), H$_2$O (0.5 mL) was heated to 90° C. for 16 hours under N$_2$. LCMS showed 6d was consumed completely and the desired MS was detected. The mixture was filtered and the filtrate was concentrated. The residue was purified by Prep-TLC (Ethyl acetate: MeOH) to give 10a. MS mass calculated for [M+1]$^+$ (C$_{17}$H$_{12}$Cl$_3$N$_5$O$_3$) requires m/z 440.0, LCMS found m/z 440.1. $^1$H NMR (400 MHz, DMSO-d6) δ 8.16-8.10 (m, 2H), 7.51 (s, 1H), 3.58 (s, 4H), 1.22-1.20 (m, 1H), 1.23-1.20 (m, 1H), 1.19-1.14 (m, 1H), 1.19-1.14 (m, 1H), 1.11-1.05 (m, 1H), 1.10-1.05 (m, 1H).

6-(3,5-dichloro-4-((5-cyclopropyl-6-oxo-1,6-dihydropyridazin-3-yl)oxy)phenyl)-2-methyl-1,2,4-triazine-3,5(2H,4H)-dione (10

A mixture of 6-(3,5-dichloro-4-((6-chloro-5-cyclopropylpyridazin-3-yl)oxy)phenyl)-2-methyl-1,2,4-triazine-3,5 (2H,4H)-dione (10a) (28 mg, 63.54 umol) and NaOAc (26.06 mg, 317.70 umol) in HOAc (1 mL) was heated to 110° C. for 16 hours. LCMS showed the 10a was consumed completely and desired MS was detected. The mixture was concentrated. The residue was purified by Prep-HPLC (column: Welch Ultimate AQ-C18 150*30 mm*5 um; mobile phase: [water (0.1% TFA)-ACN]) to give 10. MS mass calculated for [M+1]$^+$ (C$_{17}$H$_{13}$Cl$_2$N$_5$O$_4$) requires m/z 422.0, LCMS found m/z 422.0. $^1$H NMR (400 MHz, DMSO-d6) δ 12.43 (s, 1H), 12.17 (s, 1H), 8.07 (s, 2H), 7.16 (s, 1H), 3.57 (s, 3H), 2.19-2.10 (m, 1H), 1.11-1.05 (m, 2H), 1.01 (td, J=2.8, 5.2 Hz, 2H).

Example S11: 6-(3,5-dichloro-4-((5-cyclopropyl-1-methyl-6-oxo-1,6-dihydropyridazin-3-yl)oxy)phenyl)-1,2,4-triazine-3,5(2H,4H)-dione (Compound 11

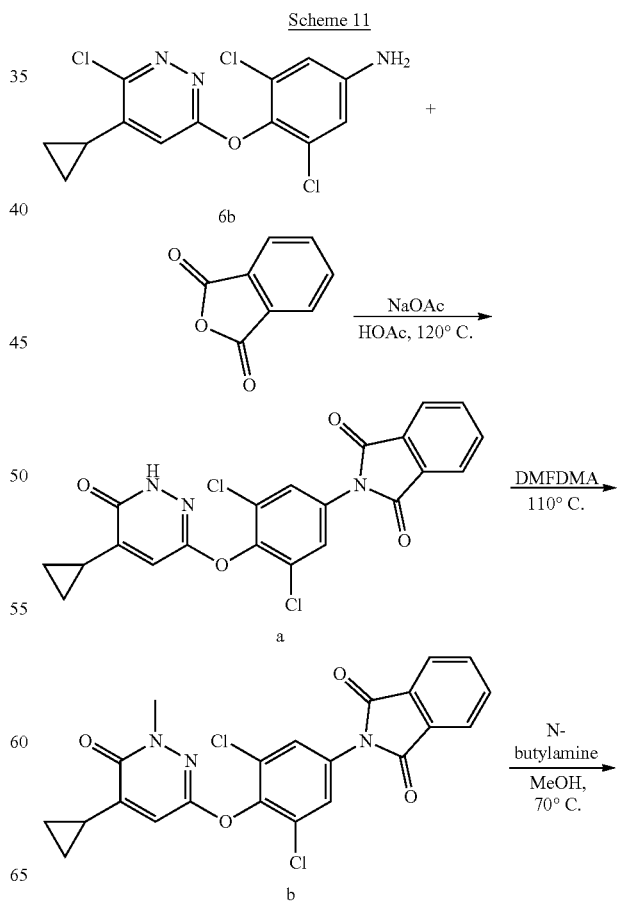

Example S11, with 3A according to the reaction conditions used for the preparation of Compound 7.

Example S13: 6-(3,5-dichloro-4-(5-isopropyl-6-oxo-1,6-dihydropyridazine-3-carbonyl)phenyl)-2-methyl-1,2,4-triazine-3,5(2H,4H)-dione (Compound 13

Scheme 13

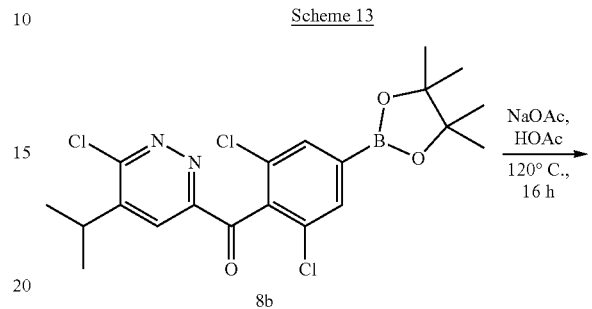

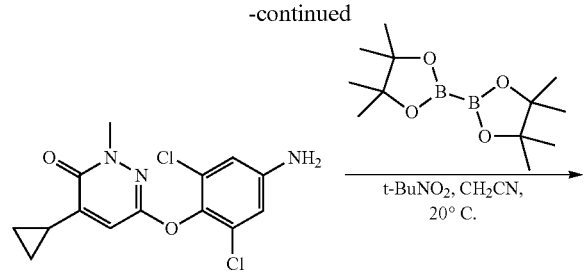

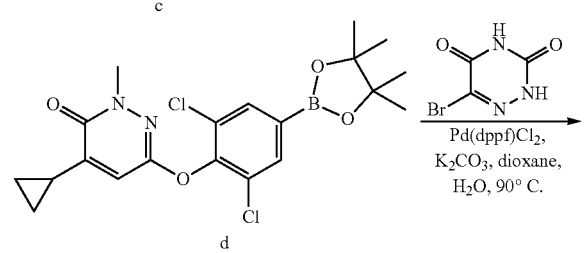

Compound 11 can be prepared using intermediate 6b according to the procedure described for Example S5 by replacing 5a with 6b and following the remaining synthetic sequence.

Example S12: 6-(3,5-dichloro-4-((5-cyclopropyl-1-methyl-6-oxo-1,6-dihydropyridazin-3-yl)oxy)phenyl)-2-methyl-1,2,4-triazine-3,5(2H,4H)-dione (Compound 12

Scheme 12

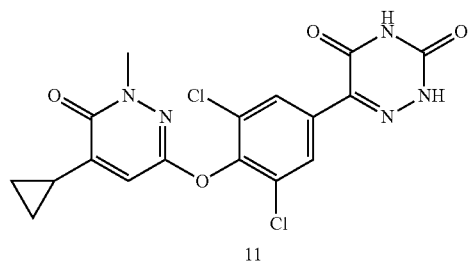 [SMILES: Cn1nc(Oc2c(Cl)cc(-c3n[nH]c(=O)[nH]c3=O)cc2Cl)cc(C2CC2)c1=O]

Compound 12 can be prepared by reaction of the boronic ester derivative d, the synthesis of which is outlined in 6-(2,6-dichloro-4-(4,4,5,5-tetramethyl-1,3,2-dioxaborolan-2-yl)benzoyl)-4-isopropylpyridazin-3(2H)-one (13a To a solution of (6-chloro-5-isopropylpyridazin-3-yl)(2,6-dichloro-4-(4,4,5,5-tetramethyl-1,3,2-dioxaborolan-2-yl)phenyl)methanone (8b) (200 mg, 439.01 umol) in HOAc (10 mL) was added NaOAc (180.07 mg, 2.20 mmol). The mixture was stirred at 120° C. for 16 hours. LCMS showed one major peak with the desired mass was formed. The reaction mixture was concentrated under reduced pressure. The residue was extracted with Ethyl acetate (10 mL*3) and H$_2$O (10 mL). The combined organic layers were washed with NaHCO$_3$ (10 mL), dried over Na$_2$SO$_4$, filtered and concentrated under reduced pressure. The residue was purified by Prep-TLC (SiO$_2$, Petroleum ether:Ethyl acetate) to give 13a. MS mass calculated for [M+1]$^+$ (C$_{20}$H$_{23}$BCl$_2$N$_2$O$_4$) requires m/z 437.1, LCMS found m/z 437.1. $^1$H NMR (400 MHz, CD$_3$OD) δ 7.90 (s, 1H), 7.68-7.70 (m, 1H), 7.43-7.46 (m, 1H), 3.13-3.20 (m, 1H), 1.29-1.30 (m, 6H), 1.20 (s, 12H).

6-(3,5-dichloro-4-(5-isopropyl-6-oxo-1,6-dihydro-pyridazine-3-carbonyl)phenyl)-2-methyl-1,2,4-triazine-3,5(2H,4H)-dione (Compound 13

A mixture of 6-(2,6-dichloro-4-(4,4,5,5-tetramethyl-1,3,2-dioxaborolan-2-yl)benzoyl)-4-isopropylpyridazin-3(2H)-one (13a) (60 mg, 137.26 umol), 6-bromo-2-methyl-1,2,4-triazine-3,5(2H,4H)-dione (3a) (28.28 mg, 137.26 umol), Pd(dppf)Cl$_2$ (10.04 mg, 13.73 umol), and K$_2$CO$_3$ (56.91 mg, 411.78 umol) in dioxane (4 mL) and H$_2$O (1 mL) was degassed and purged with N$_2$ for 3 times, and then the mixture was stirred at 90° C. for 16 hours under N$_2$ atmosphere. LCMS showed one major peak with the desired mass was formed. The reaction mixture was concentrated under reduced pressure. The residue was purified by Prep-HPLC (column: Welch Ultimate AQ-C18 150*30 mm*5 um; mobile phase: [water (0.225% FA)-ACN]) to give 13. MS mass calculated for [M+1]$^+$ (C$_{18}$H$_{15}$Cl$_2$N$_5$O$_4$) requires m/z 436.1, LCMS found m/z 436.0. $^1$H NMR (400 MHz, CD$_3$OD) δ 8.14-8.17 (m, 2H), 7.90-7.93 (m, 1H), 3.67-3.70 (m, 3H), 3.35 (s, 3H), 3.13-3.21 (m, 1H), 1.30 (d, J=6.8 Hz, 6H).

Example 14: 6-(3,5-dichloro-4-(5-isopropyl-1-methyl-6-oxo-1,6-dihydropyridazine-3-carbonyl)phenyl)-2-methyl-1,2,4-triazine-3,5(2H,4H)-dione (Compound 14

Scheme 14

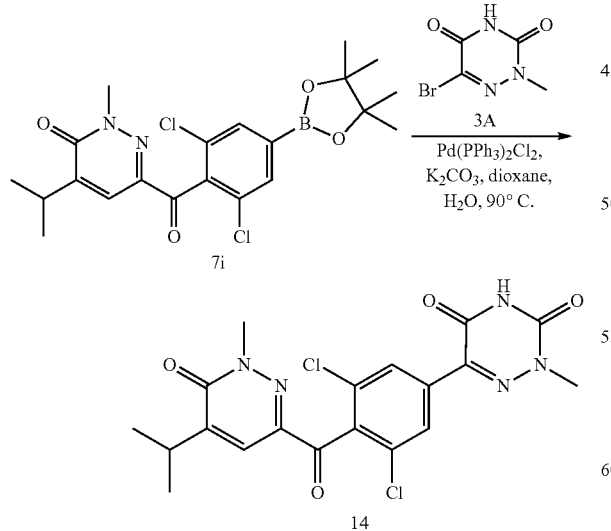

Compound 14 can be prepared by reaction of 7i with 3A according to the reaction conditions used for the preparation of Compound 7.

Example S15: 6-(3,5-dichloro-4-((5-isopropyl-6-oxo-1,6-dihydropyridazin-3-yl)methyl)phenyl)-1,2,4-triazine-3,5(2H,4H)-dione (Compound 15

Scheme 15

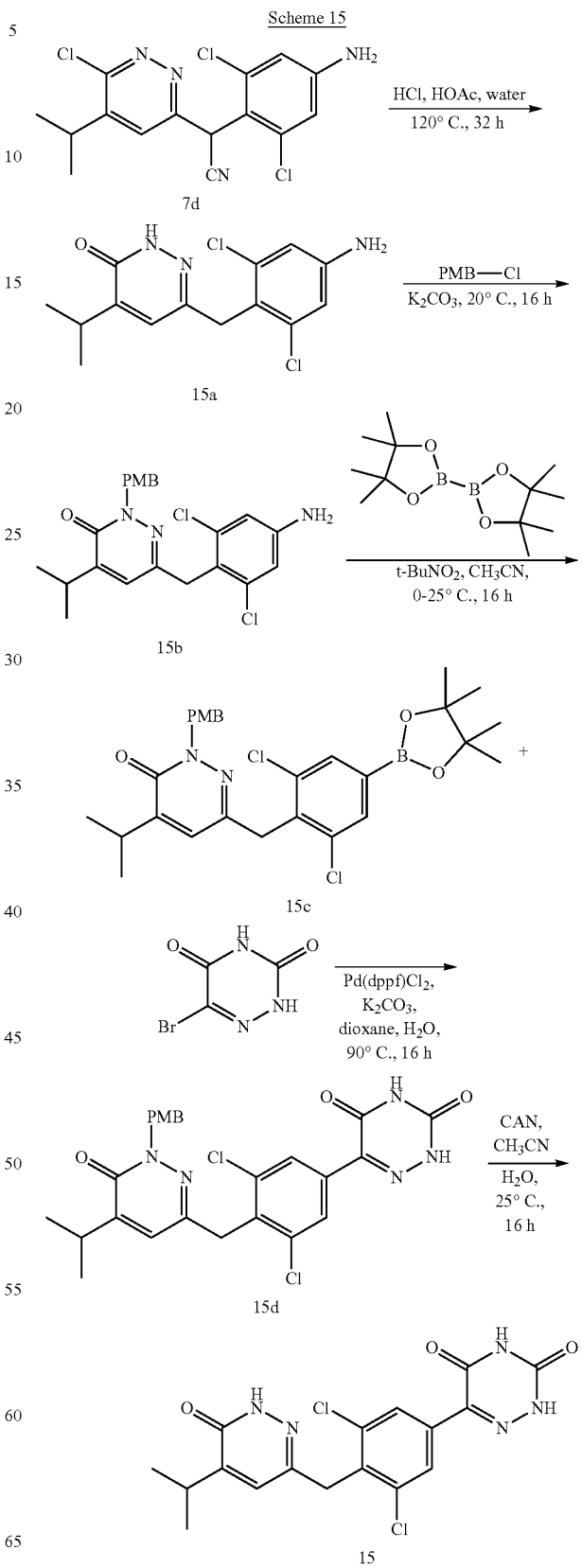

6-(4-amino-2,6-dichlorobenzyl)-4-isopropylpyridazin-3(2H)-one (15a

A solution of 2-(4-amino-2,6-dichlorophenyl)-2-(6-chloro-5-isopropylpyridazin-3-yl)acetonitrile (7d) (0.15 g, 421.76 umol) in HOAc (0.6 mL), $H_2O$ (0.6 mL) and conc. HCl (2.4 mL) was heated to 120° C. for 32 hours. LCMS showed the reaction was completed, and desired MS was detected. After cooling, the mixture was adjusted to pH-7 with 4M NaOH at 0° C., the solid was filtered and dried to give 15a (0.12 g, crude). MS mass calculated for $[M+1]^+$ ($C_{14}H_{15}Cl_2N_3O$) requires m/z 312.1, LCMS found m/z 312.1.

6-(4-amino-2,6-dichlorobenzyl)-4-isopropyl-2-(4-methoxybenzyl)pyridazin-3(2H)-one (15b To a solution of 6-(4-amino-2,6-dichlorobenzyl)-4-isopropylpyridazin-3(2H)-one (15a) (200 mg, 640.63 umol) in DMF (5 mL) was added PMB-$C_1$ (120.39 mg, 768.75 umol, 104.69 uL) and $K_2CO_3$ (106.25 mg, 768.75 umol). The mixture was stirred at 20° C. for 16 hours. TLC showed ~10% of 15a was remained and one new spot was formed. The suspension was filtered through a pad of Celite and the pad cake was washed with EtOH (5 mL*3). The combined filtrates were concentrated in vacuum. The residue was purified by Prep-TLC ($SiO_2$, Petroleum ether:Ethyl acetate) to give 15b. $^1H$ NMR (400 MHz, DMSO-d6) δ 7.17 (d, J=8.6 Hz, 2H), 7.04 (s, 1H), 6.85-6.80 (m, 2H), 6.65 (s, 2H), 5.63 (s, 2H), 5.02 (s, 2H), 4.01 (s, 2H), 3.71 (s, 3H), 2.97 (td, J=6.8, 13.5 Hz, 1H), 1.07 (d, J=7.0 Hz, 6H).

6-(2,6-dichloro-4-(4,4,5,5-tetramethyl-1,3,2-dioxaborolan-2-yl)benzyl)-4-isopropyl-2-(4-methoxybenzyl)pyridazin-3(2H)-one (15c To a solution of 6-(4-amino-2,6-dichlorobenzyl)-4-isopropyl-2-(4-methoxybenzyl)pyridazin-3(2H)-one (15b) (70 mg, 161.91 umol) and 4,4,5,5-tetramethyl-2-(4,4,5,5-tetramethyl-1,3,2-dioxaborolan-2-yl)-1,3,2-dioxaborolane (822.29 mg, 3.24 mmol) in $CH_3CN$ (2 mL) was added t-BuONO (33.39 mg, 323.82 umol, 38.51 uL) at 0° C., then the mixture was stirred at 0° C. for 4 hours. Then the mixture was stirred at 25° C. for another 12 hours. TLC indicated reactant 15b was consumed completely and many new spots were formed. The reaction mixture was diluted with water (5 mL), and extracted with ethyl acetate (5 mL). The organic phase was separated, washed with brine (5 mL*3), dried over $Na_2SO_4$, filtered and concentrated under reduced pressure. The residue was purified by column chromatography ($SiO_2$, Petroleum teeth: Ethyl acetate) to give 15c (100 mg, crude). MS mass calculated for $[M+1]^+$ ($C_{28}H_{33}BCl_2N_2O_4$) requires m/z 543.2, LCMS found m/z 543.1.

6-(3,5-dichloro-4-((5-isopropyl-1-(4-methoxybenzyl)-6-oxo-1,6-dihydropyridazin-3-yl)methyl)phenyl)-1,2,4-triazine-3,5(2H,4H)-dione (15d To a solution of 6-(2,6-dichloro-4-(4,4,5,5-tetramethyl-1,3,2-dioxaborolan-2-yl)benzyl)-4-isopropyl-2-(4-methoxybenzyl)pyridazin-3(2H)-one (15c) (20 mg, 36.81 umol) and 6-bromo-2H-1,2,4-triazine-3,5-dione (10.60 mg, 55.22 umol) in dioxane (2 mL) and $H_2O$ (0.5 mL) were added Pd(dppf)$Cl_2$ (2.69 mg, 3.68 umol) and $K_2CO_3$ (15.26 mg, 110.44 umol). The mixture was stirred at 90° C. for 12 hours. LCMS showed the 15c was consumed and desired MS was detected. The reaction mixture was partitioned between ethyl acetate 5 mL and $H_2O$ 5 mL. The organic phase was separated, washed with brine (3 mL*3), dried over $Na_2SO_4$, filtered and concentrated under reduced pressure. The residue was purified by Prep-TLC ($SiO_2$) to give 15d. MS mass calculated for $[M+1]^+$ ($C_{25}H_{23}Cl_2N_5O_4$) requires m/z 528.1, LCMS found m/z 528.0.

6-(3,5-dichloro-4-((5-isopropyl-6-oxo-1,6-dihydropyridazin-3-yl)methyl)phenyl)-1,2,4-triazine-3,5(2H,4H)-dione (15

To a solution of 6-(3,5-dichloro-4-((5-isopropyl-1-(4-methoxybenzyl)-6-oxo-1,6-dihydropyridazin-3-yl)methyl)phenyl)-1,2,4-triazine-3,5 (2H,4H)-dione (15d) (15 mg, 28.39 umol) in $CH_3CN$ (2 mL) and $H_2O$ (0.5 mL) was added CAN (77.82 mg, 141.94 umol, 70.74 uL). The mixture was stirred at 25° C. for 16 hours. LC-MS showed 15d was consumed completely and one main peak with desired m/z. The mixture was concentrated under reduced pressure. The residue was purified by Prep-HPLC to give 15. MS mass calculated for $[M+1]^+$ ($C_{17}H_{15}Cl_2N_5O_3$) requires m/z 408.1, LCMS found m/z 408.0. $^1H$ NMR (400 MHz, MeOH-d4) δ 8.10-8.13 (m, 2H), 7.24-7.27 (m, 1H), 4.36 (s, 2H), 3.07-3.15 (m, 1H), 1.19-1.23 (m, 6H).

Example S16: 6-(3,5-dichloro-4-((5-isopropyl-6-oxo-1,6-dihydropyridazin-3-yl)methyl)phenyl)-2-methyl-1,2,4-triazine-3,5(2H,4H)-dione (Compound 16

Scheme 16

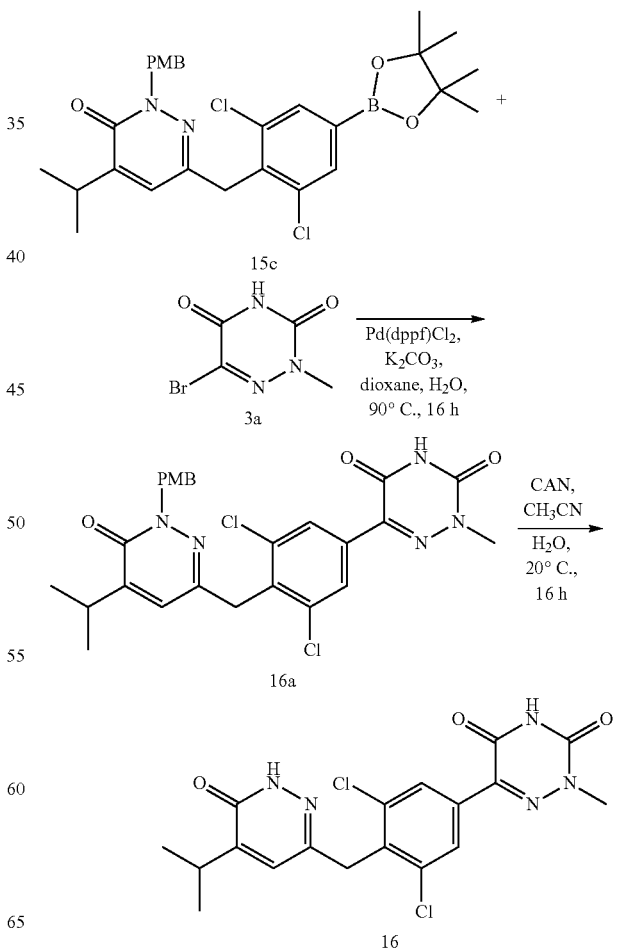

6-(3,5-dichloro-4-((5-isopropyl-1-(4-methoxybenzyl)-6-oxo-1,6-dihydropyridazin-3-yl)methyl)phenyl)-2-methyl-1,2,4-triazine-3,5(2H,4H)-dione (16a A mixture of 6-(2,6-dichloro-4-(4,4,5,5-tetramethyl-1,3,2-dioxaborolan-2-yl)benzyl)-4-isopropyl-2-(4-methoxybenzyl)pyridazin-3(2H)-one (15c) (130 mg, 239.28 umol), 6-bromo-2-methyl-1,2,4-triazine-3,5(2H,4H)-dione (3a) (73.94 mg, 358.93 umol), Pd(dppf)Cl$_2$ (17.51 mg, 23.93 umol), and K$_2$CO$_3$ (99.21 mg, 717.85 umol) in dioxane (4 mL) and H$_2$O (1 mL) was degassed and purged with N$_2$ for 3 times, and then the mixture was stirred at 90° C. for 16 hours under N$_2$ atmosphere. LCMS showed one peak with the desired mass was formed. The reaction mixture was extracted with ethyl acetate (10 mL*3) and H$_2$O (10 mL). The combined organic layers were washed with brine (5 mL), dried over anhydrous Na$_2$SO$_4$, filtered and concentrated under reduced pressure. The residue was purified by Prep-TLC (Dichloromethane: Methanol) to give 16a. MS mass calculated for [M+1]$^+$ (C$_{26}$H$_{25}$Cl$_2$N$_5$O$_4$) requires m/z 542.1, LCMS found m/z 542.1.

6-(3,5-dichloro-4-((5-isopropyl-6-oxo-1,6-dihydropyridazin-3-yl)methyl)phenyl)-2-methyl-1,2,4-triazine-3,5(2H,4H)-dione (16

To a solution of 6-(3,5-dichloro-4-((5-isopropyl-1-(4-methoxybenzyl)-6-oxo-1,6-dihydropyridazin-3-yl)methyl)phenyl)-2-methyl-1,2,4-triazine-3,5(2H,4H)-dione (16a) (20 mg, 36.87 umol) in CH$_3$CN (2 mL) and H$_2$O (0.5 mL) was added CAN (80.86 mg, 147.49 umol, 73.51 uL) at 20° C. And the mixture was stirred at 20° C. for 16 hours. TLC and LCMS showed one main peak with the desired mass was detected. The reaction mixture was concentrated under reduced pressure. The residue was purified by Prep-HPLC (column: Luna C18 100*30 5 u; mobile phase: [water (0.225% FA)-ACN) to give 16. MS mass calculated for [M+1]$^+$ (C$_{18}$H$_{17}$Cl$_2$N$_5$O$_3$) requires m/z 422.1, LCMS found m/z 422.0. $^1$H NMR (400 MHz, CD$_3$OD) δ 8.12-8.14 (m, 2H), 7.24-7.26 (m, 1H), 4.35-4.37 (m, 2H), 3.66-3.68 (m, 3H), 3.12-3.15 (m, 1H), 1.21 (d, J=6.8 Hz, 6H).

Example S17: 6-(3,5-dichloro-4-((5-isopropyl-1-methyl-6-oxo-1,6-dihydropyridazin-3-yl)methyl)phenyl)-1,2,4-triazine-3,5(2H,4H)-dione (Compound 17

Scheme 17

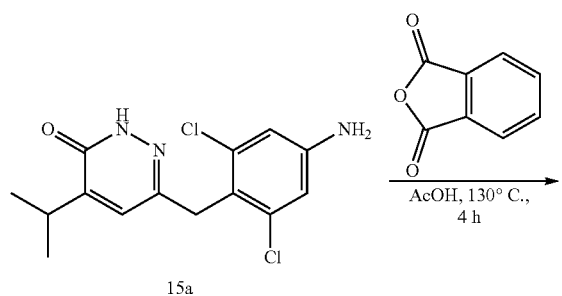

15a

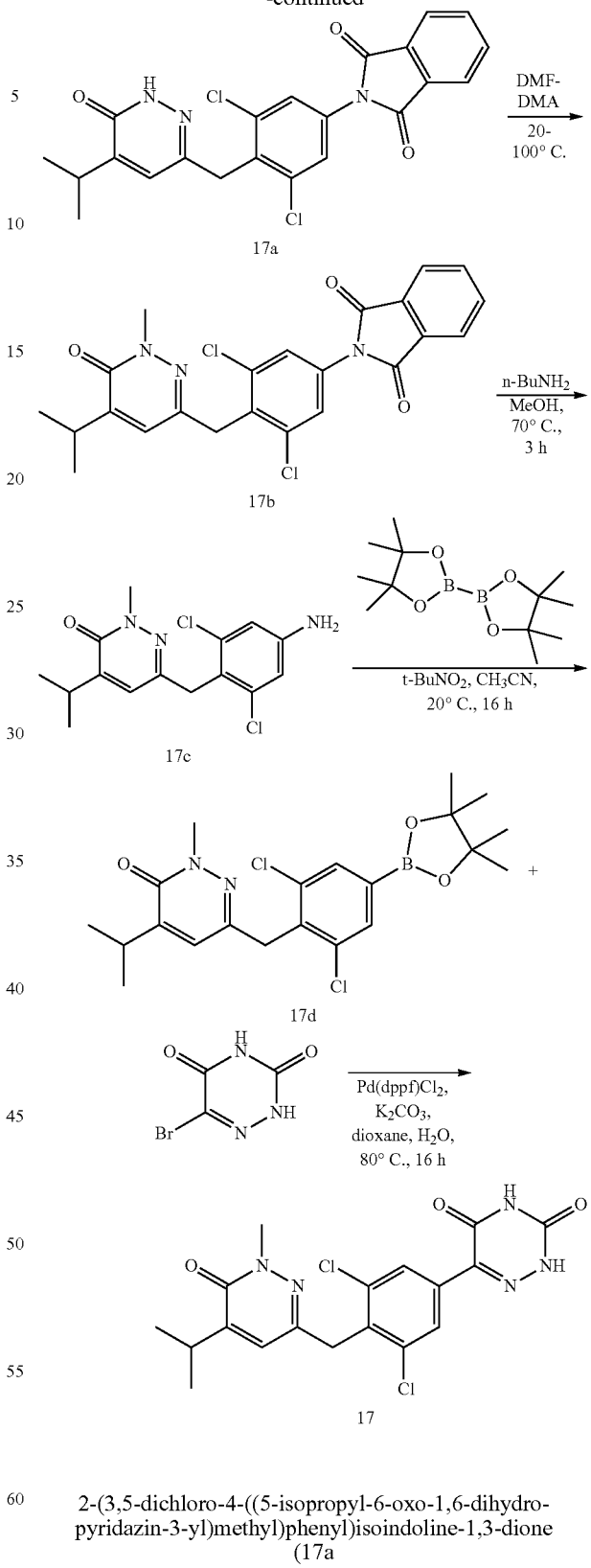

2-(3,5-dichloro-4-((5-isopropyl-6-oxo-1,6-dihydropyridazin-3-yl)methyl)phenyl)isoindoline-1,3-dione (17a To a solution of 6-(4-amino-2,6-dichlorobenzyl)-4-isopropylpyridazin-3(2H)-one (15a) (450 mg, 1.44 mmol) in HOAc (5 mL) was added isobenzofuran-1,3-dione (213.50 mg, 1.44 mmol). The mixture was stirred at 130° C. for 4 hours. LCMS showed one peak with the desired mass was detected. The reaction mixture was concentrated under reduced pressure to remove HOAc. This mixture was extracted with water (50 mL) and ethyl acetate (50 mL), and then washed with NaHCO$_3$(20 mL*3), dried over Na$_2$SO$_4$, filtered and concentrated under reduced pressure to give 17a. MS mass calculated for [M+1]$^+$(C$_{22}$H$_{17}$Cl$_2$N$_3$O$_3$) requires m/z 442.1, LCMS found m/z 442.1.

2-(3,5-dichloro-4-((5-isopropyl-1-methyl-6-oxo-1,6-dihydropyridazin-3-yl)methyl)phenyl)isoindoline-1,3-dione (17b A mixture of 2-(3,5-dichloro-4-((5-isopropyl-6-oxo-1,6-dihydropyridazin-3-yl)methyl)phenyl)isoindoline-1,3-dione (17a) (600 mg, 1.36 mmol) and DMF-DMA (5 mL) was heated to 105° C. for 3 hours. LCMS showed one peak with the desired mass was formed. The reaction mixture was and concentrated under reduced pressure to give 17b. MS mass calculated for [M+1]$^+$ (C$_{23}$H$_{19}$Cl$_2$N$_3$O$_3$) requires m/z 456.1, LCMS found m/z 456.1.

6-(4-amino-2,6-dichlorobenzyl)-4-isopropyl-2-methylpyridazin-3(2H)-one (17c

A solution of 2-(3,5-dichloro-4-((5-isopropyl-1-methyl-6-oxo-1,6-dihydropyridazin-3-yl)methyl)phenyl)isoindoline-1,3-dione (17b) (600 mg, 1.31 mmol) in N-BUTYLANILINE (981.11 mg, 6.57 mmol, 1.05 mL) and MeOH (3 mL) was heated to 70° C. for 3 hours. LCMS showed one peak with the desired mass was formed. The reaction mixture concentrated under reduced pressure. The residue was purified by column chromatography (SiO$_2$, Petroleum ether: Ethyl acetate) to give 17c. MS mass calculated for [M+1]$^+$ (C$_{15}$H$_{17}$Cl$_2$N$_3$O) requires m/z 326.1, LCMS found m/z 326.1. $^1$H NMR (400 MHz, CD$_3$OD) δ 7.04-7.08 (m, 1H), 6.69-6.72 (m, 2H), 4.13 (s, 2H), 3.70 (s, 3H), 3.06-3.14 (m, 1H), 1.15 (d, J=6.8 Hz, 6H).

6-(2,6-dichloro-4-(4,4,5,5-tetramethyl-1,3,2-dioxaborolan-2-yl)benzyl)-4-isopropyl-2-methylpyridazin-3(2H)-one (17d To a solution of 6-(4-amino-2,6-dichlorobenzyl)-4-isopropyl-2-methylpyridazin-3(2H)-one (17c) (33 mg, 101.16 umol) and 4,4,4',4',5,5,5',5'-octamethyl-2,2'-bi(1,3,2-dioxaborolane) (77.06 mg, 303.48 umol) in MeCN (1 mL) was added t-BuONO (20.86 mg, 202.32 umol, 24.06 uL). The mixture was stirred at 20° C. for 16 hours. LCMS showed one peak with the desired mass was formed. The reaction mixture was extracted with ethyl acetate (20 mL*3) and H$_2$O (20 mL). The combined organic layers were washed with brine (10 mL), dried over anhydrous Na$_2$SO$_4$, filtered and concentrated under reduced pressure. The residue was purified by Prep-TLC (Petroleum ether:Ethyl acetate) to give 17d. MS mass calculated for [M+1]$^+$ (C$_{21}$H$_{27}$BCl$_2$N$_2$O$_3$) requires m/z 437.1, LCMS found m/z 437.1. $^1$H NMR (400 MHz, CDCl$_3$) δ 7.75 (s, 2H), 6.88 (s, 1H), 4.27 (s, 2H), 3.71 (s, 3H), 3.16 (td, J=7.0, 13.8 Hz, 1H), 1.36 (s, 12H), 1.15 (d, J=6.8 Hz, 6H).

6-(3,5-dichloro-4-((5-isopropyl-1-methyl-6-oxo-1,6-dihydropyridazin-3-yl)methyl)phenyl)-1,2,4-triazine-3,5(2H,4H)-dione (17

A mixture of 6-(2,6-dichloro-4-(4,4,5,5-tetramethyl-1,3,2-dioxaborolan-2-yl)benzyl)-4-isopropyl-2-methylpyridazin-3 (2H)-one (17d) (24.7 mg, 56.50 umol), 6-bromo-1,2,4-triazine-3,5(2H,4H)-dione (10.85 mg, 56.50 umol), Pd(dppf)Cl$_2$ (4.13 mg, 5.65 umol) and K$_2$CO$_3$ (23.43 mg, 169.50 umol, 3 eq) in dioxane (1 mL) and H$_2$O (0.5 mL) was degassed and purged with N$_2$ for 3 times, and then the mixture was stirred at 90° C. for 16 hours under N$_2$ atmosphere. LCMS showed one peak with the desired mass was formed. The mixture was added palladium scavenger Si-TMT (3 g) and stirred at 20° C. for 1 hour, then filtered and concentrated under reduced pressure. The residue was purified by Prep-HPLC (column: Luna C18 100*30 5 u; mobile phase: [water (0.225% FA)-ACN]) to give 17. MS mass calculated for [M+1]$^+$ (C$_{18}$H$_{17}$Cl$_2$N$_5$O$_3$) requires m/z 422.1, LCMS found m/z 422.1. $^1$H NMR (400 MHz, MeOH-d4) δ 8.10-8.14 (m, 2H), 7.21-7.23 (m, 1H), 4.35-4.37 (m, 2H), 3.64 (s, 3H), 3.13 (quin, J=6.9 Hz, 1H), 1.19 (d, J=6.8 Hz, 6H).

Example S18: 6-(3,5-dichloro-4-((5-isopropyl-1-methyl-6-oxo-1,6-dihydropyridazin-3-yl)methyl) phenyl)-2-methyl-1,2,4-triazine-3,5(2H,4H)-dione (Compound 18

Scheme 18

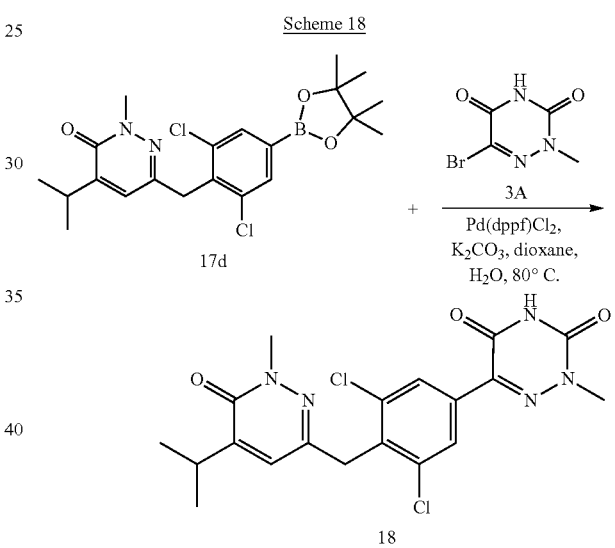

Compound 18 can be prepared by reaction of 17d with 3A according to the procedure described for Example S17.

Example S19: 6-(3,5-dichloro-4-((5-isopropyl-6-oxo-1,6-dihydropyridazin-3-yl)oxy)phenyl)-2-ethyl-1,2,4-triazine-3,5(2H,4H)-dione (Compound 19

Scheme 19

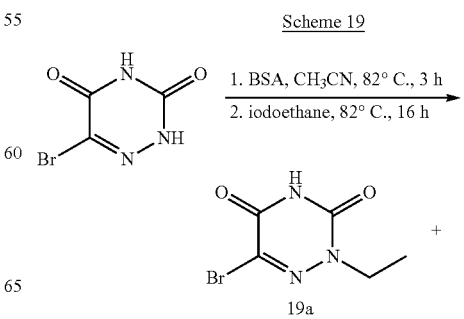

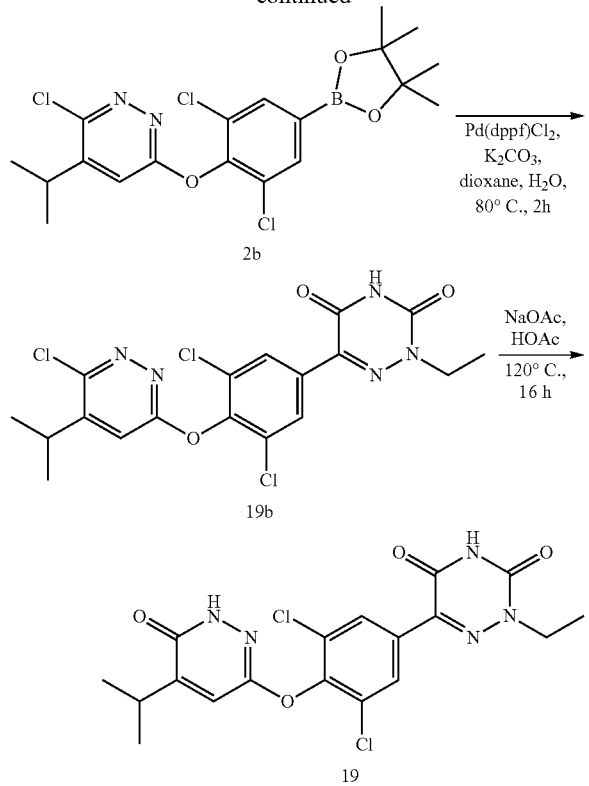

6-bromo-2-ethyl-1,2,4-triazine-3,5(2H, 4H)-dione (19a

To a solution of 6-bromo-1,2,4-triazine-3,5(2H, 4H)-dione (50 mg, 260.46 umol) in CH$_3$CN (2 mL) was added BSA (132.46 mg, 651.15 umol, 160.95 uL). Then the mixture was stirred at 82° C. for 3 hours. Then iodoethane (60.93 mg, 390.69 umol, 31.25 uL) was added in the mixture. The resulting mixture was stirred at 82° C. for another 16 hours. LCMS and TLC showed the starting material was consumed, and the desired MS was detected. The mixture was concentrated in vacuum. The residue were purified by Prep-TLC (Dichloromethane:Methanol) to give 19a. MS mass calculated for [M+1]$^+$ (C$_5$H$_6$BrN$_3$O$_2$) requires m/z 220.0, LCMS found m/z 219.9. $^1$H NMR (400 MHz, DMSO-d6) δ 12.45 (br s, 1H), 3.79-3.89 (m, 2H), 1.19 (t, J=7.2 Hz, 3H).

6-(3,5-dichloro-4-((6-chloro-5-isopropylpyridazin-3-yl) oxy) phenyl)-2-ethyl-1,2,4-triazine-3,5(2H, 4H)-dione (19b To a solution of 3-chloro-6-(2,6-dichloro-4-(4,4,5,5-tetramethyl-1,3,2-dioxaborolan-2-yl)phenoxy)-4-isopropylpyridazine (2b) (40 mg, 90.18 umol) and 6-bromo-2-ethyl-1,2,4-triazine-3,5(2H, 4H)-dione (19a). (19.84 mg, 90.18 umol) in dioxane (4 mL) and H$_2$O (1 mL) was added K$_2$CO$_3$ (37.39 mg, 270.54 umol) and Pd(dppf)Cl$_2$ (659.85 ug). Then the mixture was stirred at 80° C. for 2 hours under N$_2$. LCMS showed the 19a was completed. The mixture was concentrated in vacuum. The residue was extracted with Ethyl acetate (10 mL*2) and H$_2$O (5 mL). The combined organic layer was concentrated in vacuum. The residue was purified by Prep-TLC (Dichloromethane:Methanol) to give 19b (20 mg, crude). The product was used directly in next step. MS mass calculated for [M+1]$^+$ (C$_{18}$H$_{16}$C$_{13}$N$_5$O$_3$) requires m/z 456.0, LCMS found m/z 456.1.

6-(3,5-dichloro-4-((5-isopropyl-6-oxo-1,6-dihydropyridazin-3-yl)oxy)phenyl)-2-ethyl-1,2,4-triazine-3,5(2H,4H)-dione (19

To a solution of 6-(3,5-dichloro-4-((6-chloro-5-isopropylpyridazin-3-yl) oxy) phenyl)-2-ethyl-1,2,4-triazine-3,5(2H, 4H)-dione (19b) (20 mg, 43.79 umol) in AcOH (3 mL) was added NaOAc (17.96 mg, 218.96 umol). Then the mixture was stirred at 120° C. for 16 hours. LCMS and HPLC showed the 19b was completed, and desired was found in the major peak. The mixture was concentrated in vacuum. The residue was purified by Prep-HPLC (column: Nano-Micro UniSil 5-100 C18 ULTRA 100*250 mm 5 um; mobile phase: [water (0.1% TFA)-ACN]) to give 19. MS mass calculated for [M+1]$^+$ (C$_{18}$H$_{17}$Cl$_2$N$_5$O$_4$) requires m/z 438.1, LCMS found m/z 438.0. $^1$H NMR (400 MHz, MeOH-d4) δ 8.18 (s, 2H), 7.36 (s, 1H), 4.10 (q, J=7.2 Hz, 2H), 3.15 (d, J=13.2 Hz, 1H), 1.39 (t, J=7.0 Hz, 3H), 1.29 (d, J=7.0 Hz, 6H).

Example S20: ethyl 2-(6-(3,5-dichloro-4-((5-isopropyl-6-oxo-1,6-dihydropyridazin-3-yl)oxy)phenyl)-3,5-dioxo-4,5-dihydro-1,2,4-triazin-2(3H)-yl)acetate (Compound 20

Scheme 20

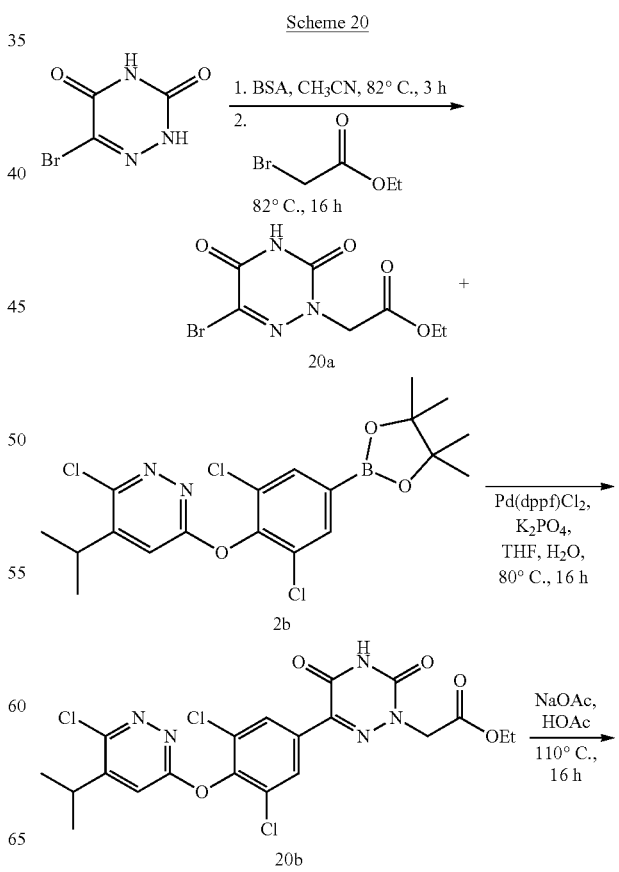

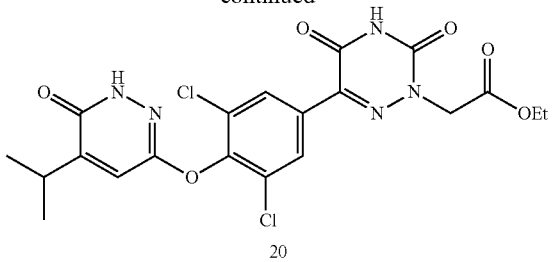

Ethyl 2-(6-bromo-3,5-dioxo-4,5-dihydro-1,2,4-triazin-2(3H)-yl) acetate (20a

BSA (1.32 g, 6.51 mmol, 1.61 mL) was added to a mixture of 6-bromo-1,2,4-triazine-3,5(2H,4H)-dione (500 mg, 2.60 mmol) in CH$_3$CN (5 mL) at 82° C. for 3 hours, Then ethyl 2-bromoacetate (652.45 mg, 3.91 mmol, 432.08 uL) was added, the resulting mixture was stirred at 82° C. for 16 hours. LCMS showed the starting material was consumed completely and desired MS was detected. The mixture was concentrated in vacuum. The residue was partitioned between ethyl acetate (10 mL*2) and H$_2$O (3 mL). The combined organic phase was washed with brine (5 mL*3), dried with anhydrous Na$_2$SO$_4$, filtered and concentrated in vacuum. The residue was purified by Prep-TLC (SiO$_2$, DCM:MeOH) to give 20a. MS mass calculated for [M+1]$^+$ (C$_7$H$_8$BrN$_3$O$_4$) requires m/z 278.0, LCMS found m/z 278.0. $^1$H NMR (400 MHz, MeOH-d4) δ 4.70 (s, 2H), 4.25 (q, J 7.2 Hz, 2H), 1.29 (t, J 7.2 Hz, 3H).

Ethyl 2-(6-(3,5-dichloro-4-((6-chloro-5-isopropylpyridazin-3-yl)oxy)phenyl)-3,5-dioxo-4,5-dihydro-1,2,4-triazin-2(3H)-yl)acetate (20b To a solution of ethyl 2-(6-bromo-3,5-dioxo-4,5-dihydro-1,2,4-triazin-2(3H)-yl)acetate (20a) (80 mg, 287.71 umol) and 3-chloro-6-(2,6-dichloro-4-(4,4,5,5-tetramethyl-1,3,2-dioxaborolan-2-yl)phenoxy)-4-isopropylpyridazine (2b) (128.20 mg, 287.71 umol) in THF (2 mL) was added Pd(dppf)Cl$_2$ (18.75 mg, 28.77 umol) and K$_3$PO$_4$ (122.14 mg, 575.42 umol) in H$_2$O (0.5 mL). The mixture was stirred at 80° C. for 16 hours under N$_2$. LCMS showed the 20a was consumed completely and desired MS was detected. The mixture was concentrated in vacuum. The residue was partitioned between ethyl acetate (10 mL*2) and H$_2$O (3 mL). The combined organic phase was washed with brine (5 mL*3), dried with anhydrous Na$_2$SO$_4$, filtered and concentrated in vacuum. The residue was purified by Prep-TLC (Petroleum ether:Ethyl acetate) to give 20b. MS mass calculated for [M+1]$^+$ (C$_{20}$H$_{18}$Cl$_3$N$_5$O$_5$) requires m/z 514.0, LCMS found m/z 514.0.

Ethyl 2-(6-(3,5-dichloro-4-((5-isopropyl-6-oxo-1,6-dihydropyridazin-3-yl)oxy)phenyl)-3,5-dioxo-4,5-dihydro-1,2,4-triazin-2(3H)-yl)acetate (20

A mixture of ethyl 2-(6-(3,5-dichloro-4-((6-chloro-5-isopropylpyridazin-3-yl)oxy)phenyl)-3,5-dioxo-4,5-dihydro-1,2,4-triazin-2(3H)-yl)acetate (20b) (48 mg, 93.25 umol) and NaOAc (38.25 mg, 466.25 umol) in HOAc (3 mL) was heated to 110° C. and stirred for 16 hours. LCMS showed 20b was consumed completely and the desired MS was detected. The mixture was concentrated. The residue was purified by Prep-HPLC (column: Luna C18 100*30 5 u; mobile phase: [water (0.225% FA)-ACN]) to give 20. MS mass calculated for [M+1]+(C$_{20}$H$_{19}$Cl$_2$N$_5$O$_6$) requires m/z 496.1, LCMS found m/z 496.1. $^1$H NMR (400 MHz, DMSO-d6) δ 12.67 (s, 1H), 12.21 (s, 1H), 8.09 (s, 2H), 7.43 (s, 1H), 4.83 (s, 2H), 4.19 (q, J=7.2 Hz, 2H), 3.05 (td, J=6.8, 13.5 Hz, 1H), 1.25-1.18 (m, 9H).

Example S21: 6-(3,5-dichloro-4-((5-isopropyl-6-oxo-1,6-dihydropyridazin-3-yl)oxy)phenyl)-2-(2,2,2-trifluoroethyl)-1,2,4-triazine-3,5(2H,4H)-dione (Compound 21

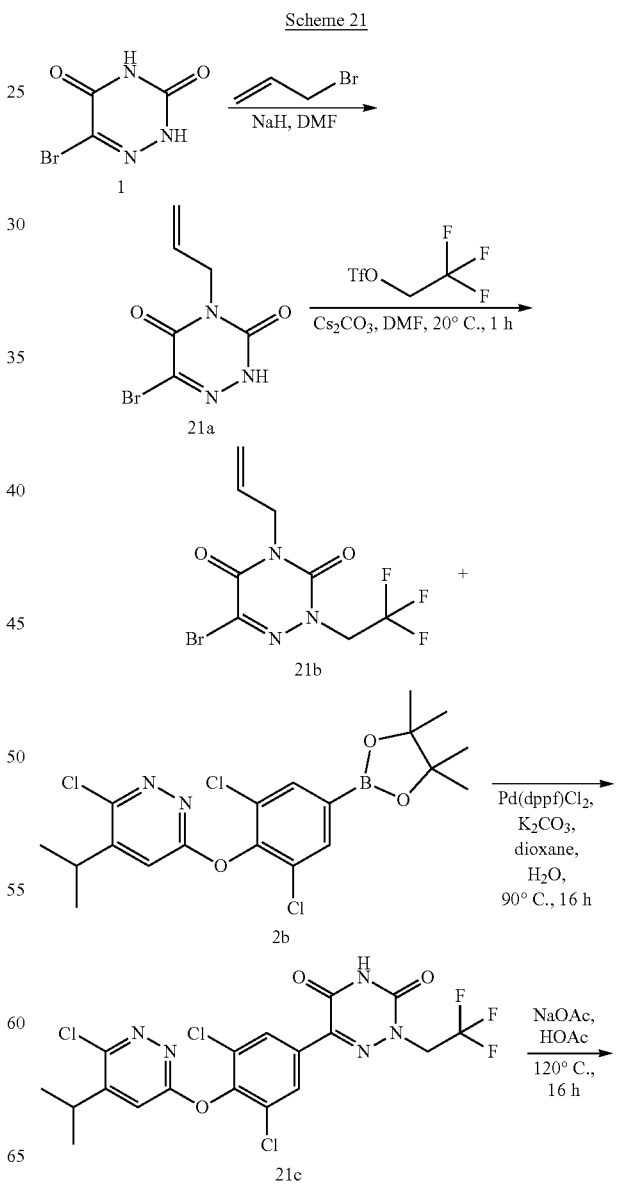

-continued

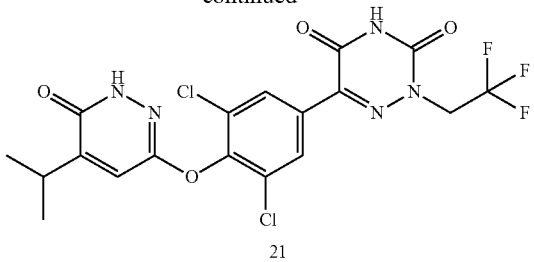

21

4-allyl-6-bromo-1,2,4-triazine-3,5(2H,4H)-dione (21a

To a solution of 6-bromo-2H-1,2,4-triazine-3,5-dione (1) (200 mg, 1.04 mmol) and 3-bromoprop-1-ene (126.04 mg, 1.04 mmol) in DMSO (2.5 mL) was added portion-wise NaH (41.67 mg, 1.04 mmol, 60% purity) at 25° C. The reaction mixture was stirred for 1 hour. LCMS showed the starting material was consumed completely and desired MS was detected. The reaction mixture was diluted with water (10 mL) and extracted with ethyl acetate (10 mL*2). The combined organic layers was washed with brine (10 mL), dried over Na$_2$SO$_4$, filtered and concentrated under reduced pressure. The residue was purified by Prep-TLC (Petroleum ether:Ethyl acetate) to give 21a. $^1$H NMR (400 MHz, MeOH-d4) δ 5.85-5.90 (m, 1H), 5.19-5.28 (m, 2H), 4.49-4.50 (d, 2H).

4-allyl-6-bromo-2-(2,2,2-trifluoroethyl)-1,2,4-triazine-3,5(2H,4H)-dione (21b

To a solution of 4-allyl-6-bromo-1,2,4-triazine-3,5(2H,4H)-dione (21a) (55 mg, 237.03 umol) in DMF (2 mL) was added Cs$_2$CO$_3$ (154.46 mg, 474.07 umol). Then 2,2,2-trifluoroethyl trifluoromethanesulfonate (66.02 mg, 284.44 umol, 25.00 uL) was added in the mixture. And the resulting mixture was stirred at 20° C. for 1 hour. TLC showed the reaction was completed, and one new spot was formed. The mixture was concentrated in vacuum. The residue was purified by Prep-TLC (SiO$_2$, Petroleum ether:Ethyl acetate) to give 21b. $^1$H NMR (400 MHz, CDCl$_3$) δ 7.28-7.98 (m, 1H), 5.86 (ddt, J=17.0, 10.4, 6.2, 6.2 Hz, 1H), 5.24-5.47 (m, 2H), 4.53-4.66 (m, 4H).

6-(3,5-dichloro-4-((6-chloro-5-isopropylpyridazin-3-yl)oxy)phenyl)-2-(2,2,2-trifluoroethyl)-1,2,4-triazine-3,5(2H,4H)-dione (21c To a solution of 4-allyl-6-bromo-2-(2,2,2-trifluoroethyl)-1,2,4-triazine-3,5(2H,4H)-dione (21b) (20 mg, 63.68 umol) and 3-chloro-6-(2,6-dichloro-4-(4,4,5,5-tetramethyl-1,3,2-dioxaborolan-2-yl)phenoxy)-4-isopropylpyridazine (2b) (33.90 mg, 76.42 umol) in dioxane (3 mL) and H$_2$O (1 mL) was added K$_2$CO$_3$ (17.60 mg, 127.36 umol) and Pd(dppf)Cl$_2$ (4.66 mg, 6.37 umol) under N$_2$. Then the mixture was stirred at 90° C. for 16 hours under N$_2$. LCMS and TLC showed the reaction was completed and desired MS was detected. The mixture was concentrated in vacuum. The residue was extracted with ethyl acetate (10 mL) and brine (5 mL). The organic layer was concentrated in vacuum. The residue was purified by Prep-TLC (SiO$_2$, Dichloromethane:Methanol) to give 21c (20 mg, crude). MS mass calculated for [M+1]$^+$ (C$_{18}$H$_{13}$Cl$_3$F$_3$N$_5$O$_3$) requires m/z 510.0, LCMS found m/z 510.1.

6-(3,5-dichloro-4-((5-isopropyl-6-oxo-1,6-dihydropyridazin-3-yl)oxy)phenyl)-2-(2,2,2-trifluoroethyl)-1,2,4-triazine-3,5(2H,4H)-dione (21

To a solution of 6-(3,5-dichloro-4-((6-chloro-5-isopropylpyridazin-3-yl)oxy)phenyl)-2-(2,2,2-trifluoroethyl)-1,2,4-triazine-3,5(2H,4H)-dione (21c) (20 mg, 39.16 umol) in HOAc (3 mL) was added NaOAc (16.06 mg, 195.82 umol). Then the mixture was stirred at 120° C. for 16 hours. LCMS showed the reaction was completed. The mixture was concentrated in vacuum. The residue was extracted with ethyl acetate (10 mL*2) and H$_2$O (5 mL). The combined organic layer was dried over Na$_2$SO$_4$, filtered and concentrated in vacuum. The residue was purified by Prep-HPLC (column: Kromasil 150*25 mm*10 um; mobile phase: [water (0.04% NH$_3$H$_2$O+10 mM NH$_4$HCO$_3$)-ACN]) to give 21. MS mass calculated for [M+1]$^+$ (C$_{18}$H$_{14}$Cl$_2$F$_3$N$_5$O$_4$) requires m/z 492.0, LCMS found m/z 492.0. $^1$H NMR (400 MHz, MeOH-d4) δ 8.17 (s, 2H), 7.38 (d, J=1 Hz, 1H), 4.80 (q, J=8.6 Hz, 2H), 3.10-3.25 (m, 1H), 1.31 (d, J=7.0 Hz, 6H).

Example S22: 2-(6-(3,5-dichloro-4-((5-isopropyl-6-oxo-1,6-dihydropyridazin-3-yl)oxy)phenyl)-3,5-dioxo-4,5-dihydro-1,2,4-triazin-2(3H)-yl)acetonitrile (Compound 22

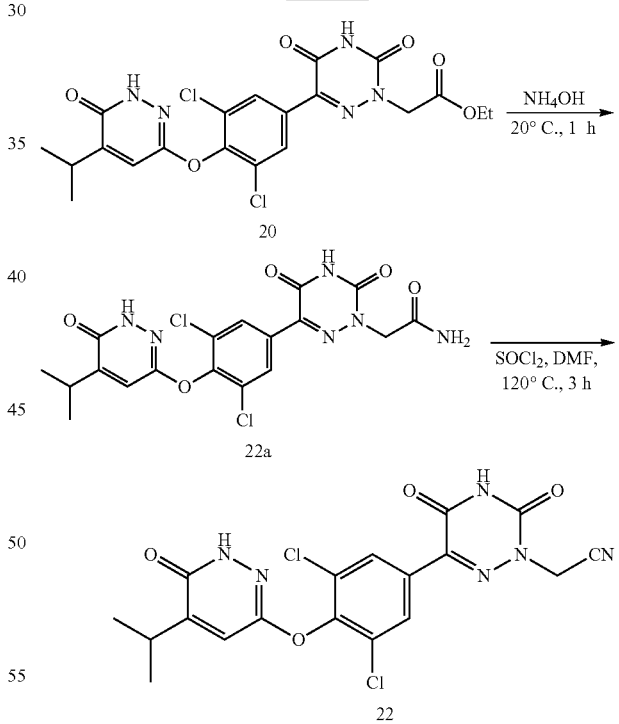

2-(6-(3,5-dichloro-4-((5-isopropyl-6-oxo-1,6-dihydropyridazin-3-yl)oxy)phenyl)-3,5-dioxo-4,5-dihydro-1,2,4-triazin-2(3H)-yl)acetamide (22a A mixture of ethyl 2-(6-(3,5-dichloro-4-((5-isopropyl-6-oxo-1,6-dihydropyridazin-3-yl)oxy)phenyl)-3,5-dioxo-4,5-dihydro-1,2,4-triazin-2(3H)-yl)acetate (27 mg, 54.40 umol) in NH$_3$.H$_2$O (3 mL) was stirred at 20° C. for 1 hour under N₂. LCMS showed 20 was consumed completely and the desired MS was detected. The mixture was concentrated to give 22a. The product was used directly for next step. MS mass calculated for [M+1]+(C₁₈H₁₆Cl₂N₆O₅) requires m/z 467.1, LCMS found m/z 467.1.

2-(6-(3,5-dichloro-4-((5-isopropyl-6-oxo-1,6-dihydropyridazin-3-yl)oxy)phenyl)-3,5-dioxo-4,5-dihydro-1,2,4-triazin-2(3H)-yl)acetonitrile (22

A solution of SOCl₂ (31.83 mg, 267.52 umol, 19.41 uL) in dry DMF (2 mL) was added drop-wise to a solution of 2-(6-(3,5-dichloro-4-((5-isopropyl-6-oxo-1,6-dihydropyridazin-3-yl)oxy)phenyl)-3,5-dioxo-4,5-dihydro-1,2,4-triazin-2(3H)-yl)acetamide (22a) (25 mg, 53.50 umol) in dry DMF (1 mL) at 25° C. under stirring. The mixture was heated to 120° C. for 3 hours. LCMS showed 22a was consumed completely and the desired MS was detected. The mixture was concentrated in vacuum. The residue was partitioned between ethyl acetate (10 mL*2) and H₂O (3 mL). The combined organic phase was washed with brine (5 mL*3), dried with anhydrous Na₂SO₄, filtered and concentrated in vacuum. The residue was purified by Prep-HPLC (condition; column: Xtimate C18 150*25 mm*5 um; mobile phase: [water (10 mM NH₄HCO₃)-ACN]) to give 22. MS mass calculated for [M+1]⁺ (C₁₈H₁₄Cl₂N₆O₄) requires m/z 449.0, LCMS found m/z 449.0. ¹H NMR (400 MHz, CDCl₃) δ 9.93 (br s, 1H), 8.08 (s, 2H), 7.18 (br s, 1H), 5.00 (s, 2H), 3.27 (br s, 1H), 1.33 (br d, J=6.4 Hz, 6H).

Example S23: 6-(3,5-dichloro-4-((5-isopropyl-6-oxo-1,6-dihydropyridazin-3-yl)oxy)phenyl)-2-(2,2-difluoroethyl)-1,2,4-triazine-3,5(2H,4H)-dione (Compound 23

Scheme 23

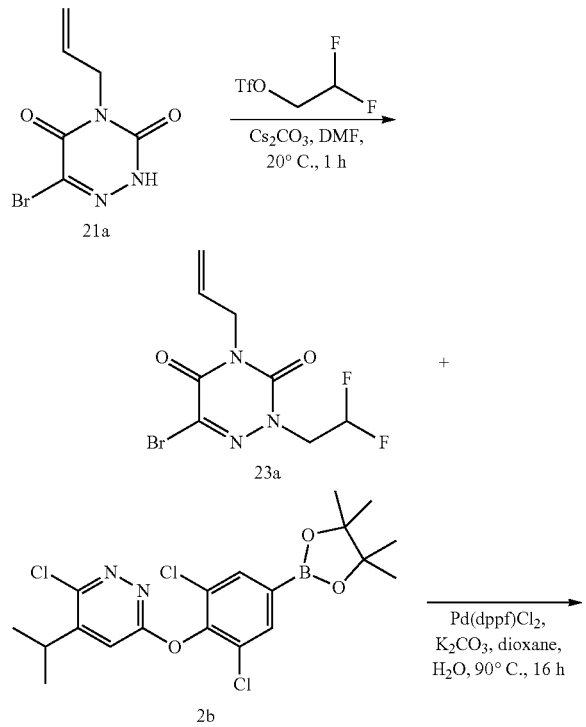

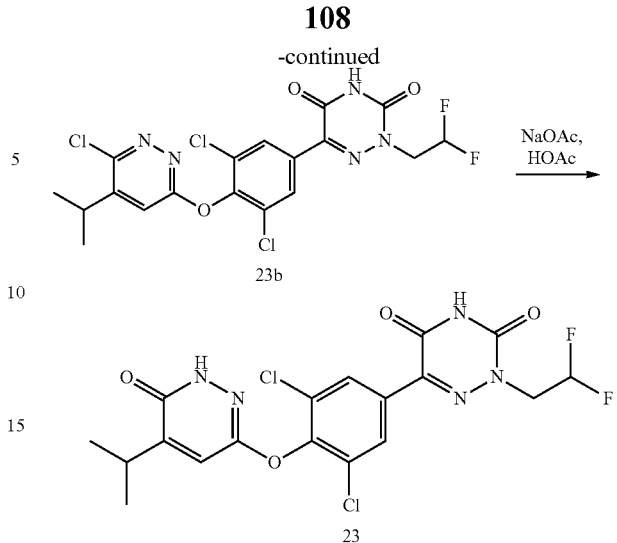

4-allyl-6-bromo-2-(2,2-difluoroethyl)-1,2,4-triazine-3,5(2H,4H)-dione (23a

To a solution of 4-allyl-6-bromo-1,2,4-triazine-3,5(2H,4H)-dione (21a) (10 mg, 43.10 umol) in DMF (1 mL) was added Cs₂CO₃ (28.08 mg, 86.19 umol). Then 2,2-difluoroethyl trifluoromethanesulfonate (11.07 mg, 51.72 umol, 25.00 uL) was added in the mixture. And the resulting mixture was stirred at 20° C. for 1 hour. TLC showed the reaction was completed, and one new spot was formed. The mixture was concentrated in vacuum. The residue was purified by Prep-TLC (Petroleum ether:Ethyl acetate) to give 23a. ¹H NMR (400 MHz, DMSO-d6) δ 12.45 (br s, 1H), 3.79-3.89 (m, 2H), 1.19 (t, J=7.2 Hz, 3H).

6-(3,5-dichloro-4-((6-chloro-5-isopropylpyridazin-3-yl)oxy)phenyl)-2-(2,2-difluoroethyl)-1,2,4-triazine-3,5(2H,4H)-dione (23b To a solution of 3-chloro-6-(2,6-dichloro-4-(4,4,5,5-tetramethyl-1,3,2-dioxaborolan-2-yl)phenoxy)-4-isopropylpyridazine (2b) (50 mg, 112.72 umol) and 4-allyl-6-bromo-2-(2,2-difluoroethyl)-1,2,4-triazine-3,5(2H,4H)-dione (23a) (36.71 mg, 124.00 umol) in dioxane (3 mL) and H₂O (1 mL) was added Pd(dppf)Cl₂ (8.25 mg, 11.27 umol) and K₂CO₃ (31.16 mg, 225.45 umol). Then the mixture was stirred at 90° C. for 16 hours under N₂. LCMS and TLC showed the reaction was completed. The mixture was concentrated in vacuum. The residue was extracted with ethyl acetate (10 mL) and brine (5 mL). The organic layer was concentrated in vacuum. The residue was purified by Prep-TLC (Dichloromethane:Methanol) to give 23b (20 mg, crude). MS mass calculated for [M+1]⁺ (C₁₈H₁₄C₁₃F₂N₅O₃) requires m/z 492.0, LCMS found m/z 492.1.

6-(3,5-dichloro-4-((5-isopropyl-6-oxo-1,6-dihydropyridazin-3-yl)oxy)phenyl)-2-(2,2-difluoroethyl)-1,2,4-triazine-3,5(2H,4H)-dione (23

To a solution of 6-(3,5-dichloro-4-((6-chloro-5-isopropylpyridazin-3-yl)oxy)phenyl)-2-(2,2-difluoroethyl)-1,2,4-triazine-3,5(2H,4H)-dione (23b) (20 mg, 40.59 umol) in HOAc (2 mL) was added NaOAc (16.65 mg, 202.97 umol). Then the mixture was stirred at 120° C. for 16 hours. LCMS showed the reaction was completed. The mixture was extracted with ethyl acetate (5 mL*2) and H₂O (5 mL). The organic layer was dried over in vacuum. The residue was purified by Prep-HPLC (column: Luna C18 100*30 5 u; mobile phase: [water (0.1% TFA)-ACN]) to give 23. MS mass calculated for [M+1]⁺ (C₁₈H₁₅Cl₂F₂N₅O₄) requires m/z 474.0, LCMS found m/z 474.0. ¹H NMR (400 MHz, MeOH-d4) δ 8.17 (s, 2H), 7.36 (s, 1H), 6.05-6.46 (m, 1H), 4.87 (s, 13H), 4.43 (td, J=13.6, 4.0 Hz, 2H), 3.17 (dt, J=13.6, 7.0 Hz, 1H), 1.29 (d, J=6.8 Hz, 6H).

Example S24: 6-(3,5-dichloro-4-((5-isopropyl-1-methyl-6-oxo-1,6-dihydropyridazin-3-yl)oxy)phenyl)-2-(2,2-difluoroethyl)-1,2,4-triazine-3,5(2H,4H)-dione (Compound 24

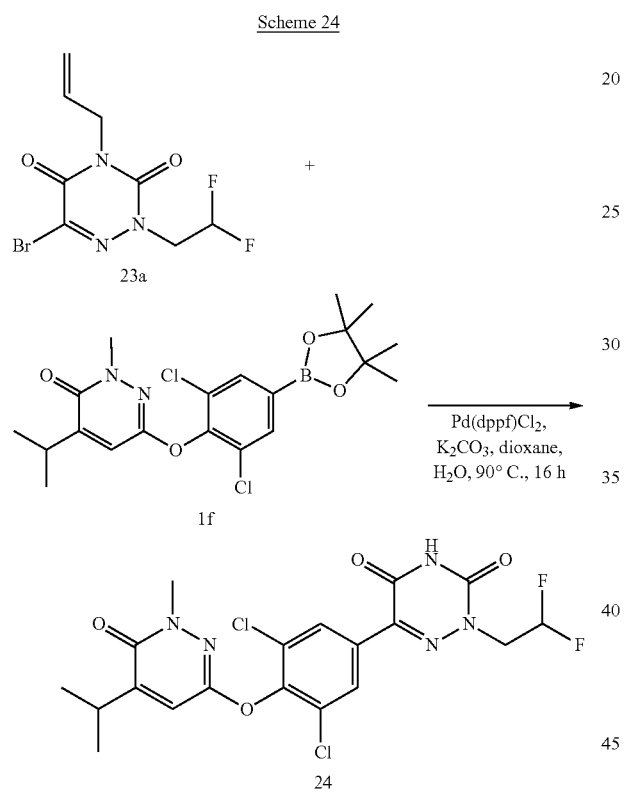

6-(3,5-dichloro-4-((5-isopropyl-1-methyl-6-oxo-1,6-dihydropyridazin-3-yl)oxy)phenyl)-2-(2,2-difluoro-ethyl)-1,2,4-triazine-3,5(2H,4H)-dione (24

To a solution of 4-allyl-6-bromo-2-(2,2-difluoroethyl)-1,2,4-triazine-3,5(2H,4H)-dione (23a) (40 mg, 135.10 umol) and 6-(2,6-dichloro-4-(4,4,5,5-tetramethyl-1,3,2-dioxaborolan-2-yl)phenoxy)-4-isopropyl-2-methylpyridazin-3(2H)-one (1f) (59.33 mg, 135.10 umol) in dioxane (3 mL) and H₂O (1 mL) was added K₂CO₃ (37.34 mg, 270.21 umol) and Pd(dppf)Cl₂ (9.89 mg, 13.51 umol) under N₂. Then the mixture was stirred at 90° C. for 16 hours under N₂. LCMS and TLC showed the reaction was completed. The mixture was concentrated in vacuum. The residue was extracted with ethyl acetate (10 mL) and brine (5 mL). The organic layer was concentrated in vacuum. The residue was purified by Prep-TLC (SiO₂, Dichloromethane:Methanol) to give 24. MS mass calculated for [M+1]⁺ (C₁₉H₁₇Cl₂F₂N₅O₄) requires m/z 488.0, LCMS found m/z 488.0. ¹H NMR (400 MHz, DMSO-d6) δ 12.62 (br s, 1H), 8.13 (s, 2H), 7.46 (s, 1H), 6.24-6.60 (m, 1H), 4.34-4.49 (m, 2H), 3.39 (s, 3H), 3.08-3.12 (m, 1H), 1.21 (d, J 7.0 Hz, 6H).

Example S25: 6-(3,5-dichloro-2-fluoro-4-((5-isopropyl-1-methyl-6-oxo-1,6-dihydropyridazin-3-yl)oxy)phenyl)-1,2,4-triazine-3,5(2H,4H)-dione (Compound 25

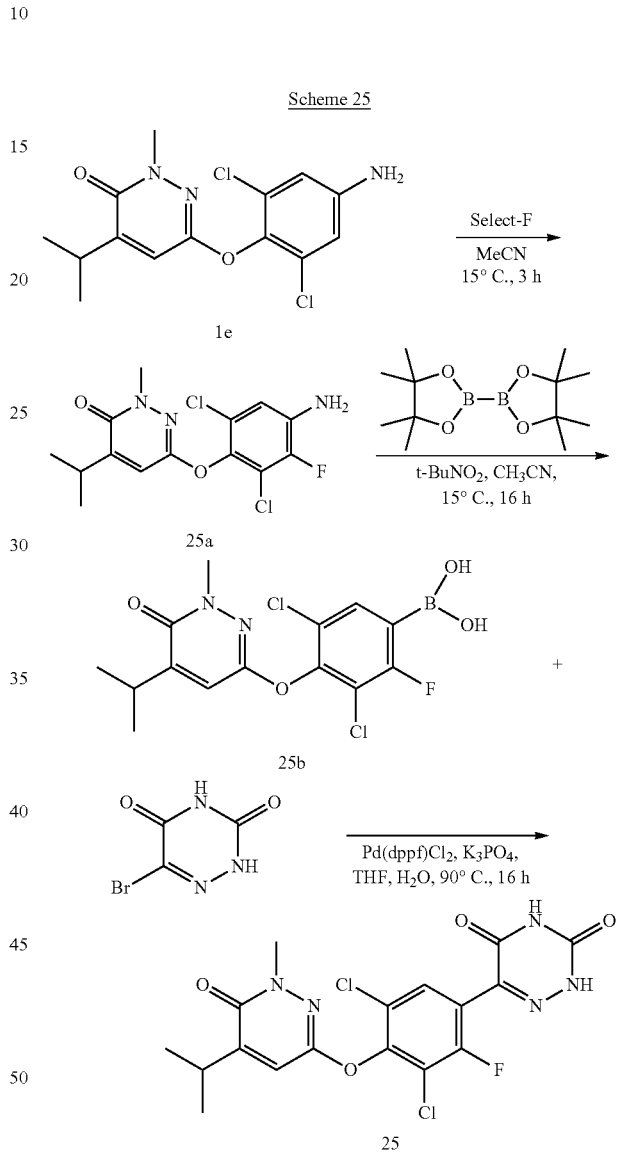

6-(4-amino-2,6-dichloro-3-fluorophenoxy)-4-isopropyl-2-methylpyridazin-3(2H)-one (25a To a solution of 6-(4-amino-2,6-dichlorophenoxy)-4-isopropyl-2-methylpyridazin-3(2H)-one (1e) (500 mg, 1.52 mmol) in MeCN (10 mL) was added Select F (593.68 mg, 1.68 mmol). The mixture was stirred at 15° C. for 3 hours. TLC and LCMS showed 1e was consumed completely and the desired MS was detected. The reaction was quenched by addition H₂O 10 mL. The reaction mixture was partitioned between ethyl acetate (20 mL) and H₂O (30 mL). The organic phase was separated, dried over Na₂SO₄, filtered and concentrated under reduced pressure. The residue was purified by column chromatography (SiO$_2$, Petroleum ether:Ethyl acetate) to give 25a. MS mass calculated for [M+1]$^+$ (C$_{14}$H$_{14}$Cl$_2$FN$_3$O$_2$) requires m/z 346.0, LCMS found m/z 346.2. $^1$H NMR (400 MHz, CDCl$_3$) δ 7.02 (d, J=0.6 Hz, 1H), 6.78-6.85 (m, 1H), 3.88 (s, 1H), 3.52-3.57 (m, 3H), 3.24 (dt, J=14.2, 7.0 Hz, 1H), 1.26 (d, J=6.8 Hz, 6H).

(3,5-dichloro-2-fluoro-4-((5-isopropyl-1-methyl-6-oxo-1,6-dihydropyridazin-3-yl)oxy)phen-yl)boronic acid (25b To a mixture of 6-(4-amino-2,6-dichloro-3-fluorophenoxy)-4-isopropyl-2-methylpyridazin-3(2H)-one (25a) (150 mg, 433.30 umol) and 4,4,4',4',5,5,5',5'-octamethyl-2,2'-bi (1,3,2-dioxaborolane) (2.20 g, 8.67 mmol) in CH$_3$CN (8 mL) was added t-BuONO (89.36 mg, 866.59 umol, 103.07 uL) at 15° C. Then the mixture was stirred at 15° C. for 16 hours. TLC, LCMS and HPLC showed 25a was consumed completely and the desired MS was detected. The mixture was concentrated in vacuum. The residue was purified by Prep-HPLC (column: Welch Ultimate AQ-C18 150*30 mm*5 um; mobile phase: [water (0.1% TFA)-ACN]) to give 25b. MS mass calculated for [M+1]$^+$ (C$_{14}$H$_{14}$BCl$_2$FN$_2$O$_4$) requires m/z 375.0, LCMS found m/z 375.1. $^1$H NMR (400 MHz, CDCl$_3$) δ 7.87 (s, 1H), 7.07 (s, 1H), 3.51 (s, 3H), 3.23-3.29 (m, 1H), 1.38 (s, 3H), 1.27-1.29 (m, 6H).

6-(3,5-dichloro-2-fluoro-4-((5-isopropyl-1-methyl-6-oxo-1,6-dihydropyridazin-3-yl)oxy)phenyl)-1,2,4-triazine-3,5(2H,4H)-dione (25

To a mixture of (3,5-dichloro-2-fluoro-4-((5-isopropyl-1-methyl-6-oxo-1,6-dihydropyridazin-3-yl)oxy)phen-yl)boronic acid (25b) (10 mg, 26.67 umol) and 6-bromo-1,2,4-triazine-3,5(2H,4H)-dione (7.68 mg, 40.00 umol) in THF (2 mL) and H$_2$O (0.5 mL) was added ditert-butyl(cyclopentyl)phosphane; dichloropalladium; iron (1.74 mg, 2.67 umol) and K$_3$PO$_4$ (11.32 mg, 53.34 umol). Then the mixture was degassed and purged with N$_2$ for 3 times, and the mixture was stirred at 90° C. for 16 hours under N$_2$ atmosphere. LCMS and HPLC showed 25b was consumed completely and the desired MS was detected. The reaction mixture was concentrated under reduced pressure. The residue was purified by Prep-HPLC (column: Luna C18 100*30 5 u; mobile phase: [water (0.1% TFA)-ACN]) to give 25. MS mass calculated for [M+1]$^+$ (C$_{17}$H$_{14}$Cl$_2$FN$_5$O$_4$) requires m/z 442.0, LCMS found m/z 442.0. $^1$H NMR (400 MHz, MeOH-d4) δ 7.72 (d, J=6.8 Hz, 1H), 7.38 (s, 1H), 3.51 (s, 3H), 3.20 (dt, J=13.6, 6.8 Hz, 1H), 1.28 (d, J=6.8 Hz, 6H).

Example S26: 6-(4-((5-isopropyl-6-oxo-1,6-dihydropyridazin-3-yl)methyl)-3,5-dimethylphenyl)-2-methyl-1,2,4-triazine-3,5(2H,4H)-dione (Compound 26

Scheme 26

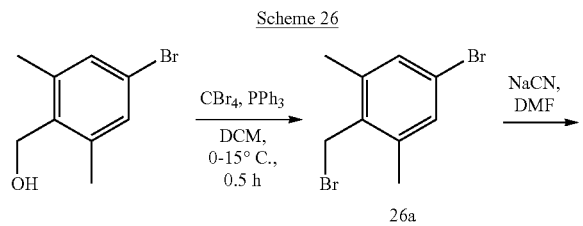

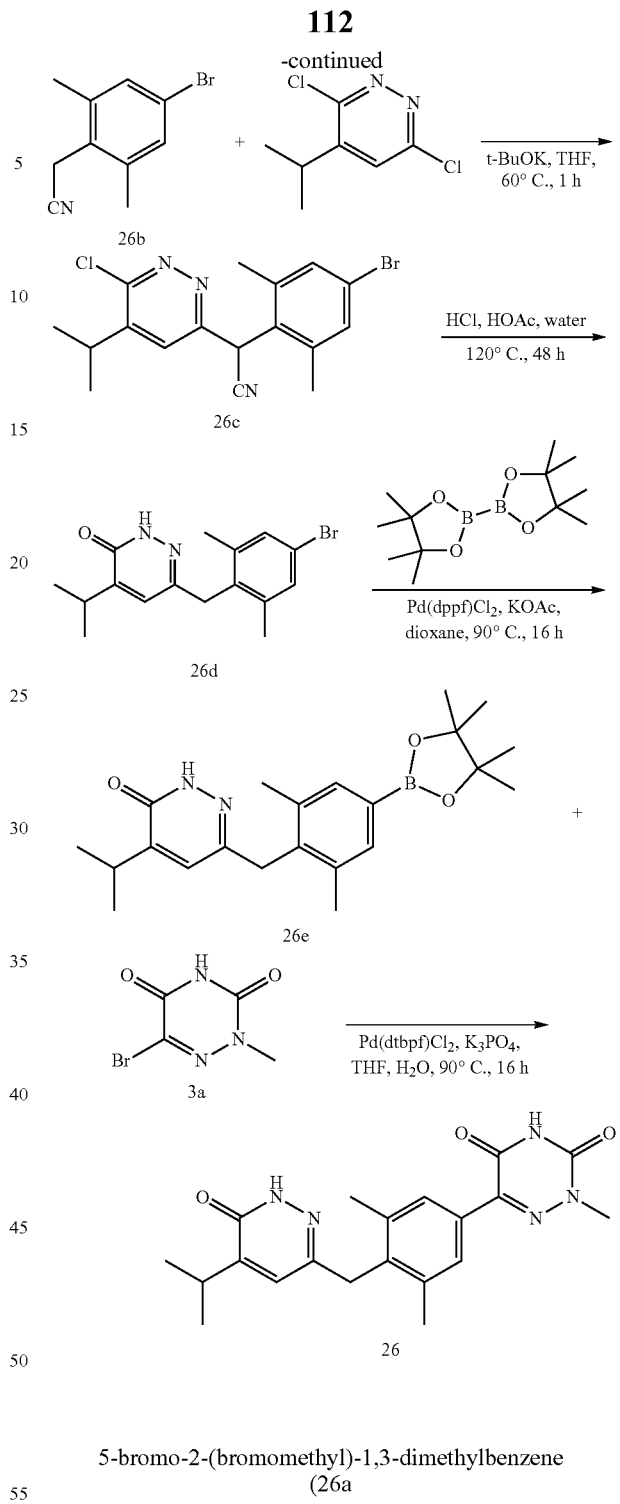

5-bromo-2-(bromomethyl)-1,3-dimethylbenzene (26a

To a solution of (4-bromo-2,6-dimethylphenyl)methanol (1 g, 4.65 mmol) in DCM (30 mL) was added PPh$_3$ (1.83 g, 6.97 mmol) under N$_2$. Then the mixture was cooled to 0-5° C. and CBr$_4$ (2.31 g, 6.97 mmol) was added to the mixture by portions. Then the mixture was stirred at 15° C. for 0.5 hours under N$_2$. TLC showed the starting material was consumed completely and one new spot was formed. The mixture was concentrated in vacuum. The residue was purified by column chromatography (SiO$_2$, Petroleum ether: Ethyl acetate) to give 26a. $^1$H NMR (400 MHz, CDCl$_3$) δ 7.21 (s, 2H), 4.50 (s, 2H), 2.39 (s, 6H).

2-(4-bromo-2,6-dimethylphenyl)acetonitrile (26b

To a solution of 5-bromo-2-(bromomethyl)-1,3-dimethylbenzene (26a) (1.26 g, 4.53 mmol) in DMF (30 mL) was added NaCN (244.35 mg, 4.99 mmol) at 15° C. Then the mixture was stirred at 15° C. for 16 hours. TLC showed 26a was consumed completely and one new spot was formed. The mixture was poured into $NH_4C_1$ aqueous solution (20 mL), and extracted with Ethyl acetate (30 mL*3). The combined organic phase was washed with brine (30 mL*2), dried with anhydrous $Na_2SO_4$, filtered and concentrated in vacuum. The residue was purified by column chromatography ($SiO_2$, Petroleum ether:Ethyl acetate) to give 26b. $^1$H NMR (400 MHz, MeOH-d4) δ 7.28 (s, 2H), 3.79 (s, 2H), 2.38 (s, 6H).

2-(4-bromo-2,6-dimethylphenyl)-2-(6-chloro-5-isopropylpyridazin-3-yl)acetonitrile (26c To a solution of 2-(4-bromo-2,6-dimethylphenyl)acetonitrile (26b) (800 mg, 3.57 mmol) and 3,6-dichloro-4-isopropylpyridazine (682.05 mg, 3.57 mmol) in THF (10 mL) was added t-BuOK (1 M, 7.14 mL) by drop-wise at 60° C., the resulting mixture was heated to 60° C. for 1 hour. TLC and LCMS showed 26b was consumed completely and the desired MS was detected. The mixture was poured into water (20 mL) and extracted with ethyl acetate (30 mL*2). The combined organic phase was washed with brine (20 mL*3), dried with anhydrous $Na_2SO_4$, filtered and concentrated. The residue was purified by column chromatography ($SiO_2$, Petroleum ether:Ethyl acetate) to give 26c. MS mass calculated for $[M+1]^+$ ($C_{17}H_{17}BrClN_3$) requires m/z 378.0, LCMS found m/z 378.2. $^1$H NMR (400 MHz, MeOH-d4) δ 7.34 (s, 3H), 7.21 (s, 1H), 6.28 (s, 1H), 3.01 (dt, J=13.4, 6.8 Hz, 1H), 2.89 (dt, J=13.8, 6.8 Hz, 1H), 2.27 (s, 6H), 1.30-1.27 (m, 6H).

6-(4-bromo-2,6-dimethylbenzyl)-4-isopropylpyridazin-3(2H)-one (26d

A solution of 2-(4-bromo-2,6-dimethylphenyl)-2-(6-chloro-5-isopropylpyridazin-3-yl)acetonitrile (26c) (1 g, 2.78 mmo) in AcOH (10 mL), $H_2O$ (10 mL) and HCl (40 mL) was heated to 120° C. for 48 hours. LCMS showed 26c was consumed completely and the desired MS was detected. The mixture was adjusted to pH-7 with 3M NaOH at 15° C., and lots the solid was collected by filtration and dried to give 26d. MS mass calculated for $[M+1]^+$ ($C_{16}H_{19}BrN_2O$) requires m/z 335.1, LCMS found m/z 335.2. $^1$H NMR (400 MHz, DMSO-d6) δ 12.56 (s, 1H), 7.24 (s, 2H), 7.11 (s, 1H), 3.90 (s, 2H), 2.97 (quin, J=6.8 Hz, 1H), 2.21 (s, 6H), 1.11 (d, J=6.8 Hz, 6H).

6-(2,6-dimethyl-4-(4,4,5,5-tetramethyl-1,3,2-dioxaborolan-2-yl)benzyl)-4-isopropylpyridazin-3(2H)-one (26e To a solution of 6-(4-bromo-2,6-dimethylbenzyl)-4-isopropylpyridazin-3(2H)-one (26d) (50 mg, 149.15 umol) and 4,4,5,5-tetramethyl-2-(4,4,5,5-tetramethyl-1,3,2-dioxaborolan-2-yl)-1,3,2-dioxaborolane (113.62 mg, 447.44 umol) in dioxane (3 mL) was added KOAc (73.19 mg, 745.74 umol) and Pd(dppf)Cl$_2$ (10.91 mg, 14.91 umol). The mixture was degassed and purged with $N_2$ for 3 times and stirred at 90° C. for 16 hours. TLC and LCMS showed 26d was consumed completely and the desired MS was detected. The mixture was poured into water (10 mL) and extracted with ethyl acetate (20 mL*2). The combined organic phase was washed with brine (10 mL*2), dried with anhydrous $Na_2SO_4$, filtered and concentrated in vacuum. The residue was purified by Prep-TLC (Petroleum ether:Ethyl acetate) to give 26e. MS mass calculated for $[M+1]^+$ ($C_{22}H_{31}BN_2O_3$) requires m/z 383.2, LCMS found m/z 383.4. $^1$H NMR (400 MHz, MeOH-d4) δ 7.42 (s, 2H), 6.98 (s, 1H), 4.05 (s, 2H), 3.06 (dt, J=13.6, 6.8 Hz, 1H), 2.29 (s, 6H), 1.34 (s, 12H), 1.14 (d, J=6.8 Hz, 6H).

6-(4-((5-isopropyl-6-oxo-1,6-dihydropyridazin-3-yl)methyl)-3,5-dimethylphenyl)-2-methyl-1,2,4-triazine-3,5(2H,4H)-dione (26

To a mixture of 6-(2,6-dimethyl-4-(4,4,5,5-tetramethyl-1,3,2-dioxaborolan-2-yl)benzyl)-4-isopropylpyridazin-3(2H)-one (26e) (32 mg, 83.70 umol) and 6-bromo-2-methyl-1,2,4-triazine-3,5(2H,4H)-dione (3a) (25.86 mg, 125.55 umol) in THF (4 mL) and $H_2O$ (1 mL) was added Pd(dppf)Cl$_2$ (5.46 mg, 8.37 umol) and $K_3PO_4$ (35.53 mg, 167.41 umol). Then the mixture was degassed and purged with $N_2$ for 3 times. Then the mixture was stirred at 90° C. for 16 hours under $N_2$ atmosphere. HPLC and LCMS showed 26e was consumed completely and the desired MS was detected. The reaction mixture was concentrated under reduced pressure. The residue was purified by Prep-HPLC (column: Waters Xbridge 150*25 5 u; mobile phase: [water (10 mM $NH_4HCO_3$)-ACN]) to give 26. MS mass calculated for $[M+1]^+$ ($C_{20}H_{23}N_5O_3$) requires m/z 382.2, LCMS found m/z 382.2. $^1$H NMR (400 MHz, MeOH-d4) δ 7.68 (s, 2H), 7.04 (s, 1H), 4.07 (s, 2H), 3.65 (s, 3H), 3.07 (dt, J=13.8, 6.6 Hz, 1H), 2.33 (s, 6H), 1.15 (d, J=6.8 Hz, 6H).

Example S27: 6-(3,5-dichloro-4-((6-oxo-5-(pentan-3-yl)-1,6-dihydropyridazin-3-yl)oxy)phenyl)-2-methyl-1,2,4-triazine-3,5(2H,4H)-dione (Compound 27

Scheme 27

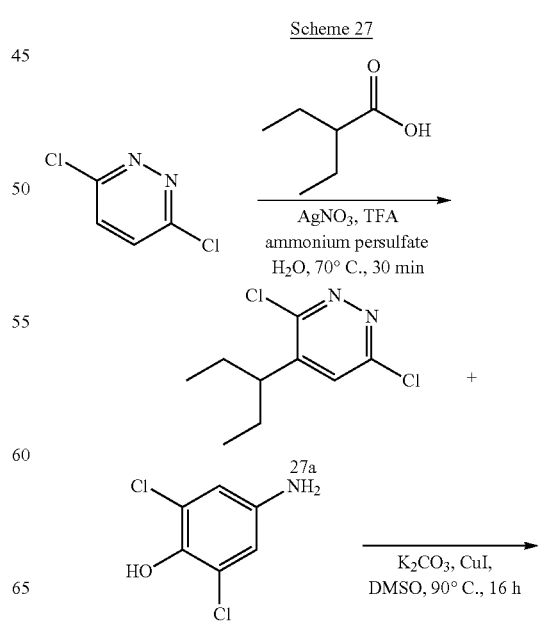

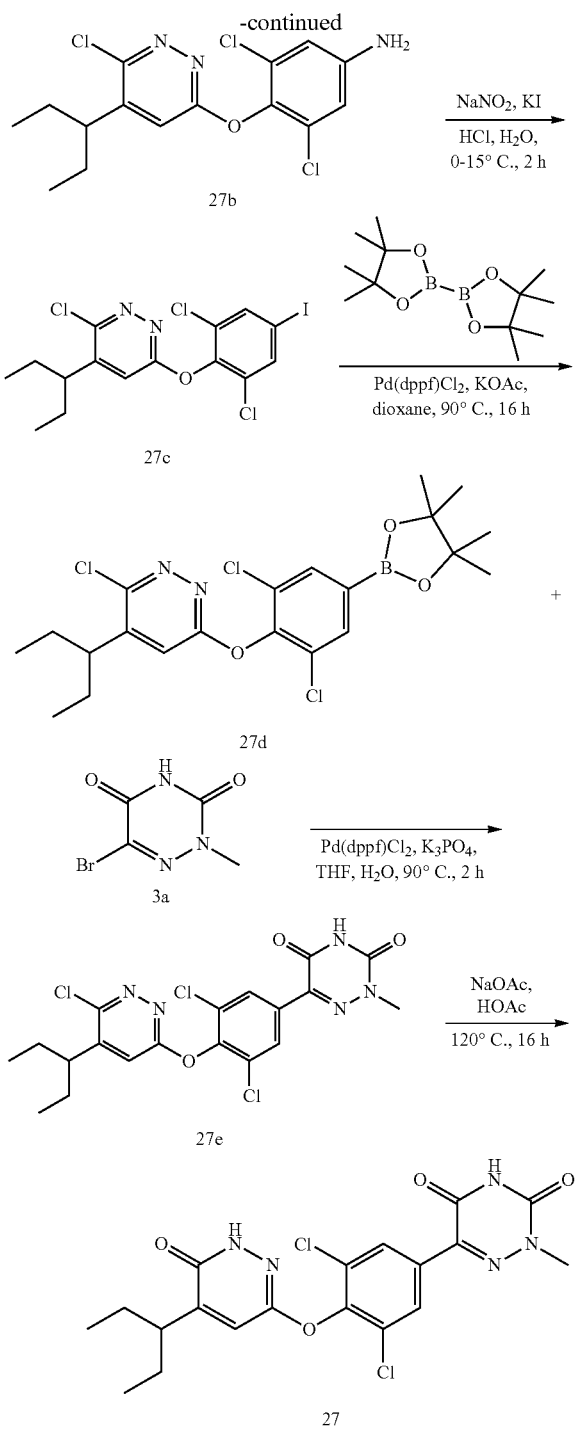

(30 mL*2). The combined organic phase was washed with brine (2 mL*2), dried with anhydrous $Na_2SO_4$, filtered and concentrated in vacuum. The residue was purified by column chromatography ($SiO_2$, Petroleum ether:Ethyl acetate) to give 27a. $^1$H NMR (400 MHz, $CDCl_3$) δ 7.23 (s, 1H), 2.89-2.98 (m, 1H), 1.67-1.80 (m, 2H), 1.55-1.64 (m, 2H), 0.82 (t, J=7.4 Hz, 6H).

3,5-dichloro-4-((6-chloro-5-(pentan-3-yl)pyridazin-3-yl)oxy)aniline (27b

To a solution of 3,6-dichloro-4-(pentan-3-yl)pyridazine (27a) (530 mg, 2.42 mmol) and 4-amino-2,6-dichlorophenol (516.72 mg, 2.90 mmol) in DMSO (20 mL) was added $K_2CO_3$ (1.34 g, 9.68 mmol) and CuI (276.40 mg, 1.45 mmol). The reaction mixture was degassed and purged with $N_2$ for 3 times, and then stirred at 90° C. for 16 hours under $N_2$ atmosphere. TLC and LCMS showed 27a was consumed completely and the desired MS was detected. The mixture was concentrated in vacuum. The residue was extracted with ethyl acetate (50 mL*2) and $H_2O$ (20 mL). The combined organic phase was washed with brine (20 mL*3), dried with anhydrous $Na_2SO_4$, filtered and concentrated in vacuum. The residue was purified by column chromatography ($SiO_2$, Petroleum ether:Ethyl acetate) to give 27b. MS mass calculated for $[M+1]^+$ ($C_{15}H_{16}C_{13}N_{30}$) requires m/z 360.0, LCMS found m/z 360.1. $^1$H NMR (400 MHz, MeOH-d4) δ 7.40 (s, 1H), 6.74 (s, 2H), 4.86 (s, 4H), 2.96-3.05 (m, 1H), 1.65-1.88 (m, 4H), 0.87 (t, J=7.4 Hz, 6H).

3-chloro-6-(2,6-dichloro-4-iodophenoxy)-4-(pentan-3-yl)pyridazine (27c

To a solution of 3,5-dichloro-4-((6-chloro-5-(pentan-3-yl)pyridazin-3-yl)oxy)aniline (27b) (575 mg, 1.59 mmol) in HCl (5 mL) was added $NaNO_2$ (132.00 mg, 1.91 mmol) at 0° C., and the mixture was stirred at 0° C. for 0.5 hours. Then a solution of KI (529.31 mg, 3.19 mmol) in $H_2O$ (5 mL) was added in the reaction mixture, and the mixture was stirred at 15° C. for another 1.5 hours. TLC and LCMS showed 27b was consumed completely and the desired mass was detected. The mixture was extracted with ethyl acetate (100 mL*2) and $H_2O$ (50 mL). The combined organic phase was washed with brine (50 mL*3), dried with anhydrous $Na_2SO_4$, filtered and concentrated in vacuum. The residue was purified by column chromatography ($SiO_2$, Petroleum ether:Ethyl acetate) to give 27c. MS mass calculated for $[M+1]^+$ ($C_{15}H_{14}Cl_3IN_2O$) requires m/z 470.9, LCMS found m/z 470.8. $^1$H NMR (400 MHz, $CDCl_3$) δ 7.73 (s, 2H), 7.13 (s, 1H), 2.96-3.05 (m, 1H), 1.61-1.87 (m, 4H), 0.89 (t, J 7.46 Hz, 6H).

3-chloro-6-(2,6-dichloro-4-(4,4,5,5-tetramethyl-1,3,2-dioxaborolan-2-yl)phenoxy)-4-(pentan-3-yl)pyridazine (27d To a solution of 3-chloro-6-(2,6-dichloro-4-iodophenoxy)-4-(pentan-3-yl)pyridazine (27c) (500 mg, 1.06 mmol) and 4,4,5,5-tetramethyl-2-(4,4,5,5-tetramethyl-1,3,2-dioxaborolan-2-yl)-1,3,2-dioxaborolane (807.78 mg, 3.18 mmol) in dioxane (15 mL) was added KOAc (520.32 mg, 5.30 mmol) and Pd(dppf)$Cl_2$ (77.59 mg, 106.03 umol). The mixture was degassed and purged with $N_2$ for 3 times and stirred at 90° C. for 16 hours. TLC and LCMS showed 27d was consumed completely and the desired mass was detected. The mixture was extracted with ethyl acetate (50 mL*2) and $H_2O$ (20 mL). The combined organic phase was 3,6-dichloro-4-(pentan-3-yl)pyridazine (27a To a mixture of 3,6-dichloropyridazine (1 g, 6.71 mmol) and 2-ethylbutanoic acid (779.70 mg, 6.71 mmol, 845.66 uL) in $H_2O$ (20 mL) was added $AgNO_3$ (1.14 g, 6.71 mmol) and TFA (2.30 g, 20.14 mmol, 1.49 mL) in one portion at 50° C., Then a solution of $(NH_4)_2S_2O_8$ (4.60 g, 20.14 mmol, 4.38 mL) in $H_2O$ (10 mL) was added in the mixture, and the mixture was stirred at 70° C. for 30 minutes. LCMS showed the reaction was completed. The reaction mixture was poured into water (20 mL) and extracted with Ethyl acetate washed with brine (20 mL*3), dried with anhydrous Na₂SO₄, filtered and concentrated in vacuum. The residue was purified by column chromatography (SiO₂, Petroleum ether:Ethyl acetate) to give 27d. MS mass calculated for [M+1]⁺ (C₂₁H₂₆BCl₃N₂O₃) requires m/z 471.1, LCMS found m/z 471.1. ¹H NMR (400 MHz, CDCl₃) δ 7.81 (s, 2H), 7.13 (s, 1H), 2.94-3.04 (m, 1H), 1.62-1.86 (m, 4H), 1.35 (s, 11H), 0.89 (t, J=7.4 Hz, 6H).

6-(3,5-dichloro-4-((6-chloro-5-(pentan-3-yl) pyridazin-3-yl)oxy)phenyl)-2-methyl-1,2,4-triazine-3,5(2H,4H)-dione (27e To a mixture of 3-chloro-6-(2,6-dichloro-4-(4,4,5,5-tetramethyl-1,3,2-dioxaborolan-2-yl)phenoxy)-4-(pentan-3-yl)pyridazine (27d) (150 mg, 318.06 umol) and 6-bromo-2-methyl-1,2,4-triazine-3,5(2H,4H)-dione (98.28 mg, 477.09 umol) in THF (4 mL) and H₂O (1 mL) was added Pd(dppf)Cl₂ (20.73 mg, 31.81 umol) and K₃PO₄ (135.03 mg, 636.12 umol) was degassed and purged with N₂ for 3 times, and then the mixture was stirred at 90° C. for 2 hours under N₂ atmosphere. TLC and LCMS showed 27d was consumed completely and the desired MS was detected. The reaction mixture was dissolved in water and the pH was adjusted to 4 with HCl (1M, 1 mL). Then the mixture was partitioned with ethyl acetate (20 mL*2). The combined organic phase was washed with brine (10 mL*3), dried with anhydrous Na₂SO₄, filtered and concentrated in vacuum. The residue was purified by Prep-TLC (Petroleum ether:Ethyl acetate) to give 27e. MS mass calculated for [M+1]⁺ (C₁₉H₁₈C₁₃N₅O₃) requires m/z 470.0, LCMS found m/z 470.1. ¹H NMR (400 MHz, MeOH-d4) δ 8.25 (s, 2H), 7.61 (s, 1H), 4.10 (q, J=7.2 Hz, 1H), 3.69 (s, 3H), 1.71-1.90 (m, 5H), 0.90 (t, J=7.4 Hz, 7H).

6-(3,5-dichloro-4-((6-oxo-5-(pentan-3-yl)-1,6-dihydropyridazin-3-yl)oxy)phenyl)-2-methyl-1,2,4-triazine-3,5(2H,4H)-dione (27

To a solution of 6-(3,5-dichloro-4-((6-chloro-5-(pentan-3-yl)pyridazin-3-yl)oxy)phenyl)-2-methyl-1,2,4-triazine-3,5(2H,4H)-dione (27e) (80 mg, 169.95 umol) in AcOH (5 mL) was added NaOAc (69.71 mg, 849.73 umol) at 15° C. Then the mixture was stirred at 120° C. for 16 hours. LCMS and HPLC showed 27e was consumed completely and the desired MS was detected. The reaction mixture was concentrated under reduced pressure. The residue was purified by Prep-HPLC (column: Luna C18 100*30 5 u; mobile phase: [water (0.225% FA)-ACN]) to give 27. MS mass calculated for [M+1]⁺ (C₁₉H₁₉Cl₂N₅O₄) requires m/z 452.1, LCMS found m/z 452.1. ¹H NMR (400 MHz, DMSO-d6) δ 12.44 (br s, 1H), 12.19 (s, 1H), 8.09 (s, 2H), 7.43 (s, 1H), 3.57 (s, 3H), 2.78 (quin, J=7.0 Hz, 1H), 1.59-1.68 (m, 4H), 0.79 (t, J=7.4 Hz, 6H).

Example S28: 6-(3,5-dichloro-4-((5-ethyl-6-oxo-1,6-dihydropyridazin-3-yl)oxy)phenyl)-2-methyl-1,2,4-triazine-3,5(2H,4H)-dione (Compound 28

Scheme 28

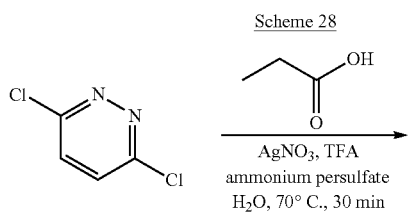

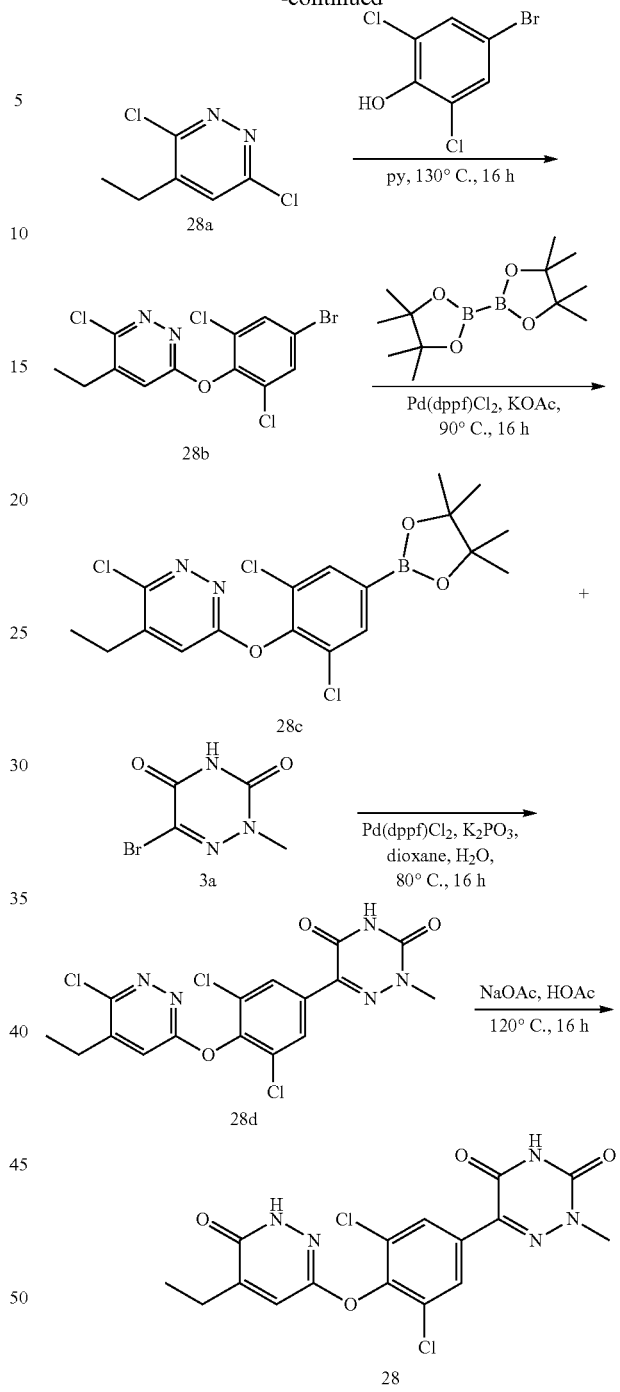

3,6-dichloro-4-ethylpyridazine (28a

To a mixture of 3,6-dichloropyridazine (1 g, 6.71 mmol) and propionic acid (497.24 mg, 6.71 mmol, 500.75 uL) in H₂O (30 mL) was added TFA (2.30 g, 20.14 mmol, 1.49 mL) and AgNO₃ (1.14 g, 6.71 mmol) and (NH₄)₂S₂O₈ (4.60 g, 20.14 mmol, 4.38 mL) in one portion at 50° C. The mixture was stirred at 70° C. for 30 minutes. LCMS showed 3,6-dichloropyridazine was completed. The residue was poured into NaHCO₃(20 mL). The aqueous phase was extracted with ethyl acetate (30 mL*2). The combined organic phase was washed with brine (15 mL*2), dried with anhydrous Na$_2$SO$_4$, filtered and concentrated in vacuum. The residue was purified by column chromatography (SiO$_2$, Petroleum ether:Ethyl acetate) to give 28a. MS mass calculated for [M+1]$^+$ (C$_6$H$_6$Cl$_2$N$_2$) requires m/z 177.0, LCMS found m/z 177.0. $^1$H NMR (400 MHz, CDCl$_3$) δ 8.12-8.16 (m, 2H), 7.90-7.92 (m, 1H), 3.12-3.21 (m, 1H), 1.29 (d, J=7.0 Hz, 6H).

6-(4-bromo-2,6-dichlorophenoxy)-3-chloro-4-ethylpyridazine (28b

A solution of 3,6-dichloro-4-ethylpyridazine (28a) (340 mg, 1.92 mmol) and 4-bromo-2,6-dichlorophenol (511.04 mg, 2.11 mmol) in Py (5 mL) was stirred at 130° C. for 16 hours in microwave tube. LCMS and TLC (Petroleum ether:Ethyl acetate=5:1, Rf=0.5) showed 28a was consumed completely, and desired MS was detected. The residue was poured into water (5 mL). The aqueous phase was extracted with ethyl acetate (10 mL*2). The combined organic phase was washed with brine (5 mL*2), dried with anhydrous Na$_2$SO$_4$, filtered and concentrated in vacuum. The residue was purified by Prep-TLC (Petroleum ether:Ethyl acetate) to give 28b (200 mg, crude). MS mass calculated for [M+1]+ (C$_{12}$H$_8$BrCl$_3$N$_2$O) requires m/z 380.9, LCMS found m/z 380.9. $^1$H NMR (400 MHz, CDCl$_3$) δ 7.44 (s, 4H), 7.15 (s, 1H), 7.10 (s, 1H), 2.72-2.80 (m, 3H), 2.66-2.71 (m, 2H), 1.22-1.31 (m, 7H), 1.17 (br t, J=7.58 Hz, 3H).

3-chloro-6-(2,6-dichloro-4-(4,4,5,5-tetramethyl-1,3,2-dioxaborolan-2-yl)phenoxy)-4-ethylpyridazine (28c To a solution of 6-(4-bromo-2,6-dichlorophenoxy)-3-chloro-4-ethylpyridazine (28b) (150 mg, 392.19 umol) and 4,4,5,5-tetramethyl-2-(4,4,5,5-tetramethyl-1,3,2-dioxaborolan-2-yl)-1,3,2-dioxaborolane (298.78 mg, 1.18 mmol) in dioxane (6 mL) was added Pd(dppf)Cl$_2$ (28.70 mg, 39.22 umol) and KOAc (192.45 mg, 1.96 mmol). The mixture was stirred at 90° C. for 16 hours under N$_2$ atmosphere. TLC (Petroleum ether:Ethyl acetate) indicated 28b was consumed completely. The suspension was filtered through a pad of Celite and the pad cake was washed with ethyl acetate (15 mL*3). The combined filtrates were concentrated in vacuum. The residue was purified by Prep-TLC (SiO$_2$, Petroleum ether:Ethyl acetate) to give 28c. MS mass calculated for [M+1]$^+$ (C$_{18}$H$_{20}$BCl$_3$N$_2$O$_3$) requires m/z 429.1, LCMS found m/z 429.1.

6-(3,5-dichloro-4-((6-chloro-5-ethylpyridazin-3-yl)oxy)phenyl)-2-methyl-1,2,4-triazine-3,5(2H,4H)-dione (28d To a solution of 3-chloro-6-(2,6-dichloro-4-(4,4,5,5-tetramethyl-1,3,2-dioxaborolan-2-yl)phenoxy)-4-ethylpyridazine (28c) (160 mg, 372.50 umol) and 6-bromo-2-methyl-1,2,4-triazine-3,5(2H,4H)-dione (3a) (115.10 mg, 558.75 umol) in THF (4 mL) was added Pd(dppf)Cl$_2$ (24.28 mg, 37.25 umol) and K$_3$PO$_4$ (158.14 mg, 745.00 umol) in H$_2$O (1 mL). The mixture was stirred at 80° C. for 16 hours. LCMS showed 28c was consumed completely and the desired MS was detected. The mixture was filtered and concentrated under reduced pressure. The residue was purified by Prep-HPLC (column: Luna C18 100*30 5 u; mobile phase: [water (0.2% FA)-ACN]) to give 28d. MS mass calculated for [M+1]+(C$_{16}$H$_{12}$C$_{13}$N$_5$O$_3$) requires m/z 428.0, LCMS found m/z 428.0. $^1$H NMR (400 MHz, MeOH-d4) δ 8.25 (s, 2H), 7.59 (s, 1H), 3.69 (s, 3H), 2.83-2.90 (m, 2H), 1.36 (t, J=7.6 Hz, 3H).

6-(3,5-dichloro-4-((5-ethyl-6-oxo-1,6-dihydropyridazin-3-yl)oxy)phenyl)-2-methyl-1,2,4-triazine-3,5(2H,4H)-dione (28

To a solution of 6-(3,5-dichloro-4-((6-chloro-5-ethylpyridazin-3-yl)oxy)phenyl)-2-methyl-1,2,4-triazine-3,5 (2H,4H)-dione (28d) (78 mg, 181.96 umol) in HOAc (3 mL) was added NaOAc (74.64 mg, 909.82 umol). The mixture was stirred at 120° C. for 16 hours. LCMS showed 28d was consumed completely and the desired mass was detected. The reaction mixture was concentrated under reduced pressure to remove AcOH. The residue was purified by Prep-HPLC (column: Luna C18 100*30 5 u; mobile phase: [water (0.225% FA)-ACN]) to give 28. MS mass calculated for [M+1]+(C$_{16}$H$_{13}$Cl$_2$N$_5$O$_4$) requires m/z 410.0, LCMS found m/z 410.0; $^1$H NMR (400 MHz, DMSO-d6) δ 8.32 (br s, 1H), 8.14 (s, 2H), 7.46 (s, 1H), 3.54 (s, 3H), 1.17 (t, J=7.4 Hz, 3H).

Example S29: 6-(3,5-dichloro-4-((5-(1-hydroxypropan-2-yl)-6-oxo-1,6-dihydropyridazin-3-yl)oxy)phenyl)-2-methyl-1,2,4-triazine-3,5(2H,4H)-dione (29

Scheme 29a

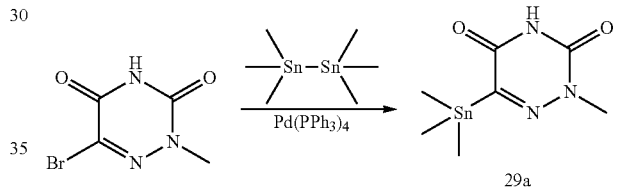

2-methyl-6-(trimethylstannyl)-1,2,4-triazine-3,5(2H,4H)-dione (29a

To a solution of 6-bromo-2-methyl-1,2,4-triazine-3,5(2H,4H)-dione (900 mg, 4.37 mmol) in toluene (15 mL) was added trimethyl(trimethylstannyl)stannane (1.72 g, 5.24 mmol, 1.09 mL), Pd(PPh$_3$)$_4$ (504.86 mg, 436.90 umol), the mixture was stirred at 110° C. for 16 hours under N$_2$ atmosphere. TLC indicated trace of starting material was remained, and one new spot was formed. The reaction mixture was concentrated in vacuum, and then diluted with ethyl acetate (15 mL) and washed with KF aqueous (10 mL*2), dried over with Na$_2$SO$_4$, filtered and concentrated under reduced pressure. The residue was purified by column chromatography (SiO$_2$, Petroleum ether:Ethyl acetate) to give 29a. MS mass calculated for [M+1]$^+$ (C$_7$H$_{13}$N$_3$O$_2$Sn) requires m/z 292.0, LCMS found m/z 292.2.

Scheme 29b

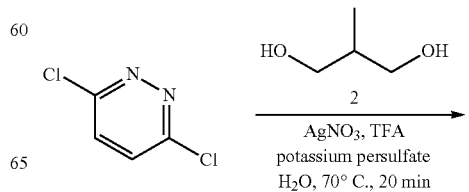

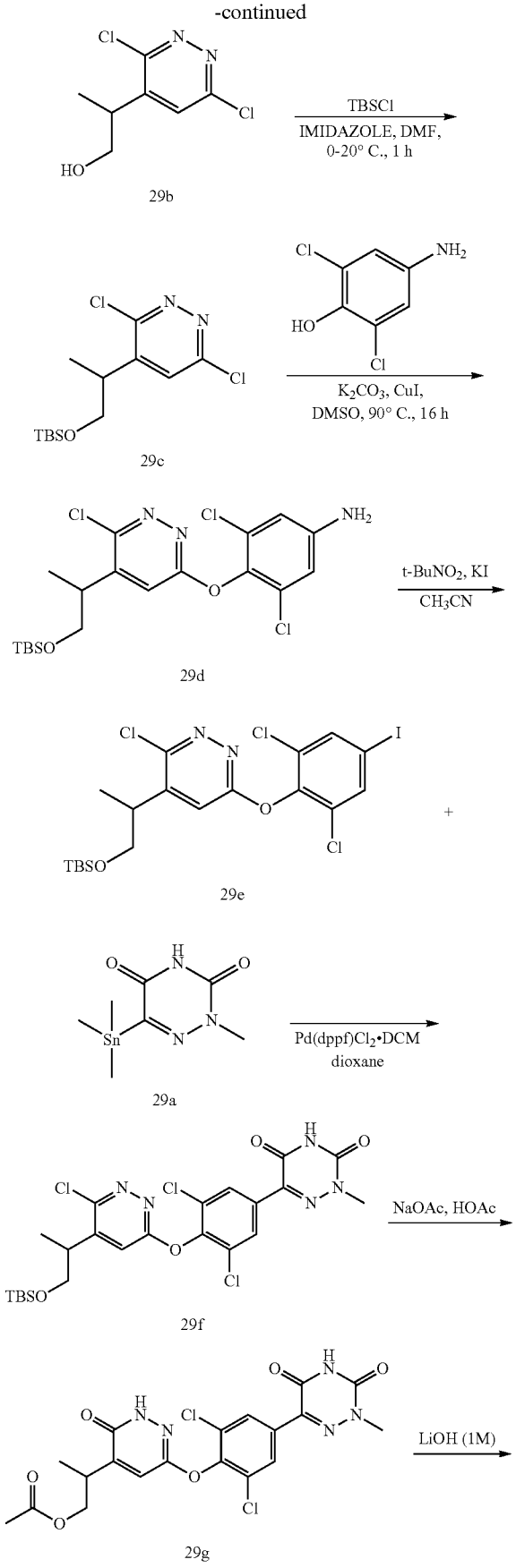

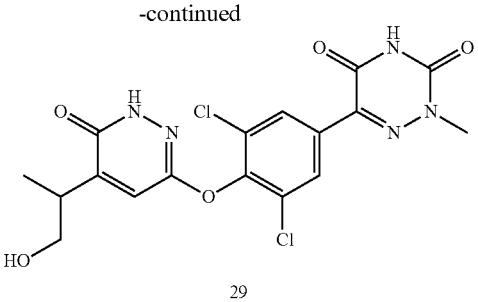

2-(3,6-dichloropyridazin-4-yl)propan-1-ol (29b

To a mixture of 3,6-dichloropyridazine (2 g, 13.42 mmol) and 2-methylpropane-1,3-diol (2.65 g, 29.40 mmol, 2.62 mL) in $H_2O$ (10 mL) was added TFA (1.88 g, 16.48 mmol, 1.22 mL) and $AgNO_3$ (3.07 g, 18.07 mmol) at 80° C. Then $(NH_4)_2S_2O_8$ (6.72 g, 10.93 mmol) was added in the mixture by one portion at 80° C. The mixture was stirred at 80° C. for 30 minutes. TLC showed the starting material was consumed completely. The residue was poured into water (10 mL). The aqueous phase was extracted with ethyl acetate (10 mL*2). The combined organic phase was washed with brine (5 mL*2), dried with anhydrous $Na_2SO_4$, filtered and concentrated in vacuum. The residue was purified by column chromatography ($SiO_2$, Petroleum ether:Ethyl acetate) to give 29b. $^1H$ NMR (400 MHz, $CDCl_3$) δ 7.51 (s, 1H), 3.84-3.91 (m, 2H), 3.33-3.42 (m, 1H), 1.35 (d, J=7.0 Hz, 3H).

4-(1-((tert-butyldimethylsilyl)oxy)propan-2-yl)-3,6-dichloropyridazine (29c

To a solution of 2-(3,6-dichloropyridazin-4-yl)propan-1-ol (29b) (700 mg, 3.38 mmol) and tert-butyl-chloro-dimethyl-silane (509.55 mg, 3.38 mmol, 414.26 uL) in DMF (15 mL) was added imidazole (276.18 mg, 4.06 mmol). The mixture was stirred at 25° C. for 1 hour under $N_2$ atmosphere. TLC indicated 29b was consumed completely. The reaction mixture was diluted with water (50 mL) and extracted with ethyl acetate (50 mL*3), The combined organic phase was washed with brine (50 mL*2), dried with anhydrous $Na_2SO_4$, filtered and concentrated in vacuum to give 29c. The product was used directly for the next step without further purification. MS mass calculated for $[M+1]^+$ ($C_{13}H_{22}Cl_2N_2OSi$) requires m/z 321.1, LCMS found m/z 321.2. $^1H$ NMR (400 MHz, $CDCl_3$) δ 7.48 (s, 1H), 3.73-3.81 (m, 2H), 3.29-3.39 (m, 1H), 1.32 (d, J=7.2 Hz, 3H), 0.84 (s, 9H), 0.01 (s, 3H), −0.04 (s, 3H).

4-((5-(1-((tert-butyldimethylsilyl)oxy)propan-2-yl)-6-chloropyridazin-3-yl)oxy)-3,5-dichloroaniline (29d To a solution of 4-(1-((tert-butyldimethylsilyl)oxy)propan-2-yl)-3,6-dichloropyridazine (29c) (300 mg, 933.66 umol) in DMSO (10 mL) was added 4-amino-2,6-dichlorophenol (225.85 mg, 933.66 umol), $K_2CO_3$ (387.12 mg, 2.80 mmol) and CuI (106.69 mg, 560.19 umol). The mixture was stirred at 90° C. for 6 hours under $N_2$ atmosphere. LCMS indicated 29c was consumed completely and the desired mass was detected. The suspension was filtered through a pad of Celite and the pad cake was washed with Ethyl acetate (50 mL). The reaction mixture was quenched by addition H₂O (30 mL) at 20° C., and then diluted with ethyl acetate (50 mL) and extracted with ethyl acetate (50 mL*5). The combined organic layers were washed with brine (50 mL*2), dried over Na₂SO₄, filtered and concentrated under reduced pressure. The residue was purified by Prep-HPLC (column: Welch Xtimate C18 150*25 mm*5 um; mobile phase: [water (10 mM NH₄HCO₃)-ACN]) to give 29d. MS mass calculated for [M+1]⁺ (C₁₉H₂₆Cl₃N₃O₂Si) requires m/z 462.1, LCMS found m/z 462.1. ¹H NMR (400 MHz, MeOH-d4) δ 7.44 (s, 1H), 6.73 (s, 2H), 3.83-3.92 (m, 2H), 3.37-3.45 (m, 1H), 1.34 (d, J=7.0 Hz, 3H), 0.83 (s, 9H), −0.01 (d, J=7.2 Hz, 6H).

4-(1-((tert-butyldimethylsilyl)oxy)propan-2-yl)-3-chloro-6-(2,6-dichloro-4-iodophenoxy)pyridazine (29e To a solution of 4-((5-(1-((tert-butyldimethylsilyl)oxy)propan-2-yl)-6-chloropyridazin-3-yl)oxy)-3,5-dichloroaniline (29d) (50 mg, 108.02 umol) in ACN (1 mL) was added tertbutylnitrite (22.28 mg, 216.04 umol) and KI (35.86 mg, 216.04 umol). Then the reaction mixture was degassed and purged with N₂ for 3 times. The mixture was stirred at 20° C. for 2 hours. TLC indicated 29d was consumed completely. The reaction mixture was concentrated under reduced pressure. The residue was diluted in H₂O (5 mL) and ethyl acetate (10 mL). The mixture was extracted with ethyl acetate (5 mL*3). The combined organic layers were washed with brine (10 mL), dried over Na₂SO₄, filtered and concentrated under reduced pressure. The residue was purified by Prep-TLC (SiO₂, Petroleum ether:Ethyl acetate) to give 29e. MS mass calculated for [M+1]⁺ (C₁₉H₂₄Cl₃₁N₂O₂Si) requires m/z 573.0, LCMS found m/z 573.0.

6-(4-((5-(1-((tert-butyldimethylsilyl)oxy)propan-2-yl)-6-chloropyridazin-3-yl)oxy)-3,5-dichlorophenyl)-2-methyl-1,2,4-triazine-3,5(2H,4H)-dione (29f To a solution of 4-(1-((tert-butyldimethylsilyl)oxy)propan-2-yl)-3-chloro-6-(2,6-dichloro-4-iodophenoxy)pyridazine (29e) (27 mg, 47.06 umol) in dioxane (1 mL) were added 2-methyl-6-(tributylstannyl)-1,2,4-triazine-3,5(2H,4H)-dione (29a) (13.92 mg, 48.00 umol) and Pd(dppf)Cl₂.CH₂Cl₂ (3.84 mg, 4.71 umol). Then the mixture was degassed and purged with N₂ for 3 times, and then the mixture was stirred at 110° C. for 16 hours under N₂ atmosphere. LCMS indicated 40% of 29e remained and the desired mass was detected. The suspension was filtered through a pad of Celite and the pad cake was washed with ethyl acetate (5 mL*3). The combined filtrates were concentrated in vacuum. The residue was purified by Prep-TLC (SiO₂, Petroleum ether:Ethyl acetate) to give 29f. MS mass calculated for [M+1]⁺ (C₂₃H₂₈Cl₁₃N₅O₄Si) requires m/z 572.1, LCMS found m/z 572.1.

2-(6-(2,6-dichloro-4-(2-methyl-3,5-dioxo-2,3,4,5-tetrahydro-1,2,4-triazin-6-yl)phenoxy)-3-oxo-2,3-dihydropyridazin-4-yl)propyl acetate (29g To a solution of 6-(4-((5-(1-((tert-butyldimethylsilyl)oxy)propan-2-yl)-6-chloropyridazin-3-yl)oxy)-3,5-dichlorophenyl)-2-methyl-1,2,4-triazine-3,5(2H,4H)-dione (29f) (19 mg, 33.16 umol) in HOAc (1 mL) was added NaOAc (13.60 mg, 165.81 umol). The mixture was stirred at 120° C. for 16 hours. LCMS showed 29f was consumed completely and one main peak with the desired MS was detected. The reaction mixture was concentrated under reduced pressure to remove AcOH to give 29g (30 mg, crude). The product was used into the next step without further purification. MS mass calculated for [M+1]⁺ (C₁₉H₁₇Cl₂N₅O₆) requires m/z 482.1, LCMS found m/z 482.1.

6-(3,5-dichloro-4-((5-(1-hydroxypropan-2-yl)-6-oxo-1,6-dihydropyridazin-3-yl)oxy)phenyl)-2-methyl-1,2,4-triazine-3,5(2H,4H)-dione (29

To a solution of 2-(6-(2,6-dichloro-4-(2-methyl-3,5-dioxo-2,3,4,5-tetrahydro-1,2,4-triazin-6-yl)phenoxy)-3-oxo-2,3-dihydropyridazin-4-yl)propyl acetate (29g) (30 mg, 62.21 umol) in THF (1 mL) was added LiOH.H₂O (1 M, 3 mL). The mixture was stirred at 20° C. for 16 hours. LCMS showed 29g was consumed completely and the desired mass was detected. The reaction mixture was concentrated under reduced pressure. The residue was purified by Prep-HPLC (column: Nano-micro Kromasil C18 100*30 mm 5 um; mobile phase: [water (0.225% FA)-ACN]) to give 29. MS mass calculated for [M+1]⁺ (C₁₇H₁₅Cl₂N₅O₅) requires m/z 440.0, LCMS found m/z 440.0. ¹H NMR (400 MHz, MeOH-d4) δ 8.18 (s, 2H), 7.39 (s, 1H), 3.78-3.86 (m, 1H), 3.64-3.74 (m, 4H), 3.21-3.27 (m, 1H), 1.30 (d, J=7.0 Hz, 3H).

Example S30: 6-(3,5-dichloro-4-((5-(1-hydroxypropyl)-6-oxo-1,6-dihydropyridazin-3-yl)oxy)phenyl)-2-methyl-1,2,4-triazine-3,5(2H,4H)-dione (Compound 30

Scheme 30

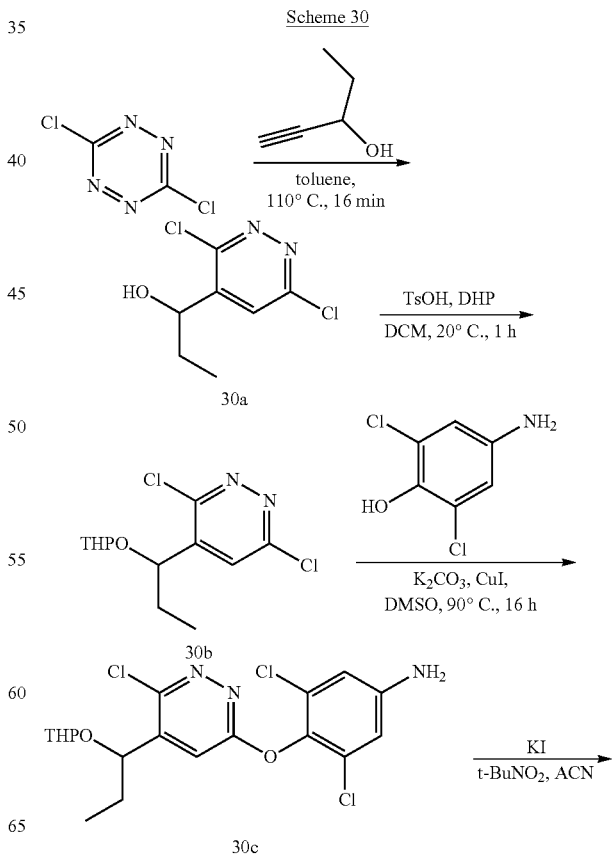

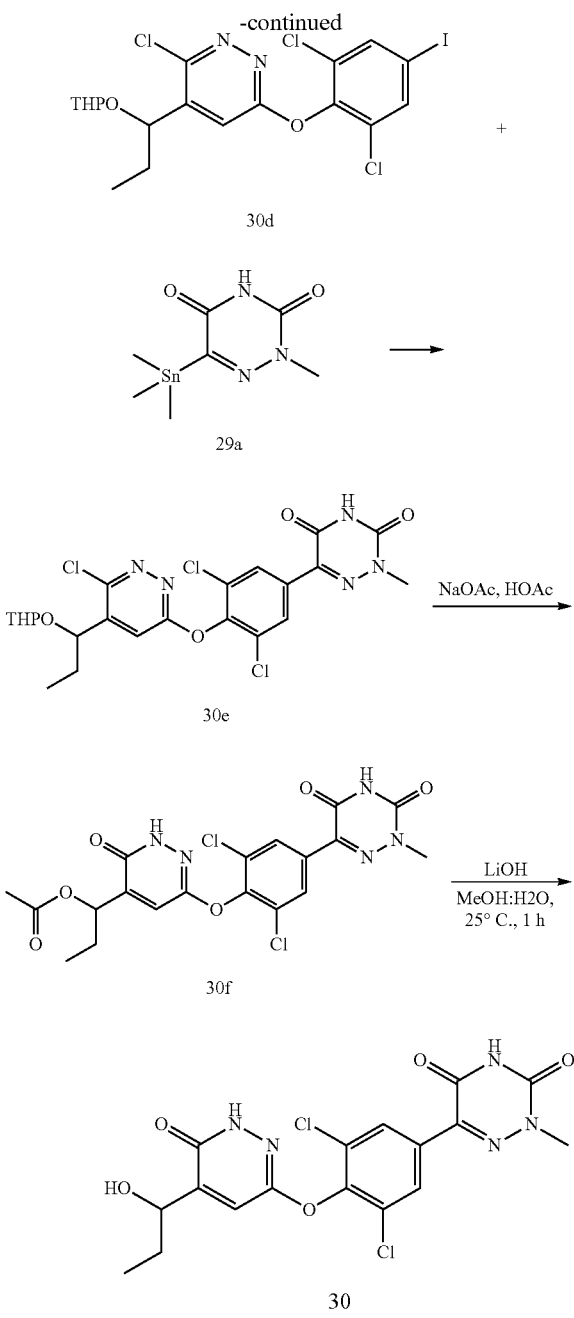

1-(3,6-dichloropyridazin-4-yl)propan-1-ol (30a

To a solution of 3,6-dichloro-1,2,4,5-tetrazine (300 mg, 1.99 mmol) in Tol. (5 mL) was added pent-1-yn-3-ol (334.34 mg, 3.97 mmol, 342.91 uL). The mixture was stirred at 110° C. for 16 hours in a sealed tube. TLC showed the starting material was consumed completely and many new spots were formed. LCMS showed the desired MS was detected. The reaction mixture was concentrated under reduced pressure. The residue was purified by Prep-TLC (SiO$_2$, Petroleum ether:Ethyl acetate) to give 30a. MS mass calculated for [M+1]$^+$ (C$_7$H$_8$Cl$_2$N$_2$O) requires m/z 207.0, LCMS found m/z 207.1. $^1$H NMR (400 MHz, CDCl$_3$) δ ppm 7.77 (s, 1H), 4.91-4.96 (m, 1H), 2.31 (d, J=4.0 Hz, 1H), 1.95 (dqd, J 14.4, 7.4, 7.4, 7.4, 3.4 Hz, 1H), 1.67 (dquin, J=14.6, 7.4, 7.4, 7.4, 7.4 Hz, 1H), 1.06 (t, J=7.4 Hz, 3H).

3,6-dichloro-4-(1-((tetrahydro-2H-pyran-2-yl)oxy) propyl)pyridazine (30b

To a solution of 1-(3,6-dichloropyridazin-4-yl)propan-1-ol (30a) (370 mg, 1.79 mmol) and DHP (751.56 mg, 8.93 mmol, 816.91 uL) in DCM (8 mL) was added TsOH (15.39 mg, 89.35 umol). The mixture was stirred at 20° C. for 1 hour. LCMS and TLC showed 30a was consumed completely and desired MS was detected. The reaction mixture was concentrated under reduced pressure. The residue was purified by Prep-TLC (SiO$_2$, Petroleum ether:Ethyl acetate) to give 30b. MS mass calculated for [M+1]$^+$ (C$_{12}$H$_{16}$Cl$_2$N$_2$O$_2$) requires m/z 291.1, LCMS found m/z 291.1. $^1$H NMR (400 MHz, CDCl$_3$) δ ppm 7.71 (s, 1H), 7.56 (s, 1H), 4.97 (dt, J=7.8, 4.0 Hz, 3H), 4.78 (dd, J=7.0, 4.0 Hz, 1H), 4.68-4.71 (m, 1H), 4.58 (br s, 6H), 4.40 (t, J=3.4 Hz, 1H), 1.02-1.09 (m, 4H), 0.95 (t, J=7.4 Hz, 3H).

3,5-dichloro-4-((6-chloro-5-(1-((tetrahydro-2H-pyran-2-yl)oxy)propyl)pyridazin-3-yl)oxy)aniline (30c To a solution of 3,6-dichloro-4-(1-((tetrahydro-2H-pyran-2-yl)oxy)propyl)pyridazine (30b) (500 mg, 1.72 mmol) and 4-amino-2,6-dichlorophenol (305.69 mg, 1.72 mmol) in DMSO (15 mL) was added K$_2$CO$_3$ (949.33 mg, 6.87 mmol) and CuI (196.22 mg, 1.03 mmol) was degassed and purged with N$_2$ for 3 times, and then the mixture was stirred at 90° C. for 16 hours under N$_2$ atmosphere. TLC showed 30b was consumed completely and one new spot was formed. LCMS showed desired MS was detected. The mixture was diluted in Ethyl acetate (5 mL) and the filtrate was extracted with ethyl acetate (10 mL*3) and H$_2$O (5 mL). The combined organic phase was washed with brine (10 mL*2), dried with anhydrous Na$_2$SO$_4$, filtered and concentrated in vacuum. The mixture was purified by Prep-TLC (Petroleum ether: Ethyl acetate) to give 30c. MS mass calculated for [M+1]$^+$ (C$_{18}$H$_{20}$Cl$_3$N$_3$O$_3$) requires m/z 432.1, LCMS found m/z 432.0. $^1$H NMR (400 MHz, CDCl$_3$) δ ppm 7.48 (s, 1H), 7.29 (s, 1H), 6.69 (s, 2H), 4.97 (dd, J=7.2, 3.8 Hz, 1H), 4.76-4.83 (m, 1H), 4.58 (br s, 1H), 4.46 (br s, 1H), 3.98 (br d, J=7.6 Hz, 1H), 3.79 (br d, J=3.6 Hz, 2H), 3.33-3.63 (m, 3H), 1.06 (br t, J=7.2 Hz, 2H), 0.96 (br t, J=7.2 Hz, 2H).

3-chloro-6-(2,6-dichloro-4-iodophenoxy)-4-(1-((tetrahydro-2H-pyran-2-yl)oxy)propyl)pyridazine (30d A solution of 3,5-dichloro-4-((6-chloro-5-(1-((tetrahydro-2H-pyran-2-yl)oxy)propyl)pyridazin-3-yl)oxy)aniline (30c) (170 mg, 392.86 umol) in ACN (3 mL) was added KI (130.43 mg, 785.71 umol) and t-BuONO (202.56 mg, 1.96 mmol, 233.63 uL). The mixture was stirred at 20° C. for 2 hours. TLC showed 30c was consumed completely and one new spot was formed. LCMS showed desired MS. The reaction mixture was concentrated under reduced pressure. The residue was purified by Prep-TLC (SiO$_2$, Petroleum ether:Ethyl acetate) to give 30d. MS mass calculated for [M+1]$^+$ (C$_{18}$H$_{18}$Cl$_3$IN$_2$O$_3$) requires m/z 542.9, LCMS found m/z 542.9. $^1$H NMR (400 MHz, CDCl$_3$) δ 7.73 (s, 2H), 7.57 (s, 1H), 4.94 (dt, J=7.6, 3.8 Hz, 1H), 2.19 (d, J=4.0 Hz, 1H), 2.03-1.94 (m, 1H), 1.85 (dt, J=14.6, 7.2 Hz, 1H), 1.70 (dquin, J=14.6, 7.34, 7.4, 7.4, 7.4 Hz, 1H), 1.27 (t, J=7.2 Hz, 1H), 1.12-1.05 (m, 3H).

6-(3,5-dichloro-4-((6-chloro-5-(1-((tetrahydro-2H-pyran-2-yl)oxy)propyl)pyridazin-3-yl)oxy)phenyl)-2-methyl-1,2,4-triazine-3,5(2H,4H)-dione (30e To a solution of 3-chloro-6-(2,6-dichloro-4-iodophenoxy)-4-(1-((tetrahydro-2H-pyran-2-yl)oxy)propyl)pyridazine (30d) (70 mg, 128.77 umol) and 2-methyl-6-(trimethylstannyl)-1,2,4-triazine-3,5(2H,4H)-dione (29a) (41.06 mg, 141.65 umol) in dioxane (4 mL) was added Pd(dppf)Cl$_2$·CH$_2$Cl$_2$ (10.52 mg, 12.88 umol). The mixture was degassed and purged with N$_2$ for 3 times and stirred at 110° C. for 16 hours. TLC and LCMS showed ~⅔ of 30d was remained, and desired MS was detected. The mixture was poured into water (10 mL) and extracted with ethyl acetate (20 mL*2). The combined organic phase was washed with brine (10 mL*3), dried with anhydrous Na$_2$SO$_4$, filtered and concentrated in vacuum. The residue was purified by Prep-TLC (Petroleum ether:Ethyl acetate) to give 30e. MS mass calculated for [M+1]$^+$ (C$_{22}$H$_{22}$Cl$_3$N$_5$O$_5$) requires m/z 542.1, LCMS found m/z 452.1. $^1$H NMR (400 MHz, CDCl$_3$) δ 8.20 (s, 1H), 7.58 (s, 1H), 7.40 (s, 1H), 7.40-7.41 (m, 1H), 5.00 (dd, J=7.4, 3.6 Hz, 1H), 4.77-4.85 (m, 1H), 4.48-4.52 (m, 1H), 3.94-4.02 (m, 1H), 3.76 (s, 2H), 3.56-3.67 (m, 1H), 3.36-3.43 (m, 1H), 1.51-2.01 (m, 6H), 1.19-1.32 (m, 1H), 1.19-1.32 (m, 1H), 1.08 (t, J=7.4 Hz, 1H), 0.98 (t, J=7.4 Hz, 1H).

1-(6-(2,6-dichloro-4-(2-methyl-3,5-dioxo-2,3,4,5-tetrahydro-1,2,4-triazin-6-yl)phenoxy)-3-oxo-2,3-dihydropyridazin-4-yl)propyl acetate (30f To a solution of 6-(3,5-dichloro-4-((6-chloro-5-(1-((tetrahydro-2H-pyran-2-yl)oxy)propyl)pyridazin-3-yl)oxy)phenyl)-2-methyl-1,2,4-triazine-3,5(2H,4H)-dione (30e) (15 mg, 27.63 umol) in HOAc (2 mL) was added NaOAc (11.33 mg, 138.17 umol). The mixture was stirred at 120° C. for 16 hours. LCMS showed 30e was consumed completely and the desired MS was detected. The reaction mixture was concentrated under reduced pressure to give 30f (20 mg, crude). MS mass calculated for [M+1]+(C$_{19}$H$_{17}$Cl$_2$N$_5$O$_6$) requires m/z 482.1, LCMS found m/z 482.0.

6-(3,5-dichloro-4-((5-(1-hydroxypropyl)-6-oxo-1,6-dihydropyridazin-3-yl)oxy)phenyl)-2-methyl-1,2,4-triazine-3,5(2H,4H)-dione (30

To a solution of 1-(6-(2,6-dichloro-4-(2-methyl-3,5-dioxo-2,3,4,5-tetrahydro-1,2,4-triazin-6-yl)phenoxy)-3-oxo-2,3-dihydropyridazin-4-yl)propyl acetate (30f) (20 mg, 41.47 umol) in MeOH (3 mL) and H$_2$O (0.5 mL) was added LiOH·H$_2$O (1 M, 82.94 uL). The mixture was stirred at 25° C. for 1 hour. HPLC and LCMS showed 30f was consumed completely and the desired MS was detected. The reaction mixture was concentrated under reduced pressure to remove AcOH. The residue was diluted with water (5 mL) and extracted with ethyl acetate (15 mL*3). The combined organic layers were dried over anhydrous Na$_2$SO$_4$, filtered and concentrated under reduced pressure. The residue was purified by Prep-HPLC (column: Phenomenex Luna C18 100*30 mm*5 um; mobile phase: [water (0.2% FA)-ACN]) to give 30. MS mass calculated for [M+1]$^+$ (C$_{17}$H$_{15}$Cl$_2$N$_5$O$_5$) requires m/z 440.0, LCMS found m/z 440.1. $^1$H NMR (400 MHz, MeOH-d4) δ 8.19 (s, 2H), 7.50 (d, J=1.0 Hz, 1H), 4.74 (dd, J=7.6, 2.8 Hz, 1H), 3.68 (s, 3H), 1.89-2.00 (m, 1H), 1.59 (dquin, J=14.2, 7.2, 7.2, 7.2, 7.2 Hz, 1H), 1.03 (t, J=7.4 Hz, 3H).

Example S31: 6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione (Compound 31

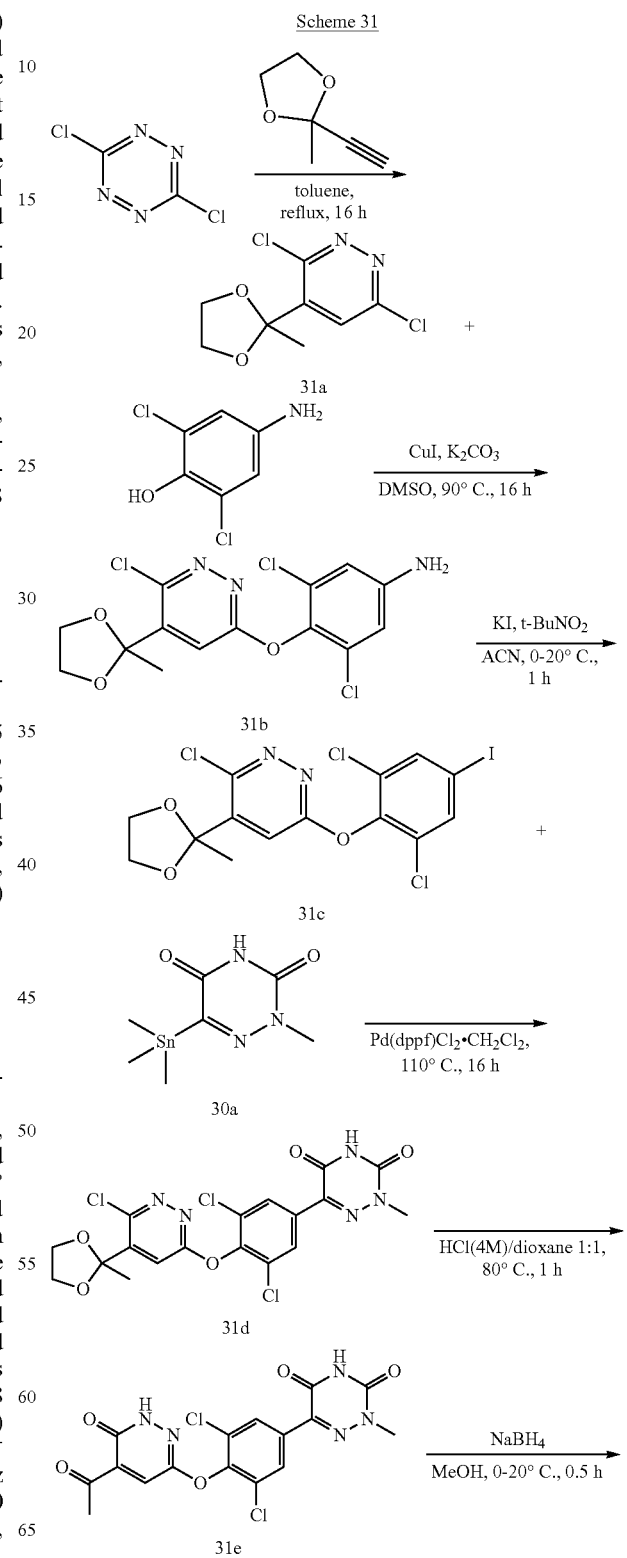

Scheme 31

-continued

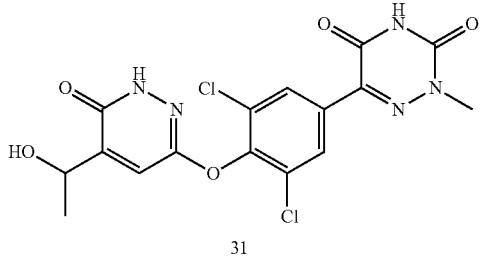 [SMILES: CC(O)c1cc(Oc2c(Cl)cc(-c3nn(C)c(=O)[nH]c3=O)cc2Cl)n[nH]c1=O]

3,6-dichloro-4-(2-methyl-1,3-dioxolan-2-yl)
pyridazine (31a

To a solution of 3,6-dichloro-1,2,4,5-tetrazine (1000 mg, 6.62 mmol) in Tol. (15 mL) was added 2-ethynyl-2-methyl-1,3-dioxolane (1.49 g, 13.25 mmol, 311.62 uL). The mixture was stirred at 110° C. for 16 hours in a sealed tube. TLC indicated the starting material was consumed completely. The reaction mixture was concentrated under reduced pressure. The residue was purified by column chromatography (SiO$_2$, Petroleum ether:Ethyl acetate) to give 31a. $^1$H NMR (400 MHz, CDCl$_3$) δ 7.74 (s, 1H), 4.19-4.08 (m, 2H), 3.89-3.77 (m, 2H), 1.80 (s, 3H).

3,5-dichloro-4-((6-chloro-5-(2-methyl-1,3-dioxolan-2-yl)pyridazin-3-yl)oxy)aniline (31b To a solution of 4-amino-2,6-dichlorophenol (591.45 mg, 3.32 mmol) and 3,6-dichloro-4-(2-methyl-1,3-dioxolan-2-yl)pyridazine (31a) (710 mg, 3.02 mmol) in DMSO (25 mL) was added K$_2$CO$_3$ (1.25 g, 9.06 mmol) and CuI (345.14 mg, 1.81 mmol) was degassed and purged with N$_2$ for 3 times, and then the mixture was stirred at 90° C. for 16 hours under N$_2$ atmosphere. TLC showed reactants were consumed completely. The reaction mixture was diluted with H$_2$O (50 mL), and then the pH was adjusted to 4-6 with HCl (1M). The mixture was extracted with Ethyl acetate 150 mL (50 mL*3). The combined organic layers were washed with brine 50 mL, dried over anhydrous Na$_2$SO$_4$, filtered and concentrated under reduced pressure. The residue was purified by column chromatography (SiO$_2$, Petroleum ether:Ethyl acetate) to give 31b. $^1$H NMR (400 MHz, CDCl$_3$) δ 7.50 (s, 1H), 6.69 (s, 2H), 4.20-4.11 (m, 2H), 3.93-3.85 (m, 2H), 3.79 (br s, 2H), 1.83 (s, 3H).

3-chloro-6-(2,6-dichloro-4-iodophenoxy)-4-(2-methyl-1,3-dioxolan-2-yl)pyridazine (31c To a solution of 3,5-dichloro-4-((6-chloro-5-(2-methyl-1, 3-dioxolan-2-yl)pyridazin-3-yl)oxy)aniline (31b) (600 mg, 1.59 mmol) in ACN (30 mL) was added t-BuONO (821.41 mg, 7.97 mmol, 947.41 uL) and KI (528.91 mg, 3.19 mmol) at 0° C. And then the mixture was stirred at 20° C. for 1 hour. TLC showed 31b was consumed completely and one major new spot was formed. The reaction mixture was concentrated under reduced pressure. The residue was purified by column chromatography (SiO$_2$, Petroleum ether:Ethyl acetate) to give 31c. $^1$H NMR (400 MHz, CDCl$_3$) δ 7.74 (s, 2H), 7.57 (s, 1H), 4.21-4.11 (m, 2H), 3.95-3.84 (m, 2H), 1.84 (s, 3H).

6-(3,5-dichloro-4-((6-chloro-5-(2-methyl-1,3-dioxolan-2-yl)pyridazin-3-yl)oxy)phenyl)-2-methyl-1,2,4-triazine-3,5(2H,4H)-dione (31d A mixture of 3-chloro-6-(2,6-dichloro-4-iodophenoxy)-4-(2-methyl-1,3-dioxolan-2-yl)pyridazine (31c) (200 mg, 410.25 umol), 2-methyl-6-(trimethylstannyl)-1,2,4-triazine-3,5(2H,4H)-dione (30a) (237.87 mg, 820.51 umol), Pd(dppf)Cl$_2$.CH$_2$Cl$_2$ (33.50 mg, 41.03 umol) in dioxane (10 mL) was degassed and purged with N$_2$ for 3 times, and then the mixture was stirred at 110° C. for 16 hours under N$_2$ atmosphere. TLC and LCMS indicated 31c was consumed completely. The reaction mixture was concentrated under reduced pressure. The residue was diluted with ethyl acetate (10 mL), and then filtered to give 31d (162 mg, crude). MS mass calculated for [M+1]$^+$ (C$_{18}$H$_{14}$C$_{l3}$N$_5$O$_5$) requires m/z 486.0, LCMS found m/z 486.0. $^1$H NMR (400 MHz, DMSO-d6) δ 12.46 (s, 1H), 8.19-8.13 (m, 2H), 7.83-7.80 (m, 1H), 4.08 (brt, J=7.0 Hz, 2H), 3.87-3.82 (m, 2H), 3.61-3.55 (m, 3H), 1.77-1.74 (m, 3H).

6-(4-((5-acetyl-6-oxo-1,6-dihydropyridazin-3-yl)oxy)-3,5-dichlorophenyl)-2-methyl-1,2,4-triazine-3,5 (2H,4H)-dione (31e To a solution of 6-(3,5-dichloro-4-((6-chloro-5-(2-methyl-1,3-dioxolan-2-yl)pyridazin-3-yl)oxy)phenyl)-2-methyl-1,2,4-triazine-3,5(2H,4H)-dione (31d) (160 mg, 328.75 umol) in dioxane (4 mL) was added HCl (4 M, 4.11 mL). The mixture was stirred at 80° C. for 1 hour. LCMS showed one main peak with desired MS was formed. The suspension was filtered through a pad of Celite and the pad cake was washed with ethyl acetate (5 mL*3). The combined filtrates were extracted with ethyl acetate (10 mL*3). The combined organic layers were washed with brine 10 mL, dried over Na$_2$SO$_4$, filtered and concentrated under reduced pressure to give 31e (80 mg, crude). MS mass calculated for [M+1]$^+$ (C$_{16}$H$_{11}$Cl$_2$N$_5$O$_5$) requires m/z 424.0, LCMS found m/z 424.0.

6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione (31

To a solution of 6-(4-((5-acetyl-6-oxo-1,6-dihydropyridazin-3-yl)oxy)-3,5-dichlorophenyl)-2-methyl-1,2,4-triazine-3,5(2H,4H)-dione (31e) (80 mg, 141.44 umol) in MeOH (5 mL) was added NaBH$_4$ (26.75 mg, 707.22 umol) at 0° C. The mixture was stirred at 0-20° C. for 0.5 hour. LCMS showed 31e was consumed completely and the desired MS was detected. The reaction mixture was concentrated under reduced pressure to remove MeOH. The residue was diluted with water (15 mL) and extracted with ethyl acetate 30 mL (10 mL*3). The combined organic layers were washed with brine 15 mL, dried over anhydrous Na$_2$SO$_4$, filtered and concentrated under reduced pressure. The residue was purified by Prep-HPLC (column: Phenomenex Luna C18 200*40 mm*10 um; mobile phase: [water (0.225% FA)-ACN]) to give 31. MS mass calculated for [M+1]$^+$(C$_{16}$H$_{13}$Cl$_2$N$_5$O$_5$) requires m/z 426.0, LCMS found m/z 426.0. $^1$H NMR (400 MHz, DMSO-d6) δ 12.44 (br s, 1H), 12.29 (br s, 1H), 8.10 (s, 2H), 7.43 (d, J=1.0 Hz, 1H), 4.75-4.68 (m, 1H), 3.58 (s, 3H), 3.57 (br s, 1H), 1.34 (d, J 6.8 Hz, 3H).

Example S31 P1 and P2: (S)-6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione and (R)-6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione (Compounds 31 P1 and 31 P2

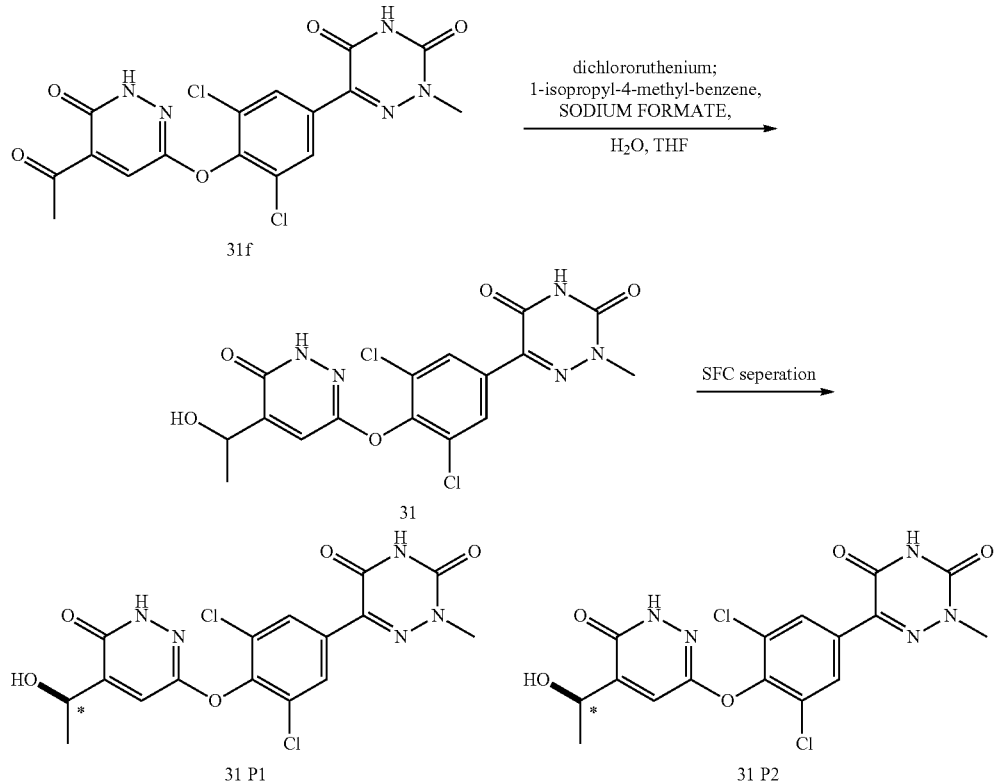

6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione (31

Dichloro (p-cymene) ruthenium(II) dimer (1.08 mg, 1.77 umol) was suspended in degassed H$_2$O (2 mL) and the mixture was degassed with nitrogen for 10 min. A solution of 6-(4-((5-acetyl-6-oxo-1,6-dihydropyridazin-3-yl)oxy)-3,5-dichlorophenyl)-2-methyl-1,2,4-triazine-3,5 (2H,4H)-dione (31f) (20 mg, 35.36 umol) in degassed THF (1 mL) and sodium formate (4.81 mg, 70.72 umol, 3.82 uL) was added in the mixture. The reaction mixture was degassed with nitrogen 5 minutes and stirred at 20° C. for 30 minutes. TLC and LCMS showed 31f was consumed completely. The mixture was diluted with water (5 mL) and extracted with ethyl acetate 30 mL (10 mL*3). The combined organic layers were washed with brine (5 mL), dried over anhydrous Na$_2$SO$_4$, filtered and concentrated under reduced pressure. The residue was purified by Prep-HPLC (column: Welch Ultimate AQ-C18 150*30 mm*5 um; mobile phase: [water (0.1% TFA)-ACN]) to give 31. MS calculated for [M+1]$^+$ (C$_{16}$H$_{13}$Cl$_2$N$_5$O$_5$) requires m/z 426.0, LCMS found m/z 426.0. $^1$H NMR (400 MHz, MeOH-d4) δ 8.21 (s, 2H), 7.54 (d, J=1.0 Hz, 1H), 4.96-4.92 (m, 1H), 3.70 (s, 3H), 1.48 (d, J=6.4 Hz, 3H).

(S)-6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione (31 P1) and (R)-6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione (31 P2

The 6-(3,5-dichloro-4-((5-(1-hydroxyethyl)-6-oxo-1,6-dihydropyridazin-3-yl)oxy)phenyl)-2-methyl-1,2,4-triazine-3,5(2H,4H)-dione (31) (4.8 mg, 9.20 umol) was separated by SFC (column: DAICEL CHIRALPAK AS (250 mm*30 mm, 10 um); mobile phase: [Neu-EtOH]; B %: 30%-30%, 8 min) to give 31 P1 (1.05 mg, 2.43 umol): MS mass calculated for [M+1]+(C$_{16}$H$_{13}$Cl$_2$N$_5$O$_5$) requires m/z 426.0, LCMS found m/z 426.0; $^1$H NMR (400 MHz, MeOH-d4) δ 8.20 (s, 2H), 7.53 (d, J 1.1 Hz, 1H), 4.94-4.92 (m, 1H), 3.69 (s, 3H), 1.47 (d, J=6.4 Hz, 3H); and 31 P2 (1.57 mg, 3.68 umol): MS mass calculated for [M+1]$^+$ (C$_{16}$H$_{13}$Cl$_2$N$_5$O$_5$) requires m/z 426.0, LCMS found m/z 426.0; $^1$H NMR (400 MHz, MeOH-d4) (8.19 (s, 2H), 7.52 (s, 1H), 4.94-4.90 (m, 1H), 3.68 (s, 3H), 1.46 (d, J=6.4 Hz, 3H). In this Example, the isomers 31 P1 and 31 P2 were separated by chiral chromatography but the absolute chirality of each isomer was not determined. Elution order was used to track the individual isomers.

Example S32: 6-(4-((5-(sec-butyl)-6-oxo-1,6-dihydropyridazin-3-yl)oxy)-3,5-dichlorophenyl)-2-methyl-1,2,4-triazine-3,5(2H,4H)-dione (Compound 32

Scheme 32

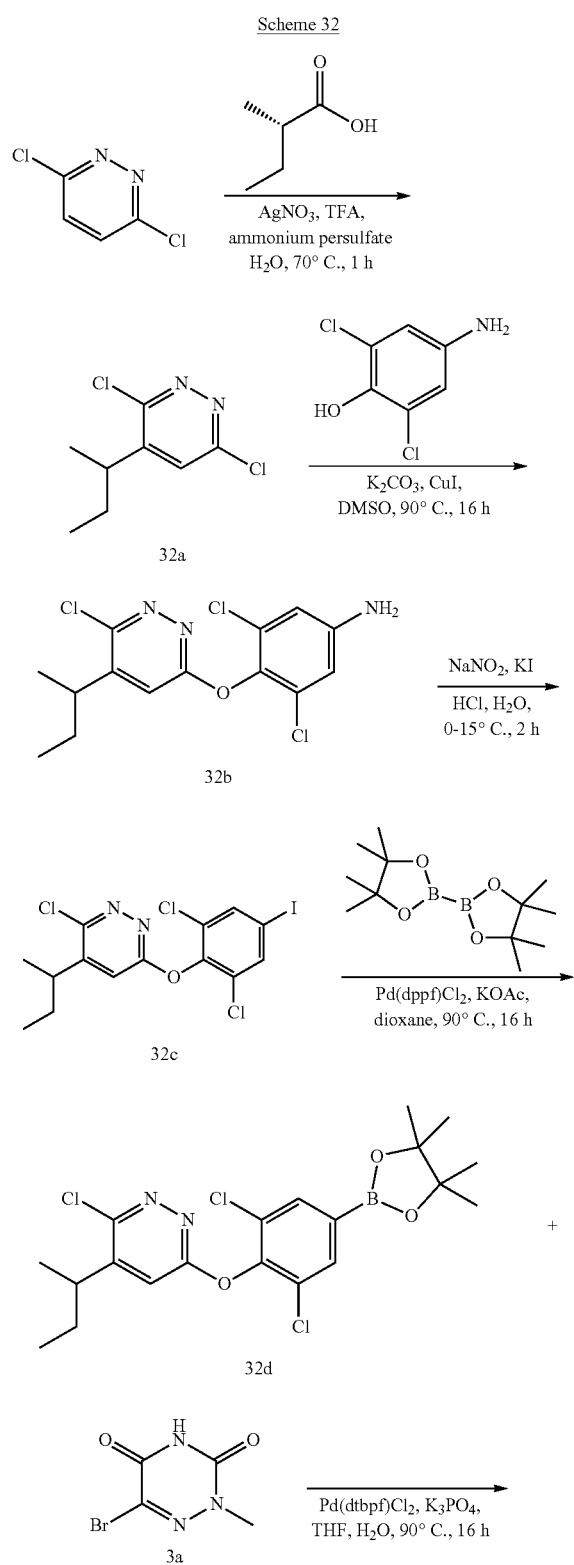

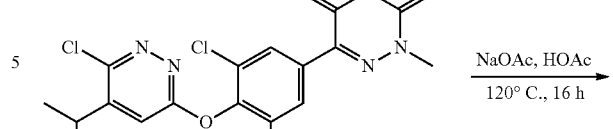

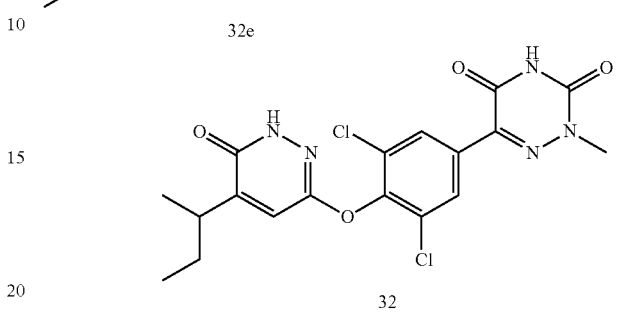

4-(sec-butyl)-3,6-dichloropyridazine (32a

To a mixture of 3,6-dichloropyridazine (200 mg, 1.34 mmol) and (2S)-2-methylbutanoic acid (137.11 mg, 1.34 mmol, 146.17 uL) in H$_2$O (2 mL) was added AgNO$_3$ (228.05 mg, 1.34 mmol) and TFA (459.22 mg, 4.03 mmol, 298.20 uL) in one portion at 50° C. Then added (NH$_4$)$_2$S$_2$O$_8$ (919.07 mg, 4.03 mmol, 875.30 uL) in H$_2$O (2 mL) at 70° C. The mixture was stirred at 70° C. for 1 hour. TLC showed the starting material was consumed completely, and one new spot was formed. The mixture was poured into water (15 mL) and extracted with ethyl acetate (20 mL*2). The combined organic phase was washed with brine (10 mL*2), dried with anhydrous Na$_2$SO$_4$, filtered and concentrated in vacuum. The residue was purified by Prep-TLC (Petroleum ether:Ethyl acetate) to give 32a. $^1$H NMR (400 MHz, CDCl$_3$) δ 7.34 (s, 1H), 3.08 (sxt, J=7.0 Hz, 1H), 1.59-1.76 (m, 1H), 1.58-1.61 (m, 1H), 1.28 (d, J=6.8 Hz, 2H), 1.26-1.31 (m, 1H), 0.95 (t, J=7.4 Hz, 3H).

4-((5-(sec-butyl)-6-chloropyridazin-3-yl)oxy)-3,5-dichloroaniline (32b

To a solution of 4-(sec-butyl)-3,6-dichloropyridazine (32a) (100 mg, 487.61 umol) and 4-amino-2,6-dichlorophenol (104.16 mg, 585.13 umol) in DMSO (5 mL) was added K$_2$CO$_3$ (269.57 mg, 1.95 mmol) and CuI (55.72 mg, 292.56 umol). The reaction mixture degassed and purged with N$_2$ for 3 times, and then the mixture was stirred at 90° C. for 16 hours under N$_2$ atmosphere. TLC and LCMS showed 32a was consumed completely and desired MS was detected. The mixture was concentrated in vacuum. The mixture was extracted with Ethyl acetate (30 mL*2) and H$_2$O (10 mL). The combined organic phase was washed with brine (10 mL*3), dried with anhydrous Na$_2$SO$_4$, filtered and concentrated in vacuum. The mixture was purified by Prep-TLC (Petroleum ether:Ethyl acetate) to give 32b. MS mass calculated for [M+1]+(C$_{14}$H$_{14}$C$_{13}$N$_3$O) requires m/z 346.0, LCMS found m/z 346.1. $^1$H NMR (400 MHz, MeOH-d4) δ 7.42 (s, 1H), 6.72-6.76 (m, 2H), 3.06-3.15 (m, 1H), 1.62-1.84 (m, 2H), 1.32 (d, J=7.0 Hz, 3H), 0.93-0.98 (m, 3H).

4-(sec-butyl)-3-chloro-6-(2,6-dichloro-4-iodophenoxy)pyridazine (32c

To a solution of 4-((5-(sec-butyl)-6-chloropyridazin-3-yl)oxy)-3,5-dichloroaniline (32b) (80 mg, 230.79 umol) in HCl (3 mL) was added NaNO$_2$ (19.11 mg, 276.95 umol) at 0° C., the mixture was stirred for 0.5 hours. Then the mixture was added a solution of KI (76.62 mg, 461.58 umol) in H$_2$O (3 mL), the mixture was stirred at 15° C. for another 1.5 hours. TLC and LCMS indicated 32b was consumed completely and the desired mass was detected. The mixture was extracted with ethyl acetate (20 mL*2) and H$_2$O 10 mL. The combined organic phase was washed with brine (10 mL*3), dried with anhydrous Na$_2$SO$_4$, filtered and concentrated in vacuum. The residue was purified by Prep-TLC (Petroleum ether:Ethyl acetate) to give 32c. MS mass calculated for [M+1]$^+$ (C$_{14}$H$_{12}$Cl$_{131}$N$_2$O) requires m/z 456.9, LCMS found m/z 457.0. $^1$H NMR (400 MHz, CDCl$_3$) δ 7.73 (s, 2H), 7.18 (s, 1H), 3.05-3.12 (m, 1H), 1.59-1.83 (m, 2H), 1.32 (d, J=6.6 Hz, 3H), 0.97 (t, J=7.4 Hz, 3H).

4-(sec-butyl)-3-chloro-6-(2,6-dichloro-4-(4,4,5,5-tetramethyl-1,3,2-dioxaborolan-2-yl)phen-oxy)pyridazine (32d To a solution of 4-(sec-butyl)-3-chloro-6-(2,6-dichloro-4-iodophenoxy)pyridazine (32c) (60 mg, 131.14 umol) and 4,4,5,5-tetramethyl-2-(4,4,5,5-tetramethyl-1,3,2-dioxaborolan-2-yl)-1,3,2-dioxaborolane (99.91 mg, 393.43 umol) in dioxane (4 mL) was added KOAc (64.35 mg, 655.71 umol) and Pd(dppf)Cl$_2$ (9.60 mg, 13.11 umol). The mixture was degassed and purged with N$_2$ for 3 times and stirred at 90° C. for 16 hours. TLC and LCMS showed 32c was consumed completely and the desired mass was detected. The mixture was extracted with ethyl acetate (20 mL*2) and H$_2$O (10 mL). The combined organic phase was washed with brine (10 mL*3), dried with anhydrous Na$_2$SO$_4$, filtered and concentrated in vacuum. The residue was purified by Prep-TLC (Petroleum ether:Ethyl acetate) to give 32d. MS mass calculated for [M+1]$^+$ (C$_{20}$H$_{24}$BCl$_3$N$_2$O$_3$) requires m/z 457.1, LCMS found m/z 457.2. $^1$H NMR (400 MHz, CDCl$_3$) δ 7.81 (s, 2H), 7.17 (s, 1H), 3.04-3.12 (m, 1H), 1.59-1.81 (m, 3H), 1.27 (s, 102H), 0.94-1.00 (m, 1H), 0.97 (t, J=7.4 Hz, 3H).

6-(4-((5-(sec-butyl)-6-chloropyridazin-3-yl)oxy)-3,5-dichlorophenyl)-2-methyl-1,2,4-triazine-3,5(2H,4H)-dione (32e To a mixture of 4-(sec-butyl)-3-chloro-6-(2,6-dichloro-4-(4,4,5,5-tetramethyl-1,3,2-dioxaborolan-2-yl)phenoxy)pyridazine (32d) (60 mg, 131.12 umol) and 6-bromo-2-methyl-1,2,4-triazine-3,5(2H,4H)-dione (3a) (40.52 mg, 196.68 umol) in THF (4 mL) and H$_2$O (1 mL) was added ditert-butyl(cyclopentyl)phosphane; dichloropalladium; iron (8.55 mg, 13.11 umol) and K$_3$PO$_4$ (55.67 mg, 262.25 umol) was degassed and purged with N$_2$ for 3 times, and then the mixture was stirred at 90° C. for 16 hours under N$_2$ atmosphere. TLC and LCMS showed 32d was consumed completely and the desired MS was detected. The reaction mixture was dissolved in water and the pH was adjusted to 4 with HCl (1M, 1 mL). Then the mixture was extracted with ethyl acetate (15 mL*2). The combined organic phase was washed with brine (10 mL*3), dried with anhydrous Na$_2$SO$_4$, filtered and concentrated in vacuum. The residue was purified by Prep-TLC (Petroleum ether:Ethyl acetate) to give 32e. MS mass calculated for [M+1]$^+$ (C$_{18}$H$_{16}$Cl$_3$N$_5$O$_3$) requires m/z 456.0, LCMS found m/z 455.8. $^1$H NMR (400 MHz, MeOH-d4) δ 8.23-8.27 (m, 2H), 7.60 (s, 1H), 3.68 (s, 3H), 3.09-3.18 (m, 1H), 1.65-1.88 (m, 2H), 1.35 (d, J=6.8 Hz, 3H), 0.97 (t, J=7.4 Hz, 3H).

6-(4-((5-(sec-butyl)-6-oxo-1,6-dihydropyridazin-3-yl)oxy)-3,5-dichlorophenyl)-2-methyl-1,2,4-triazine-3,5(2H,4H)-dione (32

To a solution of 6-(4-((5-(sec-butyl)-6-chloropyridazin-3-yl)oxy)-3,5-dichlorophenyl)-2-methyl-1,2,4-triazine-3,5 (2H,4H)-dione (32e) (40 mg, 87.58 umol) in AcOH (3 mL) was added NaOAc (35.92 mg, 437.91 umol) at 15° C. Then the mixture was stirred at 120° C. for 16 hours. LCMS and HPLC showed 32e was consumed completely and desired MS was detected. The reaction mixture was concentrated under reduced pressure. The residue was purified by Prep-HPLC (column: Luna C18 100*30 5 u; mobile phase: [water (0.225% FA)-ACN]) to give 32. MS mass calculated for [M+1]$^+$ (C$_{18}$H$_{17}$Cl$_2$N$_5$O$_4$) requires m/z 438.1, LCMS found m/z 438.0. $^1$H NMR (400 MHz, DMSO-d6) δ 12.45 (br s, 1H), 12.20 (s, 1H), 8.10 (s, 2H), 7.43 (s, 1H), 3.58 (s, 3H), 2.85-2.94 (m, 1H), 1.46-1.76 (m, 2H), 1.18 (d, J=7.0 Hz, 3H), 0.86 (t, J=7.4 Hz, 3H).

Example S33 P1 and P2: (R)-6-(4-((5-(sec-butyl)-6-oxo-1,6-dihydropyridazin-3-yl)oxy)-3,5-dichlorophenyl)-1,2,4-triazine-3,5(2H,4H)-dione and (S)-6-(4-((5-(sec-butyl)-6-oxo-1,6-dihydropyridazin-3-yl)oxy)-3,5-dichlorophenyl)-1,2,4-triazine-3,5(2H,4H)-dione (Compounds 33 P1 and 33 P2

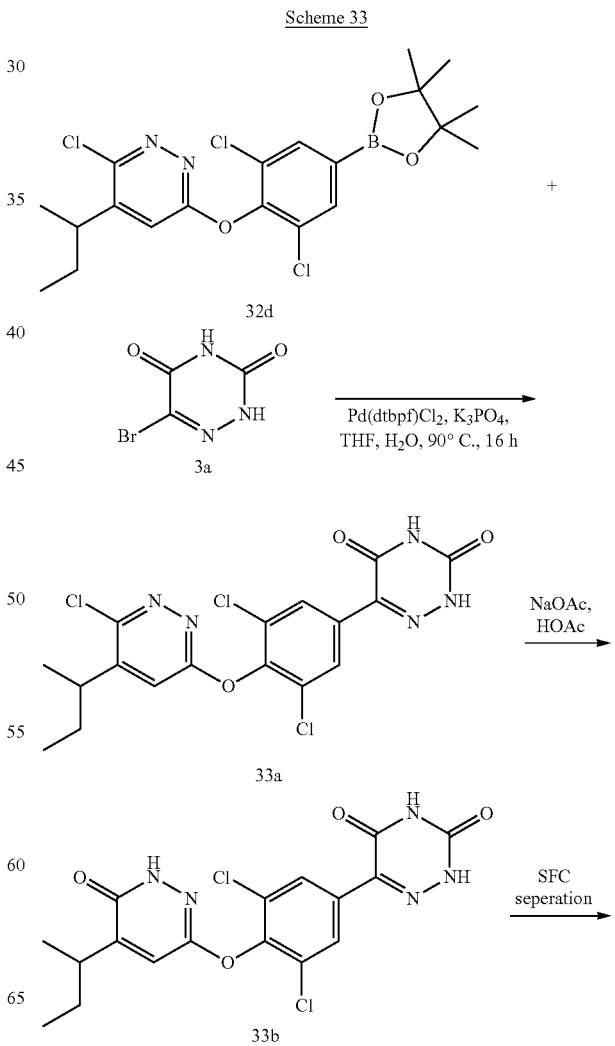

Scheme 33

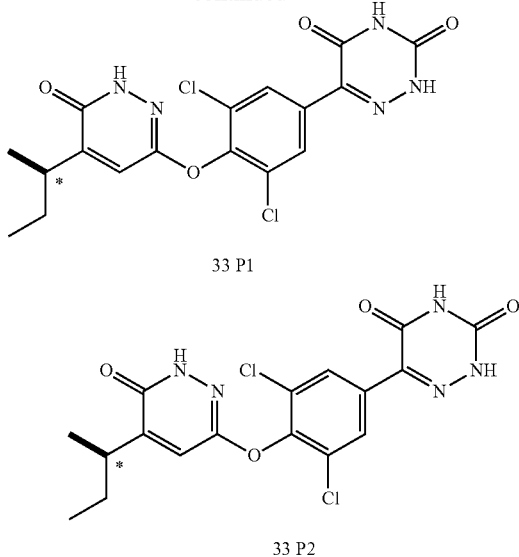

33 P1

33 P2

6-(4-((5-(sec-butyl)-6-chloropyridazin-3-yl)oxy)-3,5-dichlorophenyl)-1,2,4-triazine-3,5(2H,4H)-dione (33a To a mixture of 4-(sec-butyl)-3-chloro-6-(2,6-dichloro-4-(4,4,5,5-tetramethyl-1,3,2-dioxaborolan-2-yl)phenoxy)pyridazine (32d) (280 mg, 611.91 umol) and 6-bromo-1,2,4-triazine-3,5(2H,4H)-dione (3a) (176.20 mg, 917.86 umol) in THF (4 mL) and H$_2$O (1 mL) was added Pd(dppf)Cl$_2$ (39.88 mg, 61.19 umol) and K$_3$PO$_4$ (259.78 mg, 1.22 mmol). The mixture was degassed and purged with N$_2$ for 3 times, and then the mixture was stirred at 90° C. for 2 hours under N$_2$ atmosphere. TLC and LCMS showed 32d were consumed completely and desired MS was detected. The mixture was extracted with ethyl acetate (50 mL*2) and H$_2$O (15 mL). The combined organic phase was washed with brine (15 mL*3), dried with anhydrous Na$_2$SO$_4$, filtered and concentrated in vacuum. The residue was purified by Prep-TLC (Petroleum ether:Ethyl acetate) to give 33a. MS mass calculated for [M+1]+(C$_{20}$H$_{24}$BCl$_3$N$_2$O$_3$) requires m/z 457.1, LCMS found m/z 457.2. $^1$H NMR (400 MHz, MeOH-d4) δ 8.21-8.24 (m, 1H), 7.60 (s, 1H), 3.10-3.16 (m, 1H), 1.66-1.86 (m, 2H), 1.35 (d, J 6.84 Hz, 3H), 0.97 (t, J 7.39 Hz, 3H).

6-(4-((5-(sec-butyl)-6-oxo-1,6-dihydropyridazin-3-yl)oxy)-3,5-dichlorophenyl)-1,2,4-triazine-3,5(2H,4H)-dione (33b To a solution of 6-(4-((5-(sec-butyl)-6-chloropyridazin-3-yl)oxy)-3,5-dichlorophenyl)-1,2,4-triazine-3,5(2H,4H)-dione (33a) (175 mg, 395.32 umol) in AcOH (8 mL) was added NaOAc (162.14 mg, 1.98 mmol) at 15° C. Then the mixture was stirred at 120° C. for 16 hours. HPLC and LCMS showed 33a was consumed completely and desired MS was detected. The reaction mixture was concentrated under reduced pressure to remove AcOH. The residue was diluted with water (5 mL). The suspension was extracted with ethyl acetate (30 mL*3), the combined organic layers were dried over anhydrous Na$_2$SO$_4$, filtered and concentrated under reduced pressure. The residue was purified by Prep-HPLC (column: Luna C18 100*30 5 u; mobile phase: [water (0.2% FA)-ACN]) to give 33b. MS mass calculated for [M+1]$^+$ (C$_{17}$H$_{15}$Cl$_2$N$_5$O$_4$) requires m/z 424.1, LCMS found m/z 424.2. $^1$H NMR (400 MHz, DMSO-d6) δ 8.16 (s, 1H), 7.34 (s, 1H), 2.97-3.04 (m, 1H), 1.55-1.82 (m, 2H), 1.26 (d, J=7.0 Hz, 3H), 0.96 (t, J=7.4 Hz, 3H).

(R)-6-(4-((5-(sec-butyl)-6-oxo-1,6-dihydropyridazin-3-yl)oxy)-3,5-dichlorophenyl)-1,2,4-triazine-3,5(2H,4H)-dione and (S)-6-(4-((5-(sec-butyl)-6-oxo-1,6-dihydropyridazin-3-yl)oxy)-3,5-dichlorophenyl)-1,2,4-triazine-3,5(2H,4H)-dione (Compounds 33 P1 and 33 P2

6-(4-((5-(sec-butyl)-6-oxo-1,6-dihydropyridazin-3-yl)oxy)-3,5-dichlorophenyl)-1,2,4-triazine-3,5(2H,4H)-dione (33b) (28 mg, 66.00 umol) was separated by SFC separation (column: DAICEL CHIRALPAK AD (250 mm*30 mm, 10 um); mobile phase: [0.1% NH$_3$H$_2$O IPA]; B %: 45%-45%) to give 33 P1 (11.36 mg, 26.78 umol, 40.57% yield): MS mass calculated for [M+1]+(C$_{17}$H$_{15}$Cl$_2$N$_5$O$_4$) requires m/z 424.1, LCMS found m/z 424.0; $^1$H NMR (400 MHz, MeOH-d4) δ 8.15 (s, 2H), 7.33 (s, 1H), 3.35 (s, 1H), 2.97-3.04 (m, 1H), 1.54-1.82 (m, 2H), 1.26 (d, J 7.0 Hz, 3H), 0.95 (t, J=7.4 Hz, 3H); and 33 P2 (11.17 mg, 26.33 umol, 39.89% yield): MS mass calculated for [M+1]+ (C$_{17}$H$_{15}$Cl$_2$N$_5$O$_4$) requires m/z 424.1, LCMS found m/z 424.0; $^1$H NMR (400 MHz, MeOH-d4) δ 8.16 (s, 2H), 7.33 (s, 1H), 2.97-3.04 (m, 1H), 1.54-1.83 (m, 2H), 1.26 (d, J=7.0 Hz, 3H), 0.95 (t, J=7.4 Hz, 3H).). In this Example, the isomers 33 P1 and 33 P2 were separated by chiral chromatography, but the absolute chirality of each isomer was not determined. Elution order was used to track the individual isomers.

Example S34: (6-(3,5-dichloro-4-((5-(1-hydroxyethyl)-6-oxo-1,6-dihydropyridazin-3-yl)oxy)phenyl)-1,2,4-triazine-3,5(2H,4H)-dione (Compound 34

Scheme 34

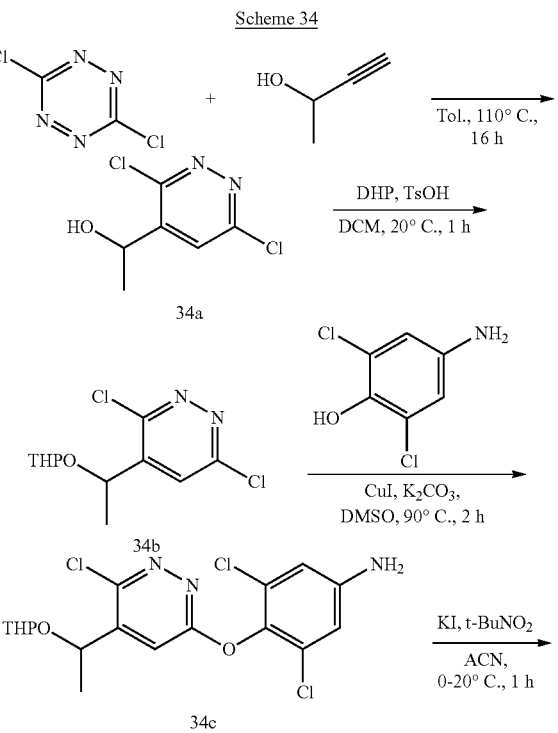

-continued

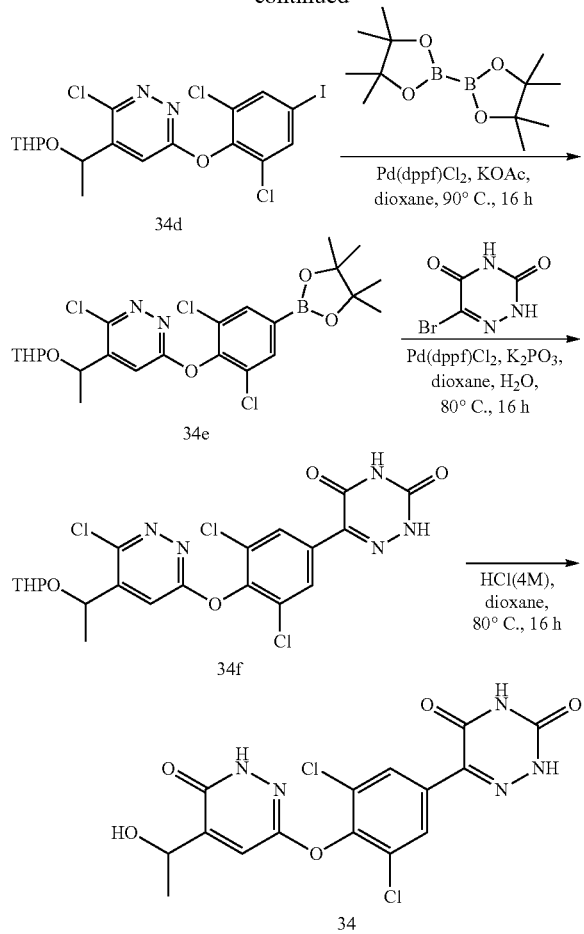

1-(3,6-dichloropyridazin-4-yl)ethanol (34a

To a solution of 3,6-dichloro-1,2,4,5-tetrazine (500 mg, 3.31 mmol) in Tol. (3 mL) was added but-3-yn-2-ol (278.59 mg, 3.97 mmol, 311.62 uL). The reaction mixture was sealed tube and stirred at 110° C. for 16 hours. TLC indicated starting material was consumed completely. The reaction mixture was concentrated under reduced pressure. The residue was purified by Prep-TLC (SiO$_2$, Petroleum ether:Ethyl acetate) to give 34a. $^1$H NMR (400 MHz, CDCl$_3$) δ 7.82 (d, J=1.0 Hz, 1H), 5.14 (dq, J=4.2, 6.3 Hz, 1H), 2.38 (d, J=3.4 Hz, 1H), 1.56 (d, J=6.4 Hz, 3H).

3,6-dichloro-4-(1-((tetrahydro-2H-pyran-2-yl)oxy) ethyl)pyridazine (34b

To a solution of 1-(3,6-dichloropyridazin-4-yl)ethanol (34a) (300 mg, 1.55 mmol) and DHP (653.68 mg, 7.77 mmol, 710.52 uL) in DCM (10 mL) was added TsOH (13.38 mg, 77.71 umol). The mixture was stirred at 20° C. for 1 hour. TLC showed reactant was consumed completely and many new spot was formed. The reaction mixture was concentrated under reduced pressure. The residue was purified by Prep-TLC (SiO$_2$, Petroleum ether:Ethyl acetate) to give 34b. $^1$H NMR (400 MHz, CDCl$_3$) (7.77 (s, 1H), 7.63 (s, 1H), 5.10 (q, J=6.4 Hz, 1H), 4.98 (q, J=6.6 Hz, 1H), 4.81 (br d, J=4.6 Hz, 1H), 4.47 (br s, 1H), 3.99-3.90 (m, 1H), 3.67-3.53 (m, 2H), 3.47-3.40 (m, 1H), 1.95-1.55 (m, 12H), 1.53 (d, J=6.4 Hz, 3H), 1.46 (d, J 6.4 Hz, 3H).

3,5-dichloro-4-((6-chloro-5-(1-((tetrahydro-2H-pyran-2-yl)oxy)ethyl)pyridazin-3-yl)oxy)aniline (34c To a solution of 3,6-dichloro-4-(1-((tetrahydro-2H-pyran-2-yl)oxy)ethyl)pyridazine (34b) (167.00 mg, 938.13 umol) and 4-amino-2,6-dichlorophenol (200 mg, 721.64 umol) in DMSO (5 mL) was added K$_2$CO$_3$ (299.21 mg, 2.16 mmol) and CuI (82.46 mg, 432.98 umol). Then the reaction mixture was degassed and purged with N$_2$ for 3 times. The mixture was stirred at 90° C. for 2 hours under N$_2$ atmosphere. TLC and LCMS showed 34b was consumed completely. The reaction mixture was diluted with H$_2$O (5 mL) and extracted with ethyl acetate (10 mL*3). The combined organic layers were washed with brine (10 mL), dried over anhydrous Na$_2$SO$_4$, filtered and concentrated under reduced pressure. The residue was purified by Prep-TLC (SiO$_2$, Petroleum ether:Ethyl acetate) to give 34c. $^1$H NMR (400 MHz, CDCl$_3$) δ 7.55 (s, 1H), 7.37 (s, 1H), 6.68 (s, 4H), 5.10 (q, J 6.6 Hz, 1H), 5.00 (q, J 6.4 Hz, 1H), 4.90-4.85 (m, 1H), 4.52 (t, J 3.6 Hz, 1H), 3.96 (ddd, J 3.8, 7.5, 11.2 Hz, 1H), 3.81 (br d, J 2.4 Hz, 4H), 3.65 (ddd, J 3.2, 8.0, 11.3 Hz, 1H), 3.61-3.54 (m, 1H), 3.47-3.40 (m, 1H), 1.96-1.60 (m, 12H), 1.55 (d, J 6.4 Hz, 3H), 1.49 (d, J 6.4 Hz, 3H).

3-chloro-6-(2,6-dichloro-4-iodophenoxy)-4-(1-((tetrahydro-2H-pyran-2-yl)oxy)ethyl)pyridazine (34d To a solution of 3,5-dichloro-4-((6-chloro-5-(1-((tetrahydro-2H-pyran-2-yl)oxy)ethyl)pyridazin-3-yl)oxy)aniline (34c) (165 mg, 394.08 umol) in ACN (5 mL) was added t-BuONO (609.56 mg, 5.91 mmol, 703.06 uL) and KI (130.83 mg, 788.15 umol) at 0° C. And then the mixture was stirred at 20° C. for 1 hour. TLC and LCMS showed 34d was consumed completely and many new spots were formed. The reaction mixture was concentrated under reduced pressure. The residue was diluted with water (10 mL) and extracted with ethyl acetate (10 mL*3). The combined organic layers were washed with brine (10 mL), dried over anhydrous Na$_2$SO$_4$, filtered and concentrated under reduced pressure. The residue was purified by Prep-TLC (SiO$_2$, Petroleum ether:Ethyl acetate) to give 34d. MS mass calculated for [M+1]$^+$ (C$_{17}$H$_{16}$C$_{13}$IN$_2$O$_3$) requires m/z 528.9, LCMS found m/z 528.9.

3-chloro-6-(2,6-dichloro-4-(4,4,5,5-tetramethyl-1,3,2-dioxaborolan-2-yl)phenoxy)-4-(1-((tetrahydro-2H-pyran-2-yl)oxy)ethyl)pyridazine (34e A mixture of 3-chloro-6-(2,6-dichloro-4-iodophenoxy)-4-(1-((tetrahydro-2H-pyran-2-yl)oxy)ethyl)pyridazine (34d) (53 mg, 100.08 umol), BPD (76.24 mg, 300.24 umol), AcOK (49.11 mg, 500.39 umol) and Pd(dppf)Cl$_2$ (7.32 mg, 10.01 umol) in dioxane (3 mL). The mixture was degassed and purged with N$_2$ for 3 times, and then the mixture was stirred at 90° C. for 16 hours under N$_2$ atmosphere. TLC and LCMS showed 34d was consumed completely. The reaction mixture was concentrated under reduced pressure. The residue was diluted with H$_2$O (10 mL) and extracted with ethyl acetate (10 mL*3). The combined organic layers were washed with brine (10 mL), dried over anhydrous Na$_2$SO$_4$, filtered and concentrated under reduced pressure to give 34e (75 mg, crude). The crude used directly in next step. MS mass calculated for [M+1]⁺ ($C_{23}H_{28}BCl_3N_2O_5$) requires m/z 529.1, LCMS found m/z 447.0.

6-(3,5-dichloro-4-((6-chloro-5-(1-((tetrahydro-2H-pyran-2-yl)oxy)ethyl)pyridazin-3-yl)oxy)phenyl)-1,2,4-triazine-3,5(2H,4H)-dione (34f)

To a solution of 3-chloro-6-(2,6-dichloro-4-(4,4,5,5-tetramethyl-1,3,2-dioxaborolan-2-yl)phenoxy)-4-(1-((tetrahydro-2H-pyran-2-yl)oxy)ethyl)pyridazine (34e) (75 mg, 141.60 umol), 6-bromo-1,2,4-triazine-3,5(2H,4H)-dione (32.62 mg, 169.92 umol) in THF (2.4 mL) and $H_2O$ (0.6 mL) was added $K_3PO_4$ (60.12 mg, 283.21 umol) and Pd(dppf)Cl₂ (9.23 mg, 14.16 umol). The mixture was degassed and purged with N₂ for 3 times, and then the mixture was stirred at 80° C. for 16 hours under N₂ atmosphere. TLC and LCMS showed reactant 34e was consumed completely. The reaction mixture was concentrated under reduced pressure, and the residue was diluted with water (10 mL) and extracted with ethyl acetate (10 mL*3). The combined organic layers were washed with brine (10 mL), dried over anhydrous Na₂SO₄, filtered and concentrated under reduced pressure. The residue was purified by Prep-TLC (SiO₂, DCM:MeOH) to give 34f. MS mass calculated for [M+1]+ ($C_{20}H_{18}C_{13}N_5O_5$) requires m/z 514.0, LCMS found m/z 514.0.

6-(3,5-dichloro-4-((5-(1-hydroxyethyl)-6-oxo-1,6-dihydropyridazin-3-yl)oxy)phenyl)-1,2,4-triazine-3,5(2H,4H)-dione (34)

To a solution of 6-(3,5-dichloro-4-((6-chloro-5-(1-((tetrahydro-2H-pyran-2-yl)oxy)ethyl)pyridazin-3-yl)oxy)phenyl)-1,2,4-triazine-3,5(2H,4H)-dione (34f) (43 mg, 66.83 umol) in dioxane (1 mL) was added HCl (4 M, 835.36 uL). The mixture was stirred at 80° C. for 16 hours. LCMS showed the reaction was completed, and desired MS was detected. The reaction mixture was concentrated under reduced pressure. The residue was diluted with water (10 mL) and extracted with ethyl acetate (10 mL*3). The combined organic layers were washed with brine (10 mL), dried over anhydrous Na₂SO₄, filtered and concentrated under reduced pressure. The residue was purified by Prep-HPLC (column: Welch Ultimate AQ-C18 150*30 mm*5 um; mobile phase: [water (0.1% TFA)-ACN]) to give 34. MS mass calculated for [M+1]⁺ ($C_{15}H_{11}Cl_2N_5O_5$) requires m/z 412.0, LCMS found m/z 412.0. ¹H NMR (400 MHz, MeOH-d4) δ 8.19-8.13 (m, 2H), 7.52 (d, J=1.2 Hz, 1H), 4.93-4.88 (m, 1H), 1.46 (d, J=6.6 Hz, 3H).

Example S35: 6-(4-((5-acetyl-1-methyl-6-oxo-1,6-dihydropyridazin-3-yl)oxy)-3,5-dichlorophenyl)-1,2,4-triazine-3,5(2H,4H)-dione (Compound 35)

Scheme 35

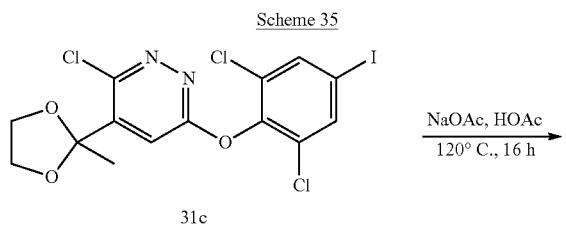

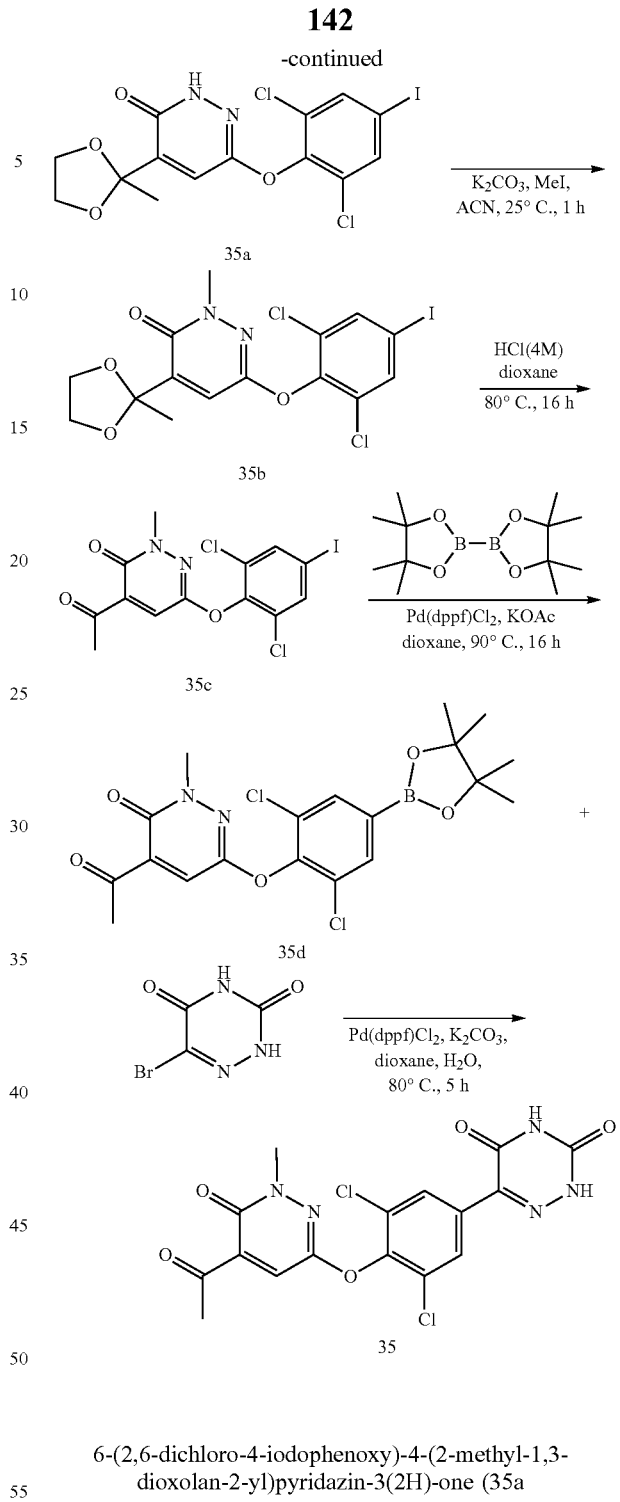

6-(2,6-dichloro-4-iodophenoxy)-4-(2-methyl-1,3-dioxolan-2-yl)pyridazin-3(2H)-one (35a)

To a solution of 3-chloro-6-(2,6-dichloro-4-iodophenoxy)-4-(2-methyl-1,3-dioxolan-2-yl)pyridazine (31c) (150 mg, 307.69 umol) in AcOH (3 mL) was added NaOAc (126.20 mg, 1.54 mmol). The mixture was stirred at 120° C. for 16 hours. LCMS showed 31c was consumed completely and the desired mass was detected. The reaction mixture was concentrated under reduced pressure to remove AcOH. The crude product was triturated with H₂O (5 mL) at 20° C. for 15 minutes, then the crude product was triturated with Petroleum ether:Ethyl acetate=20:1 (5 mL) at 20° C. for 30 minutes to give 35a, which was obtained as a white solid.

MS mass calculated for [M+1]⁺ (C₁₄H₁₁C₂₁N₂O₄) requires m/z 468.9, LCMS found m/z 468.9.

6-(2,6-dichloro-4-iodophenoxy)-2-methyl-4-(2-methyl-1,3-dioxolan-2-yl)pyridazin-3(2H)-one (35b A mixture of 6-(2,6-dichloro-4-iodophenoxy)-2-methyl-1,3-dioxolan-2-yl)pyridazin-3(2H)-one (35a) (80 mg, 170.55 umol), K₂CO₃ (47.14 mg, 341.11 umol), CH₃I (29.05 mg, 204.67 umol, 12.74 uL) in ACN (5 mL) was degassed and purged with N₂ for 3 times, and then the mixture was stirred at 25° C. for 1 hour under N₂ atmosphere. LCMS showed 35a was consumed completely and the desired mass was detected. The reaction mixture was concentrated under reduced pressure. The residue was triturated with H₂O (5 mL) and stirred at 20° C. for 1 hour. Then the mixture was filtered to collect solid. The solid was triturated with a solution of Petroleum ether:Ethyl acetate=5:1 (5 mL) and filtered to give 35b. MS mass calculated for [M+1]+(C₁₅H₁₃Cl₂₁N₂O₄) requires m/z 482.9, LCMS found m/z 483.0.

4-acetyl-6-(2,6-dichloro-4-iodophenoxy)-2-methylpyridazin-3(2H)-one (35c

To a solution of 6-(2,6-dichloro-4-iodophenoxy)-2-methyl-4-(2-methyl-1,3-dioxolan-2-yl)pyridazin-3(2H)-one (35b) (70 mg, 144.90 umol) in dioxane (2 mL) was added HCl (4 M, 2 mL). The mixture was stirred at 80° C. for 16 hours. LCMS indicated 35b was consumed completely and the desired mass was detected. The reaction mixture was concentrated under reduced pressure. The residue was triturated with a solution of Petroleum ether:Ethyl acetate and stirred at 20° C. for 1 hour. The mixture was filtered to give 35c. MS mass calculated for [M+1]+(C₁₃H₉Cl₂IN₂O₃) requires m/z 438.9, LCMS found m/z 438.9; ¹H NMR (400 MHz, MeOH-d4) δ 7.89 (s, 2H), 7.78 (s, 1H), 3.54 (s, 3H), 2.66 (s, 3H).

4-acetyl-6-(2,6-dichloro-4-(4,4,5,5-tetramethyl-1,3,2-dioxaborolan-2-yl)phenoxy)-2-methylpyridazin-3(2H)-one (35d To a solution of 4-acetyl-6-(2,6-dichloro-4-iodophenoxy)-2-methylpyridazin-3(2H)-one (35c) (60 mg, 136.66 umol) and 4,4,4',4',5,5,5',5'-octamethyl-2,2'-bi(1,3,2-dioxaborolane) (104.11 mg, 409.99 umol) in dioxane (3 mL) was added Pd(dppf)Cl₂ (10.00 mg, 13.67 umol) and KOAc (67.06 mg, 683.32 umol) under N₂. The mixture was stirred at 90° C. for 16 hours under N₂ atmosphere. LCMS indicated ~40% of 35c was remained and the desired mass was detected. The suspension was filtered through a pad of Celite and the pad cake was washed with ethyl acetate (10 mL*3). The combined organic layers were washed with H₂O (10 mL), dried over Na₂SO₄, filtered and concentrated under reduced pressure. The residue was purified by Prep-TLC (SiO₂, Petroleum ether:Ethyl acetate) to give 35d. MS mass calculated for [M+1]⁺ (C₁₉H₂₁BCl₂N₂O₅) requires m/z 439.1, LCMS found m/z 439.1. ¹H NMR (400 MHz, CDCl₃) δ 7.80 (s, 2H), 7.71 (s, 1H), 3.56-3.60 (m, 3H), 2.75-2.77 (m, 3H), 1.34-1.39 (m, 12H).

6-(4-((5-acetyl-1-methyl-6-oxo-1,6-dihydropyridazin-3-yl)oxy)-3,5-dichlorophenyl)-1,2,4-triazine-3,5(2H,4H)-dione (35

To a solution of 4-acetyl-6-(2,6-dichloro-4-(4,4,5,5-tetramethyl-1,3,2-dioxaborolan-2-yl)phenoxy)-2-methylpyridazin-3 (2H)-one (35d) (40 mg, 91.10 umol) and 6-bromo-2H-1,2,4-triazine-3,5-dione (34.98 mg, 182.19 umol) in THF (2 mL) and H₂O (0.5 mL) was added Pd(dppf)Cl₂ (5.94 mg, 9.11 umol) and K₃PO₄ (38.67 mg, 182.19 umol) under N₂. The mixture was stirred at 80° C. for 5 hours under N₂ atmosphere. LCMS indicated 35d was consumed completely and the desired mass was detected. The suspension was filtered through a pad of Celite and the pad cake was washed with ethyl acetate (10 mL*3). The combined filtrates were concentrated in vacuum. The residue was purified by Prep-HPLC (column: Xtimate C18 100*30 mm*3 um; mobile phase: [water (0.225% FA)-ACN]) to give 35. MS mass calculated for [M+1]⁺ (C₁₆H₁₁Cl₂N₅O₅) requires m/z 424.0, LCMS found m/z 424.0; ¹H NMR (400 MHz, MeOH-d4) δ 8.18-8.21 (m, 2H), 7.79 (s, 1H), 3.54 (s, 3H), 3.50-3.51 (m, 1H), 2.67 (s, 3H).

Biological Examples: Biological Screening

Example B1: Time-Resolved Fluorescence Resonance Energy Transfer (TR-FRET) Assay for Thyroid Hormone Receptor Agonist Screening LanthaScreen™ TR-FRET Thyroid Receptor alpha Coactivator Assay kit (ThermoFisher) and LanthaScreen™ TR-FRET Thyroid Receptor beta Coactivator Assay kit (ThermoFisher) were used for agonist compound screening. Compounds in DMSO were diluted using ECHO Liquid Handler (Labcyte Inc.) into 384 plates in 10-point 3-fold series in duplicate (5 micro M final top concentration). Buffer C (ThermoFisher) was added to each well before the 4× mixture of fluorescein-SCR2-2 coactivator (200 nM final concentration), Terbium-labeled anti-GST antibody (2 nM final concentration), and THR alpha-LBD (0.4 nM final concentration) or THR beta-LBD (1.0 nM final concentration) was added. After 2 hours incubation at room temperature in the dark, the TR-FRET signal was measured on an EnVision plate reader (PerkinElmer) with excitation at 340 nm and dual emission readout at 495 and 520 nm with the delay time of 100 micro second and the integration time of 200 micro second. The ratio of emission signal at 520 and at 495 was used to calculate EC₅₀ using GraphPad Prism (GraphPad Software). In every batch of compound screening, T3 (L-3,3',5-Triiodothyronine sodium salt, >95%) (Calbiochem) was used as reference compound. The EC₅₀ of T3 measured were within 3-fold of the reference value provided by the assay kit manufacturer (ThermoFisher Scientific). The Z' factors measured in every batch of screening using T3 as high percent effect (HPE) control and 0.5% DMSO as zero percent effect (ZPE) control were in the range of 0.5 to 0.8. Compounds' THR-beta selectivity values in Table 2 are derived from T3-selectivity normalized data. Data obtained using the TR-FRET assay for certain compounds disclosed herein is listed in Table 2.

TABLE 2

| Compound No. | EC₅₀ THRβ-FRET [nM]ᵃ | EC₅₀ THRα-FRET [nM]ᵃ | THRβ-Selectivity |
|---|---|---|---|
| 1 | 24.7 | 79.2 | 17 |
| 2 | 141.1 | 681 | 27.7 |
| 3 | 114.3 | 1234.4 | 69.8 |
| 4* | >5000 | >5000 | >3.0 |
| 5 | 98.6 | 62.6 | 2.3 |
| 6 | 196.2 | 981.4 | 23.6 |
| 7 | 136.2 | 434.6 | 15.3 |
| 8 | 1448.1 | 3672.3 | 9.5 |

TABLE 2-continued

| Compound No. | EC$_{50}$ THRβ-FRET [nM]$^a$ | EC$_{50}$ THRα-FRET [nM]$^a$ | THRβ-Selectivity |
|---|---|---|---|
| 9 | 23.9 | 160.9 | 25.5 |
| 10 | 524.1 | 3322.5 | 22.7 |
| 13 | 750.4 | >5000 | >27.4 |
| 15 | 380.7 | 3342 | 31.2 |
| 16 | 162.9 | 1213.5 | 28.3 |
| 17 | 34.6 | 99.6 | 11.1 |
| 19 | 1415 | >5000 | 13.9 |
| 20 | 1933 | 1328 | 2.7 |
| 21 | 2883 | >5000 | >9.5 |
| 22 | 1170 | 3436 | 12.9 |
| 23 | 1381 | 3229 | 9.2 |
| 24 | 1189 | 1485 | 4.7 |
| 25 | 22.2 | 25 | 4.4 |
| 26 | 1421.5 | 4265 | 10.9 |
| 27 | 213.4 | 1746 | 33.9 |
| 28 | 669.7 | 3443.5 | 19.2 |
| 29 | 2074.5 | 4043 | 7.105 |
| 30 | 214.2 | 1311.5 | 24.7 |
| 31 | 986.9 | 2673 | 14.4 |
| 31 P1 | 1196.4 | >5000 | >26.2 |
| 31 P2 | 451.6 | 3076 | 21.7 |
| 32 | 230.9 | 1132.7 | 20.9 |
| 33 P1 | 696.4 | 2427.9 | 11.3 |
| 33 P2 | 65.7 | 274.3 | 14.1 |
| 34 | 399.7 | 1161 | 8.6 |
| 35 | 664.8 | 1866 | 10.6 |

*Compound 4 does not fall within the scope of formula (I) and is provided for comparative purposes only.
$^a$all compounds were run in duplicate multiple times, and the average data is reported.

All publications, including patents, patent applications, and scientific articles, mentioned in this specification are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

The invention claimed is:

1. A compound of formula (I):

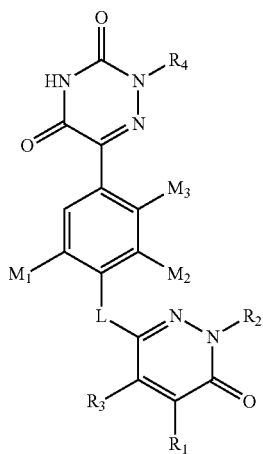

wherein:
$R_1$ is substituted or unsubstituted $C_1$-$C_6$ alkyl, substituted or unsubstituted $C_3$-$C_6$ cycloalkyl, —C(O)N($R_7$)($R_8$), —N($R_9$)C(O)($R_{10}$), or halo;

$R_2$ is H, substituted or unsubstituted $C_1$-$C_6$ alkyl, or substituted or unsubstituted $C_3$-$C_6$ cycloalkyl;
$R_3$ is H or halo;
$R_4$ is H, or substituted or unsubstituted linear $C_1$-$C_3$ alkyl;
L is —O—, —S—, —S(O)—, —S(O)$_2$—, —C(O)—, or —C($R_5$)($R_6$)—;
$R_5$ and $R_6$ are independently H, halo, —CN, or substituted or unsubstituted $C_1$-$C_6$ alkyl, or $R_5$ and $R_6$ are taken together with the carbon atom to which they are attached to form a substituted or unsubstituted $C_3$-$C_6$ cycloalkyl;
$R_7$ and $R_8$ are independently H, or substituted or unsubstituted $C_1$-$C_6$ alkyl, or $R_7$ and $R_8$ are taken together with the nitrogen atom to which they are attached to form a substituted or unsubstituted 3- to 7-membered heterocycloalkyl;
$R_9$ is H, substituted or unsubstituted $C_1$-$C_6$ alkyl, or substituted or unsubstituted $C_3$-$C_6$ cycloalkyl;
$R_{10}$ is substituted or unsubstituted $C_1$-$C_6$ alkyl, substituted or unsubstituted $C_3$-$C_6$ cycloalkyl, —N($R_7$)($R_8$), or —O($R_{11}$);
$R_{11}$ is substituted or unsubstituted $C_1$-$C_6$ alkyl, or substituted or unsubstituted $C_3$-$C_6$ cycloalkyl;
$M_1$ and $M_2$ are independently halo, or substituted or unsubstituted $C_1$-$C_6$ alkyl; and
$M_3$ is H, halo, or substituted or unsubstituted $C_1$-$C_6$ alkyl, or $M_3$ is taken together with $M_2$ and the carbon atoms to which they are attached to form a 5- to 7-membered ring containing 0, 1, or 2 heteroatoms selected from the group consisting of N, O, and S,
or a pharmaceutically acceptable salt thereof.

2. The compound of claim 1, or a pharmaceutically acceptable salt thereof, wherein:
$R_1$ is $C_1$-$C_6$ alkyl, $C_3$-$C_6$ cycloalkyl, —C(O)N($R_7$)($R_8$), —N($R_9$)C(O)($R_{10}$), or halo, wherein $C_1$-$C_6$ alkyl and $C_3$-$C_6$ cycloalkyl are optionally substituted by 1-5 substituents selected from the group consisting of —OH, oxo, —CN, and halo;
$R_2$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;
$R_3$ is H or halo;
$R_4$ is H or linear $C_1$-$C_3$ alkyl optionally substituted by 1-5 substituents selected from the group consisting of —OH, oxo, —CN, halo, and —O($C_1$-$C_2$ alkyl);
L is —O—, —S—, —S(O)—, —S(O)$_2$—, —C(O)—, or —C($R_5$)($R_6$)—;
$R_5$ and $R_6$ are independently H, halo, —CN, or $C_1$-$C_6$ alkyl, or $R_5$ and $R_6$ are taken together with the carbon atom to which they are attached to form a $C_3$-$C_6$ cycloalkyl, wherein each $C_1$-$C_6$ alkyl or $C_3$-$C_6$ cycloalkyl is optionally independently substituted by 1-5 substituents selected from the group consisting of —OH, —CN, and halo;
$R_7$ and $R_8$ are independently H or $C_1$-$C_6$ alkyl, or $R_7$ and $R_8$ are taken together with the nitrogen atom to which they are attached to form a 3- to 7-membered heterocycloalkyl, wherein each $C_1$-$C_6$ alkyl or 3- to 7-membered heterocycloalkyl is optionally independently substituted by 1-5 substituents selected from the group consisting of —OH, —CN, and halo;
$R_9$ is H, $C_1$-$C_6$ alkyl, or $C_3$-$C_6$ cycloalkyl, wherein $C_1$-$C_6$ alkyl and $C_3$-$C_6$ cycloalkyl are optionally substituted by 1-5 substituents selected from the group consisting of —OH, —CN, and halo;

$R_{10}$ is $C_1$-$C_6$ alkyl, $C_3$-$C_6$ cycloalkyl, —N($R_7$)($R_8$), or —O($R_{11}$), wherein $C_1$-$C_6$ alkyl and $C_3$-$C_6$ cycloalkyl are optionally substituted by 1-5 substituents selected from the group consisting of —OH, —CN, and halo;

$R_{11}$ is $C_1$-$C_6$ alkyl or $C_3$-$C_6$ cycloalkyl, each of which is optionally substituted by 1-5 substituents selected from the group consisting of —OH, —CN, and halo;

$M_1$ and $M_2$ are independently halo or $C_1$-$C_6$ alkyl optionally substituted by 1-5 substituents selected from the group consisting of —OH, —CN, and halo; and $M_3$ is H, halo, or $C_1$-$C_6$ alkyl optionally substituted by 1-5 substituents selected from the group consisting of —OH, —CN, and halo, or $M_3$ is taken together with $M_2$ and the carbon atoms to which they are attached to form a 5- to 7-membered ring containing 0, 1, or 2 heteroatoms selected from the group consisting of N, O, and S.

3. The compound of claim 1, or a pharmaceutically acceptable salt thereof, wherein:

$R_1$ is $C_1$-$C_6$ alkyl or $C_3$-$C_6$ cycloalkyl, each of which is optionally substituted by 1-5 substituents selected from the group consisting of —OH, oxo, —CN, and halo.

4. The compound of claim 3, or a pharmaceutically acceptable salt thereof, wherein:

$R_1$ is cyclopropyl, isopropyl, ethyl, —CH($CH_2CH_3$)$_2$, —CH($CH_3$)($CH_2OH$), —CH(OH)($CH_2CH_3$), —CH(OH)($CH_3$), —CH($CH_3$)($CH_2CH_3$), or —C(O)($CH_3$).

5. The compound of claim 1, or a pharmaceutically acceptable salt thereof, wherein:

$R_2$ is H or $C_1$-$C_6$ alkyl optionally substituted by 1-5 substituents selected from the group consisting of —OH, —CN, and halo.

6. The compound of claim 5, or a pharmaceutically acceptable salt thereof, wherein:

$R_2$ is H or methyl.

7. The compound of claim 1, or a pharmaceutically acceptable salt thereof, wherein:

$R_3$ is H.

8. The compound of claim 1, or a pharmaceutically acceptable salt thereof, wherein:

$R_4$ is H or linear $C_1$-$C_3$ alkyl optionally substituted by 1-3 substituents selected from the group consisting of —OH, oxo, —CN, halo, and —O($C_1$-$C_2$ alkyl).

9. The compound of claim 8, or a pharmaceutically acceptable salt thereof, wherein:

$R_4$ is H, methyl, ethyl, —$CH_2C(O)OCH_2CH_3$, —$CH_2CF_3$, —$CH_2CN$, or —$CH_2CHF_2$.

10. The compound of claim 1, or a pharmaceutically acceptable salt thereof, wherein:

L is —O—, —C(O)—, or —$CH_2$—.

11. The compound of claim 1, or a pharmaceutically acceptable salt thereof, wherein:

$M_1$ and $M_2$ are independently halo or $C_1$-$C_3$ alkyl optionally substituted by 1-3 substituents selected from the group consisting of —OH, —CN, and halo.

12. The compound of claim 11, or a pharmaceutically acceptable salt thereof, wherein:

$M_1$ and $M_2$ are independently halo or methyl.

13. The compound of claim 12, or a pharmaceutically acceptable salt thereof, wherein:

$M_1$ and $M_2$ are each chloro.

14. The compound of claim 12, or a pharmaceutically acceptable salt thereof, wherein:

$M_1$ and $M_2$ are each methyl.

15. The compound of claim 1, or a pharmaceutically acceptable salt thereof, $M_3$ is H, halo, or $C_1$-$C_3$ alkyl optionally substituted by 1-3 substituents selected from the group consisting of —OH, —CN, and halo.

16. The compound of claim 15, or a pharmaceutically acceptable salt thereof, wherein:

$M_3$ is H, F, or methyl.

17. A compound, or a pharmaceutically acceptable salt thereof, wherein the compound is selected from the group consisting of:

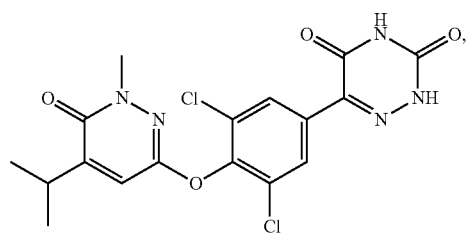

1

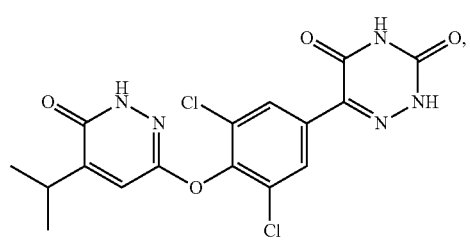

2

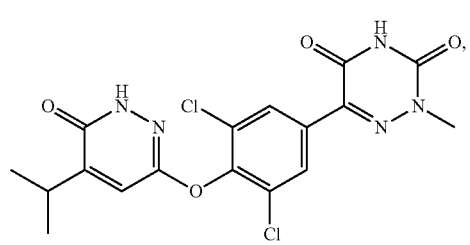

3

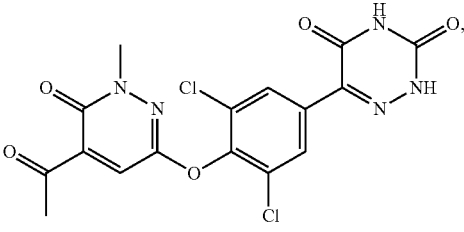

35

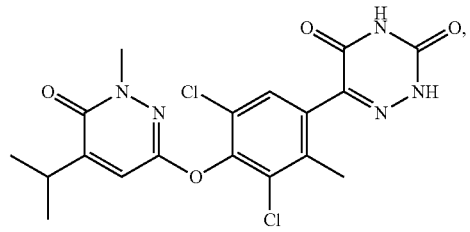

5

6
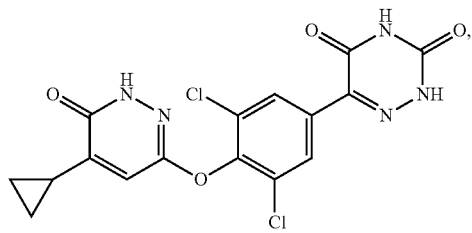
12
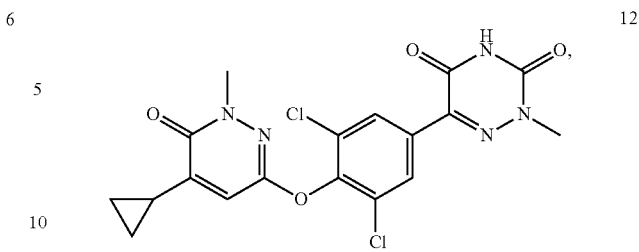
7
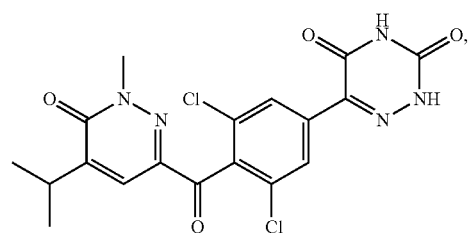
13
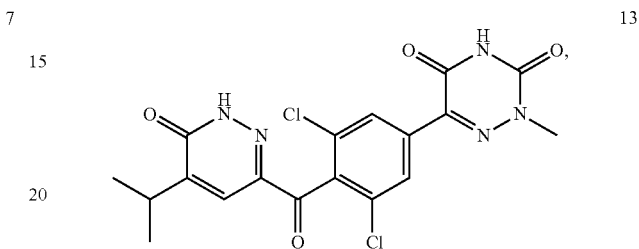
8
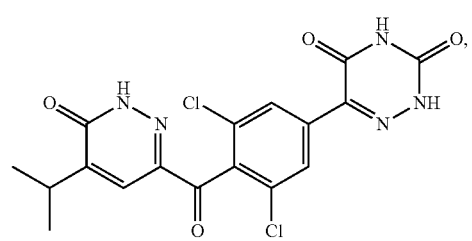
14
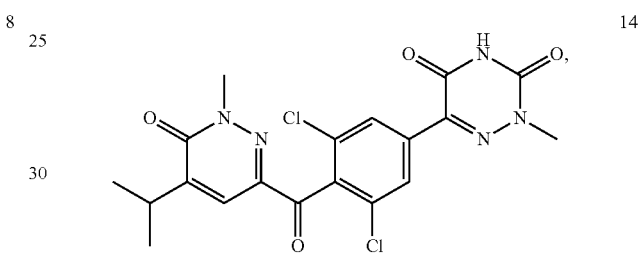
9
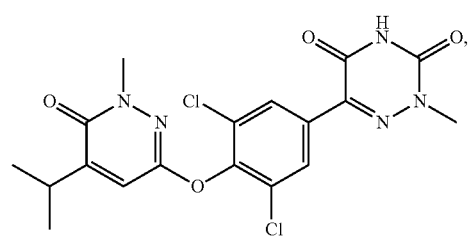
15
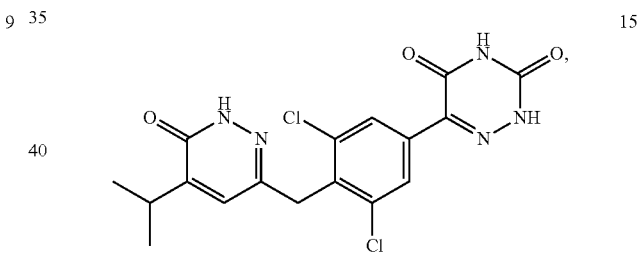
10
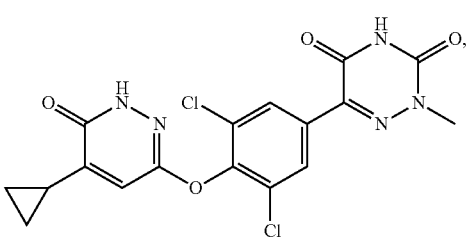
16
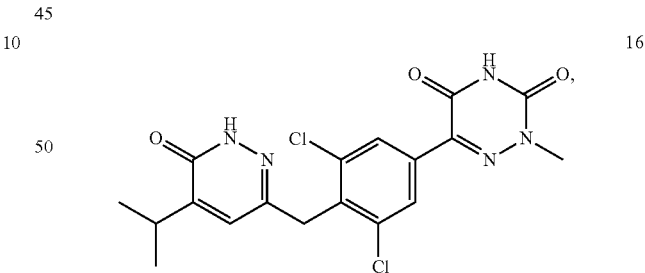
11
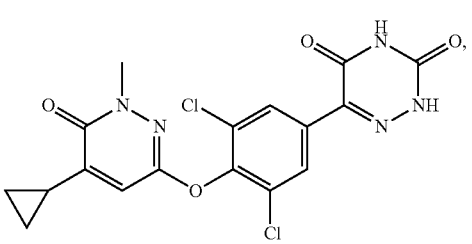
17
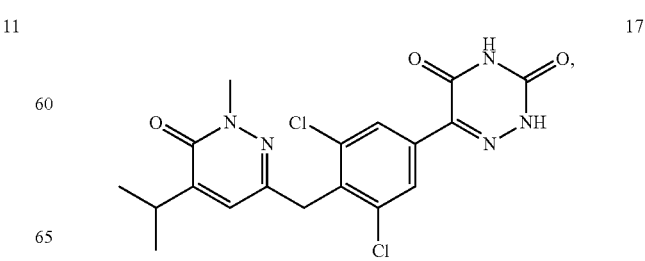

18
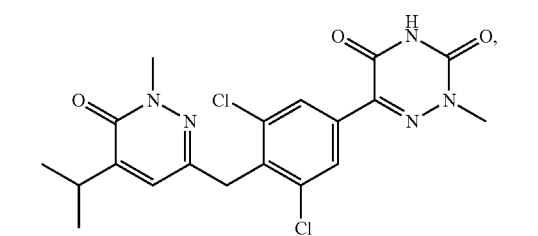
19
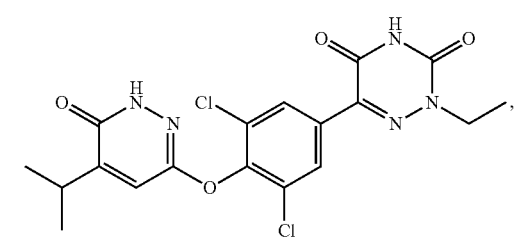
20
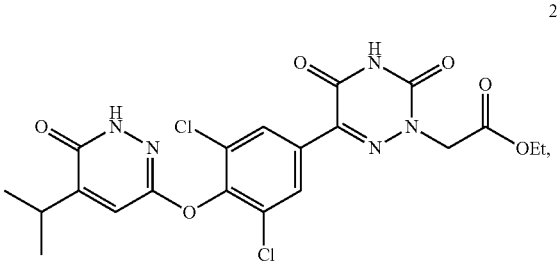
21
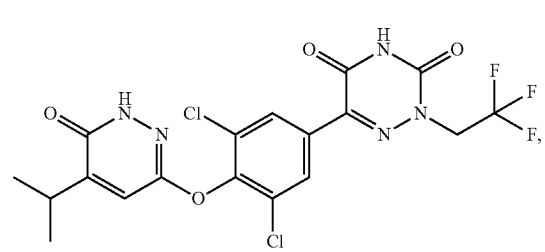
22
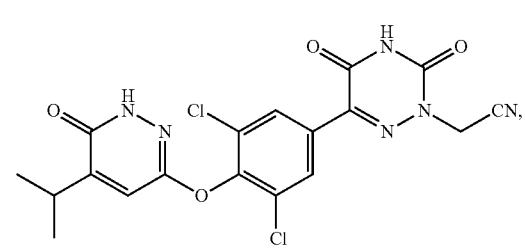
23
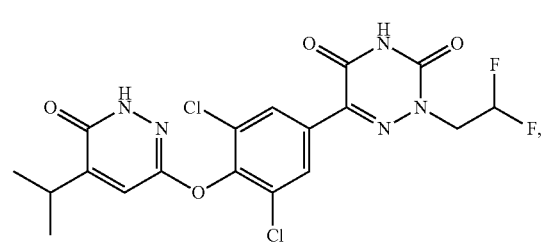
24
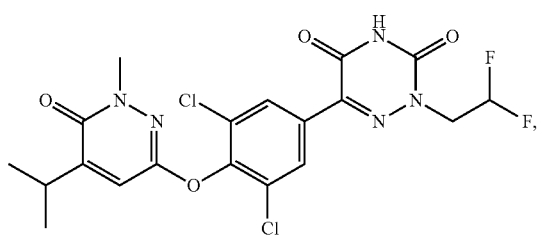
25
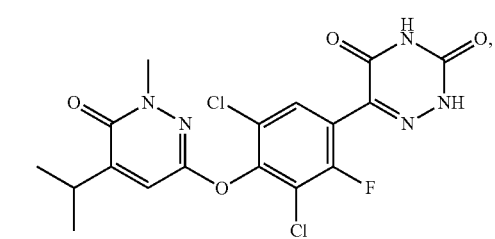
26
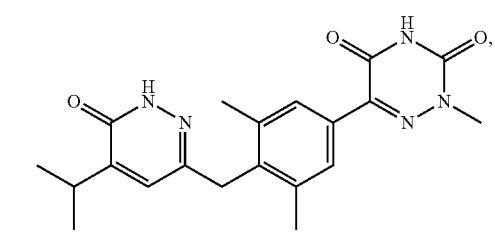
27
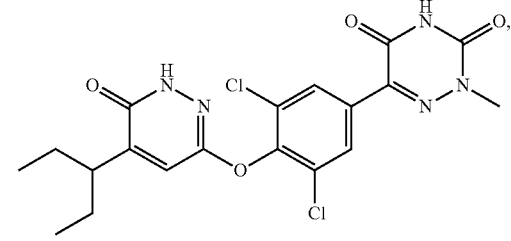
28
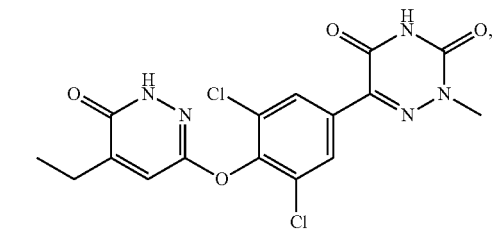
29
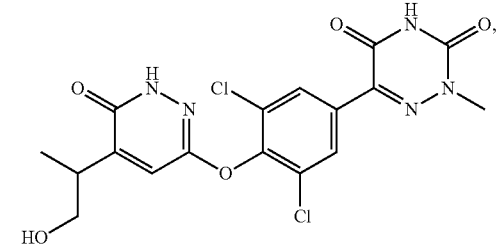

-continued

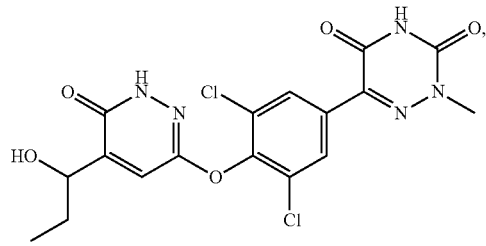
30

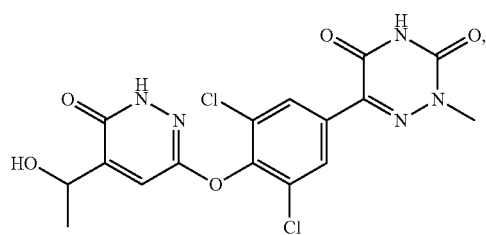
31

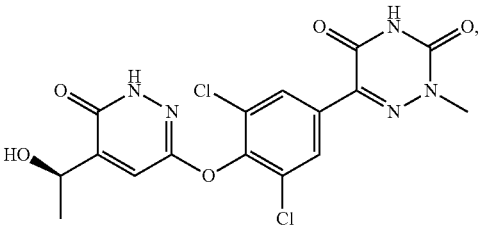
31 P1

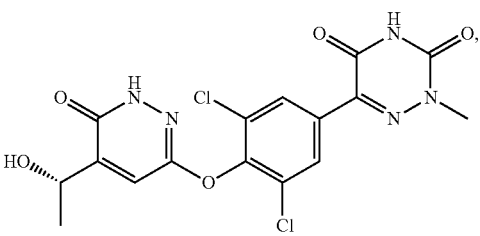
31 P2

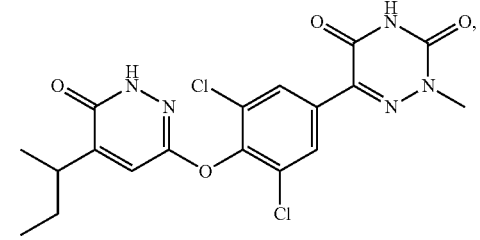
32

-continued

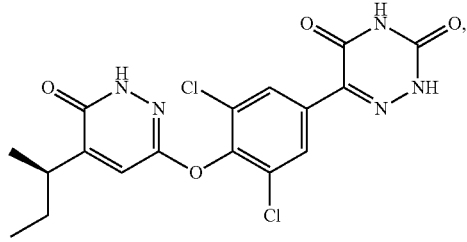
33 P1

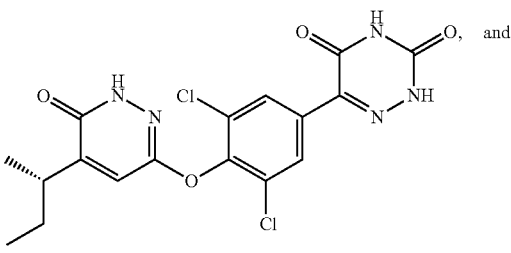
33 P2

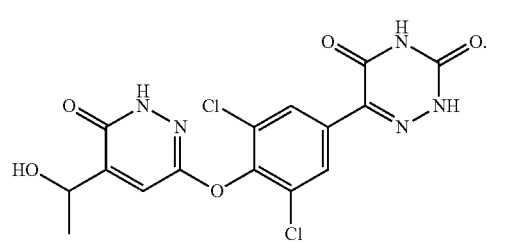
34

18. A pharmaceutical composition comprising the compound of claim 1, or a pharmaceutically acceptable salt thereof, and a pharmaceutically acceptable excipient.

19. A method of agonizing thyroid hormone receptor beta (THR beta) comprising contacting an effective amount of the compound of claim 1, or a pharmaceutically acceptable salt thereof, with the THR beta.

20. A method of treating a disorder which is mediated by THR beta in a patient in need thereof, comprising administering to the patient a therapeutically effective amount of the compound of claim 1, or a pharmaceutically acceptable salt thereof, wherein the disorder is non-alcoholic steatohepatitis (NASH), non-alcoholic fatty liver disease (NAFLD), dyslipidemia, metabolic syndrome, hypertriglyceridemia, or hypercholesterolemia.

21. The method of claim 20, wherein the disorder is non-alcoholic steatohepatitis (NASH).

* * * * *